US012637668B2

(12) United States Patent
Ronzitti et al.

(10) Patent No.: US 12,637,668 B2
(45) Date of Patent: May 26, 2026

(54) MINI-GDE FOR THE TREATMENT OF GLYCOGEN STORAGE DISEASE III

(71) Applicants: GENETHON, Evry-Courcouronnes (FR); INSTITUT NATIONAL DE LA SANTE ET DE LA RECHERCHE MEDICALE, Paris (FR); SORBONNE UNIVERSITÉ, Paris (FR); UNIVERSITE D'EVRY VAL D'ESSONNE, Evry-Courcouronnes (FR); ASSOCIATION INSTITUT DE MYOLOGIE, Paris (FR)

(72) Inventors: Giuseppe Ronzitti, Fontainebleau (FR); Patrice Vidal, Ris-Orangis (FR); Federico Mingozzi, Philadelphia, PA (US)

(73) Assignees: GENETHON, Evry-Courcouronnes (FR); INSTITUT NATIONAL DE LA SANTE ET DE LA RECHERCHE MEDICALE, Paris (FR); SORBONNE UNIVERSITÉ, Paris (FR); UNIVERSITE D'EVRY VAL D'ESSONE, Evry-Courcouronnes (FR); ASSOCIATION INSTITUT DE MYOLOGIE, Paris (FR)

( * ) Notice: Subject to any disclaimer, the term of this patent is extended or adjusted under 35 U.S.C. 154(b) by 1031 days.

(21) Appl. No.: 17/265,528

(22) PCT Filed: Aug. 6, 2019

(86) PCT No.: PCT/EP2019/071158
§ 371 (c)(1),
(2) Date: Feb. 3, 2021

(87) PCT Pub. No.: WO2020/030661
PCT Pub. Date: Feb. 13, 2020

(65) Prior Publication Data

US 2021/0292724 A1 Sep. 23, 2021

(30) Foreign Application Priority Data

Aug. 8, 2018 (EP) .................................... 18306088

(51) Int. Cl.
*C12N 9/44* (2006.01)
*A61K 38/00* (2006.01)
(Continued)

(52) U.S. Cl.
CPC ......... *C12N 9/2451* (2013.01); *C12N 9/1051* (2013.01); *C12N 15/86* (2013.01);
(Continued)

(58) Field of Classification Search
None
See application file for complete search history.

(56) References Cited

FOREIGN PATENT DOCUMENTS

WO WO 2014/130722 8/2014

OTHER PUBLICATIONS

Ghaffari et al., 2015 (BLOSUM62 Accession No. KT001453, computer printout, pp. 1-8).*

(Continued)

*Primary Examiner* — Teresa E Knight
(74) *Attorney, Agent, or Firm* — SALIWANCHIK, LLOYD & EISENCHENK

(57) ABSTRACT

The present invention relates to a mini-glycogen debranching enzyme ((GDE); mini-GDE) for the treatment of glycogen storage disease III (GSDIII (Cori disease). Also disclosed are functional truncated human GDE polypeptides, functional non-human GDE polypeptides, nucleic acid molecules, nucleic acid constructs, or vectors encoding functional truncated human GDE or non-human GDE polypeptides as well as host cells expressing functional truncated human GDE or non-human GDE polypeptides. In a further aspect, the disclosure provides functional truncated human (Continued)

Figure 1:
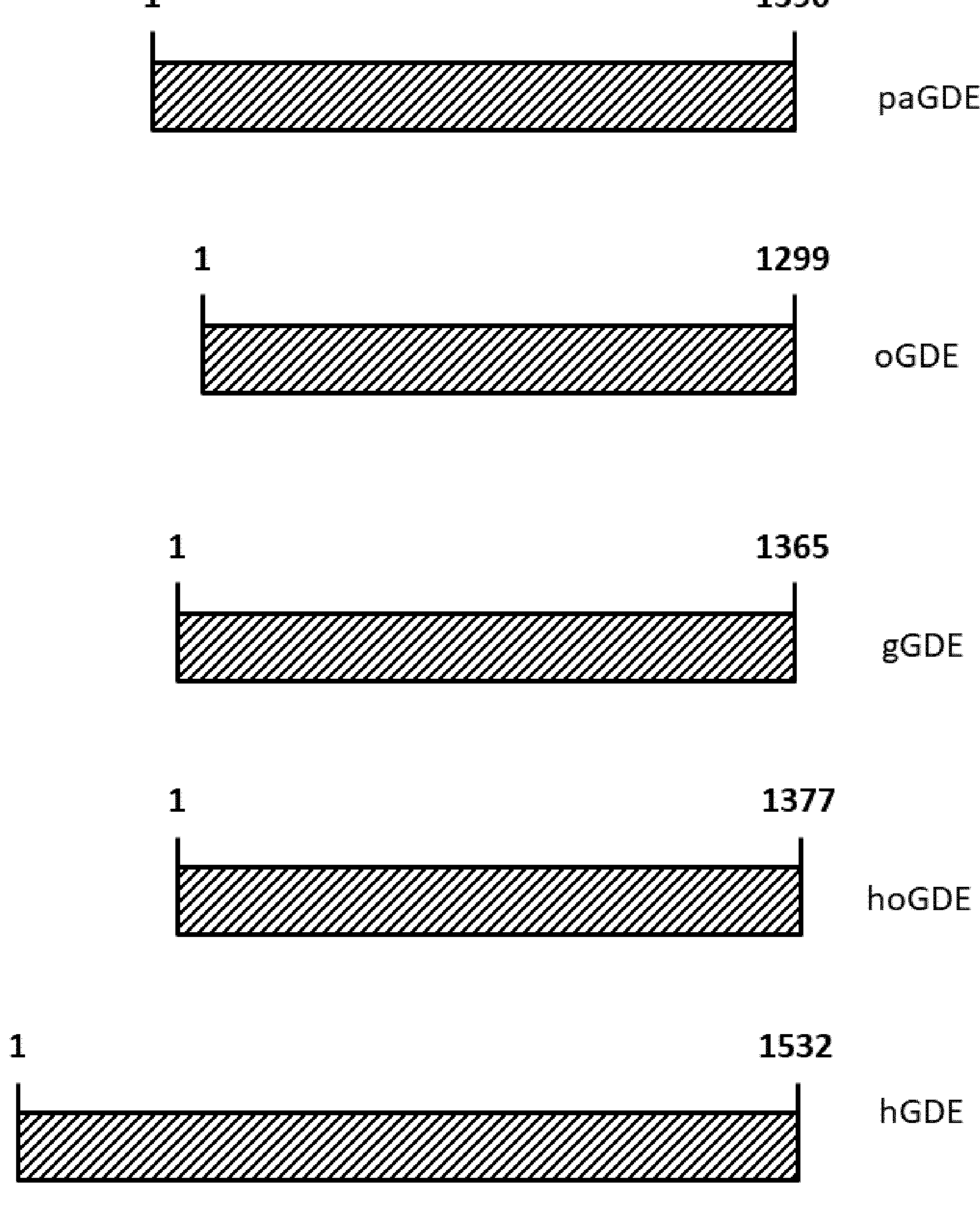

GDE polypeptides, functional non-human GDE polypeptides, nucleic acid molecules, nucleic acid constructs, vectors, or cells of the invention for use in a method for treating GSDIII (Cori disease).

18 Claims, 7 Drawing Sheets

Specification includes a Sequence Listing.

(51) Int. Cl.
*C12N 9/10* (2006.01)
*C12N 15/86* (2006.01)

(52) U.S. Cl.
CPC .... *A61K 38/00* (2013.01); *C12N 2750/14143* (2013.01); *C12N 2830/50* (2013.01); *C12Y 204/01025* (2013.01); *C12Y 302/01033* (2013.01)

(56) References Cited

OTHER PUBLICATIONS

Liu et al., 2014 (Molecular Genetics and Metabolism, vol. 111, p. 467-476).*

Nagase et al., 2016 (BLOSUM62 Accession No. AB384755, computer printout, pp. 1-5).*

Xu et al., 2018 (Stem Cell Research, vol. 27, p. 38-41, Available online Dec. 13, 2017).*

Maqbool et al., 2015 (Biochemical Society Transactions, vol. 43, No. 5, p. 1011-1017).*

Cruz et al., 2017 (Methods in Molecular Biology, vol. 1654, Chapter 5, pp. 55-75).*

Yan et al., 2023 (Computers in Biology and Medicine, 154: 106466, p. 1-12).*

Del Rio, Gabriel, 2021 (Computation, 9, 39, p. 1-11).*

Chamberlain, K. et al. "Expressing Transgenes That Exceed the Packaging Capacity of Adeno-Associated Virus Capsids" *Human Gene Therapy Methods*, 2016, pp. 1-12, vol. 27, No. 1.

Sun, B. et al. "Preclinical Development of New Therapy for Glycogen Storage Diseases" *Curr Gene Ther.*, 2015, pp. 1-20, vol. 15, No. 4.

Vidal, P. et al. "Rescue of GSDIII Phenotype with Gene Transfer Requires Liver- and Muscle-Targeted GDE Expression" *Molecular Therapy, American Society of Gene & Cell Therapy*, Mar. 2018, pp. 890-901, vol. 26, No. 3.

Vidal, P. et al. "Adeno associated vector-based gene therapy strategy for type 3 glycogen storage disease" *Abstracts, Neuromuscular Disorders*, 2017, p. S246, TH.O.18, vol. 27, abstract only.

Written Opinion in International Application No. PCT/EP2019/071158, Oct. 2, 2019, pp. 1-11.

* cited by examiner

FIGURE 10
Truncated GDEs
Δ13 Δ2/3
Δ10 Δ2/3
Δ9 Δ2/3
Δ2/3
CMV GDEfs
Aspecific band
150 KDa

MINI-GDE FOR THE TREATMENT OF GLYCOGEN STORAGE DISEASE III

CROSS-REFERENCE TO RELATED APPLICATION

This application is the U.S. national stage application of International Patent Application No. PCT/EP2019/071158, filed Aug. 6, 2019.

The Sequence Listing for this application is labeled "Seq-List.txt" which was created on Jan. 19, 2021, and is 461 KB. The entire content of the sequence listing is incorporated herein by reference in its entirety.

The present invention relates to the treatment of glycogen storage disease III (GSDIII).

BACKGROUND OF THE INVENTION

Mutations in the AGL gene cause genetic deficiency of glycogen debranching enzyme (GDE), or "amylo-alpha-1, 6-glucosidase, 4-alpha-glucanotransferase", an enzyme involved in glycogen degradation. GDE has two independent catalytic activities which occur at different sites on the protein: a 4-alpha-glucotransferase activity and an amylo-1,6-glucosidase activity. Genetic deficiency of GDE causes an incomplete glycogenolysis in glycogen storage disease III (GSD III), resulting in accumulation of abnormal glycogen with short outer chain in various organs, mostly liver and muscle. The disease is characterized by hepatomegaly, hypoglycemia, short stature, variable myopathy and cardiomyopathy. Most patients have diseases involving both liver and muscle (type IIIa), while some patients (~15 percent) have only liver involvement (type IIIb). Liver symptoms normally occur in childhood. Liver cirrhosis and hepatocellular carcinoma have been reported in some cases (Chen et al., 2009, Scriver's Online Metabolic & Molecular Bases of inherited Disease, New York: McGraw-Hill; Kishnani et al., 2010, Genet Med 12, 446-463). Muscle weakness could be present during childhood. It becomes more prevalent in adults with onset in the third or fourth decade. There is significant morbidity from progressive muscle weakness and patients in later stages can become wheel chair bound. Patients can also develop cardiomyopathy. There is significant clinical variability in the severity of the symptoms that these patients develop. The progressive myopathy and/or cardiomyopathy and/or peripheral neuropathy are major causes of morbidity in adults (Kishnani et al., 2010, Genet Med 12, 446-463; Cornelio et al., 1984, Arch Neurol 41, 1027-1032; Coleman et al., 1992, Ann Intern Med 116, 896-900). Reports of possible neurological manifestations associated with the disease derive from clinicians working with GSDIII patients, who reported attention fluctuations, deficiencies in executive functions and impaired emotional skills (Michon et al., 2015, J Inherit Metab Dis, 38 (3): 573-580). Accordingly, in the GDE−/− mouse model of the disease, an extensive accumulation of glycogen throughout the nervous system was documented (Pagliarani et al., 2014, Biochim Biophys Acta, 1842 (11): 2318-2328; Liu et al., 2014, Mol Genet Metab, 111 (4): 467-476) although a careful characterization of the phenotype associated with the accumulation of glycogen is still missing. Current treatment is symptomatic, and there is no effective therapy for the disease. Hypoglycemia can be controlled by frequent meals high in carbohydrates with cornstarch supplements or nocturnal gastric drip feedings. Patients with myopathy have been treated with a diet high in protein during the daytime plus overnight enteral infusion. In some patients transient improvement in symptoms has been documented, but there are no systemic studies or long-term data demonstrating that the high protein diet prevents or treats the progressive myopathy (Kishnani et al., 2010, Genet Med 12, 446-463). These approaches do little to alter the long term course and morbidity of these diseases.

Therefore, there is still a need for a long-term treatment of GSD III. Gene therapy aiming to stably replace the GDE protein in the affected tissues appears as a potential therapeutic approach. However, the large size of the GDE transgene constitutes a major impediment since it cannot fit the size limit of most gene therapy vectors. Indeed, the human AGL gene is 85 kb in length and composed of 35 exons, encoding a 7.4-kb mRNA that includes a 4596-bp coding region and a 2371-bp 3' untranslated sequence to express a 175 kDa GDE protein (Bao Y et al., 1996, Genomics., 38 (2): 155-65). This constitutes a real issue since the minimum size of a GDE expression cassette (including for example at least a promoter, the GDE coding sequence, a polyA signal and the two ITRs for an AAV vector) would be larger than 5 kb, the genome size limit that can be packaged into an AAV gene therapy vector for in vivo gene delivery. The inventors have previously proposed the use of dual AAV vectors to overcome this size limitation. Following this approach, two vectors, each containing a portion of the large transgene coding sequence, are used to transduce the same cell. Although the use of dual AAV vectors is promising, it would be preferable to provide a gene therapy strategy implementing only one viral vector for both economic and practical reasons.

There is therefore a need for novel strategies to improve gene therapy in the treatment of GSD III.

SUMMARY OF THE INVENTION

A first aspect of the invention relates to a functional truncated human GDE polypeptide, which is deleted of at least about 10, 20, 30, 40, 50, 60, 75, 90, 100, 125, 150, 175, 190, 200, 225, 250, 275, 300, 325, 350, 375, 400, 425, 450, 475, 500 or at least about 525 amino acids with respect to a reference full-length human GDE sequence. In a particular embodiment, the reference full-length human GDE sequence has an amino acid sequence as shown in SEQ ID NO:1, SEQ ID NO:40 or SEQ ID NO:41.

In particular embodiments:

(i) the reference full-length human GDE sequence has an amino acid sequence as shown in SEQ ID NO: 1, and said truncated human GDE polypeptide comprises at least the amino acid residues at positions 429-666, 770-892, 1088-1194, and 1235-1532 with respect to SEQ ID NO:1;

(ii) the reference full-length human GDE sequence has an amino acid sequence as shown in SEQ ID NO:40, and said truncated human GDE polypeptide comprises at least the amino acid residues at positions 412-649, 753-875, 1071-1177, 1218-1515 with respect to SEQ ID NO:40; or (iii) the reference full-length human GDE sequence has an amino acid sequence as shown in SEQ ID NO:41, and said truncated human GDE polypeptide comprises at least the amino acid residues at positions 413-650, 754-876, 1072-1178, 1219-1516 with respect to SEQ ID NO:41.

In other embodiments:

(i) the reference full-length human GDE sequence has an amino acid sequence as shown in SEQ ID NO: 1, and the deleted amino acids are at least one amino acid at positions 1-428, 668-769, 895-1087 and/or 1195-1232 with respect to SEQ ID NO:1;

(ii) the reference full-length human GDE sequence has an amino acid sequence as shown in SEQ ID NO:40, and the deleted amino acids are at least one amino acid at positions 1-411, 651-752, 878-1070 and/or 1178-1215 with respect to SEQ ID NO:40; or (iii) the reference full-length human GDE sequence has an amino acid sequence as shown in SEQ ID NO:41, and the deleted amino acids are at least one amino acid at positions 1-412, 652-753, 879-1071 and/or 1179-1216 with respect to SEQ ID NO:41.

In yet other embodiments:

(i) the reference full-length human GDE sequence has an amino acid sequence as shown in SEQ ID NO: 1, and said truncated human GDE polypeptide is deleted of:
  - at least one amino acid selected from amino acids at positions 1 to 428 with respect to SEQ ID NO: 1, preferably at least 10, 15, 20, 30, 40, 50, 60, 80, 100, 150, 200, 250, 300, 350 or at least 400 consecutive amino acids selected from amino acids at positions 1 to 428 with respect to SEQ ID NO:1; and/or
  - at least one amino acid selected from amino acids at positions 668 to 769 with respect to SEQ ID NO: 1, preferably at least 10, 15, 20, 30, 40, 50, 80 or at least 100 consecutive amino acids selected from amino acids at positions 668 to 769 with respect to SEQ ID NO:1; and/or
  - at least one amino acid selected from amino acids at positions 895 to 1087 with respect to SEQ ID NO: 1, preferably at least 10, 15, 20, 30, 40, 50, 80, 100, 125, 150, 175, or at least 200 consecutive amino acids selected from amino acids at positions 895 to 1087 with respect to SEQ ID NO: 1; and/or
  - at least one amino acid selected from amino acids at positions 1195 to 1232 with respect to SEQ ID NO: 1, preferably at least 10, 15, 20 or at least 30 consecutive amino acids selected from amino acids at positions 1195 to 1232 with respect to SEQ ID NO:1; or (ii) the reference full-length human GDE sequence has an amino acid sequence as shown in SEQ ID NO: 40, and said truncated human GDE polypeptide is deleted of:
  - at least one amino acid selected from amino acids at positions 1 to 411 with respect to SEQ ID NO: 40, preferably at least 10, 15, 20, 30, 40, 50, 60, 80, 100, 150, 200, 250, 300, 350 or at least 400 consecutive amino acids selected from amino acids at positions 1 to 411 with respect to SEQ ID NO:40; and/or
  - at least one amino acid selected from amino acids at positions 651-752 with respect to SEQ ID NO: 40, preferably at least 10, 15, 20, 30, 40, 50, 80 or at least 100 consecutive amino acids selected from amino acids at positions 651-752 with respect to SEQ ID NO:40; and/or
  - at least one amino acid selected from amino acids at positions 878-1070 with respect to SEQ ID NO: 40, preferably at least 10, 15, 20, 30, 40, 50, 80, 100, 125, 150, 175, or at least 200 consecutive amino acids selected from amino acids at positions 878-1070 with respect to SEQ ID NO: 40; and/or
  - at least one amino acid selected from amino acids at positions 1178-1215 with respect to SEQ ID NO: 40, preferably at least 10, 15, 20 or at least 30 consecutive amino acids selected from amino acids at positions 1178-1215 with respect to SEQ ID NO:40; or (iii) the reference full-length human GDE sequence has an amino acid sequence as shown in SEQ ID NO: 41, and said truncated human GDE polypeptide is deleted of:
  - at least one amino acid selected from amino acids at positions 1 to 412 with respect to SEQ ID NO: 41, preferably at least 10, 15, 20, 30, 40, 50, 60, 80, 100, 150, 200, 250, 300, 350 or at least 400 consecutive amino acids selected from amino acids at positions 1 to 412 with respect to SEQ ID NO:41; and/or
  - at least one amino acid selected from amino acids at positions 652-753 with respect to SEQ ID NO: 41, preferably at least 10, 15, 20, 30, 40, 50, 80 or at least 100 consecutive amino acids selected from amino acids at positions 652-753 with respect to SEQ ID NO:41; and/or
  - at least one amino acid selected from amino acids at positions 879-1071 with respect to SEQ ID NO: 41, preferably at least 10, 15, 20, 30, 40, 50, 80, 100, 125, 150, 175, or at least 200 consecutive amino acids selected from amino acids at positions 879-1071 with respect to SEQ ID NO: 41; and/or
  - at least one amino acid selected from amino acids at positions 1179-1216 with respect to SEQ ID NO: 41, preferably at least 10, 15, 20 or at least 30 consecutive amino acids selected from amino acids at positions 1179-1216 with respect to SEQ ID NO:41.

In further embodiments:

(i) the reference full-length human GDE sequence has an amino acid sequence as shown in SEQ ID NO:1 and the functional truncated human GDE polypeptide comprises at least one deletion with respect to SEQ ID NO:1, wherein the deletion is selected from the group consisting of deletion of amino acids from position 1 to 156 with respect to SEQ ID NO:1;

deletion of amino acids from position 361 to 428 with respect to SEQ ID NO:1;

deletion of amino acids from position 668 to 769 with respect to SEQ ID NO:1;

deletion of amino acids from position 895 to 1087 with respect to SEQ ID NO:1;

deletion of amino acids from position 1195 to 1232 with respect to SEQ ID NO:1;

deletion of amino acids from position 223 to 320 with respect to SEQ ID NO:1;

deletion of amino acids from position 360 to 428 with respect to SEQ ID NO:1;

deletion of amino acids from position 669 to 720 with respect to SEQ ID NO:1;

deletion of amino acids from position 1 to 280 with respect to SEQ ID NO:1;

deletion of amino acids from position 1 to 425 with respect to SEQ ID NO:1;

deletion of amino acids from position 1 to 230 with respect to SEQ ID NO:1;

deletion of amino acids from position 1 to 15 with respect to SEQ ID NO:1;

deletion of amino acids from position 1 to 30 with respect to SEQ ID NO:1;

deletion of amino acids from position 1 to 81 with respect to SEQ ID NO:1;

deletion of amino acids from position 1 to 103 with respect to SEQ ID NO: 1; and deletion of amino acids from position 1 to 129 with respect to SEQ ID NO:1; or (ii) the reference full-length human GDE sequence has an amino acid sequence as shown in SEQ ID NO:40 and the functional truncated human GDE polypeptide comprises at least one deletion with respect to SEQ ID NO:40, wherein the deletion is selected from the group consisting of:

deletion of amino acids from position 1 to 139 with respect to SEQ ID NO:40;

deletion of amino acids from position 344 to 411 with respect to SEQ ID NO:40;

deletion of amino acids from position 651 to 752 with respect to SEQ ID NO:40;

deletion of amino acids from position 878 to 1070 with respect to SEQ ID NO:40;

deletion of amino acids from position 1178 to 1215 with respect to SEQ ID NO:40;

deletion of amino acids from position 206 to 303 with respect to SEQ ID NO:40;

deletion of amino acids from position 343 to 411 with respect to SEQ ID NO:40;

deletion of amino acids from position 652 to 703 with respect to SEQ ID NO:40;

deletion of amino acids from position 1 to 263 with respect to SEQ ID NO:40;

deletion of amino acids from position 1 to 408 with respect to SEQ ID NO:40;

deletion of amino acids from position 1 to 213 with respect to SEQ ID NO:40;

deletion of amino acids from position 1 to 13 with respect to SEQ ID NO:40;

deletion of amino acids from position 1 to 64 with respect to SEQ ID NO:40;

deletion of amino acids from position 1 to 86 with respect to SEQ ID NO:40; and deletion of amino acids from position 1 to 112 with respect to SEQ ID NO:40; or (iii) the reference full-length human GDE sequence has an amino acid sequence as shown in SEQ ID NO:41 and the functional truncated human GDE polypeptide comprises at least one deletion with respect to SEQ ID NO:41, wherein the deletion is selected from the group consisting of:

deletion of amino acids from position 1 to 140 with respect to SEQ ID NO:41;

deletion of amino acids from position 345 to 412 with respect to SEQ ID NO:41;

deletion of amino acids from position 652 to 753 with respect to SEQ ID NO:41;

deletion of amino acids from position 879 to 1071 with respect to SEQ ID NO:41;

deletion of amino acids from position 1179 to 1216 with respect to SEQ ID NO:41;

deletion of amino acids from position 207 to 304 with respect to SEQ ID NO:41;

deletion of amino acids from position 344 to 412 with respect to SEQ ID NO:41;

deletion of amino acids from position 653 to 704 with respect to SEQ ID NO:41;

deletion of amino acids from position 1 to 264 with respect to SEQ ID NO:41;

deletion of amino acids from position 1 to 409 with respect to SEQ ID NO:41;

deletion of amino acids from position 1 to 214 with respect to SEQ ID NO:41;

deletion of amino acids from position 1 to 14 with respect to SEQ ID NO:41;

deletion of amino acids from position 1 to 65 with respect to SEQ ID NO:41;

deletion of amino acids from position 1 to 87 with respect to SEQ ID NO:41; and deletion of amino acids from position 1 to 113 with respect to SEQ ID NO:41.

In further particular embodiments:

(i) the reference full-length human GDE sequence has an amino acid sequence as shown in SEQ ID NO:1 and the functional truncated human GDE polypeptide comprises at least one deletion with respect to SEQ ID NO:1, wherein the deletion is selected from the group consisting of:

deletion of amino acids from position 1 to 156 with respect to SEQ ID NO:1;

deletion of amino acids from position 361 to 428 with respect to SEQ ID NO:1;

deletion of amino acids from position 668 to 769 with respect to SEQ ID NO:1;

deletion of amino acids from position 895 to 1087 with respect to SEQ ID NO:1;

deletion of amino acids from position 1195 to 1232 with respect to SEQ ID NO:1;

deletion of amino acids from position 223 to 320 with respect to SEQ ID NO:1;

deletion of amino acids from position 360 to 428 with respect to SEQ ID NO:1;

deletion of amino acids from position 669 to 720 with respect to SEQ ID NO:1;

deletion of amino acids from position 1 to 280 with respect to SEQ ID NO:1;

deletion of amino acids from position 1 to 425 with respect to SEQ ID NO:1; and deletion of amino acids from position 1 to 230 with respect to SEQ ID NO: 1; or (ii) the reference full-length human GDE sequence has an amino acid sequence as shown in SEQ ID NO:40 and the functional truncated human GDE polypeptide comprises at least one deletion with respect to SEQ ID NO:40, wherein the deletion is selected from the group consisting of:

deletion of amino acids from position 1 to 139 with respect to SEQ ID NO:40;

deletion of amino acids from position 344 to 411 with respect to SEQ ID NO:40;

deletion of amino acids from position 651 to 752 with respect to SEQ ID NO:40;

deletion of amino acids from position 878 to 1070 with respect to SEQ ID NO:40;

deletion of amino acids from position 1178 to 1215 with respect to SEQ ID NO:40;

deletion of amino acids from position 206 to 303 with respect to SEQ ID NO:40;

deletion of amino acids from position 343 to 411 with respect to SEQ ID NO:40;

deletion of amino acids from position 652 to 703 with respect to SEQ ID NO:40;

deletion of amino acids from position 1 to 263 with respect to SEQ ID NO:40;

deletion of amino acids from position 1 to 408 with respect to SEQ ID NO:40; and deletion of amino acids from position 1 to 213 with respect to SEQ ID NO:40; or (iii) the reference full-length human GDE sequence has an amino acid sequence as shown in SEQ ID NO:41 and the functional truncated human GDE polypeptide comprises at least one deletion with respect to SEQ ID NO:41, wherein the deletion is selected from the group consisting of:

deletion of amino acids from position 1 to 140 with respect to SEQ ID NO:41;

deletion of amino acids from position 345 to 412 with respect to SEQ ID NO:41;

deletion of amino acids from position 652 to 753 with respect to SEQ ID NO:41;

deletion of amino acids from position 879 to 1071 with respect to SEQ ID NO:41;

deletion of amino acids from position 1179 to 1216 with respect to SEQ ID NO:41;

deletion of amino acids from position 207 to 304 with respect to SEQ ID NO:41;

deletion of amino acids from position 344 to 412 with respect to SEQ ID NO:41;

deletion of amino acids from position 653 to 704 with respect to SEQ ID NO:41;

deletion of amino acids from position 1 to 264 with respect to SEQ ID NO:41;

deletion of amino acids from position 1 to 409 with respect to SEQ ID NO:41; and deletion of amino acids from position 1 to 214 with respect to SEQ ID NO:41.

In another particular embodiment, the functional truncated human GDE polypeptide of the invention comprises a deletion or a combination of deletions as shown in table 2 below. In a particular embodiment, the functional truncated human GDE polypeptide comprises:

(i) a deletion or a combination of deletions, as shown in table 2 below, and (ii) a deletion or a combination of deletions, as shown in table 3 below.

Such functional truncated human GDE polypeptides include, without limitation, those having a sequence selected from SEQ ID NO:2-10 and SEQ ID NO:48-52, in particular from SEQ ID NO:2-6. In a particular embodiment, the functional truncated human GDE polypeptide of the invention has a sequence comprising or consisting of the sequence selected from SEQ ID NO:2, 5 or 6. In a further particular embodiment, the functional truncated human GDE polypeptide of the invention has a sequence comprising or consisting of the sequence shown in SEQ ID NO:5.

In another aspect, the invention relates to a nucleic acid molecule encoding the functional truncated human GDE polypeptide disclosed herein.

In a further aspect, the invention relates to a nucleic acid construct, comprising, preferably in this order:

a promoter;

optionally, an intron;

the nucleic acid molecule disclosed herein, encoding the functional truncated human polypeptide of the invention; and a polyadenylation signal.

In yet another aspect, the invention relates to a vector comprising:

the nucleic acid molecule of the invention; or the nucleic acid construct of the invention.

In certain embodiments, the vector may be a viral vector.

According to a further aspect, the invention relates to a viral vector comprising a nucleic acid construct encoding a functional non-human GDE polypeptide, wherein the functional non-human GDE polypeptide comprises less than about 1500 amino acids. The functional non-human GDE polypeptide may be selected, without limitation, in the group consisting of: horse GDE polypeptide of SEQ ID NO: 11, gorilla GDE polypeptide of SEQ ID NO:12, orangutan GDE polypeptide of SEQ ID NO:13, Pteropus alecto GDE polypeptide of SEQ ID NO:14, sooty mangabey GDE polypeptide of SEQ ID NO: 15, platypus GDE polypeptide of SEQ ID NO:16, and duck GDE polypeptide of SEQ ID NO:17. In a particular embodiment, the functional non-human GDE polypeptide is the gorilla GDE polypeptide of SEQ ID NO:12.

In particular embodiments of the vectors of the invention, said vectors may be AAV vectors or retroviral vectors, such as a lentiviral vectors. In a particular embodiment, the vector is an AAV vector, such as a single-stranded or double-stranded self-complementary AAV vector, preferably an AAV vector with an AAV-derived capsid, such as an AAV1, AAV2, variant AAV2, AAV3, variant AAV3, AAV3B, variant AAV3B, AAV4, AAV5, AAV6, variant AAV6, AAV7, AAV8, AAV9, AAV9P1, AAV10 such as AAVcy10 and AAVrh10, AAVrh74, AAVdj, AAV-Anc80, AAV-LK03, AAV2i8, and porcine AAV, such as AAVpo4 and AAVpo6 capsid or with a chimeric capsid. In a particular embodiment, the AAV vector has an AAV9, AAV9P1 or AAV6 capsid.

In a further aspect, the invention relates to an isolated cell transformed with the nucleic acid molecule, the nucleic acid construct or the vector of the invention. The cell may be, for example, a liver cell, a muscle cell, a cardiac cell or a CNS cell.

Yet in another aspect, the invention relates to a pharmaceutical composition, comprising, in a pharmaceutically acceptable carrier, the functional truncated human GDE polypeptide, the nucleic acid molecule, the nucleic acid construct, the vector, or the cell of the invention.

The invention also relates, in a particular aspect, to the functional truncated human GDE polypeptide, the functional non-human GDE polypeptide, the nucleic acid molecule, the nucleic acid construct, the vector, or the cell of the invention, for use as a medicament.

In a further aspect, the invention relates to the functional truncated human GDE polypeptide, the functional non-human GDE polypeptide, the nucleic acid molecule, the nucleic acid construct, the vector, or the cell of the invention, for use in a method for treating GSDIII (Cori disease).

The present invention also relates to the gorilla GDE polypeptide of SEQ ID NO:12, for use in a method for treating GSDIII (Cori disease).

LEGENDS TO THE FIGURES

FIG. 1. Reduced size of non-human mammalian GDE sequences. The size, expressed as amino acids number, of different mammalian GDE proteins is reported (paGDE: Pteropus Alecto GDE sequence, oGDE: orangutan GDE sequence, gGDE: gorilla GDE sequence, hoGDE: horse GDE sequence, hGDE: human isoform 1 GDE sequence).

Figure 2:
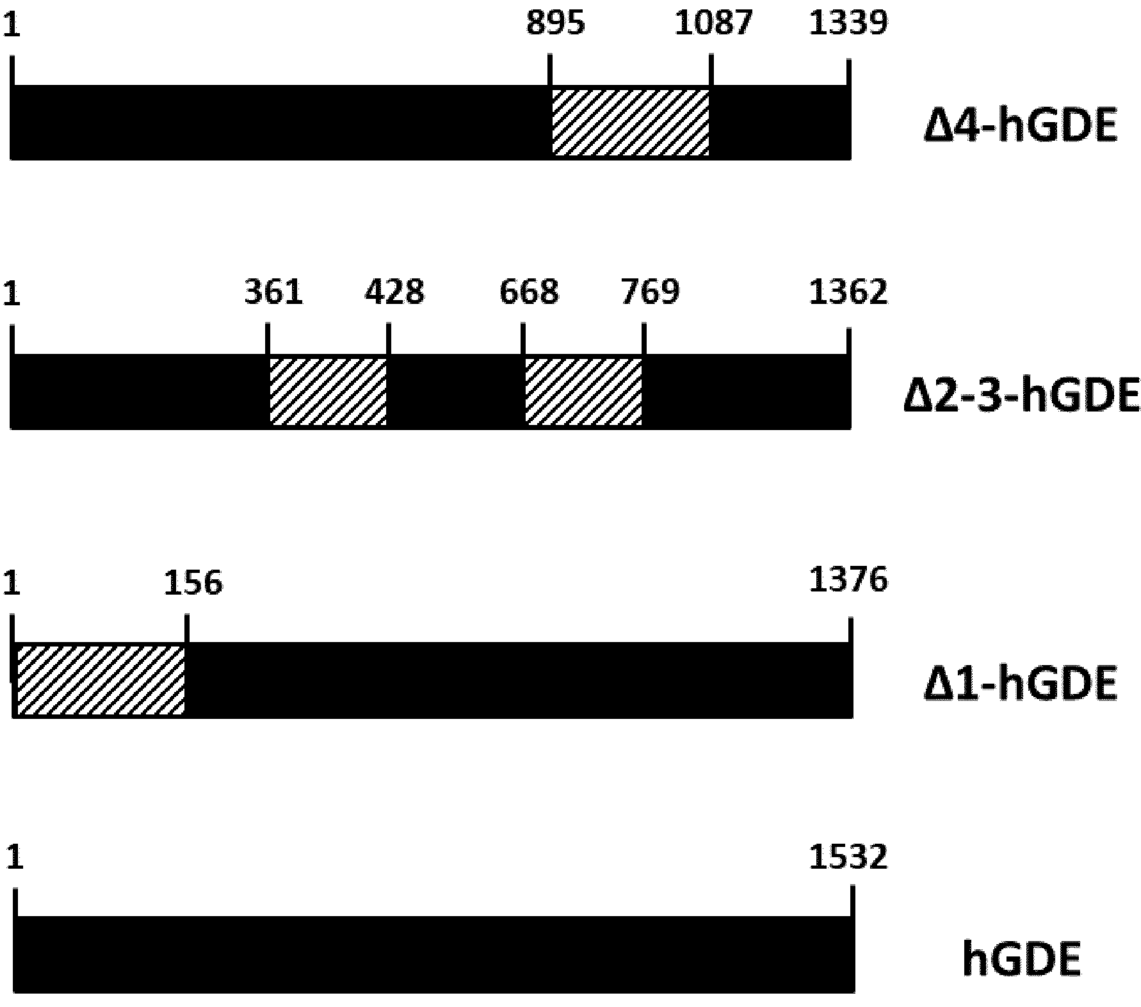

FIG. 2. Schematic representation of the different truncations on the human GDE sequence. Three different human GDE truncations, Δ1, Δ2-3 and Δ4 are reported.

Figure 3:
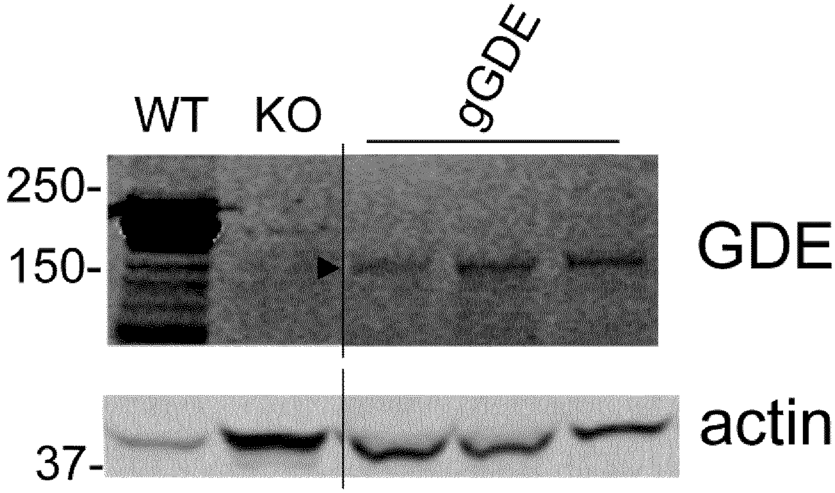

FIG. 3. gGDE protein expression. GDE knock-out (KO) mice were injected with $1\times10^{12}$ vg/mouse of a single AAV9 vector expressing gorilla GDE (gGDE). Three months after vector injection, animals were sacrificed and GDE was detected by western-blot in the heart. Wild-type (WT) GDE-KO animals were used as positive and negative controls, respectively.

Figure 4:
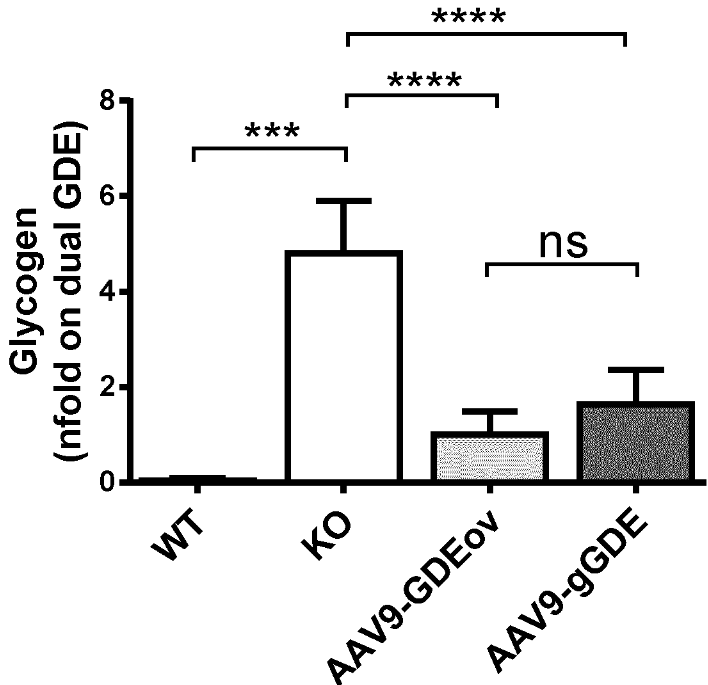

FIG. 4. AAV9-gGDE vector efficiently clears glycogen from quadriceps. GDE knock-out (KO) mice were injected with $1\times10^{12}$ vg/mouse of a single AAV9 vector expressing gorilla GDE (AAV9-gGDE) or with $2\times10^{12}$ vg/mouse of a dual AAV9 vectors expressing human GDE (AAV9-GDEov). Three months after vector injection, animals were sacrificed and glycogen accumulation was measured in the quadriceps. In parallel, glycogen was measured in age-matched wild-type (WT) and GDE knock-out (KO) animal. Statistical analysis was performed by ANOVA (*=p<0.001, **=p<0.0001, ns=not significant).

Figure 5:
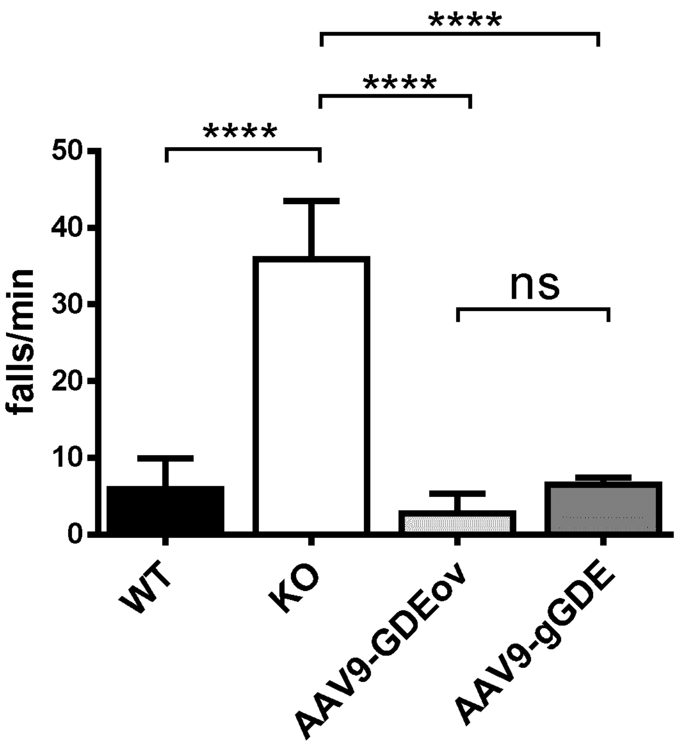

FIG. 5. AAV9-gGDE vector rescues muscle function in GSDIII mice. GDE knock-out (KO) mice were injected with $1\times10^{12}$ vg/mouse of a single AAV9 vector expressing gorilla GDE (AAV9-gGDE) or with $2\times10^{12}$ vg/mouse of a dual AAV9 vectors expressing human GDE (AAV9-GDEov). Three months after vector injection, muscle function was scored by wire-hang test. In the graph are showed wire-hang performances measured in age-matched wild-type (WT) and GDE knock-out (KO) animal. Statistical analysis was performed by ANOVA (****=p<0.0001, ns=not significant).

Figure 6:
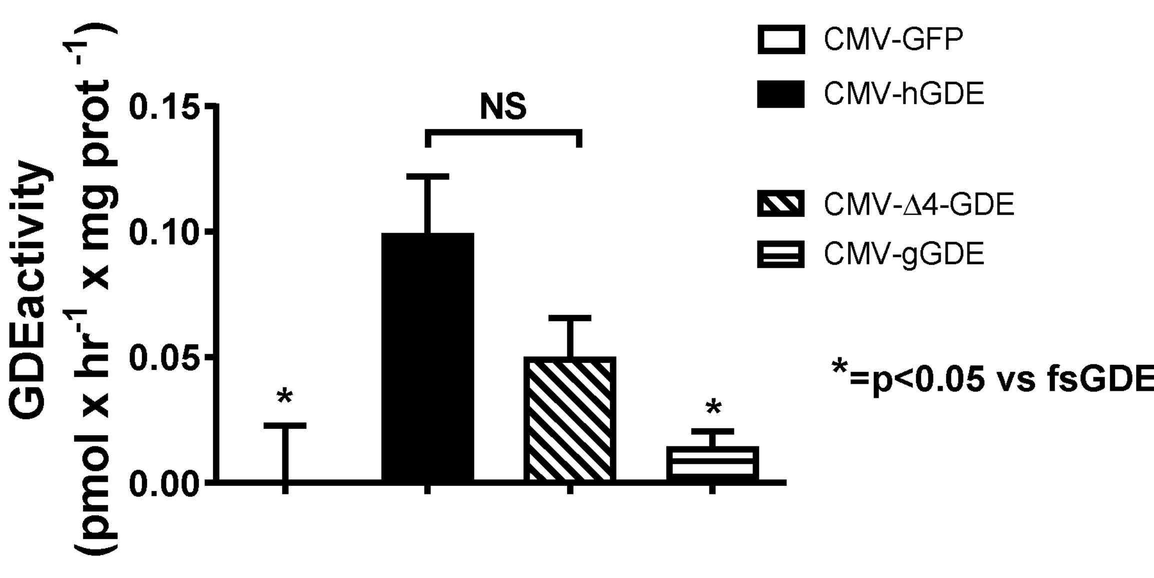

FIG. 6. Measurement of truncated GDEs activity in vitro. Huh-7 cells were transfected with plasmids expressing full-size human GDE (hGDE), one truncated human GDE (GDE 44) or gorilla GDE (gGDE) under the control of a CMV promoter. In parallel cells were transfected with a GFP-expressing plasmid as control. 48 hours after transfection, cytosolic extracts were prepared and GDE activity was measured. In the histogram are shown the levels of GDE activity expressed as glucose released from the digestion of limited dextrin. Statistical analysis was performed by ANOVA (*=p<0.05 vs CMV-hGDE).

Figure 7:
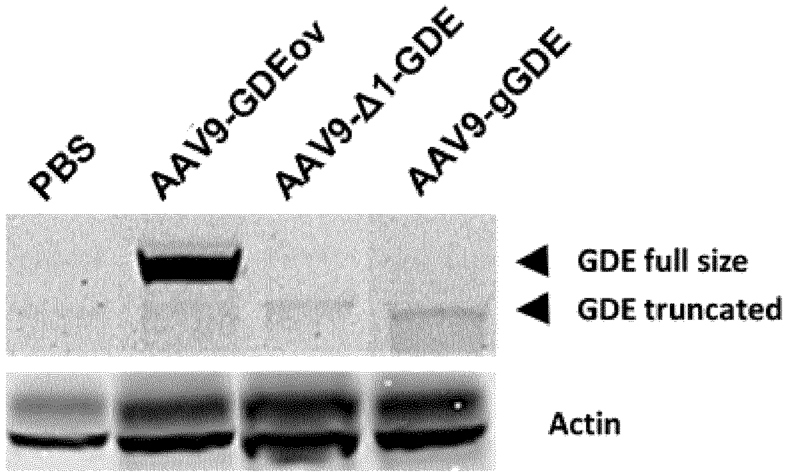

FIG. 7. Truncated GDEs are produced in vivo. Tibialis anterior (TA) muscles of GDE knock-out mice were injected with $1\times10^{11}$ vg/mouse of an AAV9 vector expressing a truncated human GDE (AAV9-Δ1-GDE) or gorilla GDE (AAV9-gGDE) or with $2\times10^{11}$ vg/mouse of a dual AAV9 vectors expressing human, full-size GDE (AAV9-GDEov). 15 days after the injection, TA were obtained and processed to analyze the expression of GDE by Western blot. Actin was used as loading control.

Figure 8:
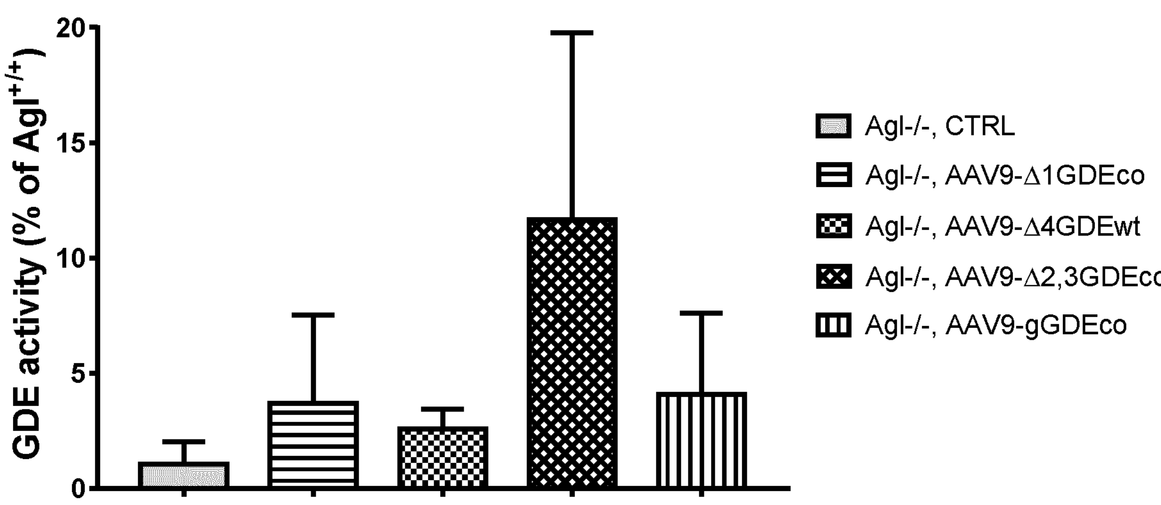

FIG. 8. Truncated GDEs are active in vivo. Tibialis anterior (TA) muscles of GDE knock-out mice were injected with $1\times10^{11}$ vg/mouse of an AAV9 vector expressing truncated human GDEs (AAV9-41-GDE, AAV9-Δ4-GDE, AAV9-Δ2/3-GDE) derived from either the wild type (wt) or a codon optimized (co) human GDE coding sequence. In parallel mice were injected with $1\times10^{11}$ vg/mouse of an AAV9 vector expressing the codon optimized gorilla GDE (AAV9-gGDEco) or with PBS as control. 15 days after the injection, TA were obtained and processed to analyze the GDE activity.

Figure 9:
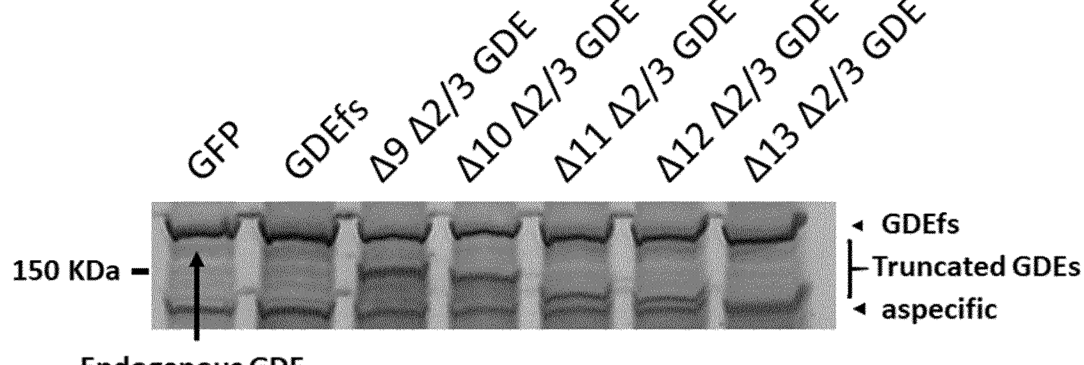

FIG. 9. Truncated GDEs are produced in vitro. HEK293T cells were transfected with plasmids expressing full-size GDE (GDEfs) or 5 truncated human GDEs (Δ9+Δ2/3; Δ10+Δ2/3; Δ11+Δ2/3; Δ12+Δ2/3; Δ13+Δ2/3). GFP transfected cells were used as control. 3 days after transfection, cells were harvested and processed to analyze the expression of GDE by Western blot.

Figure 10:

FIG. 10. Truncated GDEs are produced in vivo. Tibialis anterior (TA) muscles of GDE knock-out mice were injected with $2\times10^{11}$ vg/mouse of an AAV9 vector expressing full-size GDE (GDEfs) or 7 truncated human GDEs (Δ2/3; Δ9+Δ2/3; Δ10+Δ2/3; Δ13+Δ2/3; and Δ1). 15 days after the injection, TA were obtained and processed to analyze the expression of GDE by Western blot.

DETAILED DESCRIPTION OF THE INVENTION

As used herein with respect to any disclosed values or ranges, the term "about" indicates that the stated numerical value allows for slight imprecision, e.g., reasonably close to the value or nearly, such as plus or minus 10%, in particular such as plus or minus 5%, of the stated values or ranges.

Despite the lack of knowledge regarding the three-dimensional structure of the GDE protein, the present inventors have identified GDE polypeptides whose coding sequences are small enough to be packaged into a gene therapy vector, while preserving the GDE functionality, otherwise referred to as "mini-GDE polypeptides".

By "gene therapy vector" is meant any vector suitable for gene therapy. In particular, the gene therapy vector may be a plasmid or a recombinant virus such as a viral vector derived from a retrovirus or a lentivirus. Preferably, the viral vector is an AAV vector, such as an AAV vector suitable for transducing liver tissues or muscle cells. Extensive experience in clinical trials and in preclinical model of muscle diseases indicates adeno-associated virus (AAV) as the vector of choice for in vivo gene therapy for GSDIII. These vectors efficiently transduce liver and muscle, their production is scalable and compared to other gene therapy vectors they have a relatively low immunogenicity profile. However, one of the biggest limitations in the use of AAV for gene replacement is their limited encapsidation size limit (about 5 kb). Indeed, during recombinant AAV production, genomes larger than 5 kb are encapsidated with low efficacy and the resulting AAV may contain fragmented genomes reducing the efficacy of gene transfer.

As will be explained in details below, in the context of the present invention, the expression "mini-GDE polypeptide" encompasses either (i) functional truncated human GDE polypeptides or (ii) functional non-human GDE polypeptides.

A first aspect of the present invention is thus a functional mini-GDE polypeptide whose coding sequence is small enough to be efficiently packaged into a single AAV vector.

By "functional" GDE polypeptide is meant a polypeptide that retains, at least in part, at least one of the enzymatic activities of the GDE protein, preferably all of the enzymatic activities of the GDE protein. As a consequence, the functional GDE polypeptide implemented in the present invention is able to rescue glycogen accumulation and muscle strength in vivo. As defined above, GDE enzymatic activities are a 4-alpha-glucotransferase activity and an amylo-1, 6-glucosidase activity, involved in glycogen degradation. The transferase activity of GDE relocates three glucose units of glycogen from one chain to another. This leaves one glucose unit at the branch point, which is subsequently released as glucose by the glucosidase activity. In a particular embodiment, the functional mini-GDE polypeptide of the invention has the same functionality as a full-length GDE polypeptide, in particular as a full-length human GDE polypeptide. For example, a functional mini-GDE polypeptide of the invention may have an activity of at least 50%, 60%, 70%, 80%, 90%, 95%, or at least 99% in relation to one, preferably both, enzymatic activities described above, or at least 100%, as compared to a full-length human GDE protein, in particular the full-length human GDE protein of SEQ ID NO:1, SEQ ID NO:40 or SEQ ID NO: 41. The activity of the mini-GDE protein of the invention may even be of more than 100%, such as of more than 110%, 120%, 130%, 140%, 150%, 200%, 500%, 700%, or even more than 1000% of the activity of a full-length human GDE protein, in particular the full-length human GDE protein of SEQ ID NO:1, SEQ ID NO:40 or SEQ ID NO:41.

A skilled person is readily able to determine whether a polypeptide is a functional GDE polypeptide. Suitable methods would be apparent to those skilled in the art. For example, one suitable in vitro method involves inserting a nucleic acid encoding a polypeptide into a vector, such as a plasmid or viral vector, transfecting or transducing host cells, such as 293T or Hela cells, or other cells such as Huh7, with the vector, and assaying for GDE activity. Suitable methods are described in more details in the experimental part below. For example, GDE activity may be determined by measuring the glucose produced after incubating homogenized mouse tissues with limit dextrin. Other methods include testing the GDE activity by determining GDE expression in tissues of a GDE KO animal, such as by western-blot, by following the glucose produced from glycogen phosphorylase-digested glycogen, by evaluating muscle strength of treated GDE-KO animals by wire-hang after administration of the vectors, such as after one, two or three months after administration, or by evaluating the rescue of glycogen accumulation in muscle and/or cardiac tissue.

In a first variant of the first aspect of the invention, the mini-GDE polypeptide is a functional truncated human GDE polypeptide, which is truncated with respect to a reference full-length human GDE sequence.

The term "truncated human GDE polypeptide" encompasses any human GDE polypeptide that is rendered shorter by amino acid deletion, with respect to a reference full-length human GDE sequence from which the truncated human GDE is derived. In particular, the functional truncated human GDE polypeptide is deleted of at least 1 amino acid with respect to a reference full-length human GDE sequence. Preferably, the functional truncated human GDE polypeptide is deleted of at least about 10, 20, 30, 40, 50, 60, 75, 90, 100, 125, 150, 175, 190, 200, 225, 250, 275, 300, 325, 350, 375, 400, 425, 450, 475, 500 or at least about 525 amino acids with respect to a reference full-length human GDE sequence. In a preferred embodiment, the functional truncated human GDE polypeptide is deleted of at least about 50, 100 or 150 amino acids with respect to a reference full-length human GDE sequence.

In a particular embodiment, the functional truncated human GDE polypeptide that is truncated with respect to a reference full-length human GDE sequence may comprise one or more additional amino acid modifications with respect to said reference full-length human GDE sequence. In particular, in addition to the deletion(s) that are further described below, the functional truncated human GDE polypeptide may comprise one or more amino acid modifications such as amino acid insertion, deletion and/or substitution as compared to the reference full-length human GDE sequence. For example, the functional truncated human GDE polypeptide may comprise from 1 to 10 (e.g. 1, 2, 3, 4, 5, 6, 7, 8, 9 or 10) additional amino acid modifications, in particular from 1 to 5 (e.g. 1, 2, 3, 4 or 5) additional amino acid modifications, as long as the functionality of the truncated human GDE polypeptide is preserved. In a particular embodiment, when the functional truncated human GDE polypeptide comprises a N-terminal deletion, a methionine can be added at the N-terminal end.

In the context of the present invention, "a reference full-length human GDE sequence" encompasses all native isoforms of human GDE. Bao and colleagues (Genomics, 1997, 38, 155-165) identified the presence of six transcript variants encoding for three GDE protein isoforms. Transcript variants 1~4 encode for the same protein, namely GDE isoform 1. Transcript variants 5 and 6 encode for GDE isoforms 2 and 3 respectively.

The term "reference full-length human GDE polypeptide" thus encompasses all native isoforms of human GDE including the precursor form, as well as modified or mutated by insertion(s), deletion(s) and/or substitution(s) GDE proteins or fragments thereof that are functional derivatives of GDE. In particular, the reference full-length human GDE sequence is selected from the group consisting of SEQ ID NO: 1 (corresponding to GDE isoform 1), SEQ ID NO:40 (corresponding to GDE isoform 2) and SEQ ID NO:41 (corresponding to GDE isoform 3).

In a particular embodiment, the reference full-length human GDE sequence has an amino acid sequence as shown in SEQ ID NO:1, which corresponds to the GDE isoform 1.

In a particular embodiment, the functional truncated human GDE polypeptide of the invention comprises at least the amino acid residues at positions 429-666, 770-892, 1088-1194, 1235-1532 with respect to SEQ ID NO:1.

In a particular embodiment, the functional truncated human GDE polypeptide of the invention comprises at least the amino acid residues at positions 429-667, 770-894, 1088-1194, 1233-1532 with respect to SEQ ID NO:1.

In another particular embodiment, the functional truncated human GDE polypeptide of the invention is deleted of at least one amino acid with respect to SEQ ID NO:1, wherein the deleted amino acid(s) is at least one amino acid at positions 1-428, 668-769, 895-1087 and/or 1195-1232 with respect to SEQ ID NO: 1. In a further particular embodiment, the functional truncated human GDE polypeptide is deleted of at least about 10, 20, 30, 40, 50, 60, 75, 90, 100, 125, 150, 175, 190, 200, 225, 250, 275, 300, 325, 350, 375, 400, 425, 450, 475, 500 or at least about 525 amino acids, wherein the deleted amino acid(s) are selected from any amino acids at positions 1-428, 668-769, 895-1087, and/or 1195-1232 with respect to SEQ ID NO:1. In this embodiment, the deleted amino acids may be consecutive amino acids or non-consecutive amino acids, as long as they are selected from any amino acids at positions 1-428, 668-769, 895-1087 and/or 1195-1232 with respect to SEQ ID NO:1

In a particular embodiment, the functional truncated human GDE polypeptide of the invention is deleted of:

- at least one amino acid selected from amino acids at positions 1 to 428 with respect to SEQ ID NO: 1, preferably at least 10, 15, 20, 30, 40, 50, 60, 80, 100, 150, 200, 250, 300, 350 or at least 400 consecutive amino acids selected from amino acids at positions 1 to 428 with respect to SEQ ID NO:1; and/or
- at least one amino acid selected from amino acids at positions 668 to 769 with respect to SEQ ID NO: 1, preferably at least 10, 15, 20, 30, 40, 50, 80 or at least 100 consecutive amino acids selected from amino acids at positions 668 to 769 with respect to SEQ ID NO:1; and/or
- at least one amino acid selected from amino acids at positions 895 to 1087 with respect to SEQ ID NO: 1, preferably at least 10, 15, 20, 30, 40, 50, 80, 100, 125, 150, 175, or at least 190 consecutive amino acids selected from amino acids at positions 895 to 1087 with respect to SEQ ID NO: 1; and/or
- at least one amino acid selected from amino acids at positions 1195 to 1232 with respect to SEQ ID NO: 1, preferably at least 10, 15, 20 or at least 30 consecutive amino acids selected from amino acids at positions 1195 to 1232 with respect to SEQ ID NO:1.

In a further particular embodiment, the functional truncated human GDE polypeptide of the invention is deleted of:

- at least one amino acid selected from amino acids at positions 1 to 428 with respect to SEQ ID NO: 1, preferably at least 10, 15, 20, 30, 40, 50, 60, 80, 100, 110 or at least 120 consecutive amino acids selected from amino acids at positions 1 to 428 with respect to SEQ ID NO:1; and/or at least one amino acid selected from amino acids at positions 668 to 769 with respect to SEQ ID NO: 1, preferably at least 10, 15, 20, 30, 40, 50, 80 or at least 100 consecutive amino acids selected from amino acids at positions 668 to 769 with respect to SEQ ID NO:1; and/or at least one amino acid selected from amino acids at positions 895 to 1087 with respect to SEQ ID NO: 1, preferably at least 10, 15, 20, 30, 40, 50, 80, 100, 125, 150, 175, or at least 190 consecutive amino acids selected from amino acids at positions 895 to 1087 with respect to SEQ ID NO: 1; and/or at least one amino acid selected from amino acids at positions 1195 to 1232 with respect to SEQ ID NO: 1, preferably at least 10, 15, 20 or at least 30 consecutive amino acids selected from amino acids at positions 1195 to 1232 with respect to SEQ ID NO:1.

In a particular embodiment, the functional truncated human GDE polypeptide of the invention is deleted of:

at least one amino acid selected from amino acids at positions 1 to 156 with respect to SEQ ID NO: 1, preferably at least 15 consecutive amino acids, at least 50 consecutive amino acids or at least 100 consecutive amino acids selected from amino acids at positions 1 to 156 with respect to SEQ ID NO:1; and/or at least one amino acid selected from amino acids at positions 361 to 428 with respect to SEQ ID NO: 1, preferably at least 15 consecutive amino acids or at least 50 consecutive amino acids selected from amino acids at positions 361 to 428 with respect to SEQ ID NO:1; and/or at least one amino acid selected from amino acids at positions 668 to 769 with respect to SEQ ID NO: 1, preferably at least 15 consecutive amino acids, at least 50 consecutive amino acids or at least 100 consecutive amino acids selected from amino acids at positions 668 to 769 with respect to SEQ ID NO:1; and/or at least one amino acid selected from amino acids at positions 895 to 1087 with respect to SEQ ID NO: 1, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 895 to 1087 with respect to SEQ ID NO:1; and/or at least one amino acid selected from amino acids at positions 1195 to 1232 with respect to SEQ ID NO: 1, preferably at least 15 consecutive amino acids selected from amino acids at positions 1195 to 1232 with respect to SEQ ID NO:1; and/or at least one amino acid selected from amino acids at positions 223 to 320 with respect to SEQ ID NO: 1, preferably at least 15 consecutive amino acids or at least 50 consecutive amino acids selected from amino acids at positions 223 to 320 with respect to SEQ ID NO:1; and/or at least one amino acid selected from amino acids at positions 360 to 428 with respect to SEQ ID NO: 1, preferably at least 15 consecutive amino acids or at least 50 consecutive amino acids selected from amino acids at positions 360 to 428 with respect to SEQ ID NO:1; and/or at least one amino acid selected from amino acids at positions 669 to 720 with respect to SEQ ID NO: 1, preferably at least 15 consecutive amino acids or at least 50 consecutive amino acids selected from amino acids at positions 669 to 720 with respect to SEQ ID NO:1; and/or at least one amino acid selected from amino acids at positions 1 to 280 with respect to SEQ ID NO: 1, preferably at least 15 consecutive amino acids, at least 50 consecutive amino acids or at least 100 consecutive amino acids selected from amino acids at positions 1 to 280 with respect to SEQ ID NO:1; and/or at least one amino acid selected from amino acids at positions 1 to 425 with respect to SEQ ID NO: 1, preferably at least 15 consecutive amino acids, at least 50 consecutive amino acids or at least 100 consecutive amino acids selected from amino acids at positions 1 to 425 with respect to SEQ ID NO:1; and/or at least one amino acid selected from amino acids at positions 1 to 230 with respect to SEQ ID NO: 1, preferably at least 15 consecutive amino acids, at least 50 consecutive amino acids or at least 100 consecutive amino acids selected from amino acids at positions 1 to 230 with respect to SEQ ID NO:1; and/or at least one amino acid selected from amino acids at positions 1 to 15, with respect to SEQ ID NO: 1, preferably at least 10 consecutive amino acids selected from amino acids at positions 1 to 15 with respect to SEQ ID NO: 1; and/or at least one amino acid selected from amino acids at positions 1 to 30 with respect to SEQ ID NO: 1, preferably at least 15 consecutive amino acids or at least 25 consecutive amino acids selected from amino acids at positions 1 to 30 with respect to SEQ ID NO: 1; and/or at least one amino acid selected from amino acids at positions 1 to 81 with respect to SEQ ID NO: 1, preferably at least 15 consecutive amino acids or at least 50 consecutive amino acids selected from amino acids at positions 1 to 81 with respect to SEQ ID NO:1; and/or at least one amino acid selected from amino acids at positions 1 to 103 with respect to SEQ ID NO: 1, preferably at least 15 consecutive amino acids or at least 50 consecutive amino acids selected from amino acids at positions 1 to 103 with respect to SEQ ID NO:1; and/or at least one amino acid selected from amino acids at positions 1 to 129 with respect to SEQ ID NO: 1, preferably at least 15 consecutive amino acids, at least 50 consecutive amino acids or at least 100 consecutive amino acids selected from amino acids at positions 1 to 129 with respect to SEQ ID NO:1.

In a further particular embodiment, the functional truncated human GDE polypeptide of the invention is deleted of:

at least one amino acid selected from amino acids at positions 1 to 156 with respect to SEQ ID NO: 1, preferably at least 15 consecutive amino acids, at least 50 consecutive amino acids or at least 100 consecutive amino acids selected from amino acids at positions 1 to 156 with respect to SEQ ID NO:1; and/or at least one amino acid selected from amino acids at positions 361 to 428 with respect to SEQ ID NO: 1, preferably at least 15 consecutive amino acids or at least 50 consecutive amino acids selected from amino acids at positions 361 to 428 with respect to SEQ ID NO:1; and/or at least one amino acid selected from amino acids at positions 668 to 769 with respect to SEQ ID NO: 1, preferably at least 15 consecutive amino acids, at least 50 consecutive amino acids or at least 100 consecutive amino acids selected from amino acids at positions 668 to 769 with respect to SEQ ID NO:1; and/or at least one amino acid selected from amino acids at positions 895 to 1087 with respect to SEQ ID NO: 1, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 895 to 1087 with respect to SEQ ID NO:1; and/or at least one amino acid selected from amino acids at positions 1195 to 1232 with respect to SEQ ID NO: 1, preferably at least 15 consecutive amino acids selected from amino acids at positions 1195 to 1232 with respect to SEQ ID NO:1; and/or at least one amino acid selected from amino acids at positions 223 to 320 with respect to SEQ ID NO: 1, preferably at least 15 consecutive amino acids or at least 50 consecutive amino acids selected from amino acids at positions 223 to 320 with respect to SEQ ID NO:1; and/or at least one amino acid selected from amino acids at positions 360 to 428 with respect to SEQ ID NO: 1, preferably at least 15 consecutive amino acids or at least 50 consecutive amino acids selected from amino acids at positions 360 to 428 with respect to SEQ ID NO:1; and/or at least one amino acid selected from amino acids at positions 669 to 720 with respect to SEQ ID NO: 1, preferably at least 15 consecutive amino acids or at least 50 consecutive amino acids selected from amino acids at positions 669 to 720 with respect to SEQ ID NO: 1; and/or at least one amino acid selected from amino acids at positions 1 to 280 with respect to SEQ ID NO: 1, preferably at least 15 consecutive amino acids, at least 50 consecutive amino acids or at least 100 consecutive amino acids selected from amino acids at positions 1 to 280 with respect to SEQ ID NO:1; and/or at least one amino acid selected from amino acids at positions 1 to 425 with respect to SEQ ID NO: 1, preferably at least 15 consecutive amino acids, at least 50 consecutive amino acids or at least 100 consecutive amino acids selected from amino acids at positions 1 to 425 with respect to SEQ ID NO:1; and/or at least one amino acid selected from amino acids at positions 1 to 230 with respect to SEQ ID NO: 1, preferably at least 15 consecutive amino acids, at least 50 consecutive amino acids or at least 100 consecutive amino acids selected from amino acids at positions 1 to 230 with respect to SEQ ID NO:1.

In a further particular embodiment, the functional truncated human GDE polypeptide of the invention comprises at least one deletion with respect to SEQ ID NO:1, wherein the deletion is selected from the group consisting of:

deletion of amino acids from position 1 to 156 with respect to SEQ ID NO:1;

deletion of amino acids from position 361 to 428 with respect to SEQ ID NO:1;

deletion of amino acids from position 668 to 769 with respect to SEQ ID NO:1;

deletion of amino acids from position 895 to 1087 with respect to SEQ ID NO:1;

deletion of amino acids from position 1195 to 1232 with respect to SEQ ID NO:1;

deletion of amino acids from position 223 to 320 with respect to SEQ ID NO:1;

deletion of amino acids from position 360 to 428 with respect to SEQ ID NO:1;

deletion of amino acids from position 669 to 720 with respect to SEQ ID NO:1;

deletion of amino acids from position 1 to 280 with respect to SEQ ID NO:1;

deletion of amino acids from position 1 to 425 with respect to SEQ ID NO:1;

deletion of amino acids from position 1 to 230 with respect to SEQ ID NO:1;

deletion of amino acids from position 1 to 15 with respect to SEQ ID NO:1;

deletion of amino acids from position 1 to 30 with respect to SEQ ID NO:1;

deletion of amino acids from position 1 to 81 with respect to SEQ ID NO:1;

deletion of amino acids from position 1 to 103 with respect to SEQ ID NO:1; and deletion of amino acids from position 1 to 129 with respect to SEQ ID NO:1.

In a further particular embodiment, the functional truncated human GDE polypeptide of the invention comprises at least one deletion with respect to SEQ ID NO:1, wherein the deletion is selected from the group consisting of:

deletion of amino acids from position 1 to 156 with respect to SEQ ID NO:1;

deletion of amino acids from position 361 to 428 with respect to SEQ ID NO:1;

deletion of amino acids from position 668 to 769 with respect to SEQ ID NO:1;

deletion of amino acids from position 895 to 1087 with respect to SEQ ID NO:1;

deletion of amino acids from position 1195 to 1232 with respect to SEQ ID NO:1;

deletion of amino acids from position 223 to 320 with respect to SEQ ID NO:1;

deletion of amino acids from position 360 to 428 with respect to SEQ ID NO:1;

deletion of amino acids from position 669 to 720 with respect to SEQ ID NO:1;

deletion of amino acids from position 1 to 280 with respect to SEQ ID NO:1;

deletion of amino acids from position 1 to 425 with respect to SEQ ID NO:1; and deletion of amino acids from position 1 to 230 with respect to SEQ ID NO:1.

For the sake of clarity, in this embodiment, the deletion relates to the deletion of all consecutive amino acids in the mentioned range of positions. For example, a functional truncated human GDE polypeptide comprising the deletion of amino acids from position 1 to 156 with respect to SEQ ID NO:1 corresponds to a GDE polypeptide which is deleted of all consecutive amino acids from position 1 to 156 with respect to SEQ ID NO:1.

Also for the sake of clarity, a functional truncated human GDE polypeptide comprising for example:

the deletion of amino acids from position 1 to 156 with respect to SEQ ID NO:1; and the deletion of amino acids from position 1 to 280 with respect to SEQ ID NO:1 corresponds to a GDE polypeptide which is deleted of all consecutive amino acids from position 1 to 280, since the range 1-156 is included in the range 1-280.

In addition, a functional truncated human GDE polypeptide comprising for example:

- the deletion of amino acids from position 1 to 280 with respect to SEQ ID NO:1; and
- the deletion of amino acids from position 223 to 320 with respect to SEQ ID NO:1 corresponds to a GDE polypeptide which is deleted of all consecutive amino acids from position 1 to 320, since the range 1-280 overlaps the range 223-320.

In another embodiment, the reference full-length human GDE sequence has an amino acid sequence as shown in SEQ ID NO:40, which corresponds to GDE isoform 2.

In a particular embodiment, the functional truncated human GDE polypeptide of the invention comprises at least the amino acid residues at positions 412-649, 753-875, 1071-1177, 1218-1515 with respect to SEQ ID NO:40.

In a particular embodiment, the functional truncated human GDE polypeptide of the invention comprises at least the amino acid residues at positions 412-650, 753-877, 1071-1177, 1216-1515 with respect to SEQ ID NO:40.

In another particular embodiment, the functional truncated human GDE polypeptide of the invention is deleted of at least one amino acid with respect to SEQ ID NO:40, wherein the deleted amino acid(s) is at least one amino acid at positions 1-411, 651-752, 878-1070 and/or 1178-1215 with respect to SEQ ID NO: 40. In a further particular embodiment, the functional truncated human GDE polypeptide is deleted of at least about 10, 20, 30, 40, 50, 60, 75, 90, 100, 125, 150, 175, 190, 200, 225, 250, 275, 300, 325, 350, 375, 400, 425, 450, 475, 500 or at least about 525 amino acids, wherein the deleted amino acid(s) are selected from any amino acids at positions 1-411, 651-752, 878-1070, and/or 1178-1215 with respect to SEQ ID NO:40. In this embodiment, the deleted amino acids may be consecutive amino acids or non-consecutive amino acids, as long as they are selected from any amino acids at positions 1-411, 651-752, 878-1070 and/or 1178-1215 with respect to SEQ ID NO:40.

In a particular embodiment, the functional truncated human GDE polypeptide of the invention is deleted of:

- at least one amino acid selected from amino acids at positions 1 to 411 with respect to SEQ ID NO: 40, preferably at least 10, 15, 20, 30, 40, 50, 60, 80, 100, 150, 200, 250, 300, 350 or at least 400 consecutive amino acids selected from amino acids at positions 1 to 411 with respect to SEQ ID NO:40; and/or
- at least one amino acid selected from amino acids at positions 651-752 with respect to SEQ ID NO: 40, preferably at least 10, 15, 20, 30, 40, 50, 80 or at least 100 consecutive amino acids selected from amino acids at positions 651-752 with respect to SEQ ID NO:40; and/or
- at least one amino acid selected from amino acids at positions 878-1070 with respect to SEQ ID NO: 40, preferably at least 10, 15, 20, 30, 40, 50, 80, 100, 125, 150, 175, or at least 190 consecutive amino acids selected from amino acids at positions 878-1070 with respect to SEQ ID NO: 40; and/or
- at least one amino acid selected from amino acids at positions 1178-1215 with respect to SEQ ID NO: 40, preferably at least 10, 15, 20 or at least 30 consecutive amino acids selected from amino acids at positions 1178-1215 with respect to SEQ ID NO:40.

In a particular embodiment, the functional truncated human GDE polypeptide of the invention is deleted of:

- at least one amino acid selected from amino acids at positions 1 to 139 with respect to SEQ ID NO: 40, preferably at least 15 consecutive amino acids, at least 50 consecutive amino acids or at least 100 consecutive amino acids selected from amino acids at positions 1 to 139 with respect to SEQ ID NO:40; and/or
- at least one amino acid selected from amino acids at positions 344 to 411 with respect to SEQ ID NO: 40, preferably at least 15 consecutive amino acids or at least 50 consecutive amino acids selected from amino acids at positions 344 to 411 with respect to SEQ ID NO:40; and/or
- at least one amino acid selected from amino acids at positions 651 to 752 with respect to SEQ ID NO: 40, preferably at least 15 consecutive amino acids, at least 50 consecutive amino acids or at least 100 consecutive amino acids selected from amino acids at positions 651 to 752 with respect to SEQ ID NO:40; and/or
- at least one amino acid selected from amino acids at positions 878 to 1070 with respect to SEQ ID NO: 40, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 878 to 1070 with respect to SEQ ID NO:40; and/or
- at least one amino acid selected from amino acids at positions 1178 to 1215 with respect to SEQ ID NO: 40, preferably at least 15 consecutive amino acids selected from amino acids at positions 1178 to 1215 with respect to SEQ ID NO:40; and/or
- at least one amino acid selected from amino acids at positions 206 to 303 with respect to SEQ ID NO: 40, preferably at least 15 consecutive amino acids or at least 50 consecutive amino acids selected from amino acids at positions 206 to 303 with respect to SEQ ID NO:40; and/or
- at least one amino acid selected from amino acids at positions 343 to 411 with respect to SEQ ID NO: 40, preferably at least 15 consecutive amino acids or at least 50 consecutive amino acids selected from amino acids at positions 343 to 411 with respect to SEQ ID NO:40; and/or
- at least one amino acid selected from amino acids at positions 652 to 703 with respect to SEQ ID NO: 40, preferably at least 15 consecutive amino acids or at least 50 consecutive amino acids selected from amino acids at positions 652 to 703 with respect to SEQ ID NO:40; and/or
- at least one amino acid selected from amino acids at positions 1 to 263 with respect to SEQ ID NO: 40, preferably at least 15 consecutive amino acids, at least 50 consecutive amino acids or at least 100 consecutive amino acids selected from amino acids at positions 1 to 263 with respect to SEQ ID NO:40; and/or
- at least one amino acid selected from amino acids at positions 1 to 408 with respect to SEQ ID NO: 40, preferably at least 15 consecutive amino acids, at least 50 consecutive amino acids or at least 100 consecutive amino acids selected from amino acids at positions 1 to 408 with respect to SEQ ID NO:40; and/or
- at least one amino acid selected from amino acids at positions 1 to 213 with respect to SEQ ID NO: 40, preferably at least 15 consecutive amino acids, at least 50 consecutive amino acids or at least 100 consecutive amino acids selected from amino acids at positions 1 to 213 with respect to SEQ ID NO:40; and/or at least one amino acid selected from amino acids at positions 1 to 13 with respect to SEQ ID NO: 40, preferably at least 15 consecutive amino acids or at least 25 consecutive amino acids selected from amino acids at positions 1 to 13 with respect to SEQ ID NO:40; and/or at least one amino acid selected from amino acids at positions 1 to 64 with respect to SEQ ID NO: 40, preferably at least 15 consecutive amino acids or at least 50 consecutive amino acids selected from amino acids at positions 1 to 64 with respect to SEQ ID NO:40; and/or at least one amino acid selected from amino acids at positions 1 to 86 with respect to SEQ ID NO: 40, preferably at least 15 consecutive amino acids or at least 50 consecutive amino acids selected from amino acids at positions 1 to 86 with respect to SEQ ID NO:40; and/or at least one amino acid selected from amino acids at positions 1 to 112 with respect to SEQ ID NO: 40, preferably at least 15 consecutive amino acids, at least 50 consecutive amino acids or at least 100 consecutive amino acids selected from amino acids at positions 1 to 112 with respect to SEQ ID NO:40.

In another particular embodiment, the functional truncated human GDE polypeptide of the invention is deleted of:

at least one amino acid selected from amino acids at positions 1 to 139 with respect to SEQ ID NO: 40, preferably at least 15 consecutive amino acids, at least 50 consecutive amino acids or at least 100 consecutive amino acids selected from amino acids at positions 1 to 139 with respect to SEQ ID NO:40; and/or at least one amino acid selected from amino acids at positions 344 to 411 with respect to SEQ ID NO: 40, preferably at least 15 consecutive amino acids or at least 50 consecutive amino acids selected from amino acids at positions 344 to 411 with respect to SEQ ID NO:40; and/or at least one amino acid selected from amino acids at positions 651 to 752 with respect to SEQ ID NO: 40, preferably at least 15 consecutive amino acids, at least 50 consecutive amino acids or at least 100 consecutive amino acids selected from amino acids at positions 651 to 752 with respect to SEQ ID NO:40; and/or at least one amino acid selected from amino acids at positions 878 to 1070 with respect to SEQ ID NO: 40, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 878 to 1070 with respect to SEQ ID NO:40; and/or at least one amino acid selected from amino acids at positions 1178 to 1215 with respect to SEQ ID NO: 40, preferably at least 15 consecutive amino acids selected from amino acids at positions 1178 to 1215 with respect to SEQ ID NO:40; and/or at least one amino acid selected from amino acids at positions 206 to 303 with respect to SEQ ID NO: 40, preferably at least 15 consecutive amino acids or at least 50 consecutive amino acids selected from amino acids at positions 206 to 303 with respect to SEQ ID NO:40; and/or at least one amino acid selected from amino acids at positions 343 to 411 with respect to SEQ ID NO: 40, preferably at least 15 consecutive amino acids or at least 50 consecutive amino acids selected from amino acids at positions 343 to 411 with respect to SEQ ID NO:40; and/or at least one amino acid selected from amino acids at positions 652 to 703 with respect to SEQ ID NO: 40, preferably at least 15 consecutive amino acids or at least 50 consecutive amino acids selected from amino acids at positions 652 to 703 with respect to SEQ ID NO:40; and/or at least one amino acid selected from amino acids at positions 1 to 263 with respect to SEQ ID NO: 40, preferably at least 15 consecutive amino acids, at least 50 consecutive amino acids or at least 100 consecutive amino acids selected from amino acids at positions 1 to 263 with respect to SEQ ID NO:40; and/or at least one amino acid selected from amino acids at positions 1 to 408 with respect to SEQ ID NO: 40, preferably at least 15 consecutive amino acids, at least 50 consecutive amino acids or at least 100 consecutive amino acids selected from amino acids at positions 1 to 408 with respect to SEQ ID NO:40; and/or at least one amino acid selected from amino acids at positions 1 to 213 with respect to SEQ ID NO: 40, preferably at least 15 consecutive amino acids, at least 50 consecutive amino acids or at least 100 consecutive amino acids selected from amino acids at positions 1 to 213 with respect to SEQ ID NO:40.

In a further particular embodiment, the functional truncated human GDE polypeptide of the invention comprises at least one deletion with respect to SEQ ID NO:40, wherein the deletion is selected from the group consisting of:

deletion of amino acids from position 1 to 139 with respect to SEQ ID NO:40;

deletion of amino acids from position 344 to 411 with respect to SEQ ID NO:40;

deletion of amino acids from position 651 to 752 with respect to SEQ ID NO:40;

deletion of amino acids from position 878 to 1070 with respect to SEQ ID NO:40;

deletion of amino acids from position 1178 to 1215 with respect to SEQ ID NO:40;

deletion of amino acids from position 206 to 303 with respect to SEQ ID NO:40;

deletion of amino acids from position 343 to 411 with respect to SEQ ID NO:40;

deletion of amino acids from position 652 to 703 with respect to SEQ ID NO:40;

deletion of amino acids from position 1 to 263 with respect to SEQ ID NO:40;

deletion of amino acids from position 1 to 408 with respect to SEQ ID NO:40;

deletion of amino acids from position 1 to 213 with respect to SEQ ID NO:40;

deletion of amino acids from position 1 to 13 with respect to SEQ ID NO:40;

deletion of amino acids from position 1 to 64 with respect to SEQ ID NO:40;

deletion of amino acids from position 1 to 86 with respect to SEQ ID NO:40; and deletion of amino acids from position 1 to 112 with respect to SEQ ID NO:40.

In a further particular embodiment, the functional truncated human GDE polypeptide of the invention comprises at least one deletion with respect to SEQ ID NO:40, wherein the deletion is selected from the group consisting of:

- deletion of amino acids from position 1 to 139 with respect to SEQ ID NO:40;
- deletion of amino acids from position 344 to 411 with respect to SEQ ID NO:40;
- deletion of amino acids from position 651 to 752 with respect to SEQ ID NO:40;
- deletion of amino acids from position 878 to 1070 with respect to SEQ ID NO:40;
- deletion of amino acids from position 1178 to 1215 with respect to SEQ ID NO:40;
- deletion of amino acids from position 206 to 303 with respect to SEQ ID NO:40;
- deletion of amino acids from position 343 to 411 with respect to SEQ ID NO:40;
- deletion of amino acids from position 652 to 703 with respect to SEQ ID NO:40;
- deletion of amino acids from position 1 to 263 with respect to SEQ ID NO:40;
- deletion of amino acids from position 1 to 408 with respect to SEQ ID NO:40; and
- deletion of amino acids from position 1 to 213 with respect to SEQ ID NO:40.

For the sake of clarity, in this embodiment, the deletion relates to the deletion of all consecutive amino acids in the mentioned range of positions. For example, a functional truncated human GDE polypeptide comprising the deletion of amino acids from position 1 to 139 with respect to SEQ ID NO:40 corresponds to a GDE polypeptide which is deleted of all consecutive amino acids from position 1 to 139 with respect to SEQ ID NO:40.

Also for the sake of clarity, a functional truncated human GDE polypeptide comprising for example:

- the deletion of amino acids from position 1 to 139 with respect to SEQ ID NO:40; and
- the deletion of amino acids from position 1 to 263 with respect to SEQ ID NO:40 corresponds to a GDE polypeptide which is deleted of all consecutive amino acids from position 1 to 263, since the range 1-139 is included in the range 1-263.

In addition, a functional truncated human GDE polypeptide comprising for example:

- the deletion of amino acids from position 1 to 263 with respect to SEQ ID NO:40; and
- the deletion of amino acids from position 206 to 303 with respect to SEQ ID NO:40 corresponds to a GDE polypeptide which is deleted of all consecutive amino acids from position 1 to 303, since the range 1-263 overlaps the range 206-303.

In another embodiment, the reference full-length human GDE sequence has an amino acid sequence as shown in SEQ ID NO:41, which corresponds to GDE isoform 3.

In a particular embodiment, the functional truncated human GDE polypeptide of the invention comprises at least the amino acid residues at positions 413-650, 754-876, 1072-1178, 1219-1516 with respect to SEQ ID NO:41.

In a particular embodiment, the functional truncated human GDE polypeptide of the invention comprises at least the amino acid residues at positions 413-651, 754-878, 1072-1178, 1217-1516 with respect to SEQ ID NO:41.

In another particular embodiment, the functional truncated human GDE polypeptide of the invention is deleted of at least one amino acid with respect to SEQ ID NO:41, wherein the deleted amino acid(s) is at least one amino acid at positions 1-412, 652-753, 879-1071 and/or 1179-1216 with respect to SEQ ID NO: 41. In a further particular embodiment, the functional truncated human GDE polypeptide is deleted of at least about 10, 20, 30, 40, 50, 60, 75, 90, 100, 125, 150, 175, 190, 200, 225, 250, 275, 300, 325, 350, 375, 400, 425, 450, 475, 500 or at least about 525 amino acids, wherein the deleted amino acid(s) are selected from any amino acids at positions 1-412, 652-753, 879-1071, and/or 1179-1216 with respect to SEQ ID NO:41. In this embodiment, the deleted amino acids may be consecutive amino acids or non-consecutive amino acids, as long as they are selected from any amino acids at positions 1-412, 652-753, 879-1071 and/or 1179-1216 with respect to SEQ ID NO:41.

In a particular embodiment, the functional truncated human GDE polypeptide of the invention is deleted of:

- at least one amino acid selected from amino acids at positions 1 to 412 with respect to SEQ ID NO: 41, preferably at least 10, 15, 20, 30, 40, 50, 60, 80, 100, 150, 200, 250, 300, 350 or at least 400 consecutive amino acids selected from amino acids at positions 1 to 412 with respect to SEQ ID NO:41; and/or
- at least one amino acid selected from amino acids at positions 652-753 with respect to SEQ ID NO: 41, preferably at least 10, 15, 20, 30, 40, 50, 80 or at least 100 consecutive amino acids selected from amino acids at positions 652-753 with respect to SEQ ID NO:41; and/or
- at least one amino acid selected from amino acids at positions 879-1071 with respect to SEQ ID NO: 41, preferably at least 10, 15, 20, 30, 40, 50, 80, 100, 125, 150, 175, or at least 190 consecutive amino acids selected from amino acids at positions 879-1071 with respect to SEQ ID NO: 41; and/or
- at least one amino acid selected from amino acids at positions 1179-1216 with respect to SEQ ID NO: 41, preferably at least 10, 15, 20 or at least 30 consecutive amino acids selected from amino acids at positions 1179-1216 with respect to SEQ ID NO:41.

In a particular embodiment, the functional truncated human GDE polypeptide of the invention is deleted of:

- at least one amino acid selected from amino acids at positions 1 to 140 with respect to SEQ ID NO: 41, preferably at least 15 consecutive amino acids, at least 50 consecutive amino acids or at least 100 consecutive amino acids selected from amino acids at positions 1 to 140 with respect to SEQ ID NO:41; and/or
- at least one amino acid selected from amino acids at positions 345 to 412 with respect to SEQ ID NO: 41, preferably at least 15 consecutive amino acids or at least 50 consecutive amino acids selected from amino acids at positions 345 to 412 with respect to SEQ ID NO:41; and/or
- at least one amino acid selected from amino acids at positions 652 to 753 with respect to SEQ ID NO: 41, preferably at least 15 consecutive amino acids, at least 50 consecutive amino acids or at least 100 consecutive amino acids selected from amino acids at positions 652 to 753 with respect to SEQ ID NO:41; and/or
- at least one amino acid selected from amino acids at positions 879 to 1071 with respect to SEQ ID NO: 41, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 879 to 1071 with respect to SEQ ID NO:41; and/or at least one amino acid selected from amino acids at positions 1179 to 1216 with respect to SEQ ID NO: 41, preferably at least 15 consecutive amino acids selected from amino acids at positions 1179 to 1216 with respect to SEQ ID NO:41; and/or at least one amino acid selected from amino acids at positions 207 to 304 with respect to SEQ ID NO: 41, preferably at least 15 consecutive amino acids or at least 50 consecutive amino acids selected from amino acids at positions 207 to 304 with respect to SEQ ID NO:41; and/or at least one amino acid selected from amino acids at positions 344 to 412 with respect to SEQ ID NO: 41, preferably at least 15 consecutive amino acids or at least 50 consecutive amino acids selected from amino acids at positions 344 to 412 with respect to SEQ ID NO:41; and/or at least one amino acid selected from amino acids at positions 653 to 704 with respect to SEQ ID NO: 41, preferably at least 15 consecutive amino acids or at least 50 consecutive amino acids selected from amino acids at positions 653 to 704 with respect to SEQ ID NO:41; and/or at least one amino acid selected from amino acids at positions 1 to 264 with respect to SEQ ID NO: 41, preferably at least 15 consecutive amino acids, at least 50 consecutive amino acids or at least 100 consecutive amino acids selected from amino acids at positions 1 to 264 with respect to SEQ ID NO:41; and/or at least one amino acid selected from amino acids at positions 1 to 409 with respect to SEQ ID NO: 41, preferably at least 15 consecutive amino acids, at least 50 consecutive amino acids or at least 100 consecutive amino acids selected from amino acids at positions 1 to 409 with respect to SEQ ID NO:41;

at least one amino acid selected from amino acids at positions 1 to 214 with respect to SEQ ID NO: 41, preferably at least 15 consecutive amino acids, at least 50 consecutive amino acids or at least 100 consecutive amino acids selected from amino acids at positions 1 to 214 with respect to SEQ ID NO:41; and/or at least one amino acid selected from amino acids at positions 1 to 14 with respect to SEQ ID NO: 41, preferably at least 15 consecutive amino acids or at least 25 consecutive amino acids selected from amino acids at positions 1 to 14 with respect to SEQ ID NO:41; and/or at least one amino acid selected from amino acids at positions 1 to 65 with respect to SEQ ID NO: 41, preferably at least 15 consecutive amino acids or at least 50 consecutive amino acids selected from amino acids at positions 1 to 65 with respect to SEQ ID NO:41; and/or at least one amino acid selected from amino acids at positions 1 to 87 with respect to SEQ ID NO: 41, preferably at least 15 consecutive amino acids or at least 50 consecutive amino acids selected from amino acids at positions 1 to 87 with respect to SEQ ID NO:41; and/or at least one amino acid selected from amino acids at positions 1 to 113 with respect to SEQ ID NO: 41, preferably at least 15 consecutive amino acids, at least 50 consecutive amino acids or at least 100 consecutive amino acids selected from amino acids at positions 1 to 113 with respect to SEQ ID NO:41.

In a particular embodiment, the functional truncated human GDE polypeptide of the invention is deleted of:

at least one amino acid selected from amino acids at positions 1 to 140 with respect to SEQ ID NO: 41, preferably at least 15 consecutive amino acids, at least 50 consecutive amino acids or at least 100 consecutive amino acids selected from amino acids at positions 1 to 140 with respect to SEQ ID NO:41; and/or at least one amino acid selected from amino acids at positions 345 to 412 with respect to SEQ ID NO: 41, preferably at least 15 consecutive amino acids or at least 50 consecutive amino acids selected from amino acids at positions 345 to 412 with respect to SEQ ID NO:41; and/or at least one amino acid selected from amino acids at positions 652 to 753 with respect to SEQ ID NO: 41, preferably at least 15 consecutive amino acids, at least 50 consecutive amino acids or at least 100 consecutive amino acids selected from amino acids at positions 652 to 753 with respect to SEQ ID NO:41; and/or at least one amino acid selected from amino acids at positions 879 to 1071 with respect to SEQ ID NO: 41, preferably at least 15 consecutive amino acids, at least 50 consecutive amino acids, at least 100 consecutive amino acids, at least 150 consecutive amino acids, at least 175 consecutive amino acids or at least 190 consecutive amino acids selected from amino acids at positions 879 to 1071 with respect to SEQ ID NO:41; and/or at least one amino acid selected from amino acids at positions 1179 to 1216 with respect to SEQ ID NO: 41, preferably at least 15 consecutive amino acids selected from amino acids at positions 1179 to 1216 with respect to SEQ ID NO:41; and/or at least one amino acid selected from amino acids at positions 207 to 304 with respect to SEQ ID NO: 41, preferably at least 15 consecutive amino acids or at least 50 consecutive amino acids selected from amino acids at positions 207 to 304 with respect to SEQ ID NO:41; and/or at least one amino acid selected from amino acids at positions 344 to 412 with respect to SEQ ID NO: 41, preferably at least 15 consecutive amino acids or at least 50 consecutive amino acids selected from amino acids at positions 344 to 412 with respect to SEQ ID NO:41; and/or at least one amino acid selected from amino acids at positions 653 to 704 with respect to SEQ ID NO: 41, preferably at least 15 consecutive amino acids or at least 50 consecutive amino acids selected from amino acids at positions 653 to 704 with respect to SEQ ID NO:41; and/or at least one amino acid selected from amino acids at positions 1 to 264 with respect to SEQ ID NO: 41, preferably at least 15 consecutive amino acids, at least 50 consecutive amino acids or at least 100 consecutive amino acids selected from amino acids at positions 1 to 264 with respect to SEQ ID NO:41; and/or at least one amino acid selected from amino acids at positions 1 to 409 with respect to SEQ ID NO: 41, preferably at least 15 consecutive amino acids, at least 50 consecutive amino acids or at least 100 consecutive amino acids selected from amino acids at positions 1 to 409 with respect to SEQ ID NO:41; and/or at least one amino acid selected from amino acids at positions 1 to 214 with respect to SEQ ID NO: 41, preferably at least 15 consecutive amino acids, at least 50 consecutive amino acids or at least 100 consecutive amino acids selected from amino acids at positions 1 to 214 with respect to SEQ ID NO:41.

In a further particular embodiment, the functional truncated human GDE polypeptide of the invention comprises at least one deletion with respect to SEQ ID NO:41, wherein the deletion is selected from the group consisting of:

- deletion of amino acids from position 1 to 140 with respect to SEQ ID NO:41;
- deletion of amino acids from position 345 to 412 with respect to SEQ ID NO:41;
- deletion of amino acids from position 652 to 753 with respect to SEQ ID NO:41;
- deletion of amino acids from position 879 to 1071 with respect to SEQ ID NO:41;
- deletion of amino acids from position 1179 to 1216 with respect to SEQ ID NO:41;
- deletion of amino acids from position 207 to 304 with respect to SEQ ID NO:41;
- deletion of amino acids from position 344 to 412 with respect to SEQ ID NO:41;
- deletion of amino acids from position 653 to 704 with respect to SEQ ID NO:41;
- deletion of amino acids from position 1 to 264 with respect to SEQ ID NO:41;
- deletion of amino acids from position 1 to 409 with respect to SEQ ID NO:41;
- deletion of amino acids from position 1 to 214 with respect to SEQ ID NO:41;
- deletion of amino acids from position 1 to 14 with respect to SEQ ID NO:41;
- deletion of amino acids from position 1 to 65 with respect to SEQ ID NO:41;
- deletion of amino acids from position 1 to 87 with respect to SEQ ID NO:41; and
- deletion of amino acids from position 1 to 113 with respect to SEQ ID NO:41.

In a further particular embodiment, the functional truncated human GDE polypeptide of the invention comprises at least one deletion with respect to SEQ ID NO:41, wherein the deletion is selected from the group consisting of:

- deletion of amino acids from position 1 to 140 with respect to SEQ ID NO:41;
- deletion of amino acids from position 345 to 412 with respect to SEQ ID NO:41;
- deletion of amino acids from position 652 to 753 with respect to SEQ ID NO:41;
- deletion of amino acids from position 879 to 1071 with respect to SEQ ID NO:41;
- deletion of amino acids from position 1179 to 1216 with respect to SEQ ID NO:41;
- deletion of amino acids from position 207 to 304 with respect to SEQ ID NO:41;
- deletion of amino acids from position 344 to 412 with respect to SEQ ID NO:41;
- deletion of amino acids from position 653 to 704 with respect to SEQ ID NO:41;
- deletion of amino acids from position 1 to 264 with respect to SEQ ID NO:41;
- deletion of amino acids from position 1 to 409 with respect to SEQ ID NO:41; and
- deletion of amino acids from position 1 to 214 with respect to SEQ ID NO:41.

For the sake of clarity, in this embodiment, the deletion relates to the deletion of all consecutive amino acids in the mentioned range of positions. For example, a functional truncated human GDE polypeptide comprising the deletion of amino acids from position 1 to 140 with respect to SEQ ID NO:41 corresponds to a GDE polypeptide which is deleted of all consecutive amino acids from position 1 to 140 with respect to SEQ ID NO:41.

Also for the sake of clarity, a functional truncated human GDE polypeptide comprising for example:

- the deletion of amino acids from position 1 to 140 with respect to SEQ ID NO:41; and
- the deletion of amino acids from position 1 to 264 with respect to SEQ ID NO:41 corresponds to a GDE polypeptide which is deleted of all consecutive amino acids from position 1 to 264, since the range 1-140 is included in the range 1-264.

In addition, a functional truncated human GDE polypeptide comprising for example:

- the deletion of amino acids from position 1 to 264 with respect to SEQ ID NO:41; and
- the deletion of amino acids from position 207 to 304 with respect to SEQ ID NO:41 corresponds to a GDE polypeptide which is deleted of all consecutive amino acids from position 1 to 304, since the range 1-264 overlaps the range 207-304.

In a particular embodiment, the functional truncated human GDE polypeptide of the invention comprises a deletion or a combination of deletions with respect to SEQ ID NO:1, SEQ ID NO:40 or SEQ ID NO:41 wherein the deletion(s) is (are) selected from any deletion referred to as Δ1, Δ2, Δ3, Δ4, Δ5, Δ6, Δ7 and Δ8 in table 1:

TABLE 1

| Deletion | Position of the deleted amino acids with respect to SEQ ID NO: 1 | Position of the deleted amino acids with respect to SEQ ID NO: 40 | Position of the deleted amino acids with respect to SEQ ID NO: 41 |
|---|---|---|---|
| Δ1 | 1-156 | 1-139 | 1-140 |
| Δ2 | 361-428 | 344-411 | 345-412 |
| Δ3 | 668-769 | 651-752 | 652-753 |
| Δ4 | 895-1087 | 878-1070 | 879-1071 |
| Δ5 | 223-320 | 206-303 | 207-304 |
| Δ6 | 360-428 | 343-411 | 344-412 |
| Δ7 | 669-720 | 652-703 | 653-704 |
| Δ8 | 1-280 | 1-263 | 1-264 |

In a particular embodiment, the functional truncated human GDE polypeptide of the invention may comprise a combination of 2, 3, 4, 5, 6, 7 or 8 deletions, wherein the deletion(s) is (are) selected from any deletion referred to as Δ1, Δ2, Δ3, Δ4, Δ5, Δ6, Δ7 and Δ8 in table 1.

In a particular embodiment, the functional truncated human GDE polypeptide of the invention may comprise a deletion or a combination of deletions, as shown in table 2, wherein the deletion(s) is (are) as referred in table 1.

TABLE 2

| | | |
|---|---|---|
| Δ1 | Δ2 + Δ8 | Δ1 + Δ2 + Δ7 |
| Δ2 | Δ3 + Δ4 | Δ1 + Δ2 + Δ8 |
| Δ3 | Δ3 + Δ5 | Δ1 + Δ3 + Δ4 |
| Δ4 | Δ3 + Δ6 | Δ1 + Δ3 + Δ5 |
| Δ5 | Δ3 + Δ7 | Δ1 + Δ3 + Δ6 |
| Δ6 | Δ3 + Δ8 | Δ1 + Δ3 + Δ7 |
| Δ7 | Δ4 + Δ5 | Δ1 + Δ3 + Δ8 |
| Δ8 | Δ4 + Δ6 | Δ1 + Δ4 + Δ5 |
| Δ1 + Δ2 | Δ4 + Δ7 | Δ1 + Δ4 + Δ6 |
| Δ1 + Δ3 | Δ4 + Δ8 | Δ1 + Δ4 + Δ7 |
| Δ1 + Δ4 | Δ5 + Δ6 | Δ1 + Δ4 + Δ8 |
| Δ1 + Δ5 | Δ5 + Δ7 | Δ1 + Δ5 + Δ6 |
| Δ1 + Δ6 | Δ5 + Δ8 | Δ1 + Δ5 + Δ7 |
| Δ1 + Δ7 | Δ6 + Δ7 | Δ1 + Δ5 + Δ8 |

TABLE 2-continued

| | | |
|---|---|---|
| Δ1 + Δ8 | Δ6 + Δ8 | Δ1 + Δ6 + Δ7 |
| Δ2 + Δ3 | Δ7 + Δ8 | Δ1 + Δ6 + Δ8 |
| Δ2 + Δ4 | Δ1 + Δ2 + Δ3 | Δ1 + Δ7 + Δ8 |
| Δ2 + Δ5 | Δ1 + Δ2 + Δ4 | Δ2 + Δ3 + Δ4 |
| Δ2 + Δ6 | Δ1 + Δ2 + Δ5 | Δ2 + Δ3 + Δ5 |
| Δ2 + Δ7 | Δ1 + Δ2 + Δ6 | Δ2 + Δ3 + Δ6 |
| Δ2 + Δ3 + Δ7 | Δ1 + Δ2 + Δ3 + Δ5 | Δ1 + Δ6 + Δ7 + Δ8 |
| Δ2 + Δ3 + Δ8 | Δ1 + Δ2 + Δ3 + Δ6 | Δ2 + Δ3 + Δ4 + Δ5 |
| Δ2 + Δ4 + Δ5 | Δ1 + Δ2 + Δ3 + Δ7 | Δ2 + Δ3 + Δ4 + Δ6 |
| Δ2 + Δ4 + Δ6 | Δ1 + Δ2 + Δ3 + Δ8 | Δ2 + Δ3 + Δ4 + Δ7 |
| Δ2 + Δ4 + Δ7 | Δ1 + Δ2 + Δ4 + Δ5 | Δ2 + Δ3 + Δ4 + Δ8 |
| Δ2 + Δ4 + Δ8 | Δ1 + Δ2 + Δ4 + Δ6 | Δ2 + Δ3 + Δ5 + Δ6 |
| Δ2 + Δ5 + Δ6 | Δ1 + Δ2 + Δ4 + Δ7 | Δ2 + Δ3 + Δ5 + Δ7 |
| Δ2 + Δ5 + Δ7 | Δ1 + Δ2 + Δ4 + Δ8 | Δ2 + Δ3 + Δ5 + Δ8 |
| Δ2 + Δ5 + Δ8 | Δ1 + Δ2 + Δ5 + Δ6 | Δ2 + Δ3 + Δ6 + Δ7 |
| Δ2 + Δ6 + Δ7 | Δ1 + Δ2 + Δ5 + Δ7 | Δ2 + Δ3 + Δ6 + Δ8 |
| Δ2 + Δ6 + Δ8 | Δ1 + Δ2 + Δ5 + Δ8 | Δ2 + Δ3 + Δ7 + Δ8 |
| Δ2 + Δ7 + Δ8 | Δ1 + Δ2 + Δ6 + Δ7 | Δ2 + Δ4 + Δ5 + Δ6 |
| Δ3 + Δ4 + Δ5 | Δ1 + Δ2 + Δ6 + Δ8 | Δ2 + Δ4 + Δ5 + Δ7 |
| Δ3 + Δ4 + Δ6 | Δ1 + Δ2 + Δ7 + Δ8 | Δ2 + Δ4 + Δ5 + Δ8 |
| Δ3 + Δ4 + Δ7 | Δ1 + Δ3 + Δ4 + Δ5 | Δ2 + Δ4 + Δ6 + Δ7 |
| Δ3 + Δ4 + Δ8 | Δ1 + Δ3 + Δ4 + Δ6 | Δ2 + Δ4 + Δ6 + Δ8 |
| Δ3 + Δ5 + Δ6 | Δ1 + Δ3 + Δ4 + Δ7 | Δ2 + Δ4 + Δ7 + Δ8 |
| Δ3 + Δ5 + Δ7 | Δ1 + Δ3 + Δ4 + Δ8 | Δ2 + Δ5 + Δ6 + Δ7 |
| Δ3 + Δ5 + Δ8 | Δ1 + Δ3 + Δ5 + Δ6 | Δ2 + Δ5 + Δ6 + Δ8 |
| Δ3 + Δ6 + Δ7 | Δ1 + Δ3 + Δ5 + Δ7 | Δ2 + Δ5 + Δ7 + Δ8 |
| Δ3 + Δ6 + Δ8 | Δ1 + Δ3 + Δ5 + Δ8 | Δ2 + Δ6 + Δ7 + Δ8 |
| Δ3 + Δ7 + Δ8 | Δ1 + Δ3 + Δ6 + Δ7 | Δ3 + Δ4 + Δ5 + Δ6 |
| Δ4 + Δ5 + Δ6 | Δ1 + Δ3 + Δ6 + Δ8 | Δ3 + Δ4 + Δ5 + Δ7 |
| Δ4 + Δ5 + Δ7 | Δ1 + Δ3 + Δ7 + Δ8 | Δ3 + Δ4 + Δ5 + Δ8 |
| Δ4 + Δ5 + Δ8 | Δ1 + Δ4 + Δ5 + Δ6 | Δ3 + Δ4 + Δ6 + Δ7 |
| Δ4 + Δ6 + Δ7 | Δ1 + Δ4 + Δ5 + Δ7 | Δ3 + Δ4 + Δ6 + Δ8 |
| Δ4 + Δ6 + Δ8 | Δ1 + Δ4 + Δ5 + Δ8 | Δ3 + Δ4 + Δ7 + Δ8 |
| Δ4 + Δ7 + Δ8 | Δ1 + Δ4 + Δ6 + Δ7 | Δ3 + Δ5 + Δ6 + Δ7 |
| Δ5 + Δ6 + Δ7 | Δ1 + Δ4 + Δ6 + Δ8 | Δ3 + Δ5 + Δ6 + Δ8 |
| Δ5 + Δ6 + Δ8 | Δ1 + Δ4 + Δ7 + Δ8 | Δ3 + Δ5 + Δ7 + Δ8 |
| Δ5 + Δ7 + Δ8 | Δ1 + Δ5 + Δ6 + Δ7 | Δ3 + Δ6 + Δ7 + Δ8 |
| Δ6 + Δ7 + Δ8 | Δ1 + Δ5 + Δ6 + Δ8 | Δ4 + Δ5 + Δ6 + Δ7 |
| Δ1 + Δ2 + Δ3 + Δ4 | Δ1 + Δ5 + Δ7 + Δ8 | Δ4 + Δ5 + Δ6 + Δ8 |
| Δ4 + Δ5 + Δ7 + Δ8 | Δ1 + Δ3 + Δ6 + Δ7 + Δ8 | Δ1 + Δ2 + Δ3 + Δ4 + Δ7 + Δ8 |
| Δ4 + Δ6 + Δ7 + Δ8 | Δ1 + Δ4 + Δ5 + Δ6 + Δ7 | Δ1 + Δ2 + Δ3 + Δ5 + Δ6 + Δ7 |
| Δ5 + Δ6 + Δ7 + Δ8 | Δ1 + Δ4 + Δ5 + Δ6 + Δ8 | Δ1 + Δ2 + Δ3 + Δ5 + Δ6 + Δ8 |
| Δ1 + Δ2 + Δ3 + Δ4 + Δ5 | Δ1 + Δ4 + Δ5 + Δ7 + Δ8 | Δ1 + Δ2 + Δ3 + Δ5 + Δ7 + Δ8 |
| Δ1 + Δ2 + Δ3 + Δ4 + Δ6 | Δ1 + Δ4 + Δ6 + Δ7 + Δ8 | Δ1 + Δ2 + Δ3 + Δ6 + Δ7 + Δ8 |
| Δ1 + Δ2 + Δ3 + Δ4 + Δ7 | Δ1 + Δ5 + Δ6 + Δ7 + Δ8 | Δ1 + Δ2 + Δ4 + Δ5 + Δ6 + Δ7 |
| Δ1 + Δ2 + Δ3 + Δ4 + Δ8 | Δ2 + Δ3 + Δ4 + Δ5 + Δ6 | Δ1 + Δ2 + Δ4 + Δ5 + Δ6 + Δ8 |
| Δ1 + Δ2 + Δ3 + Δ5 + Δ6 | Δ2 + Δ3 + Δ4 + Δ5 + Δ7 | Δ1 + Δ2 + Δ4 + Δ5 + Δ7 + Δ8 |
| Δ1 + Δ2 + Δ3 + Δ5 + Δ7 | Δ2 + Δ3 + Δ4 + Δ5 + Δ8 | Δ1 + Δ2 + Δ4 + Δ6 + Δ7 + Δ8 |
| Δ1 + Δ2 + Δ3 + Δ5 + Δ8 | Δ2 + Δ3 + Δ4 + Δ6 + Δ7 | Δ1 + Δ2 + Δ5 + Δ6 + Δ7 + Δ8 |
| Δ1 + Δ2 + Δ3 + Δ6 + Δ7 | Δ2 + Δ3 + Δ4 + Δ6 + Δ8 | Δ1 + Δ3 + Δ4 + Δ5 + Δ6 + Δ7 |
| Δ1 + Δ2 + Δ3 + Δ6 + Δ8 | Δ2 + Δ3 + Δ4 + Δ7 + Δ8 | Δ1 + Δ3 + Δ4 + Δ5 + Δ6 + Δ8 |
| Δ1 + Δ2 + Δ3 + Δ7 + Δ8 | Δ2 + Δ3 + Δ5 + Δ6 + Δ7 | Δ1 + Δ3 + Δ4 + Δ5 + Δ7 + Δ8 |
| Δ1 + Δ2 + Δ4 + Δ5 + Δ6 | Δ2 + Δ3 + Δ5 + Δ6 + Δ8 | Δ1 + Δ3 + Δ4 + Δ6 + Δ7 + Δ8 |
| Δ1 + Δ2 + Δ4 + Δ5 + Δ7 | Δ2 + Δ3 + Δ5 + Δ7 + Δ8 | Δ1 + Δ3 + Δ5 + Δ6 + Δ7 + Δ8 |
| Δ1 + Δ2 + Δ4 + Δ5 + Δ8 | Δ2 + Δ3 + Δ6 + Δ7 + Δ8 | Δ1 + Δ4 + Δ5 + Δ6 + Δ7 + Δ8 |
| Δ1 + Δ2 + Δ4 + Δ6 + Δ7 | Δ2 + Δ4 + Δ5 + Δ6 + Δ7 | Δ2 + Δ3 + Δ4 + Δ5 + Δ6 + Δ7 |
| Δ1 + Δ2 + Δ4 + Δ6 + Δ8 | Δ2 + Δ4 + Δ5 + Δ6 + Δ8 | Δ2 + Δ3 + Δ4 + Δ5 + Δ6 + Δ8 |
| Δ1 + Δ2 + Δ4 + Δ7 + Δ8 | Δ2 + Δ4 + Δ5 + Δ7 + Δ8 | Δ2 + Δ3 + Δ4 + Δ5 + Δ7 + Δ8 |
| Δ1 + Δ2 + Δ5 + Δ6 + Δ7 | Δ2 + Δ4 + Δ6 + Δ7 + Δ8 | Δ2 + Δ3 + Δ4 + Δ6 + Δ7 + Δ8 |
| Δ1 + Δ2 + Δ5 + Δ6 + Δ8 | Δ2 + Δ5 + Δ6 + Δ7 + Δ8 | Δ2 + Δ3 + Δ5 + Δ6 + Δ7 + Δ8 |
| Δ1 + Δ2 + Δ5 + Δ7 + Δ8 | Δ3 + Δ4 + Δ5 + Δ6 + Δ7 | Δ2 + Δ4 + Δ5 + Δ6 + Δ7 + Δ8 |
| Δ1 + Δ2 + Δ6 + Δ7 + Δ8 | Δ3 + Δ4 + Δ5 + Δ6 + Δ8 | Δ3 + Δ4 + Δ5 + Δ6 + Δ7 + Δ8 |
| Δ1 + Δ3 + Δ4 + Δ5 + Δ6 | Δ3 + Δ4 + Δ5 + Δ7 + Δ8 | Δ1 + Δ2 + Δ3 + Δ4 + Δ5 + Δ6 + Δ7 |
| Δ1 + Δ3 + Δ4 + Δ5 + Δ7 | Δ3 + Δ4 + Δ6 + Δ7 + Δ8 | Δ1 + Δ2 + Δ3 + Δ4 + Δ5 + Δ6 + Δ8 |
| Δ1 + Δ3 + Δ4 + Δ5 + Δ8 | Δ3 + Δ5 + Δ6 + Δ7 + Δ8 | Δ1 + Δ2 + Δ3 + Δ4 + Δ5 + Δ7 + Δ8 |
| Δ1 + Δ3 + Δ4 + Δ6 + Δ7 | Δ4 + Δ5 + Δ6 + Δ7 + Δ8 | Δ1 + Δ2 + Δ3 + Δ4 + Δ6 + Δ7 + Δ8 |
| Δ1 + Δ3 + Δ4 + Δ6 + Δ8 | Δ1 + Δ2 + Δ3 + Δ4 + Δ5 + Δ6 | Δ1 + Δ2 + Δ3 + Δ5 + Δ6 + Δ7 + Δ8 |
| Δ1 + Δ3 + Δ4 + Δ7 + Δ8 | Δ1 + Δ2 + Δ3 + Δ4 + Δ5 + Δ7 | Δ1 + Δ2 + Δ4 + Δ5 + Δ6 + Δ7 + Δ8 |
| Δ1 + Δ3 + Δ5 + Δ6 + Δ7 | Δ1 + Δ2 + Δ3 + Δ4 + Δ5 + Δ8 | Δ1 + Δ3 + Δ4 + Δ5 + Δ6 + Δ7 + Δ8 |
| Δ1 + Δ3 + Δ5 + Δ6 + Δ8 | Δ1 + Δ2 + Δ3 + Δ4 + Δ6 + Δ7 | Δ2 + Δ3 + Δ4 + Δ5 + Δ6 + Δ7 + Δ8 |
| Δ1 + Δ3 + Δ5 + Δ7 + Δ8 | Δ1 + Δ2 + Δ3 + Δ4 + Δ6 + Δ8 | Δ1 + Δ2 + Δ3 + Δ4 + Δ5 + Δ6 + Δ7 + Δ8 |

For the sake of clarity, Table 2 should be understood as follows. Taking as an example the functional truncated human GDE polypeptide comprising the following combination of deletions: "Δ1+Δ2+Δ3", the functional truncated human GDE polypeptide comprises deletions Δ1, Δ2 and Δ3 with respect to SEQ ID NO:1, SEQ ID NO:40 or SEQ ID NO:41, as referred in Table 1. In other words, in this example, when the reference full-length GDE sequence is SEQ ID NO:1, the functional truncated human GDE polypeptide "Δ1+Δ2+Δ3" corresponds to a functional truncated human GDE polypeptide derived from SEQ ID NO:1, which is deleted of all consecutive amino acids from position 1 to 156, from position 361-428 and from position 668-769 with respect to SEQ ID NO:1. Accordingly, when the reference full-length GDE sequence is SEQ ID NO:40, the functional truncated human GDE polypeptide "Δ1+Δ2+Δ3" corresponds to a functional truncated human GDE polypeptide derived from SEQ ID NO:40, which is deleted of all consecutive amino acids from position 1 to 139, from position 344-411 and from position 651-752 with respect to SEQ ID NO:40.

In a particular embodiment, the functional truncated human GDE polypeptide of the invention comprises the Δ2 and Δ3 deletions referred to in table 1. In a particular embodiment, the functional truncated human GDE polypeptide of the invention comprises the Δ2 and Δ3 deletions referred to in table 1 and is derived from SEQ ID NO:1, SEQ ID NO:40 or SEQ ID NO:41, in particular from SEQ ID NO:1.

In a particular embodiment, the functional truncated human GDE polypeptide is derived from SEQ ID NO: 1 and comprises:

- (i) a deletion or a combination of deletions, as shown in table 2 with respect to SEQ ID NO:1, and
- (ii) a N-terminal deletion of at least one amino acid and of at most 132 amino acids selected from amino acids at positions 1 to 132 with respect to SEQ ID NO:1.

In a particular embodiment, the functional truncated human GDE polypeptide is derived from SEQ ID NO: 1 and comprises:

- (i) a deletion or a combination of deletions, as shown in table 2 with respect to SEQ ID NO:1, and
- (ii) a N-terminal deletion of at least one amino acid selected from amino acids at positions 1 to 132 with respect to SEQ ID NO:1, preferably at least 15 consecutive amino acids, at least 25 consecutive amino acids, at least 30 consecutive amino acids, at least 50 consecutive amino acids, at least 75 consecutive amino acids, at least 80 consecutive amino acids, at least 81 consecutive amino acids, at least 100 consecutive amino acids, at least 103 consecutive amino acids, at least 125 consecutive amino acids, or at least 132 consecutive amino acids selected from amino acids at positions 1 to 132 with respect to SEQ ID NO: 1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) a N-terminal deletion of at least one amino acid and of at most 132 amino acids selected from amino acids at positions 1 to 132 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) a N-terminal deletion of at least one amino acid selected from amino acids at positions 1 to 132 with respect to SEQ ID NO:1, preferably at least 15 consecutive amino acids, at least 25 consecutive amino acids, at least 30 consecutive amino acids, at least 50 consecutive amino acids, at least 75 consecutive amino acids, at least 80 consecutive amino acids, at least 81 consecutive amino acids, at least 100 consecutive amino acids, at least 103 consecutive amino acids, at least 125 consecutive amino acids, or at least 132 consecutive amino acids selected from amino acids at positions 1 to 132 with respect to SEQ ID NO: 1.

In a particular embodiment, the functional truncated human GDE polypeptide is derived from SEQ ID NO: 40 and comprises:

(i) a deletion or a combination of deletions, as shown in table 2 with respect to SEQ ID NO:40, and (ii) a N-terminal deletion of at least one amino acid and of at most 115 amino acids selected from amino acids at positions 1 to 115 with respect to SEQ ID NO:40.

In a particular embodiment, the functional truncated human GDE polypeptide is derived from SEQ ID NO: 40 and comprises:

(i) a deletion or a combination of deletions, as shown in table 2 with respect to SEQ ID NO:40, and (ii) a N-terminal deletion of at least one amino acid selected from amino acids at positions 1 to 115 with respect to SEQ ID NO:40, preferably at least 10 consecutive amino acids, at least 13 consecutive amino acids, at least 15 consecutive amino acids, at least 25 consecutive amino acids, at least 50 consecutive amino acids, at least 60 consecutive amino acids, at least 64 consecutive amino acids, at least 75 consecutive amino acids, at least 80 consecutive amino acids, at least 85 consecutive amino acids, at least 86 consecutive amino acids, at least 100 consecutive amino acids, at least 110 consecutive amino acids, at least 112 consecutive amino acids, or at least 115 consecutive amino acids selected from amino acids at positions 1 to 115 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) a N-terminal deletion of at least one amino acid and of at most 115 amino acids selected from amino acids at positions 1 to 115 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) a N-terminal deletion of at least one amino acid selected from amino acids at positions 1 to $Z_2$ with respect to SEQ ID NO:40, preferably at least 10 consecutive amino acids, at least 13 consecutive amino acids, at least 15 consecutive amino acids, at least 25 consecutive amino acids, at least 50 consecutive amino acids, at least 60 consecutive amino acids, at least 64 consecutive amino acids, at least 75 consecutive amino acids, at least 80 consecutive amino acids, at least 85 consecutive amino acids, at least 86 consecutive amino acids, at least 100 consecutive amino acids, at least 110 consecutive amino acids, at least 112 consecutive amino acids, or at least 115 consecutive amino acids selected from amino acids at positions 1 to 115 with respect to SEQ ID NO:40.

In a particular embodiment, the functional truncated human GDE polypeptide is derived from SEQ ID NO: 41 and comprises:

(i) the Δ2 and Δ3 deletions as referred in table 1 with respect to SEQ ID NO:41, and (ii) a N-terminal deletion of at least one amino acid and of at most 115 amino acids selected from amino acids at positions 1 to 115 with respect to SEQ ID NO:41.

In a particular embodiment, the functional truncated human GDE polypeptide is derived from SEQ ID NO: 41 and comprises:

(i) a deletion or a combination of deletions, as shown in table 2 with respect to SEQ ID NO:41, and (ii) a N-terminal deletion of at least one amino acid selected from amino acids at positions 1 to 116 with respect to SEQ ID NO:41, preferably at least 10 consecutive amino acids, at least 14 consecutive amino acids, at least 15 consecutive amino acids, at least 25 consecutive amino acids, at least 50 consecutive amino acids, at least 60 consecutive amino acids, at least 65 consecutive amino acids, at least 75 consecutive amino acids, at least 80 consecutive amino acids, at least 85 consecutive amino acids, at least 87 consecutive amino acids, at least 100 consecutive amino acids, at least 110 consecutive amino acids, at least 113 consecutive amino acids, or at least 116 consecutive amino acids selected from amino acids at positions 1 to 116 with respect to SEQ ID NO:41.

In a particular embodiment, the functional truncated human GDE polypeptide is derived from SEQ ID NO: 41 and comprises:

(i) the Δ2 and Δ3 deletions as referred in table 1 with respect to SEQ ID NO:41, and (ii) a N-terminal deletion of at least one amino acid selected from amino acids at positions 1 to 116 with respect to SEQ ID NO:41, preferably at least 10 consecutive amino acids, at least 14 consecutive amino acids, at least 15 consecutive amino acids, at least 25 consecutive amino acids, at least 50 consecutive amino acids, at least 60 consecutive amino acids, at least 65 consecutive amino acids, at least 75 consecutive amino acids, at least 80 consecutive amino acids, at least 85 consecutive amino acids, at least 87 consecutive amino acids, at least 100 consecutive amino acids, at least 110 consecutive amino acids, at least 113 consecutive amino acids, or at least 116 consecutive amino acids selected from amino acids at positions 1 to 116 with respect to SEQ ID NO:41.

In a particular embodiment, the functional truncated human GDE polypeptide comprises:

(i) a deletion or a combination of deletions, as shown in table 2 with respect to SEQ ID NO:1, SEQ ID NO: 40 or SEQ ID NO:41, and (ii) a deletion or a combination of deletions selected from any deletion referred to as Δ9, Δ10, Δ11, Δ12, and Δ13 in table 3, with respect to SEQ ID NO:1, SEQ ID NO:40 or SEQ ID NO:41.

TABLE 3

| Deletion | Position of the deleted amino acids with respect to SEQ ID NO: 1 | Position of the deleted amino acids with respect to SEQ ID NO: 40 | Position of the deleted amino acids with respect to SEQ ID NO: 41 |
|---|---|---|---|
| Δ49 | 1-15 | — | — |
| Δ10 | 1-30 | 1-13 | 1-14 |
| Δ11 | 1-81 | 1-64 | 1-65 |
| Δ12 | 1-103 | 1-86 | 1-87 |
| Δ13 | 1-129 | 1-112 | 1-113 |

In a particular embodiment, the functional truncated human GDE polypeptide is derived from SEQ ID NO: 1 and comprises:

(i) a deletion or a combination of deletions, as shown in table 2 with respect to SEQ ID NO:1, and (ii) the Δ9 deletion, as referred in Table 3 with respect to SEQ ID NO:1;

or (i) a deletion or a combination of deletions, as shown in table 2 with respect to SEQ ID NO:1, and (ii) the Δ10 deletion, as referred in Table 3 with respect to SEQ ID NO:1;

or (i) a deletion or a combination of deletions, as shown in table 2 with respect to SEQ ID NO:1, and (ii) the Δ11 deletion, as referred in Table 3 with respect to SEQ ID NO:1;

or (i) a deletion or a combination of deletions, as shown in table 2 with respect to SEQ ID NO:1, and (ii) the Δ12 deletion, as referred in Table 3 with respect to SEQ ID NO:1;

or (i) a deletion or a combination of deletions, as shown in table 2 with respect to SEQ ID NO:1 and (ii) the Δ13 deletion, as referred in Table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) a deletion or a combination of deletions selected from the Δ9, Δ10, Δ11, Δ12 and Δ13 deletions as referred in table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) the Δ9 deletion as referred in table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) the Δ10 deletion as referred in table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) the Δ11 deletion as referred in table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) the Δ12 deletion as referred in table 3 with respect to SEQ ID NO:1.

In a particular embodiment, the functional truncated human GDE polypeptide is derived from SEQ ID NO: 1 and comprises:

(i) the Δ2 and Δ3 deletions as referred in table 1 with respect to SEQ ID NO:1, and (ii) the Δ13 deletion as referred in table 3 with respect to SEQ ID NO:1.

In a further particular embodiment, the functional truncated human GDE polypeptide is derived from SEQ ID NO:1 and comprises:

(i) the Δ2 and Δ3 deletions as referred in table 1 with respect to SEQ ID NO:1, and (ii) a deletion or a combination of deletions selected from the Δ9, Δ10, and Δ13 deletions as referred in table 3 with respect to SEQ ID NO:1.

In yet another particular embodiment, the functional truncated human GDE polypeptide is derived from SEQ ID NO:1 and comprises:

(i) the Δ2 and Δ3 deletions as referred in table 1 with respect to SEQ ID NO:1, and (ii) a deletion or a combination of deletions selected from the 49 and Δ10 deletions as referred in table 3 with respect to SEQ ID NO:1.

In another particular embodiment, the functional truncated human GDE polypeptide is derived from SEQ ID NO:40 and comprises:

(i) a deletion or a combination of deletions, as shown in table 2 with respect to SEQ ID NO:40, and (ii) the Δ10 deletion, as referred in Table 3 with respect to SEQ ID NO:40;

or (i) a deletion or a combination of deletions, as shown in table 2 with respect to SEQ ID NO:40, and (ii) the Δ11 deletion, as referred in Table 3 with respect to SEQ ID NO:40;

or (i) a deletion or a combination of deletions, as shown in table 2 with respect to SEQ ID NO:40, and (ii) the Δ12 deletion, as referred in Table 3 with respect to SEQ ID NO:40;

or (i) a deletion or a combination of deletions, as shown in table 2 with respect to SEQ ID NO:40 and (ii) the Δ13 deletion, as referred in Table 3 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) a deletion or a combination of deletions selected from the Δ10, Δ11, Δ12 and Δ13 deletions as referred in table 3 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) the Δ10 deletion as referred in table 3 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) the Δ11 deletion as referred in table 3 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) the Δ12 deletion as referred in table 3 with respect to SEQ ID NO:40.

In a particular embodiment, the functional truncated human GDE polypeptide is derived from SEQ ID NO: 40 and comprises:

(i) the Δ2 and Δ3 deletions as referred in table 1 with respect to SEQ ID NO:40, and (ii) the Δ13 deletion as referred in table 3 with respect to SEQ ID NO:40.

In a further particular embodiment, the functional truncated human GDE polypeptide is derived from SEQ ID NO:40 and comprises:

(i) the Δ2 and Δ3 deletions as referred in table 1 with respect to SEQ ID NO:40, and (ii) a deletion or a combination of deletions selected from the Δ10, and Δ13 deletions as referred in table 3 with respect to SEQ ID NO:40.

In another particular embodiment, the functional truncated human GDE polypeptide is derived from SEQ ID NO:41 and comprises:

(i) a deletion or a combination of deletions, as shown in table 2 with respect to SEQ ID NO:41, and (ii) the Δ10 deletion, as referred in Table 3 with respect to SEQ ID NO:41;

or (i) a deletion or a combination of deletions, as shown in table 2 with respect to SEQ ID NO:41, and (ii) the Δ11 deletion, as referred in Table 3 with respect to SEQ ID NO:41;

or (i) a deletion or a combination of deletions, as shown in table 2 with respect to SEQ ID NO:41, and (ii) the Δ12 deletion, as referred in Table 3 with respect to SEQ ID NO:41;

or (i) a deletion or a combination of deletions, as shown in table 2 with respect to SEQ ID NO:41 and (ii) the Δ13 deletion, as referred in Table 3 with respect to SEQ ID NO:41.

In a particular embodiment, the functional truncated human GDE polypeptide is derived from SEQ ID NO: 41 and comprises:

(i) the Δ2 and Δ3 deletions as referred in table 1 with respect to SEQ ID NO:41, and (ii) a deletion or a combination of deletions selected from the Δ9, Δ10, Δ11, Δ12, and Δ13 deletions as referred in table 3 with respect to SEQ ID NO:41.

In a further particular embodiment, the functional truncated human GDE polypeptide is derived from SEQ ID NO:41 and comprises:

(i) the Δ2 and Δ3 deletions as referred in table 1 with respect to SEQ ID NO:1, and (ii) a deletion or a combination of deletions selected from the Δ10, and Δ13 deletions as referred in table 3 with respect to SEQ ID NO:41.

In another particular embodiment, the functional truncated human GDE polypeptide of the invention is selected from the group consisting of:

SEQ ID NO:2: a functional truncated human GDE polypeptide comprising a deletion of amino acids from position 1 to 156 with respect to SEQ ID NO:1;

SEQ ID NO:3: a functional truncated human GDE polypeptide comprising a deletion of amino acids from position 361 to 428 with respect to SEQ ID NO:1;

SEQ ID NO:4: a functional truncated human GDE polypeptide comprising a deletion of amino acids from position 668 to 769 with respect to SEQ ID NO:1;

SEQ ID NO:5: a functional truncated human GDE polypeptide comprising a first deletion of amino acids from position 361 to 428 and a second deletion of amino acids from position 668 to 769 with respect to SEQ ID NO:1;

SEQ ID NO:6: a functional truncated human GDE polypeptide comprising a deletion of amino acids from position 895 to 1087 with respect to SEQ ID NO:1;

SEQ ID NO:7: a functional truncated human GDE polypeptide comprising a first deletion of amino acids from position 223 to 320, a second deletion of amino acids from position 360 to 428, and a third deletion of amino acids from position 669 to 720 with respect to SEQ ID NO:1;

SEQ ID NO:8: a functional truncated human GDE polypeptide comprising a deletion of amino acids from position 1 to 280 with respect to SEQ ID NO:1;

SEQ ID NO:9: a functional truncated human GDE polypeptide comprising a deletion of amino acids from position 1 to 425 with respect to SEQ ID NO:1;

SEQ ID NO: 10: a functional truncated human GDE polypeptide comprising a deletion of amino acids from position 1 to 230 with respect to SEQ ID NO:1

SEQ ID NO:48: a functional truncated human GDE polypeptide comprising a first deletion of amino acids from position 1-15, a second deletion of amino acids from position 361 to 428 and a third deletion of amino acids from position 668 to 769 with respect to SEQ ID NO:1;

SEQ ID NO:49: a functional truncated human GDE polypeptide comprising a first deletion of amino acids from position 1-30 a second deletion of amino acids from position 361 to 428 and a third deletion of amino acids from position 668 to 769 with respect to SEQ ID NO:1;

SEQ ID NO:50: a functional truncated human GDE polypeptide comprising a first deletion of amino acids from position 1-81 a second deletion of amino acids from position 361 to 428 and a third deletion of amino acids from position 668 to 769 with respect to SEQ ID NO:1;

SEQ ID NO:51: a functional truncated human GDE polypeptide comprising a first deletion of amino acids from position 1-103 a second deletion of amino acids from position 361 to 428 and a third deletion of amino acids from position 668 to 769 with respect to SEQ ID NO: 1; and SEQ ID NO:52: a functional truncated human GDE polypeptide comprising a first deletion of amino acids from position 1-129 a second deletion of amino acids from position 361 to 428 and a third deletion of amino acids from position 668 to 769 with respect to SEQ ID NO:1.

In a further particular embodiment, the functional truncated human GDE polypeptide of the invention is selected from the group consisting of:

SEQ ID NO:2: a functional truncated human GDE polypeptide comprising a deletion of amino acids from position 1 to 156 with respect to SEQ ID NO:1;

SEQ ID NO:3: a functional truncated human GDE polypeptide comprising a deletion of amino acids from position 361 to 428 with respect to SEQ ID NO:1;

SEQ ID NO:4: a functional truncated human GDE polypeptide comprising a deletion of amino acids from position 668 to 769 with respect to SEQ ID NO:1;

SEQ ID NO:5: a functional truncated human GDE polypeptide comprising a first deletion of amino acids from position 361 to 428 and a second deletion of amino acids from position 668 to 769 with respect to SEQ ID NO:1;

SEQ ID NO:6: a functional truncated human GDE polypeptide comprising a deletion of amino acids from position 895 to 1087 with respect to SEQ ID NO:1;

SEQ ID NO:7: a functional truncated human GDE polypeptide comprising a first deletion of amino acids from position 223 to 320, a second deletion of amino acids from position 360 to 428, and a third deletion of amino acids from position 669 to 720 with respect to SEQ ID NO:1;

SEQ ID NO:8: a functional truncated human GDE polypeptide comprising a deletion of amino acids from position 1 to 280 with respect to SEQ ID NO:1;

SEQ ID NO:9: a functional truncated human GDE polypeptide comprising a deletion of amino acids from position 1 to 425 with respect to SEQ ID NO: 1; and SEQ ID NO:10: a functional truncated human GDE polypeptide comprising a deletion of amino acids from position 1 to 230 with respect to SEQ ID NO:1.

When the deletion is a N-terminal deletion, a methionine may be added at the N-terminal end of the sequence. For example, SEQ ID NO:9 comprises a deletion of amino acids from position 1 to 425 with respect to SEQ ID NO: 1 and an addition of a methionine at the N-terminal end of the sequence resulting from this deletion. The present application does disclose all the functional GDE truncated forms specifically disclosed therein, wherein said functional GDE truncated forms being with a methionine residue at its N-terminal end.

In a further particular embodiment, the functional truncated human GDE polypeptide of the invention comprises or consists of a sequence selected from SEQ ID NO:2 to 10 and SEQ ID NO:48 to 52, in particular a sequence selected from SEQ ID NO:2 to 10, in particular a sequence selected from SEQ ID NO: 2, SEQ ID NO:3, SEQ ID NO:4, SEQ ID NO:5 and SEQ ID NO:6, more particularly SEQ ID NO:5. The functional truncated human GDE polypeptide may comprise one or more amino acid modifications such as amino acid insertion, deletion and/or substitution, as compared to SEQ ID NO:2 to 10 and SEQ ID NO: 48 to 52, in particular a sequence selected from SEQ ID NO:2 to 10, in particular a sequence selected from SEQ ID NO:2, SEQ ID NO:3, SEQ ID NO:4, SEQ ID NO:5 and SEQ ID NO:6, more particularly SEQ ID NO:5. In particular, the functional truncated human GDE polypeptide may comprise 1, 2, 3, 4 or 5 amino acid modifications as compared to SEQ ID NO:2 to 10 and SEQ ID NO: 48 to 52, in particular a sequence selected from SEQ ID NO:2 to 10, in particular a sequence selected from SEQ ID NO:2, SEQ ID NO:3, SEQ ID NO:4, SEQ ID NO:5 and SEQ ID NO:6, more particularly SEQ ID NO:5. In particular, the functional truncated human GDE polypeptide may have at least 80, 85, 90, 95, 96, 97, 98 or at least 99 percent sequence identity to SEQ ID NO:2 to 10 and SEQ ID NO:48 to 52, in particular a sequence selected from SEQ ID NO:2 to 10, in particular a sequence selected from SEQ ID NO:2, SEQ ID NO:3, SEQ ID NO:4, SEQ ID NO:5 and SEQ ID NO:6, more particularly SEQ ID NO: 5.

In a second variant of the first aspect of the invention, the mini-GDE is a functional non-human GDE polypeptide.

The functional non-human GDE polypeptide of the invention can be any GDE polypeptide whose coding sequence is small enough to be packaged into a gene therapy vector, in particular into an AAV vector. Indeed, the present inventors have shown that non-human GDE polypeptides whose coding sequence is shorter than native human GDE coding sequence can be used for treating GSD III, using gene therapy vectors. In a particular embodiment, the functional non-human GDE polypeptide comprises less than about 1500, 1480, 1460, 1440, 1420, 1400, 1380, 1360, 1340, 1320, 1300, 1280, 1260, 1240, 1220, 1200, 1180, 1160, 1140, 1120, 1100, 1080, 1060, 1040, 1020, or less than about 1000 amino acids. In a particular embodiment, the functional non-human GDE polypeptide comprises between about 1000 and 1500 amino acids, between about 1000 and 1300 amino acids, between about 1300 and 1500 amino acids or between about 1300 and 1400 amino acids.

According to the invention, the functional non-human GDE polypeptide of the invention retains the biological function of human GDE polypeptide, as defined above. In particular, the non-human GDE polypeptide is able to rescue glycogen accumulation and muscle strength in vivo.

The amino acid sequence of the functional non-human GDE polypeptide or its coding sequence can derive from any non-human eukaryotic source, such as from yeast or non-human animals including non-human mammal or avian species. In a particular embodiment, the functional non-human GDE polypeptide is a non-human mammalian GDE polypeptide.

In addition, the non-human GDE polypeptide may be a functional variant of a wild type non-human GDE polypeptide, comprising one or more amino acid modifications such as amino acid insertion, deletion and/or substitution as compared to a reference native GDE polypeptide. For example, the non-human GDE polypeptide may be a functional derivative of a non-human GDE polypeptide, in particular of a non-human animal GDE polypeptide, such as the polypeptides of SEQ ID NO:11 to SEQ ID NO:17, having at least 80, 85, 90, 95, 96, 97, 98 or at least 99 percent sequence identity to these animal GDE polypeptides.

In a particular embodiment, the functional non-human GDE polypeptide or its coding sequence derives from horse, gorilla, orangutan, Pteropus alecto, sooty mangabey, platypus, duck or Tasmania devil.

In a particular embodiment, the non-human GDE polypeptide is selected in the group consisting of: horse GDE polypeptide of SEQ ID NO:11, gorilla GDE polypeptide of SEQ ID NO:12, orangutan GDE polypeptide of SEQ ID NO:13, Pteropus alecto GDE polypeptide of SEQ ID NO:14, sooty mangabey GDE polypeptide of SEQ ID NO:15, platypus GDE polypeptide of SEQ ID NO:16, and duck GDE polypeptide of SEQ ID NO:17.

In a further particular embodiment, the non-human GDE polypeptide is a gorilla GDE polypeptide, in particular the gorilla GDE polypeptide of SEQ ID NO:12.

In another aspect, the invention relates to a nucleic acid molecule encoding the mini-GDE polypeptide of the invention.

The term "nucleic acid molecule" (or nucleic acid sequence) refers to a DNA or RNA molecule in single or double stranded form, particularly a DNA encoding a functional truncated human GDE polypeptide or a functional non-human GDE polypeptide according to the invention.

According to the present invention, the nucleic acid molecule encoding the mini-GDE polypeptide is small enough to be packaged into a gene therapy vector, wherein the gene therapy vector is as defined above. In a preferred embodiment, the nucleic acid molecule encoding the mini-GDE polypeptide is small enough to be packaged into an AAV vector. Preferably, the size of the nucleic acid molecule encoding the mini-GDE polypeptide is less than about 5, 4.7, 4.5, 4.2, 4.1, 4, 3.7, 3.5, 3.2, 3, 2.7, 2.5, 2.2, 2, or 1.5 kb. Preferably, the nucleic acid molecule encoding the mini-GDE polypeptide is less than about 4.1 kb.

The sequence of the nucleic acid molecule of the invention, encoding a mini-GDE polypeptide may be optimized for expression of the GDE polypeptide in vivo. Sequence optimization may include a number of changes in a nucleic acid sequence, including codon optimization, increase of GC content, decrease of the number of CpG islands, decrease of the number of alternative open reading frames (ARFs) and decrease of the number of splice donor and splice acceptor sites. Because of the degeneracy of the genetic code, different nucleic acid molecules may encode the same protein. It is also well known that the genetic codes of different organisms are often biased towards using one of the several codons that encode the same amino acid over the others. Through codon optimization, changes are introduced in a nucleotide sequence that take advantage of the codon bias existing in a given cellular context so that the resulting codon optimized nucleotide sequence is more likely to be expressed in such given cellular context at a relatively high level compared to the non-codon optimized sequence. In a preferred embodiment of the invention, such sequence optimized nucleotide sequence encoding a mini-GDE polypeptide is codon-optimized to improve its expression in human cells compared to non-codon optimized nucleotide sequences coding for the same mini-GDE polypeptide, for example by taking advantage of the human specific codon usage bias. The nucleic acid sequence encoding the full-length human GDE isoform 1 is as shown in SEQ ID NO:37. Examples of corresponding codon optimized sequence is as shown in SEQ ID NO:38 or SEQ ID NO:39.

In a particular embodiment, the nucleic acid molecule of the invention comprises or consists of:

the sequence shown in SEQ ID NO:18, encoding the functional truncated human GDE polypeptide having the amino acid sequence shown in SEQ ID NO:2;

the sequence shown in SEQ ID NO:20, encoding the functional truncated human GDE polypeptide having the amino acid sequence shown in SEQ ID NO:3;

the sequence shown in SEQ ID NO:21, encoding the functional truncated human GDE polypeptide having the amino acid sequence shown in SEQ ID NO:4;

the sequence shown in SEQ ID NO:22, encoding the functional truncated human GDE polypeptide having the amino acid sequence shown in SEQ ID NO:5;

the sequence shown in SEQ ID NO:24, encoding the functional truncated human GDE polypeptide having the amino acid sequence shown in SEQ ID NO:6;

the sequence shown in SEQ ID NO:26, encoding the functional truncated human GDE polypeptide having the amino acid sequence shown in SEQ ID NO:7;

the sequence shown in SEQ ID NO:27, encoding the functional truncated human GDE polypeptide having the amino acid sequence shown in SEQ ID NO:8;

the sequence shown in SEQ ID NO:28, encoding the functional truncated human GDE polypeptide having the amino acid sequence shown in SEQ ID NO:9;

the sequence shown in SEQ ID NO:29, encoding the functional truncated human GDE polypeptide having the amino acid sequence shown in SEQ ID NO:10;

the sequence shown in SEQ ID NO:53 or SEQ ID NO:59, encoding the functional truncated human GDE polypeptide having the amino acid sequence shown in SEQ ID NO:48;

the sequence shown in SEQ ID NO:54 or SEQ ID NO:60, encoding the functional truncated human GDE polypeptide having the amino acid sequence shown in SEQ ID NO:49;

the sequence shown in SEQ ID NO:55 or SEQ ID NO:61, encoding the functional truncated human GDE polypeptide having the amino acid sequence shown in SEQ ID NO:50;

the sequence shown in SEQ ID NO:56 or SEQ ID NO:62, encoding the functional truncated human GDE polypeptide having the amino acid sequence shown in SEQ ID NO:51; or the sequence shown in SEQ ID NO:57 or SEQ ID NO:63, encoding the functional truncated human GDE polypeptide having the amino acid sequence shown in SEQ ID NO:52.

In a further particular embodiment, the nucleic acid molecule of the invention comprises or consists of:

the sequence shown in SEQ ID NO:18, encoding the functional truncated human GDE polypeptide having the amino acid sequence shown in SEQ ID NO:2;

the sequence shown in SEQ ID NO:20, encoding the functional truncated human GDE polypeptide having the amino acid sequence shown in SEQ ID NO:3;

the sequence shown in SEQ ID NO:21, encoding the functional truncated human GDE polypeptide having the amino acid sequence shown in SEQ ID NO:4;

the sequence shown in SEQ ID NO:22, encoding the functional truncated human GDE polypeptide having the amino acid sequence shown in SEQ ID NO:5;

the sequence shown in SEQ ID NO:24, encoding the functional truncated human GDE polypeptide having the amino acid sequence shown in SEQ ID NO:6;

the sequence shown in SEQ ID NO:26, encoding the functional truncated human GDE polypeptide having the amino acid sequence shown in SEQ ID NO:7;

the sequence shown in SEQ ID NO:27, encoding the functional truncated human GDE polypeptide having the amino acid sequence shown in SEQ ID NO:8;

the sequence shown in SEQ ID NO:28, encoding the functional truncated human GDE polypeptide having the amino acid sequence shown in SEQ ID NO:9; or the sequence shown in SEQ ID NO:29, encoding the functional truncated human GDE polypeptide having the amino acid sequence shown in SEQ ID NO:10.

As already mentioned, the above sequences may be codon-optimized. Sequences shown in SEQ ID NO: 19, SEQ ID NO:23 and SEQ ID NO:25 are examples of codon-optimized sequences corresponding to SEQ ID NO: 18, SEQ ID NO:22 and SEQ ID NO:24, respectively.

In another particular embodiment, the nucleic acid molecule of the invention comprises or consists of:

the sequence shown in SEQ ID NO:30, encoding the non-human GDE polypeptide having the amino acid sequence shown in SEQ ID NO:11;

the sequence shown in SEQ ID NO:31, encoding the non-human GDE polypeptide having the amino acid sequence shown in SEQ ID NO:12;

the sequence shown in SEQ ID NO:32, encoding the non-human GDE polypeptide having the amino acid sequence shown in SEQ ID NO:13;

the sequence shown in SEQ ID NO:33, encoding the non-human GDE polypeptide having the amino acid sequence shown in SEQ ID NO:14;

the sequence shown in SEQ ID NO:34, encoding the non-human GDE polypeptide having the amino acid sequence shown in SEQ ID NO:15;

the sequence shown in SEQ ID NO:35, encoding the non-human GDE polypeptide having the amino acid sequence shown in SEQ ID NO:16; or the sequence shown in SEQ ID NO:36, encoding the non-human GDE polypeptide having the amino acid sequence shown in SEQ ID NO:17.

The nucleic acid molecule encoding the mini-GDE polypeptide as defined above may have at least 90 or at least 95 percent identity to any of the nucleotide sequences of SEQ ID NO:18 to 26. In a particular embodiment, the nucleic acid molecule encoding the mini-GDE polypeptide as defined above may have at least 90 or at least 95 percent identity to any of the nucleotide sequences of SEQ ID NO:18 to 36 and SEQ ID NO:53 to 57. In a particular embodiment, the nucleic acid molecule of the invention has at least 95 percent identity, for example at least 96, 97, 98, 99 or 100 percent identity to any of the nucleotide sequences of SEQ ID NO:18 to 36. In a further particular embodiment, the nucleic acid molecule of the invention has at least 95 percent identity, for example at least 96, 97, 98, 99 or 100 percent identity to any of the nucleotide sequences of SEQ ID NO:18 to 36 and SEQ ID NO:53 to 57.

The term "identical" and declinations thereof refers to the sequence identity between two nucleic acid molecules or between two polypeptide molecules. When a position in both of the two compared sequences is occupied by the same base or the same amino acid, then the molecules are identical at that position. The percent of identity between two sequences is a function of the number of matching positions shared by the two sequences divided by the number of positions compared×100. For example, if 6 of 10 of the positions in two sequences are matched then the two sequences are 60% identical. Generally, a comparison is made when two sequences are aligned to give maximum identity. Various bioinformatics tools known to the one skilled in the art might be used to align nucleic acid sequences such as BLAST or FASTA.

The invention also relates to a nucleic acid construct comprising a nucleic acid molecule of the invention. The nucleic acid construct may correspond to an expression cassette comprising the nucleic acid sequence of the invention, operably linked to one or more expression control sequences and/or other sequences improving the expression. As used herein, the term "operably linked" refers to a linkage of polynucleotide elements in a functional relationship. A nucleic acid is "operably linked" when it is placed into a functional relationship with another nucleic acid sequence. For instance, a promoter, or another transcription regulatory sequence, is operably linked to a coding sequence if it affects the transcription of the coding sequence. Such expression control sequences are known in the art, such as promoters, enhancers (such as cis-regulatory modules (CRMs)), introns, polyA signals, etc.

In a particular embodiment, the expression cassette may include a promoter. The promoter may be an ubiquitous or tissue-specific promoter, in particular a promoter able to promote expression in cells or tissues in which expression of GDE is desirable such as in cells or tissues in which GDE expression is desirable in GDE-deficient patients.

In a particular embodiment, the promoter is a muscle-specific promoter. Non-limiting examples of muscle-specific promoters include the muscle creatine kinase (MCK) promoter. Non-limiting examples of suitable muscle creatine kinase promoters are human muscle creatine kinase promoters and truncated murine muscle creatine kinase [(tMCK) promoters] (Wang B et al, Construction and analysis of compact muscle-selective promoters for AAV vectors. Gene Ther. 2008 November; 15 (22): 1489-99) (representative GenBank Accession No. AF188002). Human muscle creatine kinase has the Gene ID No. 1158 (representative GenBank Accession No. NC_000019.9, accessed on Dec. 26, 2012). Other examples of muscle-specific promoters include a synthetic promoter C5.12 (spC5.12, alternatively referred to herein as "C5.12"), such as the spC5.12 or the spC5.12 promoter (disclosed in Wang et al., Gene Therapy volume 15, pages 1489-1499 (2008)), the MHCK7 promoter (Salva et al. Mol Ther. 2007 February; 15 (2): 320-9), myosin light chain (MLC) promoters, for example MLC2 (Gene ID No. 4633; representative GenBank Accession No. NG_007554.1, accessed on Dec. 26, 2012); myosin heavy chain (MHC) promoters, for example alpha-MHC (Gene ID No. 4624; representative GenBank Accession No. NG_023444.1, accessed on Dec. 26, 2012); desmin promoters (Gene ID No. 1674; representative GenBank Accession No. NG_008043.1, accessed on Dec. 26, 2012); cardiac troponin C promoters (Gene ID No. 7134; representative GenBank Accession No. NG_008963.1, accessed on Dec. 26, 2012); troponin I promoters (Gene ID Nos. 7135, 7136, and 7137; representative GenBank Accession Nos. NG_016649.1, NG_011621.1, and NG_007866.2, accessed on Dec. 26, 2012); myoD gene family promoters (Weintraub et al., Science, 251, 761 (1991); Gene ID No. 4654; representative GenBank Accession No. NM_002478, accessed on Dec. 26, 2012); alpha actin promoters (Gene ID Nos. 58, 59, and 70; representative GenBank Accession Nos. NG_006672.1, NG_011541.1, and NG_007553.1, accessed on Dec. 26, 2012); beta actin promoters (Gene ID No. 60; representative GenBank Accession No. NG_007992.1, accessed on Dec. 26, 2012); gamma actin promoters (Gene ID No. 71 and 72; representative GenBank Accession No. NG_011433.1 and NM_001199893, accessed on Dec. 26, 2012); muscle-specific promoters residing within intron 1 of the ocular form of Pitx3 (Gene ID No. 5309) (Coulon et al; the muscle-selective promoter corresponds to residues 11219-11527 of representative GenBank Accession No. NG_008147, accessed on Dec. 26, 2012); and the promoters described in US Patent Publication US 2003/0157064, and CK6 promoters (Wang et al 2008 doi: 10.1038/gt.2008.104). In another particular embodiment, the muscle-specific promoter is the E-Syn promoter described in Wang et al., Gene Therapy volume 15, pages 1489-1499 (2008), comprising the combination of a MCK-derived enhancer and of the spC5.12 promoter. In a particular embodiment of the invention, the muscle-specific promoter is selected in the group consisting of a spC5.12 promoter, the MHCK7 promoter, the E-syn promoter, a muscle creatine kinase myosin light chain (MLC) promoter, a myosin heavy chain (MHC) promoter, a cardiac troponin C promoter, a troponin I promoter, a myoD gene family promoter, an alpha actin promoter, an beta actin promoter, an gamma actin promoter, a muscle-specific promoter residing within intron 1 of the ocular form of Pitx3, a CK6 promoter, a CK8 promoter and an Acta1 promoter. In a particular embodiment, the muscle-specific promoter is selected in the group consisting of the spC5.12, desmin and MCK promoters. In a further embodiment, the muscle-specific promoter is selected in the group consisting of the spC5.12 and MCK promoters. In a particular embodiment, the muscle-specific promoter is the spC5.12 promoter.

In a particular embodiment, the promoter is a liver-specific promoter. Non-limiting examples of liver-specific promoters include the alpha-1 antitrypsin promoter (hAAT), the transthyretin promoter, the albumin promoter, the thyroxine-binding globulin (TBG) promoter, the LSP promoter (comprising a thyroid hormone-binding globulin promoter sequence, two copies of an alpha1-microglobulin/bikunin enhancer sequence, and a leader sequence—Ill, C. R., et al. (1997). Optimization of the human factor VIII complementary DNA expression plasmid for gene therapy of hemophilia A. Blood Coag. Fibrinol. 8: S23-S30.), etc. Other useful liver-specific promoters are known in the art, for example those listed in the Liver Specific Gene Promoter Database compiled the Cold Spring Harbor Laboratory (rulai.cshl.edu/LSPD/). A preferred liver-specific promoter in the context of the invention is the hAAT promoter.

In another particular embodiment, the promoter is a neuron-specific promoter. Non-limiting examples of neuron-specific promoters include, but are not limited to the following: synapsin-1 (Syn) promoter, neuron-specific enolase (NSE) promoter (Andersen et al., Cell. Mol. Neurobiol., 13:503-15 (1993)), neurofilament light-chain gene promoter (Piccioli et al., Proc. Natl. Acad. Sci. USA, 88:5611-5 (1991)), and the neuron-specific vgf gene promoter (Piccioli et al. Neuron, 15:373-84 (1995)), among others which will be apparent to the skilled artisan. In a particular embodiment, the neuron-specific promoter is the Syn promoter. Other neuron-specific promoters include, without limitation: synapsin-2 promoter, tyrosine hydroxylase promoter, dopamine β-hydroxylase promoter, hypoxanthine phosphoribosyltransferase promoter, low affinity NGF receptor promoter, and choline acetyl transferase promoter (Bejanin et al., 1992; Carroll et al., 1995; Chin and Greengard, 1994; Foss-Petter et al., 1990; Harrington et al., 1987; Mercer et al., 1991; Patei et al., 1986). Representative promoters specific for the motor neurons include, without limitation, the promoter of the Calcitonin Gene-Related Peptide (CGRP), a known motor neuron-derived factor. Other promoters functional in motor neurons include the promoters of Choline Acetyl Transferase (ChAT), Neuron Specific Enolase (NSE), Synapsin and Hb9. Other neuron-specific promoters useful in the present invention include, without limitation: GFAP (for astrocytes), Calbindin 2 (for interneurons), Mnx1 (motorneurons), Nestin (neurons), Parvalbumin, Somatostation and Plp1 (oligodendrocytes and Schwann cells).

In another particular embodiment, the promoter is a ubiquitous promoter. Representative ubiquitous promoters include the cytomegalovirus enhancer/chicken beta actin (CAG) promoter, the cytomegalovirus enhancer/promoter (CMV) (optionally with the CMV enhancer) [see, e.g., Boshart et al, Cell, 41:521-530 (1985)], the PGK promoter, the SV40 early promoter, the retroviral Rous sarcoma virus (RSV) LTR promoter (optionally with the RSV enhancer), the dihydrofolate reductase promoter, the β-actin promoter, the phosphoglycerol kinase (PGK) promoter, and the EF1 alpha promoter.

In addition, the promoter may also be an endogenous promoter such as the albumin promoter or the GDE promoter.

In a particular embodiment, the promoter is associated to an enhancer sequence, such as a cis-regulatory module (CRMs) or an artificial enhancer sequence. CRMs useful in the practice of the present invention include those described in Rincon et al., Mol Ther. 2015 January; 23 (1): 43-52, Chuah et al., Mol Ther. 2014 September; 22 (9): 1605-13 or Nair et al., Blood. 2014 May 15; 123 (20): 3195-9. Other regulatory elements that are, in particular, able to enhance muscle-specific expression of genes, in particular expression in cardiac muscle and/or skeletal muscle, are those disclosed in WO2015110449. Particular examples of nucleic acid regulatory elements that comprise an artificial sequence include the regulatory elements that are obtained by rearranging the transcription factor binding sites (TFBS) that are present in the sequences disclosed in WO2015110449. Said rearrangement may encompass changing the order of the TFBSs and/or changing the position of one or more TFBSs relative to the other TFBSs and/or changing the copy number of one or more of the TFBSs. For example, a nucleic acid regulatory element for enhancing muscle-specific gene expression, in particular cardiac and skeletal muscle-specific gene expression, may comprise binding sites for E2A, HNH 1, NF1, C/EBP, LRF, MyoD, and SREBP; or for E2A, NF1, p53, C/EBP, LRF, and SREBP; or for E2A, HNH 1, HNF3a, HNF3b, NF1, C/EBP, LRF, MyoD, and SREBP; or E2A, HNF3a, NF1, C/EBP, LRF, MyoD, and SREBP; or for E2A, HNF3a, NF1, CEBP, LRF, MyoD, and SREBP; or for HNF4, NF1, RSRFC4, C/EBP, LRF, and MyoD, or NF1, PPAR, p53, C/EBP, LRF, and MyoD. For example, a nucleic acid regulatory element for enhancing muscle-specific gene expression, in particular skeletal muscle-specific gene expression, may also comprise binding sites for E2A, NF1, SRFC, p53, C/EBP, LRF, and MyoD; or for E2A, NF1, C/EBP, LRF, MyoD, and SREBP; or for E2A, HNF3a, C/EBP, LRF, MyoD, SEREBP, and Tal1_b; or for E2A, SRF, p53, C/EBP, LRF, MyoD, and SREBP; or for HNF4, NF1, RSRFC4, C/EBP, LRF, and SREBP; or for E2A, HNF3a, HNF3b, NF1, SRF, C/EBP, LRF, MyoD, and SREBP; or for E2A, CEBP, and MyoD. In further examples, these nucleic acid regulatory elements comprise at least two, such as 2, 3, 4, or more copies of one or more of the TFBSs recited before. Other regulatory elements that are, in particular, able to enhance liver-specific expression of genes, are those disclosed in WO2009130208.

In another particular embodiment, the nucleic acid construct comprises an intron, in particular an intron placed between the promoter and the GDE coding sequence. An intron may be introduced to increase mRNA stability and the production of the protein. In a further embodiment, the intron is a human beta globin b2 (or HBB2) intron, a coagulation factor IX (FIX) intron, a SV40 intron, a hCMV intron A (hCMVI), a TPL intron (TPLI), a CHEF1 gene intron1 (CHEFI), a MVM intron (Wu et al, 2008), a FIX truncated intron 1 (Wu et al., 2008, Mol Ther, 16 (2): 280-289; Kurachi et al., 1995, J Biol Chem., 270 (10): 5276-5281), a β-globin/immunoglobin heavy chain hybrid intron (5'-donor site from a human β-globin intron and 3'-acceptor site from an immunoglobulin heavy chain variable region intron, Wu et al., 2008, Mol Ther, 16 (2): 280-289; Kurachi et al., 1995, J Biol Chem., 270 (10): 5276-5281), a hybrid intron consisting of an adenovirus splice donor and an immunoglobulin G splice (Wong et al., 1985, Chromosoma, 92 (2): 124-135; Yew et al., 1997, Hum Gene Ther, 8 (5): 575-584; Choi T. et al., 1991, Mol Cell Biol, 11 (6): 3070-3074; Huang et al., 1990, Mol Cell Biol., 10 (4): 1805-1810), a hybrid 19S/16S SV40 intron (5'-donor site from 19S intron and 3'-acceptor site from 16S intron, Yew et al., 1997, Hum Gene Ther, 8 (5): 575-584) or a chicken beta-globin intron. In another further embodiment, the intron is a modified intron (in particular a modified HBB2 or FIX intron) designed to decrease the number of, or even totally remove, alternative open reading frames (ARFs) found in said intron. Preferably, ARFs are removed whose length spans over 50 bp and have a stop codon in frame with a start codon. ARFs may be removed by modifying the sequence of the intron. For example, modification may be carried out by way of nucleotide substitution, insertion or deletion, preferably by nucleotide substitution. As an illustration, one or more nucleotides, in particular one nucleotide, in an ATG or GTG start codon present in the sequence of the intron of interest may be replaced resulting in a non-start codon. For example, an ATG or a GTG may be replaced by a CTG, which is not a start codon, within the sequence of the intron of interest.

The classical HBB2 intron is shown in SEQ ID NO:42. For example, this HBB2 intron may be modified by eliminating start codons (ATG and GTG codons) within said intron. In a particular embodiment, the modified HBB2 intron has the sequence shown in SEQ ID NO:43. The classical FIX intron is derived from the first intron of human FIX and is shown in SEQ ID NO:44. FIX intron may be modified by eliminating start codons (ATG and GTG codons) within said intron. In a particular embodiment, the modified FIX intron has the sequence shown in SEQ ID NO:45. The classical chicken-beta globin intron used in nucleic acid constructs is shown in SEQ ID NO:46. Chicken-beta globin intron may be modified by eliminating start codons (ATG and GTG codons) within said intron. In a particular embodiment, the modified chicken-beta globin intron has the sequence shown in SEQ ID NO:47.

The inventors have previously shown in WO2015/162302 that such a modified intron, in particular a modified HBB2 or FIX intron, has advantageous properties and can significantly improve the expression of a transgene.

In a particular embodiment, the nucleic acid construct of the invention is an expression cassette comprising, in the 5' to 3' orientation, a promoter optionally preceded by an enhancer, the coding sequence of the invention (i.e. the nucleic acid molecule encoding a mini-GDE polypeptide), and a polyadenylation signal such as the bovine growth hormone polyadenylation signal (bGH polyA), the SV40 polyadenylation signal, or another naturally occurring or artificial polyadenylation signal. In particular, the polyadenylation signal is the bGH polyA. In a preferred embodiment, a very short polyA signal is preferred. For example, a very short polyA signal comprising less than 20 nucleotides is preferred. In a particular embodiment, the polyadenylation signal is the human soluble neuropilin-1 (sNRP) polyadenylation signal (sNRP polyA; SEQ ID NO:58).

In a particular embodiment, the nucleic acid construct of the invention is an expression cassette comprising, in the 5' to 3' orientation, a promoter optionally preceded by an enhancer, an intron, the coding sequence of the invention, and a polyadenylation signal. In another embodiment, the nucleic acid construct of the invention is an expression cassette comprising, in the 5' to 3' orientation, a promoter, the coding sequence of the invention, and a polyadenylation signal. In another embodiment, the nucleic acid construct of the invention is an expression cassette comprising, in the 5' to 3' orientation, an enhancer, a promoter, the coding sequence of the invention, and a polyadenylation signal. In another embodiment, the nucleic acid construct of the invention is an expression cassette comprising, in the 5' to 3' orientation, a SpC5-12 promoter, the coding sequence of the invention, and a polyadenylation signal (such as a bGH polyA or a sNRP poly A, in particular a bGH polyA). In another embodiment, the nucleic acid construct of the invention is an expression cassette comprising, in the 5' to 3' orientation, an enhancer, a SpC5-12 promoter, the coding sequence of the invention, and a polyadenylation signal (such as a bGH polyA or a sNRP polyA, in particular a bGH polyA). In a further particular embodiment, the nucleic acid construct of the invention is an expression cassette comprising, in the 5' to 3' orientation, an enhancer, a promoter, an intron, the coding sequence of the invention, and a polyadenylation signal. In a further particular embodiment of the invention the expression cassette comprising, in the 5' to 3' orientation a promoter, an optional intron, the coding sequence of the invention and a polyA signal. In a further particular embodiment, the expression cassette comprises, in the 5' to 3' orientation: a SpC5-12 promoter; a SV40 intron; a sequence coding the amino acid sequence of SEQ ID NO:2, SEQ ID NO:3, SEQ ID NO:4, SEQ ID NO:5, SEQ ID NO: 6, SEQ ID NO:48, SEQ ID NO:49, SEQ ID NO:50, SEQ ID NO:51 or SEQ ID NO:52, in particular SEQ ID NO:2, SEQ ID NO:3, SEQ ID NO:4, SEQ ID NO:5 or SEQ ID NO:6, in particular SEQ ID NO:5; and a bGH polyA. In a further particular embodiment, the nucleic acid construct of the invention is an expression cassette comprising, in the 5' to 3' orientation, a promoter, the coding sequence of the invention, and a polyadenylation signal. In a further particular embodiment of the invention the expression cassette comprising, in the 5' to 3' orientation an enhancer, a promoter, the coding sequence of the invention and a polyA signal. In a further particular embodiment, the expression cassette comprises, in the 5' to 3' orientation: a SpC5-12 promoter; a sequence coding the amino acid sequence of SEQ ID NO:2, SEQ ID NO:3, SEQ ID NO:4, SEQ ID NO:5, SEQ ID NO:6, SEQ ID NO:48, SEQ ID NO:49, SEQ ID NO:50, SEQ ID NO:51 or SEQ ID NO:52, in particular SEQ ID NO:2, SEQ ID NO:3, SEQ ID NO:4, SEQ ID NO: 5 or SEQ ID NO:6, in particular SEQ ID NO:5; and a bGH polyA or sNRP polyA, in particular a bGH polyA. In another embodiment, the expression cassette comprises, in the 5' to 3' orientation: a CMV promoter; a SV40 intron; a sequence coding the amino acid sequence of SEQ ID NO: 2, SEQ ID NO:3, SEQ ID NO:4, SEQ ID NO:5, SEQ ID NO:6, SEQ ID NO:48, SEQ ID NO: 49, SEQ ID NO:50, SEQ ID NO:51 or SEQ ID NO:52, in particular SEQ ID NO:2, SEQ ID NO: 3, SEQ ID NO:4, SEQ ID NO:5 or SEQ ID NO:6, in particular SEQ ID NO:5; and a bGH polyA. In another embodiment, the expression cassette comprises, in the 5' to 3' orientation:

a CMV promoter; a sequence coding the amino acid sequence of SEQ ID NO:2, SEQ ID NO:3, SEQ ID NO: 4, SEQ ID NO:5, SEQ ID NO:6, SEQ ID NO:48, SEQ ID NO:49, SEQ ID NO:50, SEQ ID NO: 51 or SEQ ID NO:52, in particular SEQ ID NO:2, SEQ ID NO:3, SEQ ID NO:4, SEQ ID NO: 5 or SEQ ID NO:6, in particular SEQ ID NO:5; and a bGH polyA or sNRP polyA, in particular a bGH polyA. In a further particular embodiment, the expression cassette comprises, in the 5' to 3' orientation: a SpC5-12 promoter; a SV40 intron; a sequence coding the amino acid sequence of SEQ ID NO:12; and a bGH polyA. In a further particular embodiment, the expression cassette comprises, in the 5' to 3' orientation: a SpC5-12 promoter; a sequence coding the amino acid sequence of SEQ ID NO:12; and a bGH polyA or sNRP polyA, in particular a bGH polyA. In another embodiment, the expression cassette comprises, in the 5' to 3' orientation: a CMV promoter; a SV40 intron; a sequence coding the amino acid sequence of SEQ ID NO:12; and a bGH polyA. In another embodiment, the expression cassette comprises, in the 5' to 3' orientation: a CMV promoter; a sequence coding the amino acid sequence of SEQ ID NO:12; and a bGH poly A or sNRP polyA, in particular a bGH poly A.

In designing the nucleic acid construct of the invention, one skilled in the art will take care of respecting the size limit of the vector used for delivering said construct to a cell or organ. In particular, one skilled in the art knows that a major limitation of AAV vector is its cargo capacity which may vary from one AAV serotype to another but is thought to be limited to around the size of parental viral genome. For example, 5 kb, is the maximum size usually thought to be packaged into an AAV8 capsid (Wu Z. et al., Mol Ther., 2010, 18 (1): 80-86; Lai Y. et al., Mol Ther., 2010, 18 (1): 75-79; Wang Y. et al., Hum Gene Ther Methods, 2012, 23 (4): 225-33). In addition, during recombinant AAV production, genomes larger than 5 kb are encapsidated with low efficacy and the resulting AAV may contain fragmented genomes reducing the efficacy of gene transfer. Accordingly, those skilled in the art will take care in practicing the present invention to select the components of the nucleic acid construct of the invention so that the resulting nucleic acid sequence, including sequences coding AAV 5'- and 3'-ITRs to preferably not exceed 110% of the cargo capacity of the AAV vector implemented, in particular to preferably not exceed 5 kb. AAV vectors having larger cargo capacity can also be used in the context on the present invention. For example AAV particles lacking Vp2 subunit are shown to successfully package larger genomes (i.e. 6 kb) while preserving integrity of encapsidated genomes (Grieger et al., 2005, J Virol., 79 (15): 9933-9944).

The present invention also relates to a vector comprising a nucleic acid molecule or construct as disclosed herein. In a particular embodiment, the vector comprises a nucleic acid molecule or construct encoding a functional truncated human GDE polypeptide as defined above. In another particular embodiment, the vector comprises a nucleic acid molecule or construct encoding a functional non-human GDE polypeptide as defined above.

In particular, the vector of the invention is a vector suitable for protein expression, preferably for use in gene therapy. In one embodiment, the vector is a plasmid vector. In another embodiment, the vector is a nanoparticle containing a nucleic acid molecule of the invention, in particular a messenger RNA encoding the mini-GDE polypeptide of the invention. In another embodiment, the vector is a system based on transposons, allowing integration of the nucleic acid molecule or construct of the invention in the genome of the target cell, such as the hyperactive Sleeping Beauty (SB100X) transposon system (Mates et al. 2009). In another embodiment, the vector is a viral vector suitable for gene therapy, targeting any cell of interest such as liver tissue or cells, muscle cell, CNS cells (such as brain cells), or hematopoietic stem cells such as cells of the erythroid lineage (such as erythrocytes). In this case, the nucleic acid construct of the invention also contains sequences suitable for producing an efficient viral vector, as is well known in the art.

Viral vectors are preferred for delivering the nucleic acid molecule or construct of the invention, such as a retroviral vector, for example a lentiviral vector, or a non-pathogenic parvovirus, more preferably an AAV vector. The human parvovirus Adeno-Associated Virus (AAV) is a dependovirus that is naturally defective for replication which is able to integrate into the genome of the infected cell to establish a latent infection. The last property appears to be unique among mammalian viruses because the integration occurs at a specific site in the human genome, called AAVS1, located on chromosome 19 (19q13.3-qter).

Therefore, AAV vectors have arisen considerable interest as potential vectors for human gene therapy. Among the favorable properties of the virus are its lack of association with any human disease, its ability to infect both dividing and non-dividing cells, and the wide range of cell lines derived from different tissues that can be infected.

Among the serotypes of AAVs isolated from human or non-human primates (NHP) and well characterized, human serotype 2 is the first AAV that was developed as a gene transfer vector. Other currently used AAV serotypes include AAV-1, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods.), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24 (6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), −7, −8, −9, −2G9, −10 such as cy10 and −rh10, −rh74, −dj, Anc80, LK03, AAV2i8, porcine AAV serotypes such as AAVpo4 and AAVpo6, and tyrosine, lysine and serine capsid mutants of the AAV serotypes, etc. In addition, other non-natural engineered variants and chimeric AAV can also be useful.

AAV viruses may be engineered using conventional molecular biology techniques, making it possible to optimize these particles for cell specific delivery of nucleic acid sequences, for minimizing immunogenicity, for tuning stability and particle lifetime, for efficient degradation, for accurate delivery to the nucleus.

Desirable AAV fragments for assembly into vectors include the cap proteins, including the vp1, vp2, vp3 and hypervariable regions, the rep proteins, including rep 78, rep 68, rep 52, and rep 40, and the sequences encoding these proteins. These fragments may be readily utilized in a variety of vector systems and host cells.

AAV-based recombinant vectors lacking the Rep protein integrate with low efficacy into the host's genome and are mainly present as stable circular episomes that can persist for years in the target cells. Alternatively to using AAV natural serotypes, artificial AAV serotypes may be used in the context of the present invention, including, without limitation, AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV serotype, non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

In the context of the present invention, the AAV vector comprises an AAV capsid able to transduce the target cells of interest, i.e. cells of the tolerogenic tissue (for example hepatocytes) and cells of the tissue(s) of therapeutic interest such as muscle cells, CNS cells or cardiac cells.

According to a particular embodiment, the AAV vector is of the AAV-1, -2, AAV-2 variants (such as the quadruple-mutant capsid optimized AAV-2 comprising an engineered capsid with Y44+500+730F+T491V changes, disclosed in Ling et al., 2016 Jul. 18, Hum Gene Ther Methods. [Epub ahead of print]), -3 and AAV-3 variants (such as the AAV3-ST variant comprising an engineered AAV3 capsid with two amino acid changes, S663V+T492V, disclosed in Vercauteren et al., 2016, Mol. Ther. Vol. 24 (6), p. 1042), -3B and AAV-3B variants, -4, -5, -6 and AAV-6 variants (such as the AAV6 variant comprising the triply mutated AAV6 capsid Y731F/Y705F/T492V form disclosed in Rosario et al., 2016, Mol Ther Methods Clin Dev. 3, p. 16026), -7, -8, -9, -9P1, -2G9, -10 such as –cy10 and –rh10, –rh39, –rh43, –rh74, –dj, Anc80, LK03, AAV.PHP, AAV2i8, porcine AAV such as AAVpo4 and AAVpo6, and tyrosine, lysine and serine capsid mutants of AAV serotypes. In a particular embodiment, the AAV vector is of the AAV6, AAV8, AAV9, AAV9P1, AAVrh74 or AAV218 serotype (i.e. the AAV vector has a capsid of the AAV6, AAV8, AAV9, AAV9P1, AAVrh74 or AAV2i8 serotype). In a further particular embodiment, the AAV vector is a pseudotyped vector, i.e. its genome and capsid are derived from AAVs of different serotypes. For example, the pseudotyped AAV vector may be a vector whose genome is derived from one of the above mentioned AAV serotypes, and whose capsid is derived from another serotype. For example, the genome of the pseudotyped vector may have a capsid derived from the AAV6, AAV8, AAV9, AAV9P1, AAVrh74 or AAV218 serotype, and its genome may be derived from and different serotype. In a particular embodiment, the AAV vector has a capsid of the AAV6, AAV8, AAV9 or AAVrh74 serotype, in particular of the AAV6, AAV8, AAV9, or AAV9P1 serotype, more particularly of the AAV6, AAV9 or AAV9P1 serotype.

In a specific embodiment, wherein the vector is for use in delivering the therapeutic transgene to muscle cells, the AAV vector may be selected, among others, in the group consisting of AAV8, AAV9 and AAVrh74.

In another specific embodiment, wherein the vector is for use in delivering the transgene to liver cells, the AAV vector may be selected, among others, in the group consisting of AAV1, AAV5, AAV8, AAV9, AAVrh10, AAVrh39, AAVrh43, AAVrh74, AAV-LK03, AAV2G9, AAV.PHP, AAV-Anc80 and AAV3B.

In a further specific embodiment, wherein the vector is for use in delivering the transgene to the CNS, the AAV vector may be selected, among others, in the group consisting of AAV9, AAV9P1, AAV10 and AAV2G9.

In another embodiment, the capsid is a modified capsid. In the context of the present invention, a "modified capsid" may be a chimeric capsid or capsid comprising one or more variant VP capsid proteins derived from one or more wild-type AAV VP capsid proteins.

In a particular embodiment, the AAV vector is a chimeric vector, i.e. its capsid comprises VP capsid proteins derived from at least two different AAV serotypes, or comprises at least one chimeric VP protein combining VP protein regions or domains derived from at least two AAV serotypes. Examples of such chimeric AAV vectors useful to transduce liver cells are described in Shen et al., Molecular Therapy, 2007 and in Tenney et al., Virology, 2014. For example, a chimeric AAV vector can derive from the combination of an AAV8 capsid sequence with a sequence of an AAV serotype different from the AAV8 serotype, such as any of those specifically mentioned above. In another embodiment, the capsid of the AAV vector comprises one or more variant VP capsid proteins such as those described in WO2015013313, in particular the RHM4-1, RHM15-1, RHM15-2, RHM15-3/RHM15-5, RHM15-4 and RHM15-6 capsid variants, which present a high liver tropism.

In another embodiment, the modified capsid can be derived also from capsid modifications inserted by error prone PCR and/or peptide insertion (e.g. as described in Bartel et al., 2011). In a particular embodiment, the capsid is modified includes the P1 modification, as described in as disclosed in PCT/EP2019/058560. In addition, capsid variants may include single amino acid changes such as tyrosine mutants (e.g. as described in Zhong et al., 2008).

In addition, the genome of the AAV vector may either be a single stranded or self-complementary double-stranded genome (McCarty et al., Gene Therapy, 2003). Self-complementary double-stranded AAV vectors are generated by deleting the terminal resolution site from one of the AAV terminal repeats. These modified vectors, whose replicating genome is half the length of the wild type AAV genome have the tendency to package DNA dimers. In a preferred embodiment, the AAV vector implemented in the practice of the present invention has a single stranded genome, and further preferably comprises an AAV8, AAV9, AAVrh74 or AAV218 capsid, in particular an AAV8, AAV9 or AAVrh74 capsid, such as an AAV8 or AAV9 capsid, more particularly an AAV9 capsid.

The AAV vector used for packaging the GDE sequence of the invention can also be modified in order to increase its cargo capacity. For example, AAV vectors lacking Vp2 subunit are shown to successfully package larger genomes (i.e. 6 kb) while preserving integrity of encapsidated genomes (Grieger et al., 2005).

As is known in the art, additional suitable sequences may be introduced in the nucleic acid construct of the invention for obtaining a functional viral vector. Suitable sequences include AAV ITRs.

In a particular embodiment, the AAV vector comprises a muscle-specific promoter as described above, in particular a muscle-specific promoter that presents some leakage of expression into liver cells.

In another particular embodiment of the invention, the AAV vector comprises a liver-specific promoter as described above. The protolerogenic and metabolic properties of the liver are advantageously implemented thanks to this embodiment to develop highly efficient and optimized vectors to express GDE in hepatocytes and to induce immune tolerance to the protein.

The invention also relates to a cell, in particular an isolated cell, for example a liver cell, a cardiac cell, a CNS cell or a muscle cell, that is transformed or transduced with the nucleic acid molecule, the construct or the vector of the invention. In a particular embodiment, the cell is an isolated human cell. In a further particular embodiment, the cell is not a human embryonic stem cell. The cell of the invention expresses a mini-GDE polypeptide. Cells of the invention may be delivered to the subject in need thereof, such as GDE-deficient patient, by any appropriate administration route such as via injection in the liver, in the CNS, in the heart, in the muscle(s) or in the bloodstream of said subject. In a particular embodiment, the invention involves transducing liver or muscle cells, in particular liver or muscle cells of the subject to be treated, and administering said transduced liver and/or muscle cells into which the nucleic acid has been introduced to the subject. In a particular embodiment, the liver cells are liver cells from the patient to be treated, or are liver stem cells that are further transformed, and differentiated in vitro into liver cells, for subsequent administration to the patient. In another embodiment, the cell is a muscle cell from the patient to be treated, or is a muscle stem cell that is further transformed, and optionally differentiated in vitro into muscle cells, for subsequent administration to the patient.

The present invention also provides pharmaceutical compositions comprising the nucleic acid molecule, the nucleic acid construct, the vector, the mini-GDE polypeptide, or the cell of the invention. Such compositions may comprise a therapeutically effective amount of the therapeutic (the nucleic acid molecule, the nucleic acid construct, the vector, the mini-GDE polypeptide or the cell of the invention), and a pharmaceutically acceptable carrier. In a specific embodiment, the term "pharmaceutically acceptable" means approved by a regulatory agency of the Federal or a state government or listed in the U.S. or European Pharmacopcia or other generally recognized pharmacopcia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject. In a particular embodiment, the nucleic acid, vector or cell of the invention is formulated in a composition comprising phosphate-buffered saline and supplemented with 0.25% human serum albumin. In another particular embodiment, the nucleic acid, vector or cell of the invention is formulated in a composition comprising ringer lactate and a non-ionic surfactant, such as pluronic F68 at a final concentration of 0.01-0.0001%, such as at a concentration of 0.001%, by weight of the total composition. The formulation may further comprise serum albumin, in particular human serum albumin, such as human serum albumin at 0.25%. Other appropriate formulations for either storage or administration are known in the art, in particular from WO 2005/118792 or Allay et al., 2011.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, case pain at the, site of the injection.

In an embodiment, the nucleic acid molecule, the nucleic acid construct, the vector, the mini-GDE polypeptide or the cell of the invention can be delivered in a vesicle, in particular a liposome. In yet another embodiment, the nucleic acid molecule, the nucleic acid construct, the vector, the mini-GDE polypeptide or the cell of the invention can be delivered in a controlled release system.

In a particular embodiment, the nucleic acid molecule is delivered as a mRNA, corresponding to the transcript encoding the mini-GDE polypeptide of the invention. In particular, the mRNA of the invention may be delivered using liposomes such as lipid nanoparticle (LNP).

Methods of administration of the nucleic acid molecule, the nucleic acid construct, the vector, the mini-GDE polypeptide or the cell of the invention include but are not limited to intradermal, intramuscular, intraperitoneal, intravenous, subcutaneous, intranasal, epidural, and oral routes. In a particular embodiment, the administration is via the intravenous or intramuscular route. The nucleic acid molecule, the nucleic acid construct, the vector, the mini-GDE polypeptide or the cell of the invention, whether vectorized or not, may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment, e.g. the liver or the muscle. This may be achieved, for example, by means of an implant, said implant being of a porous, nonporous, or gelatinous material, including membranes, such as sialastic membranes, or fibers.

In a particular embodiment, the mini-GDE polypeptide of the invention is used in enzyme replacement therapy (ERT), in particular for treating GSDIII. The term "enzyme replacement therapy" or "ERT" generally refers to the introduction of a purified enzyme into an individual having a deficiency in such enzyme. The administered polypeptide of the invention can be obtained from natural sources, by recombinant expression, produced in vitro, or purified from isolated tissue or fluid. In particular, when used in ERT, the polypeptide of the invention may be administered parenterally, such as via intraperitoneal, intramuscular, intravascular (i.e. intravenous or intraarterial) administration. In particular the polypeptide is administered by intravenous injection. Said administration may be repeated frequently, such as every day, every week, every two weeks or every month, in particular every week or every two weeks.

The amount of the therapeutic (i.e. the nucleic acid molecule, the nucleic acid construct, the vector, the mini-GDE polypeptide or the cell of the invention) of the invention which will be effective in the treatment of GSDIII can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the nucleic acid molecule, the nucleic acid construct, the vector, the mini-GDE polypeptide or the cell of the invention administered to the subject in need thereof will vary based on several factors including, without limitation, the route of administration, the specific disease treated, the subject's age or the level of expression necessary to achieve the therapeutic effect. One skilled in the art can readily determine, based on its knowledge in this field, the dosage range required based on these factors and others. In case of a treatment comprising administering a viral vector, such as an AAV vector, to the subject, typical doses of the vector are of at least $1\times10^8$ vector genomes per kilogram body weight (vg/kg), such as at least $1\times10^9$ vg/kg, at least $1\times10^{10}$ vg/kg, at least $1\times10^{11}$ vg/kg, at least $1\times10^{12}$ vg/kg at least $1\times10^{13}$ vg/kg, or at least $1\times10^{14}$ vg/kg.

The invention also relates to a method for treating GSDIII, which comprises a step of delivering a therapeutic effective amount of the nucleic acid molecule, the nucleic acid construct, the vector, the mini-GDE polypeptide, the pharmaceutical composition or the cell of the invention to a subject in need thereof.

Cirrhosis and hepatocellular carcinoma can also develop in patients with GSD III. Thus, the invention also relates to a method for treating cirrhosis and hepatocellular carcinoma in a GSDIII patient which comprises a step of delivering a therapeutic effective amount of the nucleic acid molecule, the nucleic acid construct, the vector, the mini-GDE polypeptide, the pharmaceutical composition or the cell of the invention to a subject in need thereof.

The invention also relates to a method for treating GSD III, said method inducing no immune response to the transgene (i.e. to the mini-GDE polypeptide encoded by the nucleic acid molecule), or inducing a reduced immune response to the transgene, comprising a step of delivering a therapeutic effective amount of the nucleic acid, the vector, the mini-GDE polypeptide, the pharmaceutical composition or the cell of invention to a subject in need thereof. The invention also relates to a method for treating GSD III, said method comprising repeated administration of a therapeutic effective amount of the nucleic acid, the vector, the mini-GDE polypeptide, the pharmaceutical composition or the cell of the invention to a subject in need thereof. In this aspect, the nucleic acid molecule, the nucleic acid construct or the vector of the invention comprises a promoter which is functional in liver cells, thereby allowing immune tolerance to the expressed mini-GDE polypeptide produced therefrom. As well, in this aspect, the pharmaceutical composition used in this aspect comprises a nucleic acid molecule, a nucleic acid construct or a vector comprising a promoter which is functional in liver cells. In case of delivery of cells, in particular of liver, cardiac, CNS or muscle cells, said cells may be cells previously collected from the subject in need of the treatment and that were engineered by introducing therein the nucleic acid molecule, the nucleic acid construct or the vector of the invention to thereby make them able to produce the mini-GDE polypeptide. According to an embodiment, in the aspect comprising a repeated administration, said administration may be repeated at least once or more, and may even be considered to be done according to a periodic schedule, such as once per week, per month or per year. The periodic schedule may also comprise an administration once every 2, 3, 4, 5, 6, 7, 8, 9 or 10 year, or more than 10 years. In another particular embodiment, administration of each administration of a viral vector of the invention is done using a different virus for each successive administration, thereby avoiding a reduction of efficacy because of a possible immune response against a previously administered viral vector. For example, a first administration of an AAV vector comprising an AAV8 capsid may be done, followed by the administration of a vector comprising an AAV9 capsid.

According to the present invention, a treatment may include curative, alleviation or prophylactic effects. Accordingly, therapeutic and prophylactic treatment includes amelioration of the symptoms of GSD III or preventing or otherwise reducing the risk of developing a particular glycogen storage disease. The term "prophylactic" may be considered as reducing the severity or the onset of a particular condition. "Prophylactic" also includes preventing reoccurrence of a particular condition in a patient previously diagnosed with the condition. "Therapeutic" may also reduce the severity of an existing condition. The term "treatment" is used herein to refer to any regimen that can benefit an animal, in particular a mammal, more particularly a human subject.

The invention also relates to an ex vivo gene therapy method for the treatment of GSD III, comprising introducing the nucleic acid molecule, the nucleic acid construct or the vector of the invention into an isolated cell of a patient in need thereof, for example an isolated hematopoietic stem cell, and introducing said cell into said patient in need thereof.

The invention also relates to the nucleic acid molecule, the nucleic acid construct, the vector, the mini-GDE polypeptide, the cell or the pharmaceutical composition of the invention for use as a medicament.

The invention also relates to the nucleic acid molecule, the nucleic acid construct, the vector, the mini-GDE polypeptide, the cell or the pharmaceutical composition of the invention, for use in a method for treating a disease caused by a mutation in the GDE gene, in particular in a method for treating GSDIII (Cori disease).

The invention further relates to the use of the nucleic acid molecule, the nucleic acid construct, the vector, the mini-GDE polypeptide, the cell or the pharmaceutical composition of the invention, in the manufacture of a medicament useful for treating GSD III (Cori disease).

EXAMPLES

The invention is further described in detail by reference to the following experimental examples and the attached figures. These examples are provided for purposes of illustration only, and are not intended to be limiting.

Material and Methods

Western Blot Analysis

Mouse tissues were homogenized in DNAse/RNAse free water and protein concentration determined using a BCA Protein Assay. SDS-PAGE electrophoresis was performed in a 4-15% gradient polyacrylamide gel. After transfer, the membrane was blocked and incubated with an anti-GDE antibody and an anti-actin antibody. The membrane was washed, incubated with the appropriate secondary antibody, and visualized by Odyssey imaging system.

Enzyme Activity Measurements

Tissues homogenized as described above were incubated 3-16 hours at 37° C. with limit dextrin dissolved in phosphate buffer pH 6.9. The reaction was stopped by incubating 10 min at 95° C. and then centrifuged 10 min at 11000×g. Supernatants were used to measure the glucose produced using a commercial glucose assay kit. The reaction was stopped with concentrated H2SO4 and the resulting absorbance was measured on an EnSpire alpha plate reader (Perkin-Elmer, Waltham, MA) at 540 nm.

Measurement of Glycogen Content

Glycogen content was measured indirectly in tissue homogenates as the glucose released after total digestion with *Aspergillus Niger* amyloglucosidase (Sigma Aldrich, Saint Louis, MO). Samples were incubated for 5 min at 95° C. and then cooled at 4° C.; 25 μl of amyloglucosidase diluted 1:50 in 0.1M potassium acetate pH5.5 were then added to each sample. A control reaction without amyloglucosidase was prepared for each sample. Both sample and control reactions were incubated at 37° C. for 90 minutes. The reaction was stopped by incubating samples for 5 min at 95° C. The glucose released was determined with a commercial glucose assay kit (Sigma Aldrich, Saint Louis, MO) and the resulting absorbance was acquired on an EnSpire alpha plate reader (Perkin-Elmer, Waltham, MA) at a wavelength of 540 nm.

Muscle Function Tests

To measure the mean hanging time, a three-minute lasting hanging test on a 4-mm wire was performed. At the beginning of the test, a "falling" score of 10 is attributed to each animal. A mouse is handled by the tail and brought near the wire. The operator suspends the animal by the fore limbs only. As soon as the animal is properly suspended, a 180-see timer is started. If the animal falls, the timer is stopped, the falling score is diminished by 1 and the elapsed time is noted. The animal is then suspended by the fore limbs and the timer started again. The test is stopped either when the timer or the falling score reach 0. Results are expressed as number of falls per minute.

Results

AAV are the vector of choice for in vivo gene therapy. One of the biggest limitations in the use of AAV for gene replacement is their encapsidation size that is limited to 5 Kb. Indeed, during recombinant AAV production, genomes larger than 5 Kb are encapsidated with low efficacy and the resulting AAV may contain fragmented genomes reducing the efficacy of gene transfer. Different approaches have been developed to overcome this limitation. In particular the use of dual AAV vectors has been reported. Following this approach, two vectors, each containing a portion of the large transgene coding sequence, are used to transduce the same cell. The recombination of the two vectors may occur through i) an overlapping sequence derived from the transgene, ii) internal terminal repeats (ITR) combined with a splicing donor and acceptor or iii) an heterologous highly recombinogenic sequence coupled with a splicing donor and acceptor. However, although dual AAV vectors demonstrated efficacy in different animal models they have some drawback. Here we report the first data on the use of a gorilla GDE that fits in a single AAV and rescue glycogen accumulation and muscle function in GSDIII mice with an efficacy similar to that of dual AAV vectors at a lower dose.

FIG. 1 represents 4 different mammalian non-human GDE proteins smaller than human GDE (hGDE), this being not exhaustive.

In FIG. 2 are represented the truncated human GDE (hGDE) 41, 42-3, and 44 sequences.

First, we evaluated the effects induced in GSD III mice by a short non-human mammalian GDE. A transgene expression cassette composed of a muscle specific promoter (SpC5-12), SV40 intron, the coding sequence for gorilla GDE (gGDE) and the bGH polyA (AAV9-gGDE, total size: 5.1 Kb) was then used to produce an AAV9 vector by triple transfection and cesium chloride gradient purification.

The AAV9-gGDE vector was then injected in 3 month-old GSDIII mice at the dose of $1\times10^{12}$ vg/mouse in parallel with a dual AAV vector expressing GDE under the translational control of CMV promoter at the dose of $2\times10^{12}$ vg/mouse. Three months after vector injection, mice were sacrificed and tissues were analyzed to evaluate the biochemical correction of GSDIII. Western blot performed on the heart of mice treated as described above with an antibody specific for GDE indicates that the injection of AAV9-gGDE induces the expression of a protein smaller than GDE (estimated size ~130 KDa) and recognized by a specific anti-GDE antibody (FIG. 3). We then evaluated glycogen accumulation in the quadriceps of GDE-KO animals injected with AAV9-gGDE in comparison with a dual AAV9 vector expressing GDE under the transcriptional control of CMV (Dual-GDE). In the graph of FIG. 4 are reported the levels of glycogen measured in AAV-treated animals and in untreated wild-type (WT) and KO animals. The treatment with a single vector expressing gGDE cleared glycogen accumulation to levels comparable to those observed with dual AAV vectors. Additionally, the measurement of muscle function by wire-hang indicates that both approaches are equally efficient in the rescue of the muscle strength (FIG. 5). Taken together, these data indicate that AAV-mediated gGDE expression in the muscle rescues glycogen accumulation and muscle strength of GSDIII mice.

We then evaluated the activity of truncated forms of the human GDE sequence both in vitro and in vivo. We first transfected liver hepatoma cells (Huh-7) with plasmids encoding one truncated form derived from the human GDE under the transcriptional control of a CMV promoter. The expression cassette also contained a SV40 intron and a bGH polyadenylation signal. Two days after transfection, the activity was measured in cytosolic extracts obtained from those cells. The activity test, based on the release of glucose from limited dextrin allowed for the detection of a basal activity in the cell line, due to the endogenous expression of GDE. Full-size human GDE overexpression resulted in an increased GDE activity. Similar results were obtained with the 44 truncated human GDE but not with the gorilla GDE (FIG. 6). We then obtained results in vivo by intramuscular injection of AAV vectors expressing GDEs. GDE-KO animals were injected intramuscularly with AAV9 vectors expressing a human truncated GDE (41), the gorilla GDE or a dual vector expressing human full size GDE. 15 days after the injection, the tibialis anterior was dissected and analyzed for GDE expression and activity (FIG. 7). Western blot analysis with an anti-GDE antibody clearly demonstrated the presence of a band with a molecular weight lower than the full-size GDE (FIG. 7).

AAV vectors expressing three different truncated hGDE either wild-type (wt) or codon optimized (co) under the transcriptional control of SpC5.12 promoter were derived. These vectors were injected directly in the right tibialis anterior (TA) of female GDE-KO mice at the dose of 1E11 vg/mouse. Fifteen days after the injection, GDE activity was measured in extracts obtained from the TA of the injected mice. GDE activities measured in the left TA that did not receive any injection were used as control (Ag1−/−, CTRL). Protein extracts obtained from the TA of mice treated with single vectors AAV expressing the different truncated forms of GDE showed higher levels of GDE activity compared to the control (FIG. 8).

FIG. 9 demonstrates the successful expression of additional human truncated GDEs: Δ9+Δ2/3; Δ10+Δ2/3; Δ11+Δ2/3; Δ12+Δ2/3; Δ13+Δ2/3, by transfection in HEK293 cells.

FIG. 10 further demonstrates the successful expression of additional human truncated GDEs: Δ2/3; Δ9+Δ2/3; Δ10+Δ2/3; Δ13+Δ2/3, in the tibialis anterior of GDE-KO mice, 15 days after the injection with AAV9 vectors expressing said human truncated GDE.

Data shown clearly demonstrates that shorter forms of GDE, either truncated forms of human GDE or non-human GDE, can be expressed both in vitro and in vivo in an active form and that can be used to degrade glycogen accumulated in GSDIII mice.

The invention claimed is:

1. A nucleic acid molecule encoding a functional truncated human glycogen debranching enzyme (GDE) polypeptide, said truncated human GDE polypeptide consisting of one or more of the following combination of deletions relative to SEQ ID NO: 1:

a deletion of at least 15, at least 50 or at least 100 consecutive amino acids and at most 156 consecutive amino acids, from its N-terminal end with respect to SEQ ID NO:1; and/or a deletion of amino acids from position 1 to position 280 with respect to SEQ ID NO:1; and/or a deletion of amino acids from position 223 to position 320 with respect to SEQ ID NO:1; and/or a deletion of amino acids from position 360 to position 428 with respect to SEQ ID NO:1; and/or a deletion of amino acids from position 361 to 428 with respect to SEQ ID NO:1; and/or a deletion of amino acids from position 668 to position 769 with respect to SEQ ID NO:1; and/or a deletion of amino acids from position 669 to position 720 with respect to SEQ ID NO:1; and/or a deletion of amino acids from position 895 to position 1087 with respect to SEQ ID NO: 1.

2. The nucleic acid molecule of claim 1, said truncated human GDE polypeptide consisting of a deletion or a combination of deletions as shown in the following table:

| | | |
|---|---|---|
| Δ1 | Δ2 | Δ3 |
| Δ4 | Δ5 | Δ6 |
| Δ7 | Δ8 | Δ1 + Δ2 |
| Δ1 + Δ3 | Δ1 + Δ4 | Δ1 + Δ5 |
| Δ1 + Δ6 | Δ1 + Δ7 | Δ1 + Δ8 |
| Δ2 + Δ3 | Δ2 + Δ4 | Δ2 + Δ5 |
| Δ2 + Δ6 | Δ2 + Δ7 | Δ2 + Δ8 |
| Δ3 + Δ4 | Δ3 + Δ5 | Δ3 + Δ6 |
| Δ3 + Δ7 | Δ3 + Δ8 | Δ4 + Δ5 |
| Δ4 + Δ6 | Δ4 + Δ7 | Δ4 + Δ8 |
| Δ5 + Δ6 | Δ5 + Δ7 | Δ5 + Δ8 |
| Δ6 + Δ7 | Δ6 + Δ8 | Δ7 + Δ8 |
| Δ1 + Δ2 + Δ3 | Δ1 + Δ2 + Δ4 | Δ1 + Δ2 + Δ5 |
| Δ1 + Δ2 + Δ6 | Δ1 + Δ2 + Δ7 | Δ1 + Δ2 + Δ8 |
| Δ1 + Δ3 + Δ4 | Δ1 + Δ3 + Δ5 | Δ1 + Δ3 + Δ6 |
| Δ1 + Δ3 + Δ7 | Δ1 + Δ3 + Δ8 | Δ1 + Δ4 + Δ5 |
| Δ1 + Δ4 + Δ6 | Δ1 + Δ4 + Δ7 | Δ1 + Δ4 + Δ8 |
| Δ1 + Δ5 + Δ6 | Δ1 + Δ5 + Δ7 | Δ1 + Δ5 + Δ8 |
| Δ1 + Δ6 + Δ7 | Δ1 + Δ6 + Δ8 | Δ1 + Δ7 + Δ8 |
| Δ2 + Δ3 + Δ4 | Δ2 + Δ3 + Δ5 | Δ2 + Δ3 + Δ6 |
| Δ2 + Δ3 + Δ7 | Δ2 + Δ3 + Δ8 | Δ2 + Δ4 + Δ5 |
| Δ2 + Δ4 + Δ6 | Δ2 + Δ4 + Δ7 | Δ2 + Δ4 + Δ8 |
| Δ2 + Δ5 + Δ6 | Δ2 + Δ5 + Δ7 | Δ2 + Δ5 + Δ8 |

-continued

| | | |
|---|---|---|
| Δ2 + Δ6 + Δ7 | Δ2 + Δ6 + Δ8 | Δ2 + Δ7 + Δ8 |
| Δ3 + Δ4 + Δ5 | Δ3 + Δ4 + Δ6 | Δ3 + Δ4 + Δ7 |
| Δ3 + Δ4 + Δ8 | Δ3 + Δ5 + Δ6 | Δ3 + Δ5 + Δ7 |
| Δ3 + Δ5 + Δ8 | Δ3 + Δ6 + Δ7 | Δ3 + Δ6 + Δ8 |
| Δ3 + Δ7 + Δ8 | Δ4 + Δ5 + Δ6 | Δ4 + Δ5 + Δ7 |
| Δ4 + Δ5 + Δ8 | Δ4 + Δ6 + Δ7 | Δ4 + Δ6 + Δ8 |
| Δ4 + Δ7 + Δ8 | Δ5 + Δ6 + Δ7 | Δ5 + Δ6 + Δ8 |
| Δ5 + Δ7 + Δ8 | Δ6 + Δ7 + Δ8 | Δ1 + Δ2 + Δ3 + Δ4 |
| Δ1 + Δ2 + Δ3 + Δ5 | Δ1 + Δ2 + Δ3 + Δ6 | Δ1 + Δ2 + Δ3 + Δ7 |
| Δ1 + Δ2 + Δ3 + Δ8 | Δ1 + Δ2 + Δ4 + Δ5 | Δ1 + Δ2 + Δ4 + Δ6 |
| Δ1 + Δ2 + Δ4 + Δ7 | Δ1 + Δ2 + Δ4 + Δ8 | Δ1 + Δ2 + Δ5 + Δ6 |
| Δ1 + Δ2 + Δ5 + Δ7 | Δ1 + Δ2 + Δ5 + Δ8 | Δ1 + Δ2 + Δ6 + Δ7 |
| Δ1 + Δ2 + Δ6 + Δ8 | Δ1 + Δ2 + Δ7 + Δ8 | Δ1 + Δ3 + Δ4 + Δ5 |
| Δ1 + Δ3 + Δ4 + Δ6 | Δ1 + Δ3 + Δ4 + Δ7 | Δ1 + Δ3 + Δ4 + Δ8 |
| Δ1 + Δ3 + Δ5 + Δ6 | Δ1 + Δ3 + Δ5 + Δ7 | Δ1 + Δ3 + Δ5 + Δ8 |
| Δ1 + Δ3 + Δ6 + Δ7 | Δ1 + Δ3 + Δ6 + Δ8 | Δ1 + Δ3 + Δ7 + Δ8 |
| Δ1 + Δ4 + Δ5 + Δ6 | Δ1 + Δ4 + Δ5 + Δ7 | Δ1 + Δ4 + Δ5 + Δ8 |
| Δ1 + Δ4 + Δ6 + Δ7 | Δ1 + Δ4 + Δ6 + Δ8 | Δ1 + Δ4 + Δ7 + Δ8 |
| Δ1 + Δ5 + Δ6 + Δ7 | Δ1 + Δ5 + Δ6 + Δ8 | Δ1 + Δ5 + Δ7 + Δ8 |
| Δ1 + Δ6 + Δ7 + Δ8 | Δ2 + Δ3 + Δ4 + Δ5 | Δ2 + Δ3 + Δ4 + Δ6 |
| Δ2 + Δ3 + Δ4 + Δ7 | Δ2 + Δ3 + Δ4 + Δ8 | Δ2 + Δ3 + Δ5 + Δ6 |
| Δ2 + Δ3 + Δ5 + Δ7 | Δ2 + Δ3 + Δ5 + Δ8 | Δ2 + Δ3 + Δ6 + Δ7 |
| Δ2 + Δ3 + Δ6 + Δ8 | Δ2 + Δ3 + Δ7 + Δ8 | Δ2 + Δ4 + Δ5 + Δ6 |
| Δ2 + Δ4 + Δ5 + Δ7 | Δ2 + Δ4 + Δ5 + Δ8 | Δ2 + Δ4 + Δ6 + Δ7 |
| Δ2 + Δ4 + Δ6 + Δ8 | Δ2 + Δ4 + Δ7 + Δ8 | Δ2 + Δ5 + Δ6 + Δ7 |
| Δ2 + Δ5 + Δ6 + Δ8 | Δ2 + Δ5 + Δ7 + Δ8 | Δ2 + Δ6 + Δ7 + Δ8 |
| Δ3 + Δ4 + Δ5 + Δ6 | Δ3 + Δ4 + Δ5 + Δ7 | Δ3 + Δ4 + Δ5 + Δ8 |
| Δ3 + Δ4 + Δ6 + Δ7 | Δ3 + Δ4 + Δ6 + Δ8 | Δ3 + Δ4 + Δ7 + Δ8 |
| Δ3 + Δ5 + Δ6 + Δ7 | Δ3 + Δ5 + Δ6 + Δ8 | Δ3 + Δ5 + Δ7 + Δ8 |
| Δ3 + Δ6 + Δ7 + Δ8 | Δ4 + Δ5 + Δ6 + Δ7 | Δ4 + Δ5 + Δ6 + Δ8 |
| Δ4 + Δ5 + Δ7 + Δ8 | Δ4 + Δ6 + Δ7 + Δ8 | Δ5 + Δ6 + Δ7 + Δ8 |
| Δ1 + Δ2 + Δ3 + Δ4 + Δ5 | Δ1 + Δ2 + Δ3 + Δ4 + Δ6 | Δ1 + Δ2 + Δ3 + Δ4 + Δ7 |
| Δ1 + Δ2 + Δ3 + Δ4 + Δ8 | Δ1 + Δ2 + Δ3 + Δ5 + Δ6 | Δ1 + Δ2 + Δ3 + Δ5 + Δ7 |
| Δ1 + Δ2 + Δ3 + Δ5 + Δ8 | Δ1 + Δ2 + Δ3 + Δ6 + Δ7 | Δ1 + Δ2 + Δ3 + Δ6 + Δ8 |
| Δ1 + Δ2 + Δ3 + Δ7 + Δ8 | Δ1 + Δ2 + Δ4 + Δ5 + Δ6 | Δ1 + Δ2 + Δ4 + Δ5 + Δ7 |
| Δ1 + Δ2 + Δ4 + Δ5 + Δ8 | Δ1 + Δ2 + Δ4 + Δ6 + Δ7 | Δ1 + Δ2 + Δ4 + Δ6 + Δ8 |
| Δ1 + Δ2 + Δ4 + Δ7 + Δ8 | Δ1 + Δ2 + Δ5 + Δ6 + Δ7 | Δ1 + Δ2 + Δ5 + Δ6 + Δ8 |
| Δ1 + Δ2 + Δ5 + Δ7 + Δ8 | Δ1 + Δ2 + Δ6 + Δ7 + Δ8 | Δ1 + Δ3 + Δ4 + Δ5 + Δ6 |
| Δ1 + Δ3 + Δ4 + Δ5 + Δ7 | Δ1 + Δ3 + Δ4 + Δ5 + Δ8 | Δ1 + Δ3 + Δ4 + Δ6 + Δ7 |
| Δ1 + Δ3 + Δ4 + Δ6 + Δ8 | Δ1 + Δ3 + Δ4 + Δ7 + Δ8 | Δ1 + Δ3 + Δ5 + Δ6 + Δ7 |
| Δ1 + Δ3 + Δ5 + Δ6 + Δ8 | Δ1 + Δ3 + Δ5 + Δ7 + Δ8 | Δ1 + Δ3 + Δ6 + Δ7 + Δ8 |
| Δ1 + Δ4 + Δ5 + Δ6 + Δ7 | Δ1 + Δ4 + Δ5 + Δ6 + Δ8 | Δ1 + Δ4 + Δ5 + Δ7 + Δ8 |
| Δ1 + Δ4 + Δ6 + Δ7 + Δ8 | Δ1 + Δ5 + Δ6 + Δ7 + Δ8 | Δ2 + Δ3 + Δ4 + Δ5 + Δ6 |
| Δ2 + Δ3 + Δ4 + Δ5 + Δ7 | Δ2 + Δ3 + Δ4 + Δ5 + Δ8 | Δ2 + Δ3 + Δ4 + Δ6 + Δ7 |
| Δ2 + Δ3 + Δ4 + Δ6 + Δ8 | Δ2 + Δ3 + Δ4 + Δ7 + Δ8 | Δ2 + Δ3 + Δ5 + Δ6 + Δ7 |
| Δ2 + Δ3 + Δ5 + Δ6 + Δ8 | Δ2 + Δ3 + Δ5 + Δ7 + Δ8 | Δ2 + Δ3 + Δ6 + Δ7 + Δ8 |
| Δ2 + Δ4 + Δ5 + Δ6 + Δ7 | Δ2 + Δ4 + Δ5 + Δ6 + Δ8 | Δ2 + Δ4 + Δ5 + Δ7 + Δ8 |
| Δ2 + Δ4 + Δ6 + Δ7 + Δ8 | Δ2 + Δ5 + Δ6 + Δ7 + Δ8 | Δ3 + Δ4 + Δ5 + Δ6 + Δ7 |
| Δ3 + Δ4 + Δ5 + Δ6 + Δ8 | Δ3 + Δ4 + Δ5 + Δ7 + Δ8 | Δ3 + Δ4 + Δ6 + Δ7 + Δ8 |
| Δ3 + Δ5 + Δ6 + Δ7 + Δ8 | Δ4 + Δ5 + Δ6 + Δ7 + Δ8 | Δ1 + Δ2 + Δ3 + Δ4 + Δ5 + Δ6 |
| Δ1 + Δ2 + Δ3 + Δ4 + Δ5 + Δ7 | Δ1 + Δ2 + Δ3 + Δ4 + Δ5 + Δ8 | Δ1 + Δ2 + Δ3 + Δ4 + Δ6 + Δ7 |
| Δ1 + Δ2 + Δ3 + Δ4 + Δ6 + Δ8 | Δ1 + Δ2 + Δ3 + Δ4 + Δ7 + Δ8 | Δ1 + Δ2 + Δ3 + Δ5 + Δ6 + Δ7 |
| Δ1 + Δ2 + Δ3 + Δ5 + Δ6 + Δ8 | Δ1 + Δ2 + Δ3 + Δ5 + Δ7 + Δ8 | Δ1 + Δ2 + Δ3 + Δ6 + Δ7 + Δ8 |
| Δ1 + Δ2 + Δ4 + Δ5 + Δ6 + Δ7 | Δ1 + Δ2 + Δ4 + Δ5 + Δ6 + Δ8 | Δ1 + Δ2 + Δ4 + Δ5 + Δ7 + Δ8 |
| Δ1 + Δ2 + Δ4 + Δ6 + Δ7 + Δ8 | Δ1 + Δ2 + Δ5 + Δ6 + Δ7 + Δ8 | Δ1 + Δ3 + Δ4 + Δ5 + Δ6 + Δ7 |
| Δ1 + Δ3 + Δ4 + Δ5 + Δ6 + Δ8 | Δ1 + Δ3 + Δ4 + Δ5 + Δ7 + Δ8 | Δ1 + Δ3 + Δ4 + Δ6 + Δ7 + Δ8 |
| Δ1 + Δ3 + Δ5 + Δ6 + Δ7 + Δ8 | Δ1 + Δ4 + Δ5 + Δ6 + Δ7 + Δ8 | Δ2 + Δ3 + Δ4 + Δ5 + Δ6 + Δ7 |
| Δ2 + Δ3 + Δ4 + Δ5 + Δ6 + Δ8 | Δ2 + Δ3 + Δ4 + Δ5 + Δ7 + Δ8 | Δ2 + Δ3 + Δ4 + Δ6 + Δ7 + Δ8 |
| Δ2 + Δ3 + Δ5 + Δ6 + Δ7 + Δ8 | Δ2 + Δ4 + Δ5 + Δ6 + Δ7 + Δ8 | Δ3 + Δ4 + Δ5 + Δ6 + Δ7 + Δ8 |
| Δ1 + Δ2 + Δ3 + Δ4 + Δ5 + Δ6 + Δ7 | Δ1 + Δ2 + Δ3 + Δ4 + Δ5 + Δ6 + Δ8 | Δ1 + Δ2 + Δ3 + Δ4 + Δ5 + Δ7 + Δ8 |
| Δ1 + Δ2 + Δ3 + Δ4 + Δ6 + Δ7 + Δ8 | Δ1 + Δ2 + Δ3 + Δ5 + Δ6 + Δ7 + Δ8 | Δ1 + Δ2 + Δ4 + Δ5 + Δ6 + Δ7 + Δ8 |
| Δ1 + Δ3 + Δ4 + Δ5 + Δ6 + Δ7 + Δ8 | Δ2 + Δ3 + Δ4 + Δ5 + Δ6 + Δ7 + Δ8 | Δ1 + Δ2 + Δ3 + Δ4 + Δ5 + Δ6 + Δ7 + Δ8 |

wherein Δ1, Δ2, Δ3, Δ4, Δ5, Δ6, Δ7 and Δ8 are as defined in the following table:

| Deletion | Position of the deleted amino acids with respect to SEQ ID NO: 1 |
|---|---|
| Δ1 | 1-156 |
| Δ2 | 361-428 |
| Δ3 | 668-769 |
| Δ4 | 895-1087 |
| Δ5 | 223-320 |
| Δ6 | 360-428 |
| Δ7 | 669-720 |
| Δ8 | 1-280. |

3. The nucleic acid molecule of claim 1, said functional truncated human GDE polypeptide consisting of a sequence selected from SEQ ID NOs: 2 to 6 or SEQ ID NOs: 48 to 52, or consisting of a sequence having at least 95% sequence identity to SEQ ID NOs: 2 to 6 and SEQ ID NOs: 48 to 52.

4. The nucleic acid molecule of claim 3, said functional truncated human GDE polypeptide consisting of SEQ ID NO:2.

5. The nucleic acid molecule of claim 3, said functional truncated human GDE polypeptide consisting of a sequence having at least 95% sequence identity to SEQ ID NO:2.

6. The nucleic acid molecule of claim 1, said functional truncated human GDE polypeptide consisting of SEQ ID NO:5, or consisting of a sequence having at least 95% sequence identity to SEQ ID NO:5.

7. A nucleic acid construct, comprising:

a promoter;

optionally, an intron;

the nucleic acid molecule of claim 1; and a polyadenylation signal.

8. A vector, comprising the nucleic acid molecule of claim 1 or a nucleic acid construct comprising said nucleic acid molecule.

9. The vector of claim 8, wherein said vector is a viral vector.

10. The viral vector of claim 9, wherein the viral vector is an adeno-associated virus (AAV) vector.

11. The viral vector of claim 10, wherein the viral vector is an AAV vector with an AAV-derived capsid, selected from the group consisting of an AAV1, AAV2, variant AAV2, AAV3, variant AAV3, AAV3B, variant AAV3B, AAV4, AAV5, AAV6, variant AAV6, AAV7, AAV8, AAV9, AAV9P1, AAV10, AAVcy10, AAVrh10, AAVrh74, AAVdj, AAV-Anc80, AAV-LK03, AAV218, and porcine AAV.

12. The viral vector of claim 10, wherein the viral vector is an AAV vector with an AAV9, AAV9P1 or AAV6 capsid.

13. The viral vector of claim 10, wherein the viral vector is an AAV vector with a chimeric capsid.

14. The vector of claim 8, wherein the nucleic acid molecule comprises a nucleic acid molecule encoding a truncated human GDE polypeptide consisting of a deletion or a combination of deletions as shown in the following table:

| | | |
|---|---|---|
| Δ1 | Δ2 | Δ3 |
| Δ4 | Δ5 | Δ6 |
| Δ7 | Δ8 | Δ1 + Δ2 |
| Δ1 + Δ3 | Δ1 + Δ4 | Δ1 + Δ5 |
| Δ1 + Δ6 | Δ1 + Δ7 | Δ1 + Δ8 |
| Δ2 + Δ3 | Δ2 + Δ4 | Δ2 + Δ5 |
| Δ2 + Δ6 | Δ2 + Δ7 | Δ2 + Δ8 |
| Δ3 + Δ4 | Δ3 + Δ5 | Δ3 + Δ6 |
| Δ3 + Δ7 | Δ3 + Δ8 | Δ4 + Δ5 |
| Δ4 + Δ6 | Δ4 + Δ7 | Δ4 + Δ8 |
| Δ5 + Δ6 | Δ5 + Δ7 | Δ5 + Δ8 |
| Δ6 + Δ7 | Δ6 + Δ8 | Δ7 + Δ8 |
| Δ1 + Δ2 + Δ3 | Δ1 + Δ2 + Δ4 | Δ1 + Δ2 + Δ5 |
| Δ1 + Δ2 + Δ6 | Δ1 + Δ2 + Δ7 | Δ1 + Δ2 + Δ8 |
| Δ1 + Δ3 + Δ4 | Δ1 + Δ3 + Δ5 | Δ1 + Δ3 + Δ6 |
| Δ1 + Δ3 + Δ7 | Δ1 + Δ3 + Δ8 | Δ1 + Δ4 + Δ5 |
| Δ1 + Δ4 + Δ6 | Δ1 + Δ4 + Δ7 | Δ1 + Δ4 + Δ8 |
| Δ1 + Δ5 + Δ6 | Δ1 + Δ5 + Δ7 | Δ1 + Δ5 + Δ8 |
| Δ1 + Δ6 + Δ7 | Δ1 + Δ6 + Δ8 | Δ1 + Δ7 + Δ8 |
| Δ2 + Δ3 + Δ4 | Δ2 + Δ3 + Δ5 | Δ2 + Δ3 + Δ6 |
| Δ2 + Δ3 + Δ7 | Δ2 + Δ3 + Δ8 | Δ2 + Δ4 + Δ5 |
| Δ2 + Δ4 + Δ6 | Δ2 + Δ4 + Δ7 | Δ2 + Δ4 + Δ8 |
| Δ2 + Δ5 + Δ6 | Δ2 + Δ5 + Δ7 | Δ2 + Δ5 + Δ8 |
| Δ2 + Δ6 + Δ7 | Δ2 + Δ6 + Δ8 | Δ2 + Δ7 + Δ8 |
| Δ3 + Δ4 + Δ5 | Δ3 + Δ4 + Δ6 | Δ3 + Δ4 + Δ7 |
| Δ3 + Δ4 + Δ8 | Δ3 + Δ5 + Δ6 | Δ3 + Δ5 + Δ7 |
| Δ3 + Δ5 + Δ8 | Δ3 + Δ6 + Δ7 | Δ3 + Δ6 + Δ8 |
| Δ3 + Δ7 + Δ8 | Δ4 + Δ5 + Δ6 | Δ4 + Δ5 + Δ7 |
| Δ4 + Δ5 + Δ8 | Δ4 + Δ6 + Δ7 | Δ4 + Δ6 + Δ8 |
| Δ4 + Δ7 + Δ8 | Δ5 + Δ6 + Δ7 | Δ5 + Δ6 + Δ8 |
| Δ5 + Δ7 + Δ8 | Δ6 + Δ7 + Δ8 | Δ1 + Δ2 + Δ3 + Δ4 |
| Δ1 + Δ2 + Δ3 + Δ5 | Δ1 + Δ2 + Δ3 + Δ6 | Δ1 + Δ2 + Δ3 + Δ7 |
| Δ1 + Δ2 + Δ3 + Δ8 | Δ1 + Δ2 + Δ4 + Δ5 | Δ1 + Δ2 + Δ4 + Δ6 |
| Δ1 + Δ2 + Δ4 + Δ7 | Δ1 + Δ2 + Δ4 + Δ8 | Δ1 + Δ2 + Δ5 + Δ6 |
| Δ1 + Δ2 + Δ5 + Δ7 | Δ1 + Δ2 + Δ5 + Δ8 | Δ1 + Δ2 + Δ6 + Δ7 |
| Δ1 + Δ2 + Δ6 + Δ8 | Δ1 + Δ2 + Δ7 + Δ8 | Δ1 + Δ3 + Δ4 + Δ5 |
| Δ1 + Δ3 + Δ4 + Δ6 | Δ1 + Δ3 + Δ4 + Δ7 | Δ1 + Δ3 + Δ4 + Δ8 |
| Δ1 + Δ3 + Δ5 + Δ6 | Δ1 + Δ3 + Δ5 + Δ7 | Δ1 + Δ3 + Δ5 + Δ8 |
| Δ1 + Δ3 + Δ6 + Δ7 | Δ1 + Δ3 + Δ6 + Δ8 | Δ1 + Δ3 + Δ7 + Δ8 |
| Δ1 + Δ4 + Δ5 + Δ6 | Δ1 + Δ4 + Δ5 + Δ7 | Δ1 + Δ4 + Δ5 + Δ8 |
| Δ1 + Δ4 + Δ6 + Δ7 | Δ1 + Δ4 + Δ6 + Δ8 | Δ1 + Δ4 + Δ7 + Δ8 |
| Δ1 + Δ5 + Δ6 + Δ7 | Δ1 + Δ5 + Δ6 + Δ8 | Δ1 + Δ5 + Δ7 + Δ8 |
| Δ1 + Δ6 + Δ7 + Δ8 | Δ2 + Δ3 + Δ4 + Δ5 | Δ2 + Δ3 + Δ4 + Δ6 |
| Δ2 + Δ3 + Δ4 + Δ7 | Δ2 + Δ3 + Δ4 + Δ8 | Δ2 + Δ3 + Δ5 + Δ6 |
| Δ2 + Δ3 + Δ5 + Δ7 | Δ2 + Δ3 + Δ5 + Δ8 | Δ2 + Δ3 + Δ6 + Δ7 |
| Δ2 + Δ3 + Δ6 + Δ8 | Δ2 + Δ3 + Δ7 + Δ8 | Δ2 + Δ4 + Δ5 + Δ6 |
| Δ2 + Δ4 + Δ5 + Δ7 | Δ2 + Δ4 + Δ5 + Δ8 | Δ2 + Δ4 + Δ6 + Δ7 |
| Δ2 + Δ4 + Δ6 + Δ8 | Δ2 + Δ4 + Δ7 + Δ8 | Δ2 + Δ5 + Δ6 + Δ7 |
| Δ2 + Δ5 + Δ6 + Δ8 | Δ2 + Δ5 + Δ7 + Δ8 | Δ2 + Δ6 + Δ7 + Δ8 |
| Δ3 + Δ4 + Δ5 + Δ6 | Δ3 + Δ4 + Δ5 + Δ7 | Δ3 + Δ4 + Δ5 + Δ8 |
| Δ3 + Δ4 + Δ6 + Δ7 | Δ3 + Δ4 + Δ6 + Δ8 | Δ3 + Δ4 + Δ7 + Δ8 |
| Δ3 + Δ5 + Δ6 + Δ7 | Δ3 + Δ5 + Δ6 + Δ8 | Δ3 + Δ5 + Δ7 + Δ8 |
| Δ3 + Δ6 + Δ7 + Δ8 | Δ4 + Δ5 + Δ6 + Δ7 | Δ4 + Δ5 + Δ6 + Δ8 |
| Δ4 + Δ5 + Δ7 + Δ8 | Δ4 + Δ6 + Δ7 + Δ8 | Δ5 + Δ6 + Δ7 + Δ8 |
| Δ1 + Δ2 + Δ3 + Δ4 + Δ5 | Δ1 + Δ2 + Δ3 + Δ4 + Δ6 | Δ1 + Δ2 + Δ3 + Δ4 + Δ7 |
| Δ1 + Δ2 + Δ3 + Δ4 + Δ8 | Δ1 + Δ2 + Δ3 + Δ5 + Δ6 | Δ1 + Δ2 + Δ3 + Δ5 + Δ7 |
| Δ1 + Δ2 + Δ3 + Δ5 + Δ8 | Δ1 + Δ2 + Δ3 + Δ6 + Δ7 | Δ1 + Δ2 + Δ3 + Δ6 + Δ8 |
| Δ1 + Δ2 + Δ3 + Δ7 + Δ8 | Δ1 + Δ2 + Δ4 + Δ5 + Δ6 | Δ1 + Δ2 + Δ4 + Δ5 + Δ7 |
| Δ1 + Δ2 + Δ4 + Δ5 + Δ8 | Δ1 + Δ2 + Δ4 + Δ6 + Δ7 | Δ1 + Δ2 + Δ4 + Δ6 + Δ8 |
| Δ1 + Δ2 + Δ4 + Δ7 + Δ8 | Δ1 + Δ2 + Δ5 + Δ6 + Δ7 | Δ1 + Δ2 + Δ5 + Δ6 + Δ8 |
| Δ1 + Δ2 + Δ5 + Δ7 + Δ8 | Δ1 + Δ2 + Δ6 + Δ7 + Δ8 | Δ1 + Δ3 + Δ4 + Δ5 + Δ6 |
| Δ1 + Δ3 + Δ4 + Δ5 + Δ7 | Δ1 + Δ3 + Δ4 + Δ5 + Δ8 | Δ1 + Δ3 + Δ4 + Δ6 + Δ7 |
| Δ1 + Δ3 + Δ4 + Δ6 + Δ8 | Δ1 + Δ3 + Δ4 + Δ7 + Δ8 | Δ1 + Δ3 + Δ5 + Δ6 + Δ7 |
| Δ1 + Δ3 + Δ5 + Δ6 + Δ8 | Δ1 + Δ3 + Δ5 + Δ7 + Δ8 | Δ1 + Δ3 + Δ6 + Δ7 + Δ8 |
| Δ1 + Δ4 + Δ5 + Δ6 + Δ7 | Δ1 + Δ4 + Δ5 + Δ6 + Δ8 | Δ1 + Δ4 + Δ5 + Δ7 + Δ8 |
| Δ1 + Δ4 + Δ6 + Δ7 + Δ8 | Δ1 + Δ5 + Δ6 + Δ7 + Δ8 | Δ2 + Δ3 + Δ4 + Δ5 + Δ6 |
| Δ2 + Δ3 + Δ4 + Δ5 + Δ7 | Δ2 + Δ3 + Δ4 + Δ5 + Δ8 | Δ2 + Δ3 + Δ4 + Δ6 + Δ7 |
| Δ2 + Δ3 + Δ4 + Δ6 + Δ8 | Δ2 + Δ3 + Δ4 + Δ7 + Δ8 | Δ2 + Δ3 + Δ5 + Δ6 + Δ7 |
| Δ2 + Δ3 + Δ5 + Δ6 + Δ8 | Δ2 + Δ3 + Δ5 + Δ7 + Δ8 | Δ2 + Δ3 + Δ6 + Δ7 + Δ8 |
| Δ2 + Δ4 + Δ5 + Δ6 + Δ7 | Δ2 + Δ4 + Δ5 + Δ6 + Δ8 | Δ2 + Δ4 + Δ5 + Δ7 + Δ8 |
| Δ2 + Δ4 + Δ6 + Δ7 + Δ8 | Δ2 + Δ5 + Δ6 + Δ7 + Δ8 | Δ3 + Δ4 + Δ5 + Δ6 + Δ7 |
| Δ3 + Δ4 + Δ5 + Δ6 + Δ8 | Δ3 + Δ4 + Δ5 + Δ7 + Δ8 | Δ3 + Δ4 + Δ6 + Δ7 + Δ8 |
| Δ3 + Δ5 + Δ6 + Δ7 + Δ8 | Δ4 + Δ5 + Δ6 + Δ7 + Δ8 | Δ1 + Δ2 + Δ3 + Δ4 + Δ5 + Δ6 |
| Δ1 + Δ2 + Δ3 + Δ4 + Δ5 + Δ7 | Δ1 + Δ2 + Δ3 + Δ4 + Δ5 + Δ8 | Δ1 + Δ2 + Δ3 + Δ4 + Δ6 + Δ7 |
| Δ1 + Δ2 + Δ3 + Δ4 + Δ6 + Δ8 | Δ1 + Δ2 + Δ3 + Δ4 + Δ7 + Δ8 | Δ1 + Δ2 + Δ3 + Δ5 + Δ6 + Δ7 |
| Δ1 + Δ2 + Δ3 + Δ5 + Δ6 + Δ8 | Δ1 + Δ2 + Δ3 + Δ5 + Δ7 + Δ8 | Δ1 + Δ2 + Δ3 + Δ6 + Δ7 + Δ8 |
| Δ1 + Δ2 + Δ4 + Δ5 + Δ6 + Δ7 | Δ1 + Δ2 + Δ4 + Δ5 + Δ6 + Δ8 | Δ1 + Δ2 + Δ4 + Δ5 + Δ7 + Δ8 |
| Δ1 + Δ2 + Δ4 + Δ6 + Δ7 + Δ8 | Δ1 + Δ2 + Δ5 + Δ6 + Δ7 + Δ8 | Δ1 + Δ3 + Δ4 + Δ5 + Δ6 + Δ7 |
| Δ1 + Δ3 + Δ4 + Δ5 + Δ6 + Δ8 | Δ1 + Δ3 + Δ4 + Δ5 + Δ7 + Δ8 | Δ1 + Δ3 + Δ4 + Δ6 + Δ7 + Δ8 |
| Δ1 + Δ3 + Δ5 + Δ6 + Δ7 + Δ8 | Δ1 + Δ4 + Δ5 + Δ6 + Δ7 + Δ8 | Δ2 + Δ3 + Δ4 + Δ5 + Δ6 + Δ7 |
| Δ2 + Δ3 + Δ4 + Δ5 + Δ6 + Δ8 | Δ2 + Δ3 + Δ4 + Δ5 + Δ7 + Δ8 | Δ2 + Δ3 + Δ4 + Δ6 + Δ7 + Δ8 |
| Δ2 + Δ3 + Δ5 + Δ6 + Δ7 + Δ8 | Δ2 + Δ4 + Δ5 + Δ6 + Δ7 + Δ8 | Δ3 + Δ4 + Δ5 + Δ6 + Δ7 + Δ8 |
| Δ1 + Δ2 + Δ3 + Δ4 + Δ5 + Δ6 + Δ7 | Δ1 + Δ2 + Δ3 + Δ4 + Δ5 + Δ6 + Δ8 | Δ1 + Δ2 + Δ3 + Δ4 + Δ5 + Δ7 + Δ8 |
| Δ1 + Δ2 + Δ3 + Δ4 + Δ6 + Δ7 + Δ8 | Δ1 + Δ2 + Δ3 + Δ5 + Δ6 + Δ7 + Δ8 | Δ1 + Δ2 + Δ4 + Δ5 + Δ6 + Δ7 + Δ8 |
| Δ1 + Δ3 + Δ4 + Δ5 + Δ6 + Δ7 + Δ8 | Δ2 + Δ3 + Δ4 + Δ5 + Δ6 + Δ7 + Δ8 | Δ1 + Δ2 + Δ3 + Δ4 + Δ5 + Δ6 + Δ7 + Δ8 |

wherein Δ1, Δ2, Δ3, Δ4, Δ5, Δ6, Δ7 and Δ8 are as defined in the following table:

| Deletion | Position of the deleted amino acids with respect to SEQ ID NO: 1 |
|---|---|
| Δ1 | 1-156 |
| Δ2 | 361-428 |
| Δ3 | 668-769 |
| Δ4 | 895-1087 |
| Δ5 | 223-320 |
| Δ6 | 360-428 |
| Δ7 | 669-720 |
| Δ8 | 1-280 |

or a truncated human GDE polypeptide consisting of a sequence selected from SEQ ID NOs: 2 to 6 or SEQ ID NOs: 48 to 52, or consisting of a sequence having at least 95% sequence identity to SEQ ID NOs: 2 to 6 or SEQ ID NOs: 48 to 52.

15. An isolated cell transformed with the nucleic acid molecule of claim 1, a nucleic acid construct comprising said nucleic acid molecule or a vector comprising said nucleic acid or said nucleic acid construct.

16. The isolated cell of claim 15, wherein said cell is a liver cell, a muscle cell, a cardiac cell or a central nervous system (CNS) cell.

17. The isolated cell of claim 15, wherein said vector is a viral vector.

18. The isolated cell of claim 15, wherein the vector is an AAV vector.

* * * * *

SEQUENCE LISTING

```
<160> NUMBER OF SEQ ID NOS: 63

<210> SEQ ID NO 1
<211> LENGTH: 1532
<212> TYPE: PRT
<213> ORGANISM: Homo sapiens

<400> SEQUENCE: 1

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
    290                 295                 300
```

```
Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Lys Gly Pro Ala Ala Ile Glu
        355                 360                 365

Glu Cys Cys Asn Trp Phe His Lys Arg Met Glu Glu Leu Asn Ser Glu
    370                 375                 380

Lys His Arg Leu Ile Asn Tyr His Gln Glu Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Ile Asp Phe Ser Met Glu Glu Ser Met Ile His Leu
        435                 440                 445

Pro Asn Lys Ala Cys Phe Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asn Ser His Glu Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Ile Ser Val Val Ser
            660                 665                 670

Glu Glu Arg Phe Tyr Thr Lys Trp Asn Pro Glu Ala Leu Pro Ser Asn
        675                 680                 685

Thr Gly Glu Val Asn Phe Gln Ser Gly Ile Ile Ala Ala Arg Cys Ala
    690                 695                 700

Ile Ser Lys Leu His Gln Glu Leu Gly Ala Lys Gly Phe Ile Gln Val
705                 710                 715                 720
```

```
Tyr Val Asp Gln Val Asp Glu Asp Ile Val Ala Val Thr Arg His Ser
                725                 730                 735

Pro Ser Ile His Gln Ser Val Val Ala Val Thr Arg Thr Ala Phe Arg
            740                 745                 750

Asn Pro Lys Thr Ser Phe Tyr Ser Lys Glu Val Pro Gln Met Cys Ile
        755                 760                 765

Pro Gly Lys Ile Glu Glu Val Val Leu Glu Ala Arg Thr Ile Glu Arg
    770                 775                 780

Asn Thr Lys Pro Tyr Arg Lys Asp Glu Asn Ser Ile Asn Gly Thr Pro
785                 790                 795                 800

Asp Ile Thr Val Glu Ile Arg Glu His Ile Gln Leu Asn Glu Ser Lys
                805                 810                 815

Ile Val Lys Gln Ala Gly Val Ala Thr Lys Gly Pro Asn Glu Tyr Ile
            820                 825                 830

Gln Glu Ile Glu Phe Glu Asn Leu Ser Pro Gly Ser Val Ile Ile Phe
        835                 840                 845

Arg Val Ser Leu Asp Pro His Ala Gln Val Ala Val Gly Ile Leu Arg
    850                 855                 860

Asn His Leu Thr Gln Phe Ser Pro His Phe Lys Ser Gly Ser Leu Ala
865                 870                 875                 880

Val Asp Asn Ala Asp Pro Ile Leu Lys Ile Pro Phe Ala Ser Leu Ala
                885                 890                 895

Tyr Arg Leu Thr Leu Ala Glu Leu Asn Gln Ile Leu Tyr Arg Cys Glu
            900                 905                 910

Ser Glu Glu Lys Glu Asp Gly Gly Gly Cys Tyr Asp Ile Pro Asn Trp
        915                 920                 925

Ser Ala Leu Lys Tyr Ala Gly Leu Gln Gly Leu Met Ser Val Leu Ala
    930                 935                 940

Glu Ile Arg Pro Lys Asn Asp Leu Gly His Pro Phe Cys Asn Asn Leu
945                 950                 955                 960

Arg Ser Gly Asp Trp Met Ile Asp Tyr Val Ser Asn Arg Leu Ile Ser
                965                 970                 975

Arg Ser Gly Thr Ile Ala Glu Val Gly Lys Trp Leu Gln Ala Met Phe
            980                 985                 990

Phe Tyr Leu Lys Gln Ile Pro Arg  Tyr Leu Ile Pro Cys  Tyr Phe Asp
        995                 1000                1005

Ala Ile  Leu Ile Gly Ala Tyr  Thr Thr Leu Leu Asp  Thr Ala Trp
    1010                1015                1020

Lys Gln  Met Ser Ser Phe Val  Gln Asn Gly Ser Thr  Phe Val Lys
    1025                1030                1035

His Leu  Ser Leu Gly Ser Val  Gln Leu Cys Gly Val  Gly Lys Phe
    1040                1045                1050

Pro Ser  Leu Pro Ile Leu Ser  Pro Ala Leu Met Asp  Val Pro Tyr
    1055                1060                1065

Arg Leu  Asn Glu Ile Thr Lys  Glu Lys Glu Gln Cys  Cys Val Ser
    1070                1075                1080

Leu Ala  Ala Gly Leu Pro His  Phe Ser Ser Gly Ile  Phe Arg Cys
    1085                1090                1095

Trp Gly  Arg Asp Thr Phe Ile  Ala Leu Arg Gly Ile  Leu Leu Ile
    1100                1105                1110

Thr Gly  Arg Tyr Val Glu Ala  Arg Asn Ile Ile Leu  Ala Phe Ala
    1115                1120                1125

Gly Thr  Leu Arg His Gly Leu  Ile Pro Asn Leu Leu  Gly Glu Gly
```

```
    1130                1135                1140

Ile Tyr  Ala Arg Tyr Asn Cys  Arg Asp Ala Val Trp  Trp Trp Leu
    1145                1150                1155

Gln Cys  Ile Gln Asp Tyr Cys  Lys Met Val Pro Asn  Gly Leu Asp
    1160                1165                1170

Ile Leu  Lys Cys Pro Val Ser  Arg Met Tyr Pro Thr  Asp Asp Ser
    1175                1180                1185

Ala Pro  Leu Pro Ala Gly Thr  Leu Asp Gln Pro Leu  Phe Glu Val
    1190                1195                1200

Ile Gln  Glu Ala Met Gln Lys  His Met Gln Gly Ile  Gln Phe Arg
    1205                1210                1215

Glu Arg  Asn Ala Gly Pro Gln  Ile Asp Arg Asn Met  Lys Asp Glu
    1220                1225                1230

Gly Phe  Asn Ile Thr Ala Gly  Val Asp Glu Glu Thr  Gly Phe Val
    1235                1240                1245

Tyr Gly  Gly Asn Arg Phe Asn  Cys Gly Thr Trp Met  Asp Lys Met
    1250                1255                1260

Gly Glu  Ser Asp Arg Ala Arg  Asn Arg Gly Ile Pro  Ala Thr Pro
    1265                1270                1275

Arg Asp  Gly Ser Ala Val Glu  Ile Val Gly Leu Ser  Lys Ser Ala
    1280                1285                1290

Val Arg  Trp Leu Leu Glu Leu  Ser Lys Lys Asn Ile  Phe Pro Tyr
    1295                1300                1305

His Glu  Val Thr Val Lys Arg  His Gly Lys Ala Ile  Lys Val Ser
    1310                1315                1320

Tyr Asp  Glu Trp Asn Arg Lys  Ile Gln Asp Asn Phe  Glu Lys Leu
    1325                1330                1335

Phe His  Val Ser Glu Asp Pro  Ser Asp Leu Asn Glu  Lys His Pro
    1340                1345                1350

Asn Leu  Val His Lys Arg Gly  Ile Tyr Lys Asp Ser  Tyr Gly Ala
    1355                1360                1365

Ser Ser  Pro Trp Cys Asp Tyr  Gln Leu Arg Pro Asn  Phe Thr Ile
    1370                1375                1380

Ala Met  Val Val Ala Pro Glu  Leu Phe Thr Thr Glu  Lys Ala Trp
    1385                1390                1395

Lys Ala  Leu Glu Ile Ala Glu  Lys Lys Leu Leu Gly  Pro Leu Gly
    1400                1405                1410

Met Lys  Thr Leu Asp Pro Asp  Asp Met Val Tyr Cys  Gly Ile Tyr
    1415                1420                1425

Asp Asn  Ala Leu Asp Asn Asp  Asn Tyr Asn Leu Ala  Lys Gly Phe
    1430                1435                1440

Asn Tyr  His Gln Gly Pro Glu  Trp Leu Trp Pro Ile  Gly Tyr Phe
    1445                1450                1455

Leu Arg  Ala Lys Leu Tyr Phe  Ser Arg Leu Met Gly  Pro Glu Thr
    1460                1465                1470

Thr Ala  Lys Thr Ile Val Leu  Val Lys Asn Val Leu  Ser Arg His
    1475                1480                1485

Tyr Val  His Leu Glu Arg Ser  Pro Trp Lys Gly Leu  Pro Glu Leu
    1490                1495                1500

Thr Asn  Glu Asn Ala Gln Tyr  Cys Pro Phe Ser Cys  Glu Thr Gln
    1505                1510                1515

Ala Trp  Ser Ile Ala Thr Ile  Leu Glu Thr Leu Tyr  Asp Leu
    1520                1525                1530
```

<210> SEQ ID NO 2
<211> LENGTH: 1376
<212> TYPE: PRT
<213> ORGANISM: artificial
<220> FEATURE:
<223> OTHER INFORMATION: D1 hGDE

<400> SEQUENCE: 2

```
Met Ile His Phe Thr Pro Leu Gln Thr Leu Gly Leu Ser Arg Ser Cys
1               5                   10                  15

Tyr Ser Leu Ala Asn Gln Leu Glu Leu Asn Pro Asp Phe Ser Arg Pro
            20                  25                  30

Asn Arg Lys Tyr Thr Trp Asn Asp Val Gly Gln Leu Val Glu Lys Leu
        35                  40                  45

Lys Lys Glu Trp Asn Val Ile Cys Ile Thr Asp Val Val Tyr Asn His
    50                  55                  60

Thr Ala Ala Asn Ser Lys Trp Ile Gln Glu His Pro Glu Cys Ala Tyr
65                  70                  75                  80

Asn Leu Val Asn Ser Pro His Leu Lys Pro Ala Trp Val Leu Asp Arg
                85                  90                  95

Ala Leu Trp Arg Phe Ser Cys Asp Val Ala Glu Gly Lys Tyr Lys Glu
            100                 105                 110

Lys Gly Ile Pro Ala Leu Ile Glu Asn Asp His His Met Asn Ser Ile
        115                 120                 125

Arg Lys Ile Ile Trp Glu Asp Ile Phe Pro Lys Leu Lys Leu Trp Glu
    130                 135                 140

Phe Phe Gln Val Asp Val Asn Lys Ala Val Glu Gln Phe Arg Arg Leu
145                 150                 155                 160

Leu Thr Gln Glu Asn Arg Arg Val Thr Lys Ser Asp Pro Asn Gln His
                165                 170                 175

Leu Thr Ile Ile Gln Asp Pro Glu Tyr Arg Arg Phe Gly Cys Thr Val
            180                 185                 190

Asp Met Asn Ile Ala Leu Thr Thr Phe Ile Pro His Asp Lys Gly Pro
        195                 200                 205

Ala Ala Ile Glu Glu Cys Cys Asn Trp Phe His Lys Arg Met Glu Glu
    210                 215                 220

Leu Asn Ser Glu Lys His Arg Leu Ile Asn Tyr His Gln Glu Gln Ala
225                 230                 235                 240

Val Asn Cys Leu Leu Gly Asn Val Phe Tyr Glu Arg Leu Ala Gly His
                245                 250                 255

Gly Pro Lys Leu Gly Pro Val Thr Arg Lys His Pro Leu Val Thr Arg
            260                 265                 270

Tyr Phe Thr Phe Pro Phe Glu Glu Ile Asp Phe Ser Met Glu Glu Ser
        275                 280                 285

Met Ile His Leu Pro Asn Lys Ala Cys Phe Leu Met Ala His Asn Gly
    290                 295                 300

Trp Val Met Gly Asp Asp Pro Leu Arg Asn Phe Ala Glu Pro Gly Ser
305                 310                 315                 320

Glu Val Tyr Leu Arg Arg Glu Leu Ile Cys Trp Gly Asp Ser Val Lys
                325                 330                 335

Leu Arg Tyr Gly Asn Lys Pro Glu Asp Cys Pro Tyr Leu Trp Ala His
            340                 345                 350

Met Lys Lys Tyr Thr Glu Ile Thr Ala Thr Tyr Phe Gln Gly Val Arg
        355                 360                 365
```

-continued

```
Leu Asp Asn Cys His Ser Thr Pro Leu His Val Ala Glu Tyr Met Leu
    370                 375                 380

Asp Ala Ala Arg Asn Leu Gln Pro Asn Leu Tyr Val Val Ala Glu Leu
385                 390                 395                 400

Phe Thr Gly Ser Glu Asp Leu Asp Asn Val Phe Val Thr Arg Leu Gly
                405                 410                 415

Ile Ser Ser Leu Ile Arg Glu Ala Met Ser Ala Tyr Asn Ser His Glu
            420                 425                 430

Glu Gly Arg Leu Val Tyr Arg Tyr Gly Gly Glu Pro Val Gly Ser Phe
        435                 440                 445

Val Gln Pro Cys Leu Arg Pro Leu Met Pro Ala Ile Ala His Ala Leu
    450                 455                 460

Phe Met Asp Ile Thr His Asp Asn Glu Cys Pro Ile Val His Arg Ser
465                 470                 475                 480

Ala Tyr Asp Ala Leu Pro Ser Thr Thr Ile Val Ser Met Ala Cys Cys
                485                 490                 495

Ala Ser Gly Ser Thr Arg Gly Tyr Asp Glu Leu Val Pro His Gln Ile
            500                 505                 510

Ser Val Val Ser Glu Glu Arg Phe Tyr Thr Lys Trp Asn Pro Glu Ala
        515                 520                 525

Leu Pro Ser Asn Thr Gly Glu Val Asn Phe Gln Ser Gly Ile Ile Ala
    530                 535                 540

Ala Arg Cys Ala Ile Ser Lys Leu His Gln Glu Leu Gly Ala Lys Gly
545                 550                 555                 560

Phe Ile Gln Val Tyr Val Asp Gln Val Asp Glu Asp Ile Val Ala Val
                565                 570                 575

Thr Arg His Ser Pro Ser Ile His Gln Ser Val Val Ala Val Thr Arg
            580                 585                 590

Thr Ala Phe Arg Asn Pro Lys Thr Ser Phe Tyr Ser Lys Glu Val Pro
        595                 600                 605

Gln Met Cys Ile Pro Gly Lys Ile Glu Glu Val Val Leu Glu Ala Arg
    610                 615                 620

Thr Ile Glu Arg Asn Thr Lys Pro Tyr Arg Lys Asp Glu Asn Ser Ile
625                 630                 635                 640

Asn Gly Thr Pro Asp Ile Thr Val Glu Ile Arg Glu His Ile Gln Leu
                645                 650                 655

Asn Glu Ser Lys Ile Val Lys Gln Ala Gly Val Ala Thr Lys Gly Pro
            660                 665                 670

Asn Glu Tyr Ile Gln Glu Ile Glu Phe Glu Asn Leu Ser Pro Gly Ser
        675                 680                 685

Val Ile Ile Phe Arg Val Ser Leu Asp Pro His Ala Gln Val Ala Val
    690                 695                 700

Gly Ile Leu Arg Asn His Leu Thr Gln Phe Ser Pro His Phe Lys Ser
705                 710                 715                 720

Gly Ser Leu Ala Val Asp Asn Ala Asp Pro Ile Leu Lys Ile Pro Phe
                725                 730                 735

Ala Ser Leu Ala Tyr Arg Leu Thr Leu Ala Glu Leu Asn Gln Ile Leu
            740                 745                 750

Tyr Arg Cys Glu Ser Glu Glu Lys Glu Asp Gly Gly Gly Cys Tyr Asp
        755                 760                 765

Ile Pro Asn Trp Ser Ala Leu Lys Tyr Ala Gly Leu Gln Gly Leu Met
    770                 775                 780
```

-continued

```
Ser Val Leu Ala Glu Ile Arg Pro Lys Asn Asp Leu Gly His Pro Phe
785                 790                 795                 800

Cys Asn Asn Leu Arg Ser Gly Asp Trp Met Ile Asp Tyr Val Ser Asn
                805                 810                 815

Arg Leu Ile Ser Arg Ser Gly Thr Ile Ala Glu Val Gly Lys Trp Leu
            820                 825                 830

Gln Ala Met Phe Phe Tyr Leu Lys Gln Ile Pro Arg Tyr Leu Ile Pro
        835                 840                 845

Cys Tyr Phe Asp Ala Ile Leu Ile Gly Ala Tyr Thr Thr Leu Leu Asp
    850                 855                 860

Thr Ala Trp Lys Gln Met Ser Ser Phe Val Gln Asn Gly Ser Thr Phe
865                 870                 875                 880

Val Lys His Leu Ser Leu Gly Ser Val Gln Leu Cys Gly Val Gly Lys
                885                 890                 895

Phe Pro Ser Leu Pro Ile Leu Ser Pro Ala Leu Met Asp Val Pro Tyr
            900                 905                 910

Arg Leu Asn Glu Ile Thr Lys Glu Lys Glu Gln Cys Cys Val Ser Leu
        915                 920                 925

Ala Ala Gly Leu Pro His Phe Ser Ser Gly Ile Phe Arg Cys Trp Gly
    930                 935                 940

Arg Asp Thr Phe Ile Ala Leu Arg Gly Ile Leu Leu Ile Thr Gly Arg
945                 950                 955                 960

Tyr Val Glu Ala Arg Asn Ile Ile Leu Ala Phe Ala Gly Thr Leu Arg
                965                 970                 975

His Gly Leu Ile Pro Asn Leu Leu Gly Glu Gly Ile Tyr Ala Arg Tyr
            980                 985                 990

Asn Cys Arg Asp Ala Val Trp Trp  Trp Leu Gln Cys Ile  Gln Asp Tyr
        995                 1000                1005

Cys Lys  Met Val Pro Asn Gly  Leu Asp Ile Leu Lys  Cys Pro Val
    1010                1015                1020

Ser Arg  Met Tyr Pro Thr Asp  Asp Ser Ala Pro Leu  Pro Ala Gly
    1025                1030                1035

Thr Leu  Asp Gln Pro Leu Phe  Glu Val Ile Gln Glu  Ala Met Gln
    1040                1045                1050

Lys His  Met Gln Gly Ile Gln  Phe Arg Glu Arg Asn  Ala Gly Pro
    1055                1060                1065

Gln Ile  Asp Arg Asn Met Lys  Asp Glu Gly Phe Asn  Ile Thr Ala
    1070                1075                1080

Gly Val  Asp Glu Glu Thr Gly  Phe Val Tyr Gly Gly  Asn Arg Phe
    1085                1090                1095

Asn Cys  Gly Thr Trp Met Asp  Lys Met Gly Glu Ser  Asp Arg Ala
    1100                1105                1110

Arg Asn  Arg Gly Ile Pro Ala  Thr Pro Arg Asp Gly  Ser Ala Val
    1115                1120                1125

Glu Ile  Val Gly Leu Ser Lys  Ser Ala Val Arg Trp  Leu Leu Glu
    1130                1135                1140

Leu Ser  Lys Lys Asn Ile Phe  Pro Tyr His Glu Val  Thr Val Lys
    1145                1150                1155

Arg His  Gly Lys Ala Ile Lys  Val Ser Tyr Asp Glu  Trp Asn Arg
    1160                1165                1170

Lys Ile  Gln Asp Asn Phe Glu  Lys Leu Phe His Val  Ser Glu Asp
    1175                1180                1185

Pro Ser  Asp Leu Asn Glu Lys  His Pro Asn Leu Val  His Lys Arg
```

```
    1190                1195                1200

Gly Ile  Tyr Lys Asp Ser Tyr  Gly Ala Ser Ser Pro  Trp Cys Asp
    1205                1210                1215

Tyr Gln  Leu Arg Pro Asn Phe  Thr Ile Ala Met Val  Val Ala Pro
    1220                1225                1230

Glu Leu  Phe Thr Thr Glu Lys  Ala Trp Lys Ala Leu  Glu Ile Ala
    1235                1240                1245

Glu Lys  Lys Leu Leu Gly Pro  Leu Gly Met Lys Thr  Leu Asp Pro
    1250                1255                1260

Asp Asp  Met Val Tyr Cys Gly  Ile Tyr Asp Asn Ala  Leu Asp Asn
    1265                1270                1275

Asp Asn  Tyr Asn Leu Ala Lys  Gly Phe Asn Tyr His  Gln Gly Pro
    1280                1285                1290

Glu Trp  Leu Trp Pro Ile Gly  Tyr Phe Leu Arg Ala  Lys Leu Tyr
    1295                1300                1305

Phe Ser  Arg Leu Met Gly Pro  Glu Thr Thr Ala Lys  Thr Ile Val
    1310                1315                1320

Leu Val  Lys Asn Val Leu Ser  Arg His Tyr Val His  Leu Glu Arg
    1325                1330                1335

Ser Pro  Trp Lys Gly Leu Pro  Glu Leu Thr Asn Glu  Asn Ala Gln
    1340                1345                1350

Tyr Cys  Pro Phe Ser Cys Glu  Thr Gln Ala Trp Ser  Ile Ala Thr
    1355                1360                1365

Ile Leu  Glu Thr Leu Tyr Asp  Leu
    1370                1375


<210> SEQ ID NO 3
<211> LENGTH: 1464
<212> TYPE: PRT
<213> ORGANISM: artificial
<220> FEATURE:
<223> OTHER INFORMATION: D2 hGDE

<400> SEQUENCE: 3

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
```

```
            165                 170                 175

Asn Gln Leu Glu Leu Asn Pro Asp Phe Ser Arg Pro Asn Arg Lys Tyr
        180                 185                 190

Thr Trp Asn Asp Val Gly Gln Leu Val Glu Lys Leu Lys Lys Glu Trp
    195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
            245                 250                 255

Phe Ser Cys Asp Val Ala Glu Gly Lys Tyr Lys Glu Lys Gly Ile Pro
        260                 265                 270

Ala Leu Ile Glu Asn Asp His His Met Asn Ser Ile Arg Lys Ile Ile
    275                 280                 285

Trp Glu Asp Ile Phe Pro Lys Leu Lys Leu Trp Glu Phe Phe Gln Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
            325                 330                 335

Gln Asp Pro Glu Tyr Arg Arg Phe Gly Cys Thr Val Asp Met Asn Ile
        340                 345                 350

Ala Leu Thr Thr Phe Ile Pro His Tyr Phe Thr Phe Pro Phe Glu Glu
    355                 360                 365

Ile Asp Phe Ser Met Glu Glu Ser Met Ile His Leu Pro Asn Lys Ala
    370                 375                 380

Cys Phe Leu Met Ala His Asn Gly Trp Val Met Gly Asp Asp Pro Leu
385                 390                 395                 400

Arg Asn Phe Ala Glu Pro Gly Ser Glu Val Tyr Leu Arg Arg Glu Leu
            405                 410                 415

Ile Cys Trp Gly Asp Ser Val Lys Leu Arg Tyr Gly Asn Lys Pro Glu
        420                 425                 430

Asp Cys Pro Tyr Leu Trp Ala His Met Lys Lys Tyr Thr Glu Ile Thr
    435                 440                 445

Ala Thr Tyr Phe Gln Gly Val Arg Leu Asp Asn Cys His Ser Thr Pro
    450                 455                 460

Leu His Val Ala Glu Tyr Met Leu Asp Ala Ala Arg Asn Leu Gln Pro
465                 470                 475                 480

Asn Leu Tyr Val Val Ala Glu Leu Phe Thr Gly Ser Glu Asp Leu Asp
            485                 490                 495

Asn Val Phe Val Thr Arg Leu Gly Ile Ser Ser Leu Ile Arg Glu Ala
        500                 505                 510

Met Ser Ala Tyr Asn Ser His Glu Glu Gly Arg Leu Val Tyr Arg Tyr
    515                 520                 525

Gly Gly Glu Pro Val Gly Ser Phe Val Gln Pro Cys Leu Arg Pro Leu
    530                 535                 540

Met Pro Ala Ile Ala His Ala Leu Phe Met Asp Ile Thr His Asp Asn
545                 550                 555                 560

Glu Cys Pro Ile Val His Arg Ser Ala Tyr Asp Ala Leu Pro Ser Thr
            565                 570                 575

Thr Ile Val Ser Met Ala Cys Cys Ala Ser Gly Ser Thr Arg Gly Tyr
        580                 585                 590
```

```
Asp Glu Leu Val Pro His Gln Ile Ser Val Val Ser Glu Glu Arg Phe
        595                 600                 605

Tyr Thr Lys Trp Asn Pro Glu Ala Leu Pro Ser Asn Thr Gly Glu Val
    610                 615                 620

Asn Phe Gln Ser Gly Ile Ile Ala Ala Arg Cys Ala Ile Ser Lys Leu
625                 630                 635                 640

His Gln Glu Leu Gly Ala Lys Gly Phe Ile Gln Val Tyr Val Asp Gln
                645                 650                 655

Val Asp Glu Asp Ile Val Ala Val Thr Arg His Ser Pro Ser Ile His
            660                 665                 670

Gln Ser Val Val Ala Val Thr Arg Thr Ala Phe Arg Asn Pro Lys Thr
        675                 680                 685

Ser Phe Tyr Ser Lys Glu Val Pro Gln Met Cys Ile Pro Gly Lys Ile
    690                 695                 700

Glu Glu Val Val Leu Glu Ala Arg Thr Ile Glu Arg Asn Thr Lys Pro
705                 710                 715                 720

Tyr Arg Lys Asp Glu Asn Ser Ile Asn Gly Thr Pro Asp Ile Thr Val
                725                 730                 735

Glu Ile Arg Glu His Ile Gln Leu Asn Glu Ser Lys Ile Val Lys Gln
            740                 745                 750

Ala Gly Val Ala Thr Lys Gly Pro Asn Glu Tyr Ile Gln Glu Ile Glu
        755                 760                 765

Phe Glu Asn Leu Ser Pro Gly Ser Val Ile Ile Phe Arg Val Ser Leu
    770                 775                 780

Asp Pro His Ala Gln Val Ala Val Gly Ile Leu Arg Asn His Leu Thr
785                 790                 795                 800

Gln Phe Ser Pro His Phe Lys Ser Gly Ser Leu Ala Val Asp Asn Ala
                805                 810                 815

Asp Pro Ile Leu Lys Ile Pro Phe Ala Ser Leu Ala Tyr Arg Leu Thr
            820                 825                 830

Leu Ala Glu Leu Asn Gln Ile Leu Tyr Arg Cys Glu Ser Glu Glu Lys
        835                 840                 845

Glu Asp Gly Gly Gly Cys Tyr Asp Ile Pro Asn Trp Ser Ala Leu Lys
    850                 855                 860

Tyr Ala Gly Leu Gln Gly Leu Met Ser Val Leu Ala Glu Ile Arg Pro
865                 870                 875                 880

Lys Asn Asp Leu Gly His Pro Phe Cys Asn Asn Leu Arg Ser Gly Asp
                885                 890                 895

Trp Met Ile Asp Tyr Val Ser Asn Arg Leu Ile Ser Arg Ser Gly Thr
            900                 905                 910

Ile Ala Glu Val Gly Lys Trp Leu Gln Ala Met Phe Phe Tyr Leu Lys
        915                 920                 925

Gln Ile Pro Arg Tyr Leu Ile Pro Cys Tyr Phe Asp Ala Ile Leu Ile
    930                 935                 940

Gly Ala Tyr Thr Thr Leu Leu Asp Thr Ala Trp Lys Gln Met Ser Ser
945                 950                 955                 960

Phe Val Gln Asn Gly Ser Thr Phe Val Lys His Leu Ser Leu Gly Ser
                965                 970                 975

Val Gln Leu Cys Gly Val Gly Lys Phe Pro Ser Leu Pro Ile Leu Ser
            980                 985                 990

Pro Ala Leu Met Asp Val Pro Tyr  Arg Leu Asn Glu Ile  Thr Lys Glu
        995                 1000                1005
```

```
Lys Glu  Gln Cys Cys Val Ser  Leu Ala Ala Gly Leu  Pro His Phe
    1010                 1015                 1020

Ser Ser  Gly Ile Phe Arg Cys  Trp Gly Arg Asp Thr  Phe Ile Ala
    1025                 1030                 1035

Leu Arg  Gly Ile Leu Leu Ile  Thr Gly Arg Tyr Val  Glu Ala Arg
    1040                 1045                 1050

Asn Ile  Ile Leu Ala Phe Ala  Gly Thr Leu Arg His  Gly Leu Ile
    1055                 1060                 1065

Pro Asn  Leu Leu Gly Glu Gly  Ile Tyr Ala Arg Tyr  Asn Cys Arg
    1070                 1075                 1080

Asp Ala  Val Trp Trp Trp Leu  Gln Cys Ile Gln Asp  Tyr Cys Lys
    1085                 1090                 1095

Met Val  Pro Asn Gly Leu Asp  Ile Leu Lys Cys Pro  Val Ser Arg
    1100                 1105                 1110

Met Tyr  Pro Thr Asp Asp Ser  Ala Pro Leu Pro Ala  Gly Thr Leu
    1115                 1120                 1125

Asp Gln  Pro Leu Phe Glu Val  Ile Gln Glu Ala Met  Gln Lys His
    1130                 1135                 1140

Met Gln  Gly Ile Gln Phe Arg  Glu Arg Asn Ala Gly  Pro Gln Ile
    1145                 1150                 1155

Asp Arg  Asn Met Lys Asp Glu  Gly Phe Asn Ile Thr  Ala Gly Val
    1160                 1165                 1170

Asp Glu  Glu Thr Gly Phe Val  Tyr Gly Gly Asn Arg  Phe Asn Cys
    1175                 1180                 1185

Gly Thr  Trp Met Asp Lys Met  Gly Glu Ser Asp Arg  Ala Arg Asn
    1190                 1195                 1200

Arg Gly  Ile Pro Ala Thr Pro  Arg Asp Gly Ser Ala  Val Glu Ile
    1205                 1210                 1215

Val Gly  Leu Ser Lys Ser Ala  Val Arg Trp Leu Leu  Glu Leu Ser
    1220                 1225                 1230

Lys Lys  Asn Ile Phe Pro Tyr  His Glu Val Thr Val  Lys Arg His
    1235                 1240                 1245

Gly Lys  Ala Ile Lys Val Ser  Tyr Asp Glu Trp Asn  Arg Lys Ile
    1250                 1255                 1260

Gln Asp  Asn Phe Glu Lys Leu  Phe His Val Ser Glu  Asp Pro Ser
    1265                 1270                 1275

Asp Leu  Asn Glu Lys His Pro  Asn Leu Val His Lys  Arg Gly Ile
    1280                 1285                 1290

Tyr Lys  Asp Ser Tyr Gly Ala  Ser Ser Pro Trp Cys  Asp Tyr Gln
    1295                 1300                 1305

Leu Arg  Pro Asn Phe Thr Ile  Ala Met Val Val Ala  Pro Glu Leu
    1310                 1315                 1320

Phe Thr  Thr Glu Lys Ala Trp  Lys Ala Leu Glu Ile  Ala Glu Lys
    1325                 1330                 1335

Lys Leu  Leu Gly Pro Leu Gly  Met Lys Thr Leu Asp  Pro Asp Asp
    1340                 1345                 1350

Met Val  Tyr Cys Gly Ile Tyr  Asp Asn Ala Leu Asp  Asn Asp Asn
    1355                 1360                 1365

Tyr Asn  Leu Ala Lys Gly Phe  Asn Tyr His Gln Gly  Pro Glu Trp
    1370                 1375                 1380

Leu Trp  Pro Ile Gly Tyr Phe  Leu Arg Ala Lys Leu  Tyr Phe Ser
    1385                 1390                 1395

Arg Leu  Met Gly Pro Glu Thr  Thr Ala Lys Thr Ile  Val Leu Val
```

-continued

```
    1400                1405                1410

Lys Asn  Val Leu Ser Arg His  Tyr Val His Leu Glu  Arg Ser Pro
    1415                1420                1425

Trp Lys  Gly Leu Pro Glu Leu  Thr Asn Glu Asn Ala  Gln Tyr Cys
    1430                1435                1440

Pro Phe  Ser Cys Glu Thr Gln  Ala Trp Ser Ile Ala  Thr Ile Leu
    1445                1450                1455

Glu Thr  Leu Tyr Asp Leu
    1460


<210> SEQ ID NO 4
<211> LENGTH: 1430
<212> TYPE: PRT
<213> ORGANISM: artificial
<220> FEATURE:
<223> OTHER INFORMATION: D3 hGDE

<400> SEQUENCE: 4

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
```

```
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Lys Gly Pro Ala Ala Ile Glu
        355                 360                 365

Glu Cys Cys Asn Trp Phe His Lys Arg Met Glu Glu Leu Asn Ser Glu
    370                 375                 380

Lys His Arg Leu Ile Asn Tyr His Gln Glu Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Ile Asp Phe Ser Met Glu Glu Ser Met Ile His Leu
        435                 440                 445

Pro Asn Lys Ala Cys Phe Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asn Ser His Glu Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Gly Lys Ile Glu Glu
            660                 665                 670

Val Val Leu Glu Ala Arg Thr Ile Glu Arg Asn Thr Lys Pro Tyr Arg
        675                 680                 685

Lys Asp Glu Asn Ser Ile Asn Gly Thr Pro Asp Ile Thr Val Glu Ile
    690                 695                 700

Arg Glu His Ile Gln Leu Asn Glu Ser Lys Ile Val Lys Gln Ala Gly
705                 710                 715                 720
```

```
Val Ala Thr Lys Gly Pro Asn Glu Tyr Ile Gln Glu Ile Glu Phe Glu
                725                 730                 735

Asn Leu Ser Pro Gly Ser Val Ile Ile Phe Arg Val Ser Leu Asp Pro
            740                 745                 750

His Ala Gln Val Ala Val Gly Ile Leu Arg Asn His Leu Thr Gln Phe
        755                 760                 765

Ser Pro His Phe Lys Ser Gly Ser Leu Ala Val Asp Asn Ala Asp Pro
    770                 775                 780

Ile Leu Lys Ile Pro Phe Ala Ser Leu Ala Tyr Arg Leu Thr Leu Ala
785                 790                 795                 800

Glu Leu Asn Gln Ile Leu Tyr Arg Cys Glu Ser Glu Glu Lys Glu Asp
                805                 810                 815

Gly Gly Gly Cys Tyr Asp Ile Pro Asn Trp Ser Ala Leu Lys Tyr Ala
            820                 825                 830

Gly Leu Gln Gly Leu Met Ser Val Leu Ala Glu Ile Arg Pro Lys Asn
        835                 840                 845

Asp Leu Gly His Pro Phe Cys Asn Asn Leu Arg Ser Gly Asp Trp Met
    850                 855                 860

Ile Asp Tyr Val Ser Asn Arg Leu Ile Ser Arg Ser Gly Thr Ile Ala
865                 870                 875                 880

Glu Val Gly Lys Trp Leu Gln Ala Met Phe Phe Tyr Leu Lys Gln Ile
                885                 890                 895

Pro Arg Tyr Leu Ile Pro Cys Tyr Phe Asp Ala Ile Leu Ile Gly Ala
            900                 905                 910

Tyr Thr Thr Leu Leu Asp Thr Ala Trp Lys Gln Met Ser Ser Phe Val
        915                 920                 925

Gln Asn Gly Ser Thr Phe Val Lys His Leu Ser Leu Gly Ser Val Gln
    930                 935                 940

Leu Cys Gly Val Gly Lys Phe Pro Ser Leu Pro Ile Leu Ser Pro Ala
945                 950                 955                 960

Leu Met Asp Val Pro Tyr Arg Leu Asn Glu Ile Thr Lys Glu Lys Glu
                965                 970                 975

Gln Cys Cys Val Ser Leu Ala Ala Gly Leu Pro His Phe Ser Ser Gly
            980                 985                 990

Ile Phe Arg Cys Trp Gly Arg Asp  Thr Phe Ile Ala Leu  Arg Gly Ile
        995                 1000                1005

Leu Leu  Ile Thr Gly Arg Tyr  Val Glu Ala Arg Asn  Ile Ile Leu
    1010                1015                1020

Ala Phe  Ala Gly Thr Leu Arg  His Gly Leu Ile Pro  Asn Leu Leu
    1025                1030                1035

Gly Glu  Gly Ile Tyr Ala Arg  Tyr Asn Cys Arg Asp  Ala Val Trp
    1040                1045                1050

Trp Trp  Leu Gln Cys Ile Gln  Asp Tyr Cys Lys Met  Val Pro Asn
    1055                1060                1065

Gly Leu  Asp Ile Leu Lys Cys  Pro Val Ser Arg Met  Tyr Pro Thr
    1070                1075                1080

Asp Asp  Ser Ala Pro Leu Pro  Ala Gly Thr Leu Asp  Gln Pro Leu
    1085                1090                1095

Phe Glu  Val Ile Gln Glu Ala  Met Gln Lys His Met  Gln Gly Ile
    1100                1105                1110

Gln Phe  Arg Glu Arg Asn Ala  Gly Pro Gln Ile Asp  Arg Asn Met
    1115                1120                1125
```

```
Lys Asp  Glu Gly Phe Asn Ile  Thr Ala Gly Val Asp  Glu Glu Thr
    1130                 1135                 1140

Gly Phe  Val Tyr Gly Gly Asn  Arg Phe Asn Cys Gly  Thr Trp Met
    1145                 1150                 1155

Asp Lys  Met Gly Glu Ser Asp  Arg Ala Arg Asn Arg  Gly Ile Pro
    1160                 1165                 1170

Ala Thr  Pro Arg Asp Gly Ser  Ala Val Glu Ile Val  Gly Leu Ser
    1175                 1180                 1185

Lys Ser  Ala Val Arg Trp Leu  Leu Glu Leu Ser Lys  Lys Asn Ile
    1190                 1195                 1200

Phe Pro  Tyr His Glu Val Thr  Val Lys Arg His Gly  Lys Ala Ile
    1205                 1210                 1215

Lys Val  Ser Tyr Asp Glu Trp  Asn Arg Lys Ile Gln  Asp Asn Phe
    1220                 1225                 1230

Glu Lys  Leu Phe His Val Ser  Glu Asp Pro Ser Asp  Leu Asn Glu
    1235                 1240                 1245

Lys His  Pro Asn Leu Val His  Lys Arg Gly Ile Tyr  Lys Asp Ser
    1250                 1255                 1260

Tyr Gly  Ala Ser Ser Pro Trp  Cys Asp Tyr Gln Leu  Arg Pro Asn
    1265                 1270                 1275

Phe Thr  Ile Ala Met Val Val  Ala Pro Glu Leu Phe  Thr Thr Glu
    1280                 1285                 1290

Lys Ala  Trp Lys Ala Leu Glu  Ile Ala Glu Lys Lys  Leu Leu Gly
    1295                 1300                 1305

Pro Leu  Gly Met Lys Thr Leu  Asp Pro Asp Asp Met  Val Tyr Cys
    1310                 1315                 1320

Gly Ile  Tyr Asp Asn Ala Leu  Asp Asn Asp Asn Tyr  Asn Leu Ala
    1325                 1330                 1335

Lys Gly  Phe Asn Tyr His Gln  Gly Pro Glu Trp Leu  Trp Pro Ile
    1340                 1345                 1350

Gly Tyr  Phe Leu Arg Ala Lys  Leu Tyr Phe Ser Arg  Leu Met Gly
    1355                 1360                 1365

Pro Glu  Thr Thr Ala Lys Thr  Ile Val Leu Val Lys  Asn Val Leu
    1370                 1375                 1380

Ser Arg  His Tyr Val His Leu  Glu Arg Ser Pro Trp  Lys Gly Leu
    1385                 1390                 1395

Pro Glu  Leu Thr Asn Glu Asn  Ala Gln Tyr Cys Pro  Phe Ser Cys
    1400                 1405                 1410

Glu Thr  Gln Ala Trp Ser Ile  Ala Thr Ile Leu Glu  Thr Leu Tyr
    1415                 1420                 1425

Asp Leu
    1430
```

<210> SEQ ID NO 5
<211> LENGTH: 1362
<212> TYPE: PRT
<213> ORGANISM: artificial
<220> FEATURE:
<223> OTHER INFORMATION: D2,3 hGDE

<400> SEQUENCE: 5

```
Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30
```

```
Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Tyr Phe Thr Phe Pro Phe Glu Glu
        355                 360                 365

Ile Asp Phe Ser Met Glu Glu Ser Met Ile His Leu Pro Asn Lys Ala
    370                 375                 380

Cys Phe Leu Met Ala His Asn Gly Trp Val Met Gly Asp Asp Pro Leu
385                 390                 395                 400

Arg Asn Phe Ala Glu Pro Gly Ser Glu Val Tyr Leu Arg Arg Glu Leu
                405                 410                 415

Ile Cys Trp Gly Asp Ser Val Lys Leu Arg Tyr Gly Asn Lys Pro Glu
            420                 425                 430

Asp Cys Pro Tyr Leu Trp Ala His Met Lys Lys Tyr Thr Glu Ile Thr
        435                 440                 445

Ala Thr Tyr Phe Gln Gly Val Arg Leu Asp Asn Cys His Ser Thr Pro
```

```
    450                 455                 460

Leu His Val Ala Glu Tyr Met Leu Asp Ala Ala Arg Asn Leu Gln Pro
465                 470                 475                 480

Asn Leu Tyr Val Val Ala Glu Leu Phe Thr Gly Ser Glu Asp Leu Asp
                485                 490                 495

Asn Val Phe Val Thr Arg Leu Gly Ile Ser Ser Leu Ile Arg Glu Ala
            500                 505                 510

Met Ser Ala Tyr Asn Ser His Glu Glu Gly Arg Leu Val Tyr Arg Tyr
        515                 520                 525

Gly Gly Glu Pro Val Gly Ser Phe Val Gln Pro Cys Leu Arg Pro Leu
    530                 535                 540

Met Pro Ala Ile Ala His Ala Leu Phe Met Asp Ile Thr His Asp Asn
545                 550                 555                 560

Glu Cys Pro Ile Val His Arg Ser Ala Tyr Asp Ala Leu Pro Ser Thr
                565                 570                 575

Thr Ile Val Ser Met Ala Cys Cys Ala Ser Gly Ser Thr Arg Gly Tyr
            580                 585                 590

Asp Glu Leu Val Pro His Gln Gly Lys Ile Glu Glu Val Val Leu Glu
        595                 600                 605

Ala Arg Thr Ile Glu Arg Asn Thr Lys Pro Tyr Arg Lys Asp Glu Asn
    610                 615                 620

Ser Ile Asn Gly Thr Pro Asp Ile Thr Val Glu Ile Arg Glu His Ile
625                 630                 635                 640

Gln Leu Asn Glu Ser Lys Ile Val Lys Gln Ala Gly Val Ala Thr Lys
                645                 650                 655

Gly Pro Asn Glu Tyr Ile Gln Glu Ile Glu Phe Glu Asn Leu Ser Pro
            660                 665                 670

Gly Ser Val Ile Ile Phe Arg Val Ser Leu Asp Pro His Ala Gln Val
        675                 680                 685

Ala Val Gly Ile Leu Arg Asn His Leu Thr Gln Phe Ser Pro His Phe
    690                 695                 700

Lys Ser Gly Ser Leu Ala Val Asp Asn Ala Asp Pro Ile Leu Lys Ile
705                 710                 715                 720

Pro Phe Ala Ser Leu Ala Tyr Arg Leu Thr Leu Ala Glu Leu Asn Gln
                725                 730                 735

Ile Leu Tyr Arg Cys Glu Ser Glu Glu Lys Glu Asp Gly Gly Gly Cys
            740                 745                 750

Tyr Asp Ile Pro Asn Trp Ser Ala Leu Lys Tyr Ala Gly Leu Gln Gly
        755                 760                 765

Leu Met Ser Val Leu Ala Glu Ile Arg Pro Lys Asn Asp Leu Gly His
    770                 775                 780

Pro Phe Cys Asn Asn Leu Arg Ser Gly Asp Trp Met Ile Asp Tyr Val
785                 790                 795                 800

Ser Asn Arg Leu Ile Ser Arg Ser Gly Thr Ile Ala Glu Val Gly Lys
                805                 810                 815

Trp Leu Gln Ala Met Phe Phe Tyr Leu Lys Gln Ile Pro Arg Tyr Leu
            820                 825                 830

Ile Pro Cys Tyr Phe Asp Ala Ile Leu Ile Gly Ala Tyr Thr Thr Leu
        835                 840                 845

Leu Asp Thr Ala Trp Lys Gln Met Ser Ser Phe Val Gln Asn Gly Ser
    850                 855                 860

Thr Phe Val Lys His Leu Ser Leu Gly Ser Val Gln Leu Cys Gly Val
865                 870                 875                 880
```

-continued

```
Gly Lys Phe Pro Ser Leu Pro Ile Leu Ser Pro Ala Leu Met Asp Val
            885                 890                 895

Pro Tyr Arg Leu Asn Glu Ile Thr Lys Glu Lys Glu Gln Cys Cys Val
        900                 905                 910

Ser Leu Ala Ala Gly Leu Pro His Phe Ser Ser Gly Ile Phe Arg Cys
    915                 920                 925

Trp Gly Arg Asp Thr Phe Ile Ala Leu Arg Gly Ile Leu Leu Ile Thr
    930                 935                 940

Gly Arg Tyr Val Glu Ala Arg Asn Ile Ile Leu Ala Phe Ala Gly Thr
945                 950                 955                 960

Leu Arg His Gly Leu Ile Pro Asn Leu Leu Gly Glu Gly Ile Tyr Ala
            965                 970                 975

Arg Tyr Asn Cys Arg Asp Ala Val Trp Trp Trp Leu Gln Cys Ile Gln
        980                 985                 990

Asp Tyr Cys Lys Met Val Pro Asn  Gly Leu Asp Ile Leu  Lys Cys Pro
    995                 1000                1005

Val Ser  Arg Met Tyr Pro Thr  Asp Asp Ser Ala Pro  Leu Pro Ala
    1010                1015                1020

Gly Thr  Leu Asp Gln Pro Leu  Phe Glu Val Ile Gln  Glu Ala Met
    1025                1030                1035

Gln Lys  His Met Gln Gly Ile  Gln Phe Arg Glu Arg  Asn Ala Gly
    1040                1045                1050

Pro Gln  Ile Asp Arg Asn Met  Lys Asp Glu Gly Phe  Asn Ile Thr
    1055                1060                1065

Ala Gly  Val Asp Glu Glu Thr  Gly Phe Val Tyr Gly  Gly Asn Arg
    1070                1075                1080

Phe Asn  Cys Gly Thr Trp Met  Asp Lys Met Gly Glu  Ser Asp Arg
    1085                1090                1095

Ala Arg  Asn Arg Gly Ile Pro  Ala Thr Pro Arg Asp  Gly Ser Ala
    1100                1105                1110

Val Glu  Ile Val Gly Leu Ser  Lys Ser Ala Val Arg  Trp Leu Leu
    1115                1120                1125

Glu Leu  Ser Lys Lys Asn Ile  Phe Pro Tyr His Glu  Val Thr Val
    1130                1135                1140

Lys Arg  His Gly Lys Ala Ile  Lys Val Ser Tyr Asp  Glu Trp Asn
    1145                1150                1155

Arg Lys  Ile Gln Asp Asn Phe  Glu Lys Leu Phe His  Val Ser Glu
    1160                1165                1170

Asp Pro  Ser Asp Leu Asn Glu  Lys His Pro Asn Leu  Val His Lys
    1175                1180                1185

Arg Gly  Ile Tyr Lys Asp Ser  Tyr Gly Ala Ser Ser  Pro Trp Cys
    1190                1195                1200

Asp Tyr  Gln Leu Arg Pro Asn  Phe Thr Ile Ala Met  Val Val Ala
    1205                1210                1215

Pro Glu  Leu Phe Thr Thr Glu  Lys Ala Trp Lys Ala  Leu Glu Ile
    1220                1225                1230

Ala Glu  Lys Lys Leu Leu Gly  Pro Leu Gly Met Lys  Thr Leu Asp
    1235                1240                1245

Pro Asp  Asp Met Val Tyr Cys  Gly Ile Tyr Asp Asn  Ala Leu Asp
    1250                1255                1260

Asn Asp  Asn Tyr Asn Leu Ala  Lys Gly Phe Asn Tyr  His Gln Gly
    1265                1270                1275
```

```
Pro Glu  Trp Leu Trp Pro Ile  Gly Tyr Phe Leu Arg  Ala Lys Leu
    1280                 1285                 1290

Tyr Phe  Ser Arg Leu Met Gly  Pro Glu Thr Thr Ala  Lys Thr Ile
    1295                 1300                 1305

Val Leu  Val Lys Asn Val Leu  Ser Arg His Tyr Val  His Leu Glu
    1310                 1315                 1320

Arg Ser  Pro Trp Lys Gly Leu  Pro Glu Leu Thr Asn  Glu Asn Ala
    1325                 1330                 1335

Gln Tyr  Cys Pro Phe Ser Cys  Glu Thr Gln Ala Trp  Ser Ile Ala
    1340                 1345                 1350

Thr Ile  Leu Glu Thr Leu Tyr  Asp Leu
    1355                 1360


<210> SEQ ID NO 6
<211> LENGTH: 1339
<212> TYPE: PRT
<213> ORGANISM: artificial
<220> FEATURE:
<223> OTHER INFORMATION: D4 hGDE

<400> SEQUENCE: 6

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270
```

```
Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Lys Gly Pro Ala Ala Ile Glu
        355                 360                 365

Glu Cys Cys Asn Trp Phe His Lys Arg Met Glu Glu Leu Asn Ser Glu
    370                 375                 380

Lys His Arg Leu Ile Asn Tyr His Gln Glu Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Ile Asp Phe Ser Met Glu Glu Ser Met Ile His Leu
        435                 440                 445

Pro Asn Lys Ala Cys Phe Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asn Ser His Glu Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Ile Ser Val Val Ser
            660                 665                 670

Glu Glu Arg Phe Tyr Thr Lys Trp Asn Pro Glu Ala Leu Pro Ser Asn
        675                 680                 685

Thr Gly Glu Val Asn Phe Gln Ser Gly Ile Ile Ala Ala Arg Cys Ala
```

-continued

```
    690                 695                 700

Ile Ser Lys Leu His Gln Glu Leu Gly Ala Lys Gly Phe Ile Gln Val
705                 710                 715                 720

Tyr Val Asp Gln Val Asp Glu Asp Ile Val Ala Val Thr Arg His Ser
                725                 730                 735

Pro Ser Ile His Gln Ser Val Val Ala Val Thr Arg Thr Ala Phe Arg
            740                 745                 750

Asn Pro Lys Thr Ser Phe Tyr Ser Lys Glu Val Pro Gln Met Cys Ile
        755                 760                 765

Pro Gly Lys Ile Glu Glu Val Val Leu Glu Ala Arg Thr Ile Glu Arg
    770                 775                 780

Asn Thr Lys Pro Tyr Arg Lys Asp Glu Asn Ser Ile Asn Gly Thr Pro
785                 790                 795                 800

Asp Ile Thr Val Glu Ile Arg Glu His Ile Gln Leu Asn Glu Ser Lys
                805                 810                 815

Ile Val Lys Gln Ala Gly Val Ala Thr Lys Gly Pro Asn Glu Tyr Ile
            820                 825                 830

Gln Glu Ile Glu Phe Glu Asn Leu Ser Pro Gly Ser Val Ile Ile Phe
        835                 840                 845

Arg Val Ser Leu Asp Pro His Ala Gln Val Ala Val Gly Ile Leu Arg
    850                 855                 860

Asn His Leu Thr Gln Phe Ser Pro His Phe Lys Ser Gly Ser Leu Ala
865                 870                 875                 880

Val Asp Asn Ala Asp Pro Ile Leu Lys Ile Pro Phe Ala Ser Leu Pro
                885                 890                 895

His Phe Ser Ser Gly Ile Phe Arg Cys Trp Gly Arg Asp Thr Phe Ile
            900                 905                 910

Ala Leu Arg Gly Ile Leu Leu Ile Thr Gly Arg Tyr Val Glu Ala Arg
        915                 920                 925

Asn Ile Ile Leu Ala Phe Ala Gly Thr Leu Arg His Gly Leu Ile Pro
    930                 935                 940

Asn Leu Leu Gly Glu Gly Ile Tyr Ala Arg Tyr Asn Cys Arg Asp Ala
945                 950                 955                 960

Val Trp Trp Trp Leu Gln Cys Ile Gln Asp Tyr Cys Lys Met Val Pro
                965                 970                 975

Asn Gly Leu Asp Ile Leu Lys Cys Pro Val Ser Arg Met Tyr Pro Thr
            980                 985                 990

Asp Asp Ser Ala Pro Leu Pro Ala  Gly Thr Leu Asp Gln  Pro Leu Phe
        995                 1000                1005

Glu Val  Ile Gln Glu Ala Met  Gln Lys His Met Gln  Gly Ile Gln
    1010                1015                1020

Phe Arg  Glu Arg Asn Ala Gly  Pro Gln Ile Asp Arg  Asn Met Lys
    1025                1030                1035

Asp Glu  Gly Phe Asn Ile Thr  Ala Gly Val Asp Glu  Glu Thr Gly
    1040                1045                1050

Phe Val  Tyr Gly Gly Asn Arg  Phe Asn Cys Gly Thr  Trp Met Asp
    1055                1060                1065

Lys Met  Gly Glu Ser Asp Arg  Ala Arg Asn Arg Gly  Ile Pro Ala
    1070                1075                1080

Thr Pro  Arg Asp Gly Ser Ala  Val Glu Ile Val Gly  Leu Ser Lys
    1085                1090                1095

Ser Ala  Val Arg Trp Leu Leu  Glu Leu Ser Lys Lys  Asn Ile Phe
    1100                1105                1110
```

```
Pro Tyr  His Glu Val Thr Val  Lys Arg His Gly Lys  Ala Ile Lys
    1115                 1120                 1125

Val Ser  Tyr Asp Glu Trp Asn  Arg Lys Ile Gln Asp  Asn Phe Glu
    1130                 1135                 1140

Lys Leu  Phe His Val Ser Glu  Asp Pro Ser Asp Leu  Asn Glu Lys
    1145                 1150                 1155

His Pro  Asn Leu Val His Lys  Arg Gly Ile Tyr Lys  Asp Ser Tyr
    1160                 1165                 1170

Gly Ala  Ser Ser Pro Trp Cys  Asp Tyr Gln Leu Arg  Pro Asn Phe
    1175                 1180                 1185

Thr Ile  Ala Met Val Val Ala  Pro Glu Leu Phe Thr  Thr Glu Lys
    1190                 1195                 1200

Ala Trp  Lys Ala Leu Glu Ile  Ala Glu Lys Lys Leu  Leu Gly Pro
    1205                 1210                 1215

Leu Gly  Met Lys Thr Leu Asp  Pro Asp Asp Met Val  Tyr Cys Gly
    1220                 1225                 1230

Ile Tyr  Asp Asn Ala Leu Asp  Asn Asp Asn Tyr Asn  Leu Ala Lys
    1235                 1240                 1245

Gly Phe  Asn Tyr His Gln Gly  Pro Glu Trp Leu Trp  Pro Ile Gly
    1250                 1255                 1260

Tyr Phe  Leu Arg Ala Lys Leu  Tyr Phe Ser Arg Leu  Met Gly Pro
    1265                 1270                 1275

Glu Thr  Thr Ala Lys Thr Ile  Val Leu Val Lys Asn  Val Leu Ser
    1280                 1285                 1290

Arg His  Tyr Val His Leu Glu  Arg Ser Pro Trp Lys  Gly Leu Pro
    1295                 1300                 1305

Glu Leu  Thr Asn Glu Asn Ala  Gln Tyr Cys Pro Phe  Ser Cys Glu
    1310                 1315                 1320

Thr Gln  Ala Trp Ser Ile Ala  Thr Ile Leu Glu Thr  Leu Tyr Asp
    1325                 1330                 1335

Leu


<210> SEQ ID NO 7
<211> LENGTH: 1313
<212> TYPE: PRT
<213> ORGANISM: artificial
<220> FEATURE:
<223> OTHER INFORMATION: D5 hGDE

<400> SEQUENCE: 7

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110
```

-continued

```
Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Asn Arg
    210                 215                 220

Arg Val Thr Lys Ser Asp Pro Asn Gln His Leu Thr Ile Ile Gln Asp
225                 230                 235                 240

Pro Glu Tyr Arg Arg Phe Gly Cys Thr Val Asp Met Asn Ile Ala Leu
                245                 250                 255

Thr Thr Phe Ile Pro Tyr Phe Thr Phe Pro Phe Glu Glu Ile Asp Phe
            260                 265                 270

Ser Met Glu Glu Ser Met Ile His Leu Pro Asn Lys Ala Cys Phe Leu
        275                 280                 285

Met Ala His Asn Gly Trp Val Met Gly Asp Asp Pro Leu Arg Asn Phe
    290                 295                 300

Ala Glu Pro Gly Ser Glu Val Tyr Leu Arg Arg Glu Leu Ile Cys Trp
305                 310                 315                 320

Gly Asp Ser Val Lys Leu Arg Tyr Gly Asn Lys Pro Glu Asp Cys Pro
                325                 330                 335

Tyr Leu Trp Ala His Met Lys Lys Tyr Thr Glu Ile Thr Ala Thr Tyr
            340                 345                 350

Phe Gln Gly Val Arg Leu Asp Asn Cys His Ser Thr Pro Leu His Val
        355                 360                 365

Ala Glu Tyr Met Leu Asp Ala Ala Arg Asn Leu Gln Pro Asn Leu Tyr
    370                 375                 380

Val Val Ala Glu Leu Phe Thr Gly Ser Glu Asp Leu Asp Asn Val Phe
385                 390                 395                 400

Val Thr Arg Leu Gly Ile Ser Ser Leu Ile Arg Glu Ala Met Ser Ala
                405                 410                 415

Tyr Asn Ser His Glu Glu Gly Arg Leu Val Tyr Arg Tyr Gly Gly Glu
            420                 425                 430

Pro Val Gly Ser Phe Val Gln Pro Cys Leu Arg Pro Leu Met Pro Ala
        435                 440                 445

Ile Ala His Ala Leu Phe Met Asp Ile Thr His Asp Asn Glu Cys Pro
    450                 455                 460

Ile Val His Arg Ser Ala Tyr Asp Ala Leu Pro Ser Thr Thr Ile Val
465                 470                 475                 480

Ser Met Ala Cys Cys Ala Ser Gly Ser Thr Arg Gly Tyr Asp Glu Leu
                485                 490                 495

Val Pro His Gln Ile Tyr Val Asp Gln Val Asp Glu Asp Ile Val Ala
            500                 505                 510

Val Thr Arg His Ser Pro Ser Ile His Gln Ser Val Val Ala Val Thr
        515                 520                 525

Arg Thr Ala Phe Arg Asn Pro Lys Thr Ser Phe Tyr Ser Lys Glu Val
```

```
    530                 535                 540

Pro Gln Met Cys Ile Pro Gly Lys Ile Glu Glu Val Val Leu Glu Ala
545                 550                 555                 560

Arg Thr Ile Glu Arg Asn Thr Lys Pro Tyr Arg Lys Asp Glu Asn Ser
                565                 570                 575

Ile Asn Gly Thr Pro Asp Ile Thr Val Glu Ile Arg Glu His Ile Gln
            580                 585                 590

Leu Asn Glu Ser Lys Ile Val Lys Gln Ala Gly Val Ala Thr Lys Gly
        595                 600                 605

Pro Asn Glu Tyr Ile Gln Glu Ile Glu Phe Glu Asn Leu Ser Pro Gly
    610                 615                 620

Ser Val Ile Ile Phe Arg Val Ser Leu Asp Pro His Ala Gln Val Ala
625                 630                 635                 640

Val Gly Ile Leu Arg Asn His Leu Thr Gln Phe Ser Pro His Phe Lys
                645                 650                 655

Ser Gly Ser Leu Ala Val Asp Asn Ala Asp Pro Ile Leu Lys Ile Pro
            660                 665                 670

Phe Ala Ser Leu Ala Tyr Arg Leu Thr Leu Ala Glu Leu Asn Gln Ile
        675                 680                 685

Leu Tyr Arg Cys Glu Ser Glu Glu Lys Glu Asp Gly Gly Gly Cys Tyr
    690                 695                 700

Asp Ile Pro Asn Trp Ser Ala Leu Lys Tyr Ala Gly Leu Gln Gly Leu
705                 710                 715                 720

Met Ser Val Leu Ala Glu Ile Arg Pro Lys Asn Asp Leu Gly His Pro
                725                 730                 735

Phe Cys Asn Asn Leu Arg Ser Gly Asp Trp Met Ile Asp Tyr Val Ser
            740                 745                 750

Asn Arg Leu Ile Ser Arg Ser Gly Thr Ile Ala Glu Val Gly Lys Trp
        755                 760                 765

Leu Gln Ala Met Phe Phe Tyr Leu Lys Gln Ile Pro Arg Tyr Leu Ile
    770                 775                 780

Pro Cys Tyr Phe Asp Ala Ile Leu Ile Gly Ala Tyr Thr Thr Leu Leu
785                 790                 795                 800

Asp Thr Ala Trp Lys Gln Met Ser Ser Phe Val Gln Asn Gly Ser Thr
                805                 810                 815

Phe Val Lys His Leu Ser Leu Gly Ser Val Gln Leu Cys Gly Val Gly
            820                 825                 830

Lys Phe Pro Ser Leu Pro Ile Leu Ser Pro Ala Leu Met Asp Val Pro
        835                 840                 845

Tyr Arg Leu Asn Glu Ile Thr Lys Glu Lys Glu Gln Cys Cys Val Ser
    850                 855                 860

Leu Ala Ala Gly Leu Pro His Phe Ser Ser Gly Ile Phe Arg Cys Trp
865                 870                 875                 880

Gly Arg Asp Thr Phe Ile Ala Leu Arg Gly Ile Leu Leu Ile Thr Gly
                885                 890                 895

Arg Tyr Val Glu Ala Arg Asn Ile Ile Leu Ala Phe Ala Gly Thr Leu
            900                 905                 910

Arg His Gly Leu Ile Pro Asn Leu Leu Gly Glu Gly Ile Tyr Ala Arg
        915                 920                 925

Tyr Asn Cys Arg Asp Ala Val Trp Trp Trp Leu Gln Cys Ile Gln Asp
    930                 935                 940

Tyr Cys Lys Met Val Pro Asn Gly Leu Asp Ile Leu Lys Cys Pro Val
945                 950                 955                 960
```

```
Ser Arg Met Tyr Pro Thr Asp Asp Ser Ala Pro Leu Pro Ala Gly Thr
                965                 970                 975

Leu Asp Gln Pro Leu Phe Glu Val Ile Gln Glu Ala Met Gln Lys His
            980                 985                 990

Met Gln Gly Ile Gln Phe Arg Glu  Arg Asn Ala Gly Pro  Gln Ile Asp
        995                 1000                1005

Arg Asn  Met Lys Asp Glu Gly  Phe Asn Ile Thr Ala  Gly Val Asp
    1010                 1015                 1020

Glu Glu  Thr Gly Phe Val Tyr  Gly Gly Asn Arg Phe  Asn Cys Gly
    1025                 1030                 1035

Thr Trp  Met Asp Lys Met Gly  Glu Ser Asp Arg Ala  Arg Asn Arg
    1040                 1045                 1050

Gly Ile  Pro Ala Thr Pro Arg  Asp Gly Ser Ala Val  Glu Ile Val
    1055                 1060                 1065

Gly Leu  Ser Lys Ser Ala Val  Arg Trp Leu Leu Glu  Leu Ser Lys
    1070                 1075                 1080

Lys Asn  Ile Phe Pro Tyr His  Glu Val Thr Val Lys  Arg His Gly
    1085                 1090                 1095

Lys Ala  Ile Lys Val Ser Tyr  Asp Glu Trp Asn Arg  Lys Ile Gln
    1100                 1105                 1110

Asp Asn  Phe Glu Lys Leu Phe  His Val Ser Glu Asp  Pro Ser Asp
    1115                 1120                 1125

Leu Asn  Glu Lys His Pro Asn  Leu Val His Lys Arg  Gly Ile Tyr
    1130                 1135                 1140

Lys Asp  Ser Tyr Gly Ala Ser  Ser Pro Trp Cys Asp  Tyr Gln Leu
    1145                 1150                 1155

Arg Pro  Asn Phe Thr Ile Ala  Met Val Val Ala Pro  Glu Leu Phe
    1160                 1165                 1170

Thr Thr  Glu Lys Ala Trp Lys  Ala Leu Glu Ile Ala  Glu Lys Lys
    1175                 1180                 1185

Leu Leu  Gly Pro Leu Gly Met  Lys Thr Leu Asp Pro  Asp Asp Met
    1190                 1195                 1200

Val Tyr  Cys Gly Ile Tyr Asp  Asn Ala Leu Asp Asn  Asp Asn Tyr
    1205                 1210                 1215

Asn Leu  Ala Lys Gly Phe Asn  Tyr His Gln Gly Pro  Glu Trp Leu
    1220                 1225                 1230

Trp Pro  Ile Gly Tyr Phe Leu  Arg Ala Lys Leu Tyr  Phe Ser Arg
    1235                 1240                 1245

Leu Met  Gly Pro Glu Thr Thr  Ala Lys Thr Ile Val  Leu Val Lys
    1250                 1255                 1260

Asn Val  Leu Ser Arg His Tyr  Val His Leu Glu Arg  Ser Pro Trp
    1265                 1270                 1275

Lys Gly  Leu Pro Glu Leu Thr  Asn Glu Asn Ala Gln  Tyr Cys Pro
    1280                 1285                 1290

Phe Ser  Cys Glu Thr Gln Ala  Trp Ser Ile Ala Thr  Ile Leu Glu
    1295                 1300                 1305

Thr Leu  Tyr Asp Leu
    1310
```

<210> SEQ ID NO 8
<211> LENGTH: 1252
<212> TYPE: PRT
<213> ORGANISM: artificial
<220> FEATURE:

<223> OTHER INFORMATION: D6 hGDE

<400> SEQUENCE: 8

```
Met Asn Ser Ile Arg Lys Ile Ile Trp Glu Asp Ile Phe Pro Lys Leu
1               5                   10                  15

Lys Leu Trp Glu Phe Phe Gln Val Asp Val Asn Lys Ala Val Glu Gln
            20                  25                  30

Phe Arg Arg Leu Leu Thr Gln Glu Asn Arg Arg Val Thr Lys Ser Asp
        35                  40                  45

Pro Asn Gln His Leu Thr Ile Ile Gln Asp Pro Glu Tyr Arg Arg Phe
    50                  55                  60

Gly Cys Thr Val Asp Met Asn Ile Ala Leu Thr Thr Phe Ile Pro His
65                  70                  75                  80

Asp Lys Gly Pro Ala Ala Ile Glu Glu Cys Cys Asn Trp Phe His Lys
                85                  90                  95

Arg Met Glu Glu Leu Asn Ser Glu Lys His Arg Leu Ile Asn Tyr His
            100                 105                 110

Gln Glu Gln Ala Val Asn Cys Leu Leu Gly Asn Val Phe Tyr Glu Arg
        115                 120                 125

Leu Ala Gly His Gly Pro Lys Leu Gly Pro Val Thr Arg Lys His Pro
    130                 135                 140

Leu Val Thr Arg Tyr Phe Thr Phe Pro Phe Glu Glu Ile Asp Phe Ser
145                 150                 155                 160

Met Glu Glu Ser Met Ile His Leu Pro Asn Lys Ala Cys Phe Leu Met
                165                 170                 175

Ala His Asn Gly Trp Val Met Gly Asp Asp Pro Leu Arg Asn Phe Ala
            180                 185                 190

Glu Pro Gly Ser Glu Val Tyr Leu Arg Arg Glu Leu Ile Cys Trp Gly
        195                 200                 205

Asp Ser Val Lys Leu Arg Tyr Gly Asn Lys Pro Glu Asp Cys Pro Tyr
    210                 215                 220

Leu Trp Ala His Met Lys Lys Tyr Thr Glu Ile Thr Ala Thr Tyr Phe
225                 230                 235                 240

Gln Gly Val Arg Leu Asp Asn Cys His Ser Thr Pro Leu His Val Ala
                245                 250                 255

Glu Tyr Met Leu Asp Ala Ala Arg Asn Leu Gln Pro Asn Leu Tyr Val
            260                 265                 270

Val Ala Glu Leu Phe Thr Gly Ser Glu Asp Leu Asp Asn Val Phe Val
        275                 280                 285

Thr Arg Leu Gly Ile Ser Ser Leu Ile Arg Glu Ala Met Ser Ala Tyr
    290                 295                 300

Asn Ser His Glu Glu Gly Arg Leu Val Tyr Arg Tyr Gly Gly Glu Pro
305                 310                 315                 320

Val Gly Ser Phe Val Gln Pro Cys Leu Arg Pro Leu Met Pro Ala Ile
                325                 330                 335

Ala His Ala Leu Phe Met Asp Ile Thr His Asp Asn Glu Cys Pro Ile
            340                 345                 350

Val His Arg Ser Ala Tyr Asp Ala Leu Pro Ser Thr Thr Ile Val Ser
        355                 360                 365

Met Ala Cys Cys Ala Ser Gly Ser Thr Arg Gly Tyr Asp Glu Leu Val
    370                 375                 380

Pro His Gln Ile Ser Val Val Ser Glu Glu Arg Phe Tyr Thr Lys Trp
385                 390                 395                 400
```

-continued

```
Asn Pro Glu Ala Leu Pro Ser Asn Thr Gly Glu Val Asn Phe Gln Ser
                405                 410                 415

Gly Ile Ile Ala Ala Arg Cys Ala Ile Ser Lys Leu His Gln Glu Leu
            420                 425                 430

Gly Ala Lys Gly Phe Ile Gln Val Tyr Val Asp Gln Val Asp Glu Asp
        435                 440                 445

Ile Val Ala Val Thr Arg His Ser Pro Ser Ile His Gln Ser Val Val
    450                 455                 460

Ala Val Thr Arg Thr Ala Phe Arg Asn Pro Lys Thr Ser Phe Tyr Ser
465                 470                 475                 480

Lys Glu Val Pro Gln Met Cys Ile Pro Gly Lys Ile Glu Glu Val Val
                485                 490                 495

Leu Glu Ala Arg Thr Ile Glu Arg Asn Thr Lys Pro Tyr Arg Lys Asp
            500                 505                 510

Glu Asn Ser Ile Asn Gly Thr Pro Asp Ile Thr Val Glu Ile Arg Glu
        515                 520                 525

His Ile Gln Leu Asn Glu Ser Lys Ile Val Lys Gln Ala Gly Val Ala
    530                 535                 540

Thr Lys Gly Pro Asn Glu Tyr Ile Gln Glu Ile Glu Phe Glu Asn Leu
545                 550                 555                 560

Ser Pro Gly Ser Val Ile Ile Phe Arg Val Ser Leu Asp Pro His Ala
                565                 570                 575

Gln Val Ala Val Gly Ile Leu Arg Asn His Leu Thr Gln Phe Ser Pro
            580                 585                 590

His Phe Lys Ser Gly Ser Leu Ala Val Asp Asn Ala Asp Pro Ile Leu
        595                 600                 605

Lys Ile Pro Phe Ala Ser Leu Ala Tyr Arg Leu Thr Leu Ala Glu Leu
    610                 615                 620

Asn Gln Ile Leu Tyr Arg Cys Glu Ser Glu Glu Lys Glu Asp Gly Gly
625                 630                 635                 640

Gly Cys Tyr Asp Ile Pro Asn Trp Ser Ala Leu Lys Tyr Ala Gly Leu
                645                 650                 655

Gln Gly Leu Met Ser Val Leu Ala Glu Ile Arg Pro Lys Asn Asp Leu
            660                 665                 670

Gly His Pro Phe Cys Asn Asn Leu Arg Ser Gly Asp Trp Met Ile Asp
        675                 680                 685

Tyr Val Ser Asn Arg Leu Ile Ser Arg Ser Gly Thr Ile Ala Glu Val
    690                 695                 700

Gly Lys Trp Leu Gln Ala Met Phe Phe Tyr Leu Lys Gln Ile Pro Arg
705                 710                 715                 720

Tyr Leu Ile Pro Cys Tyr Phe Asp Ala Ile Leu Ile Gly Ala Tyr Thr
                725                 730                 735

Thr Leu Leu Asp Thr Ala Trp Lys Gln Met Ser Ser Phe Val Gln Asn
            740                 745                 750

Gly Ser Thr Phe Val Lys His Leu Ser Leu Gly Ser Val Gln Leu Cys
        755                 760                 765

Gly Val Gly Lys Phe Pro Ser Leu Pro Ile Leu Ser Pro Ala Leu Met
    770                 775                 780

Asp Val Pro Tyr Arg Leu Asn Glu Ile Thr Lys Glu Lys Glu Gln Cys
785                 790                 795                 800

Cys Val Ser Leu Ala Ala Gly Leu Pro His Phe Ser Ser Gly Ile Phe
                805                 810                 815

Arg Cys Trp Gly Arg Asp Thr Phe Ile Ala Leu Arg Gly Ile Leu Leu
```

```
            820                 825                 830

Ile Thr Gly Arg Tyr Val Glu Ala Arg Asn Ile Ile Leu Ala Phe Ala
        835                 840                 845

Gly Thr Leu Arg His Gly Leu Ile Pro Asn Leu Leu Gly Glu Gly Ile
    850                 855                 860

Tyr Ala Arg Tyr Asn Cys Arg Asp Ala Val Trp Trp Trp Leu Gln Cys
865                 870                 875                 880

Ile Gln Asp Tyr Cys Lys Met Val Pro Asn Gly Leu Asp Ile Leu Lys
                885                 890                 895

Cys Pro Val Ser Arg Met Tyr Pro Thr Asp Asp Ser Ala Pro Leu Pro
            900                 905                 910

Ala Gly Thr Leu Asp Gln Pro Leu Phe Glu Val Ile Gln Glu Ala Met
        915                 920                 925

Gln Lys His Met Gln Gly Ile Gln Phe Arg Glu Arg Asn Ala Gly Pro
    930                 935                 940

Gln Ile Asp Arg Asn Met Lys Asp Glu Gly Phe Asn Ile Thr Ala Gly
945                 950                 955                 960

Val Asp Glu Glu Thr Gly Phe Val Tyr Gly Gly Asn Arg Phe Asn Cys
                965                 970                 975

Gly Thr Trp Met Asp Lys Met Gly Glu Ser Asp Arg Ala Arg Asn Arg
            980                 985                 990

Gly Ile Pro Ala Thr Pro Arg Asp  Gly Ser Ala Val Glu  Ile Val Gly
        995                 1000                1005

Leu Ser  Lys Ser Ala Val Arg  Trp Leu Leu Glu Leu  Ser Lys Lys
    1010                1015                1020

Asn Ile  Phe Pro Tyr His Glu  Val Thr Val Lys Arg  His Gly Lys
    1025                1030                1035

Ala Ile  Lys Val Ser Tyr Asp  Glu Trp Asn Arg Lys  Ile Gln Asp
    1040                1045                1050

Asn Phe  Glu Lys Leu Phe His  Val Ser Glu Asp Pro  Ser Asp Leu
    1055                1060                1065

Asn Glu  Lys His Pro Asn Leu  Val His Lys Arg Gly  Ile Tyr Lys
    1070                1075                1080

Asp Ser  Tyr Gly Ala Ser Ser  Pro Trp Cys Asp Tyr  Gln Leu Arg
    1085                1090                1095

Pro Asn  Phe Thr Ile Ala Met  Val Val Ala Pro Glu  Leu Phe Thr
    1100                1105                1110

Thr Glu  Lys Ala Trp Lys Ala  Leu Glu Ile Ala Glu  Lys Lys Leu
    1115                1120                1125

Leu Gly  Pro Leu Gly Met Lys  Thr Leu Asp Pro Asp  Asp Met Val
    1130                1135                1140

Tyr Cys  Gly Ile Tyr Asp Asn  Ala Leu Asp Asn Asp  Asn Tyr Asn
    1145                1150                1155

Leu Ala  Lys Gly Phe Asn Tyr  His Gln Gly Pro Glu  Trp Leu Trp
    1160                1165                1170

Pro Ile  Gly Tyr Phe Leu Arg  Ala Lys Leu Tyr Phe  Ser Arg Leu
    1175                1180                1185

Met Gly  Pro Glu Thr Thr Ala  Lys Thr Ile Val Leu  Val Lys Asn
    1190                1195                1200

Val Leu  Ser Arg His Tyr Val  His Leu Glu Arg Ser  Pro Trp Lys
    1205                1210                1215

Gly Leu  Pro Glu Leu Thr Asn  Glu Asn Ala Gln Tyr  Cys Pro Phe
    1220                1225                1230
```

```
Ser Cys  Glu Thr Gln Ala Trp  Ser Ile Ala Thr Ile  Leu Glu Thr
    1235                 1240                 1245

Leu Tyr  Asp Leu
    1250


<210> SEQ ID NO 9
<211> LENGTH: 1108
<212> TYPE: PRT
<213> ORGANISM: artificial
<220> FEATURE:
<223> OTHER INFORMATION: D7 hGDE

<400> SEQUENCE: 9

Met Val Thr Arg Tyr Phe Thr Phe Pro Phe Glu Glu Ile Asp Phe Ser
1               5                   10                  15

Met Glu Glu Ser Met Ile His Leu Pro Asn Lys Ala Cys Phe Leu Met
            20                  25                  30

Ala His Asn Gly Trp Val Met Gly Asp Asp Pro Leu Arg Asn Phe Ala
        35                  40                  45

Glu Pro Gly Ser Glu Val Tyr Leu Arg Arg Glu Leu Ile Cys Trp Gly
    50                  55                  60

Asp Ser Val Lys Leu Arg Tyr Gly Asn Lys Pro Glu Asp Cys Pro Tyr
65                  70                  75                  80

Leu Trp Ala His Met Lys Lys Tyr Thr Glu Ile Thr Ala Thr Tyr Phe
                85                  90                  95

Gln Gly Val Arg Leu Asp Asn Cys His Ser Thr Pro Leu His Val Ala
            100                 105                 110

Glu Tyr Met Leu Asp Ala Ala Arg Asn Leu Gln Pro Asn Leu Tyr Val
        115                 120                 125

Val Ala Glu Leu Phe Thr Gly Ser Glu Asp Leu Asp Asn Val Phe Val
    130                 135                 140

Thr Arg Leu Gly Ile Ser Ser Leu Ile Arg Glu Ala Met Ser Ala Tyr
145                 150                 155                 160

Asn Ser His Glu Glu Gly Arg Leu Val Tyr Arg Tyr Gly Gly Glu Pro
                165                 170                 175

Val Gly Ser Phe Val Gln Pro Cys Leu Arg Pro Leu Met Pro Ala Ile
            180                 185                 190

Ala His Ala Leu Phe Met Asp Ile Thr His Asp Asn Glu Cys Pro Ile
        195                 200                 205

Val His Arg Ser Ala Tyr Asp Ala Leu Pro Ser Thr Thr Ile Val Ser
    210                 215                 220

Met Ala Cys Cys Ala Ser Gly Ser Thr Arg Gly Tyr Asp Glu Leu Val
225                 230                 235                 240

Pro His Gln Ile Ser Val Val Ser Glu Glu Arg Phe Tyr Thr Lys Trp
                245                 250                 255

Asn Pro Glu Ala Leu Pro Ser Asn Thr Gly Glu Val Asn Phe Gln Ser
            260                 265                 270

Gly Ile Ile Ala Ala Arg Cys Ala Ile Ser Lys Leu His Gln Glu Leu
        275                 280                 285

Gly Ala Lys Gly Phe Ile Gln Val Tyr Val Asp Gln Val Asp Glu Asp
    290                 295                 300

Ile Val Ala Val Thr Arg His Ser Pro Ser Ile His Gln Ser Val Val
305                 310                 315                 320

Ala Val Thr Arg Thr Ala Phe Arg Asn Pro Lys Thr Ser Phe Tyr Ser
                325                 330                 335
```

```
Lys Glu Val Pro Gln Met Cys Ile Pro Gly Lys Ile Glu Glu Val Val
            340                 345                 350

Leu Glu Ala Arg Thr Ile Glu Arg Asn Thr Lys Pro Tyr Arg Lys Asp
        355                 360                 365

Glu Asn Ser Ile Asn Gly Thr Pro Asp Ile Thr Val Glu Ile Arg Glu
    370                 375                 380

His Ile Gln Leu Asn Glu Ser Lys Ile Val Lys Gln Ala Gly Val Ala
385                 390                 395                 400

Thr Lys Gly Pro Asn Glu Tyr Ile Gln Glu Ile Glu Phe Glu Asn Leu
                405                 410                 415

Ser Pro Gly Ser Val Ile Ile Phe Arg Val Ser Leu Asp Pro His Ala
            420                 425                 430

Gln Val Ala Val Gly Ile Leu Arg Asn His Leu Thr Gln Phe Ser Pro
        435                 440                 445

His Phe Lys Ser Gly Ser Leu Ala Val Asp Asn Ala Asp Pro Ile Leu
    450                 455                 460

Lys Ile Pro Phe Ala Ser Leu Ala Tyr Arg Leu Thr Leu Ala Glu Leu
465                 470                 475                 480

Asn Gln Ile Leu Tyr Arg Cys Glu Ser Glu Glu Lys Glu Asp Gly Gly
                485                 490                 495

Gly Cys Tyr Asp Ile Pro Asn Trp Ser Ala Leu Lys Tyr Ala Gly Leu
            500                 505                 510

Gln Gly Leu Met Ser Val Leu Ala Glu Ile Arg Pro Lys Asn Asp Leu
        515                 520                 525

Gly His Pro Phe Cys Asn Asn Leu Arg Ser Gly Asp Trp Met Ile Asp
    530                 535                 540

Tyr Val Ser Asn Arg Leu Ile Ser Arg Ser Gly Thr Ile Ala Glu Val
545                 550                 555                 560

Gly Lys Trp Leu Gln Ala Met Phe Phe Tyr Leu Lys Gln Ile Pro Arg
                565                 570                 575

Tyr Leu Ile Pro Cys Tyr Phe Asp Ala Ile Leu Ile Gly Ala Tyr Thr
            580                 585                 590

Thr Leu Leu Asp Thr Ala Trp Lys Gln Met Ser Ser Phe Val Gln Asn
        595                 600                 605

Gly Ser Thr Phe Val Lys His Leu Ser Leu Gly Ser Val Gln Leu Cys
    610                 615                 620

Gly Val Gly Lys Phe Pro Ser Leu Pro Ile Leu Ser Pro Ala Leu Met
625                 630                 635                 640

Asp Val Pro Tyr Arg Leu Asn Glu Ile Thr Lys Glu Lys Glu Gln Cys
                645                 650                 655

Cys Val Ser Leu Ala Ala Gly Leu Pro His Phe Ser Ser Gly Ile Phe
            660                 665                 670

Arg Cys Trp Gly Arg Asp Thr Phe Ile Ala Leu Arg Gly Ile Leu Leu
        675                 680                 685

Ile Thr Gly Arg Tyr Val Glu Ala Arg Asn Ile Ile Leu Ala Phe Ala
    690                 695                 700

Gly Thr Leu Arg His Gly Leu Ile Pro Asn Leu Leu Gly Glu Gly Ile
705                 710                 715                 720

Tyr Ala Arg Tyr Asn Cys Arg Asp Ala Val Trp Trp Trp Leu Gln Cys
                725                 730                 735

Ile Gln Asp Tyr Cys Lys Met Val Pro Asn Gly Leu Asp Ile Leu Lys
            740                 745                 750
```

```
Cys Pro Val Ser Arg Met Tyr Pro Thr Asp Asp Ser Ala Pro Leu Pro
        755                 760                 765

Ala Gly Thr Leu Asp Gln Pro Leu Phe Glu Val Ile Gln Glu Ala Met
    770                 775                 780

Gln Lys His Met Gln Gly Ile Gln Phe Arg Glu Arg Asn Ala Gly Pro
785                 790                 795                 800

Gln Ile Asp Arg Asn Met Lys Asp Glu Gly Phe Asn Ile Thr Ala Gly
                805                 810                 815

Val Asp Glu Glu Thr Gly Phe Val Tyr Gly Gly Asn Arg Phe Asn Cys
            820                 825                 830

Gly Thr Trp Met Asp Lys Met Gly Glu Ser Asp Arg Ala Arg Asn Arg
        835                 840                 845

Gly Ile Pro Ala Thr Pro Arg Asp Gly Ser Ala Val Glu Ile Val Gly
    850                 855                 860

Leu Ser Lys Ser Ala Val Arg Trp Leu Leu Glu Leu Ser Lys Lys Asn
865                 870                 875                 880

Ile Phe Pro Tyr His Glu Val Thr Val Lys Arg His Gly Lys Ala Ile
                885                 890                 895

Lys Val Ser Tyr Asp Glu Trp Asn Arg Lys Ile Gln Asp Asn Phe Glu
            900                 905                 910

Lys Leu Phe His Val Ser Glu Asp Pro Ser Asp Leu Asn Glu Lys His
        915                 920                 925

Pro Asn Leu Val His Lys Arg Gly Ile Tyr Lys Asp Ser Tyr Gly Ala
    930                 935                 940

Ser Ser Pro Trp Cys Asp Tyr Gln Leu Arg Pro Asn Phe Thr Ile Ala
945                 950                 955                 960

Met Val Val Ala Pro Glu Leu Phe Thr Thr Glu Lys Ala Trp Lys Ala
                965                 970                 975

Leu Glu Ile Ala Glu Lys Lys Leu Leu Gly Pro Leu Gly Met Lys Thr
            980                 985                 990

Leu Asp Pro Asp Asp Met Val Tyr  Cys Gly Ile Tyr Asp  Asn Ala Leu
        995                 1000                1005

Asp Asn  Asp Asn Tyr Asn Leu  Ala Lys Gly Phe Asn  Tyr His Gln
    1010                1015                1020

Gly Pro  Glu Trp Leu Trp Pro  Ile Gly Tyr Phe Leu  Arg Ala Lys
    1025                1030                1035

Leu Tyr  Phe Ser Arg Leu Met  Gly Pro Glu Thr Thr  Ala Lys Thr
    1040                1045                1050

Ile Val  Leu Val Lys Asn Val  Leu Ser Arg His Tyr  Val His Leu
    1055                1060                1065

Glu Arg  Ser Pro Trp Lys Gly  Leu Pro Glu Leu Thr  Asn Glu Asn
    1070                1075                1080

Ala Gln  Tyr Cys Pro Phe Ser  Cys Glu Thr Gln Ala  Trp Ser Ile
    1085                1090                1095

Ala Thr  Ile Leu Glu Thr Leu  Tyr Asp Leu
    1100                1105
```

<210> SEQ ID NO 10
<211> LENGTH: 1303
<212> TYPE: PRT
<213> ORGANISM: artificial
<220> FEATURE:
<223> OTHER INFORMATION: D8 hGDE

<400> SEQUENCE: 10

```
Met His Pro Glu Cys Ala Tyr Asn Leu Val Asn Ser Pro His Leu Lys
1               5                   10                  15

Pro Ala Trp Val Leu Asp Arg Ala Leu Trp Arg Phe Ser Cys Asp Val
            20                  25                  30

Ala Glu Gly Lys Tyr Lys Glu Lys Gly Ile Pro Ala Leu Ile Glu Asn
        35                  40                  45

Asp His His Met Asn Ser Ile Arg Lys Ile Ile Trp Glu Asp Ile Phe
    50                  55                  60

Pro Lys Leu Lys Leu Trp Glu Phe Phe Gln Val Asp Val Asn Lys Ala
65                  70                  75                  80

Val Glu Gln Phe Arg Arg Leu Leu Thr Gln Glu Asn Arg Arg Val Thr
                85                  90                  95

Lys Ser Asp Pro Asn Gln His Leu Thr Ile Ile Gln Asp Pro Glu Tyr
            100                 105                 110

Arg Arg Phe Gly Cys Thr Val Asp Met Asn Ile Ala Leu Thr Thr Phe
        115                 120                 125

Ile Pro His Asp Lys Gly Pro Ala Ala Ile Glu Glu Cys Cys Asn Trp
    130                 135                 140

Phe His Lys Arg Met Glu Glu Leu Asn Ser Glu Lys His Arg Leu Ile
145                 150                 155                 160

Asn Tyr His Gln Glu Gln Ala Val Asn Cys Leu Leu Gly Asn Val Phe
                165                 170                 175

Tyr Glu Arg Leu Ala Gly His Gly Pro Lys Leu Gly Pro Val Thr Arg
            180                 185                 190

Lys His Pro Leu Val Thr Arg Tyr Phe Thr Phe Pro Phe Glu Glu Ile
        195                 200                 205

Asp Phe Ser Met Glu Glu Ser Met Ile His Leu Pro Asn Lys Ala Cys
    210                 215                 220

Phe Leu Met Ala His Asn Gly Trp Val Met Gly Asp Asp Pro Leu Arg
225                 230                 235                 240

Asn Phe Ala Glu Pro Gly Ser Glu Val Tyr Leu Arg Arg Glu Leu Ile
                245                 250                 255

Cys Trp Gly Asp Ser Val Lys Leu Arg Tyr Gly Asn Lys Pro Glu Asp
            260                 265                 270

Cys Pro Tyr Leu Trp Ala His Met Lys Lys Tyr Thr Glu Ile Thr Ala
        275                 280                 285

Thr Tyr Phe Gln Gly Val Arg Leu Asp Asn Cys His Ser Thr Pro Leu
    290                 295                 300

His Val Ala Glu Tyr Met Leu Asp Ala Ala Arg Asn Leu Gln Pro Asn
305                 310                 315                 320

Leu Tyr Val Val Ala Glu Leu Phe Thr Gly Ser Glu Asp Leu Asp Asn
                325                 330                 335

Val Phe Val Thr Arg Leu Gly Ile Ser Ser Leu Ile Arg Glu Ala Met
            340                 345                 350

Ser Ala Tyr Asn Ser His Glu Glu Gly Arg Leu Val Tyr Arg Tyr Gly
        355                 360                 365

Gly Glu Pro Val Gly Ser Phe Val Gln Pro Cys Leu Arg Pro Leu Met
    370                 375                 380

Pro Ala Ile Ala His Ala Leu Phe Met Asp Ile Thr His Asp Asn Glu
385                 390                 395                 400

Cys Pro Ile Val His Arg Ser Ala Tyr Asp Ala Leu Pro Ser Thr Thr
                405                 410                 415

Ile Val Ser Met Ala Cys Cys Ala Ser Gly Ser Thr Arg Gly Tyr Asp
```

```
            420                 425                 430

Glu Leu Val Pro His Gln Ile Ser Val Val Ser Glu Glu Arg Phe Tyr
        435                 440                 445

Thr Lys Trp Asn Pro Glu Ala Leu Pro Ser Asn Thr Gly Glu Val Asn
    450                 455                 460

Phe Gln Ser Gly Ile Ile Ala Ala Arg Cys Ala Ile Ser Lys Leu His
465                 470                 475                 480

Gln Glu Leu Gly Ala Lys Gly Phe Ile Gln Val Tyr Val Asp Gln Val
                485                 490                 495

Asp Glu Asp Ile Val Ala Val Thr Arg His Ser Pro Ser Ile His Gln
            500                 505                 510

Ser Val Val Ala Val Thr Arg Thr Ala Phe Arg Asn Pro Lys Thr Ser
        515                 520                 525

Phe Tyr Ser Lys Glu Val Pro Gln Met Cys Ile Pro Gly Lys Ile Glu
    530                 535                 540

Glu Val Val Leu Glu Ala Arg Thr Ile Glu Arg Asn Thr Lys Pro Tyr
545                 550                 555                 560

Arg Lys Asp Glu Asn Ser Ile Asn Gly Thr Pro Asp Ile Thr Val Glu
                565                 570                 575

Ile Arg Glu His Ile Gln Leu Asn Glu Ser Lys Ile Val Lys Gln Ala
            580                 585                 590

Gly Val Ala Thr Lys Gly Pro Asn Glu Tyr Ile Gln Glu Ile Glu Phe
        595                 600                 605

Glu Asn Leu Ser Pro Gly Ser Val Ile Ile Phe Arg Val Ser Leu Asp
    610                 615                 620

Pro His Ala Gln Val Ala Val Gly Ile Leu Arg Asn His Leu Thr Gln
625                 630                 635                 640

Phe Ser Pro His Phe Lys Ser Gly Ser Leu Ala Val Asp Asn Ala Asp
                645                 650                 655

Pro Ile Leu Lys Ile Pro Phe Ala Ser Leu Ala Tyr Arg Leu Thr Leu
            660                 665                 670

Ala Glu Leu Asn Gln Ile Leu Tyr Arg Cys Glu Ser Glu Glu Lys Glu
        675                 680                 685

Asp Gly Gly Gly Cys Tyr Asp Ile Pro Asn Trp Ser Ala Leu Lys Tyr
    690                 695                 700

Ala Gly Leu Gln Gly Leu Met Ser Val Leu Ala Glu Ile Arg Pro Lys
705                 710                 715                 720

Asn Asp Leu Gly His Pro Phe Cys Asn Asn Leu Arg Ser Gly Asp Trp
                725                 730                 735

Met Ile Asp Tyr Val Ser Asn Arg Leu Ile Ser Arg Ser Gly Thr Ile
            740                 745                 750

Ala Glu Val Gly Lys Trp Leu Gln Ala Met Phe Phe Tyr Leu Lys Gln
        755                 760                 765

Ile Pro Arg Tyr Leu Ile Pro Cys Tyr Phe Asp Ala Ile Leu Ile Gly
    770                 775                 780

Ala Tyr Thr Thr Leu Leu Asp Thr Ala Trp Lys Gln Met Ser Ser Phe
785                 790                 795                 800

Val Gln Asn Gly Ser Thr Phe Val Lys His Leu Ser Leu Gly Ser Val
                805                 810                 815

Gln Leu Cys Gly Val Gly Lys Phe Pro Ser Leu Pro Ile Leu Ser Pro
            820                 825                 830

Ala Leu Met Asp Val Pro Tyr Arg Leu Asn Glu Ile Thr Lys Glu Lys
        835                 840                 845
```

-continued

```
Glu Gln Cys Cys Val Ser Leu Ala Ala Gly Leu Pro His Phe Ser Ser
    850                 855                 860

Gly Ile Phe Arg Cys Trp Gly Arg Asp Thr Phe Ile Ala Leu Arg Gly
865                 870                 875                 880

Ile Leu Leu Ile Thr Gly Arg Tyr Val Glu Ala Arg Asn Ile Ile Leu
                885                 890                 895

Ala Phe Ala Gly Thr Leu Arg His Gly Leu Ile Pro Asn Leu Leu Gly
            900                 905                 910

Glu Gly Ile Tyr Ala Arg Tyr Asn Cys Arg Asp Ala Val Trp Trp Trp
        915                 920                 925

Leu Gln Cys Ile Gln Asp Tyr Cys Lys Met Val Pro Asn Gly Leu Asp
    930                 935                 940

Ile Leu Lys Cys Pro Val Ser Arg Met Tyr Pro Thr Asp Asp Ser Ala
945                 950                 955                 960

Pro Leu Pro Ala Gly Thr Leu Asp Gln Pro Leu Phe Glu Val Ile Gln
                965                 970                 975

Glu Ala Met Gln Lys His Met Gln Gly Ile Gln Phe Arg Glu Arg Asn
            980                 985                 990

Ala Gly Pro Gln Ile Asp Arg Asn  Met Lys Asp Glu Gly  Phe Asn Ile
        995                 1000                1005

Thr Ala  Gly Val Asp Glu Glu  Thr Gly Phe Val Tyr  Gly Gly Asn
    1010                1015                1020

Arg Phe  Asn Cys Gly Thr Trp  Met Asp Lys Met Gly  Glu Ser Asp
    1025                1030                1035

Arg Ala  Arg Asn Arg Gly Ile  Pro Ala Thr Pro Arg  Asp Gly Ser
    1040                1045                1050

Ala Val  Glu Ile Val Gly Leu  Ser Lys Ser Ala Val  Arg Trp Leu
    1055                1060                1065

Leu Glu  Leu Ser Lys Lys Asn  Ile Phe Pro Tyr His  Glu Val Thr
    1070                1075                1080

Val Lys  Arg His Gly Lys Ala  Ile Lys Val Ser Tyr  Asp Glu Trp
    1085                1090                1095

Asn Arg  Lys Ile Gln Asp Asn  Phe Glu Lys Leu Phe  His Val Ser
    1100                1105                1110

Glu Asp  Pro Ser Asp Leu Asn  Glu Lys His Pro Asn  Leu Val His
    1115                1120                1125

Lys Arg  Gly Ile Tyr Lys Asp  Ser Tyr Gly Ala Ser  Ser Pro Trp
    1130                1135                1140

Cys Asp  Tyr Gln Leu Arg Pro  Asn Phe Thr Ile Ala  Met Val Val
    1145                1150                1155

Ala Pro  Glu Leu Phe Thr Thr  Glu Lys Ala Trp Lys  Ala Leu Glu
    1160                1165                1170

Ile Ala  Glu Lys Lys Leu Leu  Gly Pro Leu Gly Met  Lys Thr Leu
    1175                1180                1185

Asp Pro  Asp Asp Met Val Tyr  Cys Gly Ile Tyr Asp  Asn Ala Leu
    1190                1195                1200

Asp Asn  Asp Asn Tyr Asn Leu  Ala Lys Gly Phe Asn  Tyr His Gln
    1205                1210                1215

Gly Pro  Glu Trp Leu Trp Pro  Ile Gly Tyr Phe Leu  Arg Ala Lys
    1220                1225                1230

Leu Tyr  Phe Ser Arg Leu Met  Gly Pro Glu Thr Thr  Ala Lys Thr
    1235                1240                1245
```

```
Ile Val  Leu Val Lys Asn Val  Leu Ser Arg His Tyr  Val His Leu
    1250                 1255                 1260

Glu Arg  Ser Pro Trp Lys Gly  Leu Pro Glu Leu Thr  Asn Glu Asn
    1265                 1270                 1275

Ala Gln  Tyr Cys Pro Phe Ser  Cys Glu Thr Gln Ala  Trp Ser Ile
    1280                 1285                 1290

Ala Thr  Ile Leu Glu Thr Leu  Tyr Asp Leu
    1295                 1300


<210> SEQ ID NO 11
<211> LENGTH: 1377
<212> TYPE: PRT
<213> ORGANISM: Equus caballus

<400> SEQUENCE: 11

Met Ile His Phe Thr Pro Leu Gln Thr Leu Gly Leu Ser Arg Ser Ser
1               5                   10                  15

Tyr Ser Leu Ala Asp Gln Leu Glu Leu Asn Pro Asp Phe Ser Arg Pro
            20                  25                  30

Asn Lys Lys Tyr Thr Trp His Asp Val Gly Gln Leu Val Glu Lys Leu
        35                  40                  45

Lys Lys Glu Trp Asp Ile Leu Cys Ile Thr Asp Val Val Tyr Asn His
    50                  55                  60

Thr Ala Ala Asn Ser Lys Trp Ile His Glu His Pro Glu Ser Ala Tyr
65                  70                  75                  80

Asn Leu Val Asn Ser Pro His Leu Lys Pro Ala Trp Val Leu Asp Arg
                85                  90                  95

Ala Leu Trp His Leu Ser Cys Asp Val Ala Glu Gly Lys Tyr Arg Glu
            100                 105                 110

Lys Gly Val Pro Ala Leu Ile Glu Asn Asp His Gln Met Asn Cys Ile
        115                 120                 125

Arg Lys Ile Ile Trp Glu Asp Ile Tyr Pro Lys Ile His Leu Trp Glu
    130                 135                 140

Phe Phe Gln Val Asp Val His Lys Ala Val Glu Gln Phe Arg Gly Leu
145                 150                 155                 160

Leu Thr Gln Glu Asn Arg Lys Ile Ile Ser Gln Pro Asp Pro Lys Gln
                165                 170                 175

His Leu Lys Ile Ile Gln Asp Pro Glu Tyr Arg Arg Leu Gly Cys Thr
            180                 185                 190

Val Asp Met Asn Ile Ala Leu Ala Thr Phe Ile Pro His Asp Asn Gly
        195                 200                 205

Pro Ala Ala Ile Asp Glu Cys Cys Asn Trp Phe Arg Lys Arg Ile Glu
    210                 215                 220

Glu Leu Asn Ala Glu Lys His Gln Leu Val Asn Tyr His Gln Glu Gln
225                 230                 235                 240

Ala Val Asn Cys Leu Leu Gly Asn Val Phe Tyr Glu Arg Leu Ala Gly
                245                 250                 255

His Gly Pro Lys Leu Gly Pro Val Thr Arg Lys His Pro Leu Val Thr
            260                 265                 270

Arg Tyr Phe Thr Phe Pro Phe Glu Glu Met Thr Pro Ser Thr Glu Glu
        275                 280                 285

Ser Met Ile His Leu Pro Asn Lys Ala Cys Phe Leu Met Ala His Asn
    290                 295                 300

Gly Trp Val Met Gly Asp Asp Pro Leu Arg Asn Phe Ala Glu Pro Gly
305                 310                 315                 320
```

```
Ser Asp Val Tyr Leu Arg Arg Glu Leu Ile Cys Trp Gly Asp Ser Val
                325                 330                 335

Lys Leu Arg Tyr Gly Asn Lys Pro Glu Asp Cys Pro Tyr Leu Trp Ala
            340                 345                 350

His Met Lys Lys Tyr Thr Glu Ile Thr Ala Thr His Phe Gln Gly Val
        355                 360                 365

Arg Leu Asp Asn Cys His Ser Thr Pro Ile His Val Ala Glu Tyr Met
    370                 375                 380

Leu Asp Ala Ala Arg Lys Leu Gln Pro Asn Leu Tyr Val Val Ala Glu
385                 390                 395                 400

Leu Phe Thr Gly Ser Glu Asp Leu Asp Asn Ile Phe Val Thr Arg Leu
                405                 410                 415

Gly Ile Ser Ser Leu Ile Arg Glu Ala Met Ser Ala Ala Asp Ser His
            420                 425                 430

Glu Glu Gly Arg Leu Val Tyr Arg Tyr Gly Gly Glu Pro Val Gly Ser
        435                 440                 445

Phe Val Gln Pro Cys Leu Arg Pro Leu Met Pro Ala Ile Ala His Ala
    450                 455                 460

Leu Phe Met Asp Ile Thr His Asp Asn Glu Cys Pro Ile Val His Arg
465                 470                 475                 480

Ser Ala Tyr Asp Ala Leu Pro Ser Ser Thr Ile Val Ser Met Ala Ser
                485                 490                 495

Cys Ala Ser Gly Ser Thr Lys Gly Tyr Asp Glu Leu Val Pro His Gln
            500                 505                 510

Ile Ser Val Val Ser Glu Glu Arg Phe Tyr Thr Lys Trp Asn Pro Glu
        515                 520                 525

Ala Leu Pro Ser Asn Thr Gly Glu Val Asn Phe Gln Ser Gly Ile Ile
    530                 535                 540

Ala Ala Arg Arg Ala Ile Asn Lys Leu His Gln Glu Leu Gly Ala Lys
545                 550                 555                 560

Gly Phe Ile Gln Val Tyr Val Asp Gln Val Asp Gln Asp Ile Val Ala
                565                 570                 575

Val Thr Arg His Ser Pro Ser Ile His Gln Ser Val Val Ser Val Ser
            580                 585                 590

Arg Thr Ala Phe Arg Asn Pro Lys Thr Ser Phe Tyr Ser Lys Glu Val
        595                 600                 605

Pro His Met Tyr Ile Pro Gly Lys Ile Glu Glu Val Val Leu Glu Ala
    610                 615                 620

Arg Thr Ile Glu Arg His Thr Ile Pro Tyr Lys Lys Asp Glu Asn Ser
625                 630                 635                 640

Ile Asn Gly Met Pro Asp Ile Thr Val Glu Ile Arg Glu His Ile Gln
                645                 650                 655

Leu Asn Glu Ser Lys Ile Val Lys His Ala Gly Ile Val Thr Lys Gly
            660                 665                 670

Pro Asn Glu Phe Val Gln Glu Ile Glu Phe Glu Asn Leu Thr Pro Gly
        675                 680                 685

Ser Val Ile Ile Phe Arg Val Ser Leu Asp Pro His Ala Gln Val Ala
    690                 695                 700

Val Gly Ile Leu Arg Asn His Leu Thr Gln Phe Ser Pro His Phe Lys
705                 710                 715                 720

Ser Gly Ser Leu Ala Val Asp Asn Ala Asp Pro Ile Leu Lys Ile Pro
                725                 730                 735
```

-continued

```
Phe Ala Ser Ile Ala Ser Lys Leu Thr Leu Ala Glu Leu Asn Gln Val
            740                 745                 750

Leu Tyr Arg Cys Glu Ser Glu Glu Gln Glu Asp Gly Gly Gly Cys Tyr
        755                 760                 765

Asn Ile Pro Asn Trp Ser Ser Leu Lys Tyr Ala Gly Leu Gln Gly Leu
    770                 775                 780

Met Ser Ile Leu Ala Glu Ile Arg Pro Arg Asn Asp Leu Gly His Pro
785                 790                 795                 800

Phe Cys Asp Asn Leu Arg Ser Gly Asp Trp Met Ile Asp Tyr Val Ser
                805                 810                 815

Ser Arg Leu Ile Ser Arg Ser Gly Thr Ile Ala Glu Val Gly Lys Trp
            820                 825                 830

Leu Gln Ala Met Phe Leu Tyr Leu Lys Gln Ile Pro Arg Tyr Leu Ile
        835                 840                 845

Pro Cys Tyr Phe Asp Ala Ile Leu Ile Gly Ala Tyr Thr Thr Leu Leu
    850                 855                 860

Asp Ile Ala Trp Lys Gln Met Ser Ser Phe Val Gln Asn Gly Ser Thr
865                 870                 875                 880

Phe Val Lys His Leu Ser Leu Gly Ser Val Gln Met Cys Gly Val Gly
                885                 890                 895

Lys Phe Pro Ser Leu Pro Leu Leu Ser Pro Ser Leu Thr Asp Leu Pro
            900                 905                 910

Tyr Arg Val Asn Glu Ile Thr Lys Glu Lys Glu Gln Cys Cys Gly Ser
        915                 920                 925

Leu Ala Ala Gly Leu Pro His Phe Ser Ala Gly Ile Phe Arg Cys Trp
    930                 935                 940

Gly Arg Asp Thr Phe Ile Ala Leu Arg Gly Leu Leu Leu Val Thr Gly
945                 950                 955                 960

Arg Tyr Leu Glu Ala Arg Asn Ile Ile Leu Ala Phe Ala Gly Thr Leu
                965                 970                 975

Arg His Gly Leu Ile Pro Asn Leu Leu Gly Glu Gly Thr His Ala Arg
            980                 985                 990

Tyr Asn Cys Arg Asp Ala Val Trp  Trp Trp Leu Gln Cys  Ile Gln Asp
        995                 1000                1005

Tyr Cys  Lys Ile Val Pro Asn  Gly Leu Asp Ile Leu  Arg Cys Pro
    1010                1015                1020

Val Ser  Arg Met Tyr Pro Thr  Asp Asp Ser Val Pro  Leu Ser Ala
    1025                1030                1035

Gly Thr  Val Asp Gln Pro Leu  Phe Glu Val Ile Gln  Glu Ala Met
    1040                1045                1050

Gln Arg  His Val Gln Gly Ile  Gln Phe Arg Glu Arg  Asn Ala Gly
    1055                1060                1065

Pro Gln  Ile Asp Arg Asn Met  Lys Asp Glu Gly Phe  Asn Ile Thr
    1070                1075                1080

Ala Gly  Val Asp Glu Glu Thr  Gly Phe Val Tyr Gly  Gly Asn Arg
    1085                1090                1095

Phe Asn  Cys Gly Thr Trp Met  Asp Lys Met Gly Glu  Ser Asp Arg
    1100                1105                1110

Ala Arg  Asn Arg Gly Ile Pro  Ala Thr Pro Arg Asp  Gly Ser Ala
    1115                1120                1125

Val Glu  Ile Val Gly Leu Ser  Lys Ser Ala Val Arg  Trp Leu Leu
    1130                1135                1140

Glu Leu  Ser Arg Lys Asn Ile  Phe Pro Tyr His Glu  Val Arg Val
```

```
    1145                1150                1155

Lys Arg  His Gly Lys Phe Val  Thr Val Ser Tyr Asp  Glu Trp Asn
    1160                1165                1170

Arg Lys  Ile Gln Asp Asn Phe  Glu Lys Leu Phe His  Val Ser Glu
    1175                1180                1185

Asp Pro  Ser Asp Phe Asn Glu  Lys His Pro Glu Leu  Val His Lys
    1190                1195                1200

Arg Gly  Ile Tyr Lys Asp Ser  Tyr Gly Ala Ser Ser  Pro Trp Cys
    1205                1210                1215

Asp Tyr  Gln Leu Arg Pro Asn  Phe Thr Ile Ala Met  Val Val Ala
    1220                1225                1230

Pro Glu  Leu Phe Thr Pro Glu  Lys Ala Trp Lys Ala  Leu Glu Ile
    1235                1240                1245

Ala Glu  Lys Lys Leu Leu Gly  Pro Leu Gly Met Lys  Thr Leu Asp
    1250                1255                1260

Pro Asp  Asp Met Val Tyr Cys  Gly Ile Tyr Asp Asn  Ala Leu Asp
    1265                1270                1275

Asn Asp  Asn Tyr Asn Leu Ala  Lys Gly Phe Asn Tyr  His Gln Gly
    1280                1285                1290

Pro Glu  Trp Leu Trp Pro Thr  Gly Tyr Phe Leu Arg  Ala Lys Leu
    1295                1300                1305

Tyr Phe  Ser Lys Leu Met Gly  Pro Glu Thr Asn Ala  Lys Thr Met
    1310                1315                1320

Phe Leu  Val Lys Asn Val Leu  Ser Arg His Tyr Val  His Leu Glu
    1325                1330                1335

Arg Ser  Pro Trp Lys Gly Leu  Pro Glu Leu Thr Asn  Glu Asn Gly
    1340                1345                1350

Gln Tyr  Cys Pro Phe Ser Cys  Glu Thr Gln Ala Trp  Ser Ile Ala
    1355                1360                1365

Thr Val  Leu Glu Thr Leu Tyr  Asp Leu
    1370                1375


<210> SEQ ID NO 12
<211> LENGTH: 1365
<212> TYPE: PRT
<213> ORGANISM: Gorilla gorilla

<400> SEQUENCE: 12

Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125
```

```
Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Gln Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Glu Tyr Phe Thr Phe Pro Phe Glu
        355                 360                 365

Glu Ile Asp Phe Ser Met Glu Glu Ser Met Ile His Leu Pro Asn Lys
    370                 375                 380

Ala Cys Phe Leu Met Ala His Asn Gly Trp Val Met Gly Asp Asp Pro
385                 390                 395                 400

Leu Arg Asn Phe Ala Glu Pro Gly Ser Glu Val Tyr Leu Arg Arg Glu
                405                 410                 415

Leu Ile Cys Trp Gly Asp Ser Val Lys Leu Arg Tyr Gly Asn Lys Pro
            420                 425                 430

Glu Asp Cys Pro Tyr Leu Trp Ala His Met Lys Lys Tyr Thr Glu Ile
        435                 440                 445

Thr Ala Thr Tyr Phe Gln Gly Val Arg Leu Asp Asn Cys His Ser Thr
    450                 455                 460

Pro Leu His Val Ala Glu Tyr Met Leu Asp Ala Ala Arg Asn Leu Gln
465                 470                 475                 480

Pro Asn Leu Tyr Val Val Ala Glu Leu Phe Thr Gly Ser Glu Asp Leu
                485                 490                 495

Asp Asn Val Phe Val Thr Arg Leu Gly Ile Ser Ser Leu Ile Arg Glu
            500                 505                 510

Ala Met Ser Ala Tyr Asn Ser His Glu Glu Gly Arg Leu Val Tyr Arg
        515                 520                 525

Tyr Gly Gly Glu Pro Val Gly Ser Phe Val Gln Pro Cys Leu Arg Pro
    530                 535                 540

Leu Met Pro Ala Ile Ala His Ala Leu Phe Met Asp Ile Thr His Asp
```

```
545                 550                 555                 560

Asn Glu Cys Pro Ile Val His Arg Ser Ala Tyr Asp Ala Leu Pro Ser
                565                 570                 575

Thr Thr Ile Val Ser Met Ala Cys Cys Ala Ser Gly Ser Thr Arg Gly
            580                 585                 590

Tyr Asp Glu Leu Val Pro His Gln Phe Leu Gly Lys Ile Glu Glu Val
        595                 600                 605

Val Leu Glu Ala Arg Thr Ile Glu Arg Asn Met Lys Pro Tyr Arg Lys
    610                 615                 620

Asp Glu Asn Ser Ile Asn Gly Thr Pro Asp Ile Thr Val Glu Ile Arg
625                 630                 635                 640

Glu His Ile Gln Leu Asn Glu Ser Lys Ile Val Lys Gln Ala Gly Val
                645                 650                 655

Ala Thr Lys Gly Pro Asn Glu Tyr Ile Gln Glu Ile Glu Phe Glu Asn
            660                 665                 670

Leu Ser Pro Gly Ser Val Ile Ile Phe Arg Val Ser Leu Asp Pro His
        675                 680                 685

Ala Gln Val Ala Val Gly Ile Leu Arg Asn His Leu Thr Gln Phe Ser
    690                 695                 700

Pro His Phe Lys Ser Gly Ser Leu Ala Val Asp Asn Ala Asp Pro Ile
705                 710                 715                 720

Leu Lys Ile Pro Phe Ala Ser Ile Ala Ser Arg Leu Thr Leu Ala Glu
                725                 730                 735

Leu Asn Gln Ile Leu Tyr Arg Cys Glu Ser Glu Glu Lys Glu Asp Gly
            740                 745                 750

Gly Gly Cys Tyr Asp Ile Pro Asn Trp Ser Ala Leu Lys Tyr Ala Gly
        755                 760                 765

Leu Gln Gly Leu Met Ser Val Leu Ala Glu Ile Arg Pro Lys Asn Asp
    770                 775                 780

Leu Gly His Pro Phe Cys Asn Asn Leu Arg Ser Gly Asp Trp Met Ile
785                 790                 795                 800

Asp Tyr Val Ser Asn Arg Leu Ile Ser Arg Ser Gly Thr Ile Ala Glu
                805                 810                 815

Val Gly Lys Trp Leu Gln Ala Met Phe Phe Tyr Leu Lys Gln Ile Pro
            820                 825                 830

Arg Tyr Leu Ile Pro Cys Tyr Phe Asp Ala Ile Leu Ile Gly Ala Tyr
        835                 840                 845

Thr Thr Leu Leu Asp Thr Ala Trp Lys Gln Met Ser Ser Phe Val Gln
    850                 855                 860

Asn Gly Ser Thr Phe Val Lys His Leu Ser Leu Gly Ser Val Gln Leu
865                 870                 875                 880

Cys Gly Val Gly Lys Phe Pro Ser Leu Pro Ile Leu Ser Pro Ala Leu
                885                 890                 895

Met Asp Val Pro Tyr Arg Leu Asn Glu Ile Thr Lys Glu Lys Glu Gln
            900                 905                 910

Cys Cys Val Ser Leu Ala Ala Gly Leu Pro His Phe Ser Ser Gly Ile
        915                 920                 925

Phe Arg Cys Trp Gly Arg Asp Thr Phe Ile Ala Leu Arg Gly Ile Leu
    930                 935                 940

Leu Ile Thr Gly Arg Tyr Val Glu Ala Arg Asn Ile Ile Leu Ala Phe
945                 950                 955                 960

Ala Gly Thr Leu Arg His Gly Leu Ile Pro Asn Leu Leu Gly Glu Gly
                965                 970                 975
```

```
Ile Tyr Ala Arg Tyr Asn Cys Arg Asp Ala Val Trp Trp Trp Leu Gln
            980                 985                 990

Cys Ile Gln Asp Tyr Cys Lys Met  Val Pro Asn Gly Val  Asp Ile Leu
        995                 1000                1005

Lys Cys  Pro Val Ser Arg Met  Tyr Pro Thr Asp Asp  Ser Ala Pro
    1010                 1015                 1020

Leu Pro  Ala Gly Thr Leu Asp  Gln Pro Leu Phe Glu  Val Ile Gln
    1025                 1030                 1035

Glu Ala  Met Gln Lys His Met  Gln Gly Ile Gln Phe  Arg Glu Arg
    1040                 1045                 1050

Asn Ala  Gly Pro Gln Ile Asp  Arg Asn Met Lys Asp  Glu Gly Phe
    1055                 1060                 1065

Asn Ile  Thr Ala Gly Val Asp  Glu Glu Thr Gly Phe  Val Tyr Gly
    1070                 1075                 1080

Gly Asn  Arg Phe Asn Cys Gly  Thr Trp Met Asp Lys  Met Gly Glu
    1085                 1090                 1095

Ser Asp  Arg Ala Arg Asn Arg  Gly Ile Pro Ala Thr  Pro Arg Asp
    1100                 1105                 1110

Gly Ser  Ala Val Glu Ile Val  Gly Leu Ser Lys Ser  Ala Val Arg
    1115                 1120                 1125

Trp Leu  Leu Glu Leu Ser Lys  Lys Asn Ile Phe Pro  Tyr His Glu
    1130                 1135                 1140

Val Thr  Val Lys Arg His Gly  Lys Ala Ile Lys Val  Ser Tyr Asp
    1145                 1150                 1155

Glu Trp  Asn Arg Lys Ile Gln  Asp Asn Phe Glu Lys  Leu Phe His
    1160                 1165                 1170

Val Ser  Glu Asp Pro Ser Asp  Leu Asn Glu Lys His  Pro Asn Leu
    1175                 1180                 1185

Val His  Lys Arg Gly Ile Tyr  Lys Asp Ser Tyr Gly  Ala Ser Ser
    1190                 1195                 1200

Pro Trp  Cys Asp Tyr Gln Leu  Arg Pro Asn Phe Thr  Ile Ala Met
    1205                 1210                 1215

Val Val  Ala Pro Glu Leu Phe  Thr Thr Glu Lys Ala  Trp Lys Ala
    1220                 1225                 1230

Leu Glu  Ile Ala Glu Lys Lys  Leu Leu Gly Pro Leu  Gly Met Lys
    1235                 1240                 1245

Thr Leu  Asp Pro Asp Asp Met  Val Tyr Cys Gly Ile  Tyr Asp Asn
    1250                 1255                 1260

Ala Leu  Asp Asn Asp Asn Tyr  Asn Leu Ala Lys Gly  Phe Asn Tyr
    1265                 1270                 1275

His Gln  Gly Pro Glu Trp Leu  Trp Pro Ile Gly Tyr  Phe Leu Arg
    1280                 1285                 1290

Ala Lys  Leu Tyr Phe Ser Arg  Leu Met Gly Pro Glu  Thr Thr Ala
    1295                 1300                 1305

Lys Thr  Ile Val Leu Val Lys  Asn Val Leu Ser Arg  His Tyr Val
    1310                 1315                 1320

His Leu  Glu Arg Ser Pro Trp  Lys Gly Leu Pro Glu  Leu Thr Asn
    1325                 1330                 1335

Glu Asn  Ala Gln Tyr Cys Pro  Phe Ser Cys Glu Thr  Gln Ala Trp
    1340                 1345                 1350

Ser Ile  Ala Thr Ile Leu Glu  Thr Leu Tyr Asp Leu
    1355                 1360                 1365
```

<210> SEQ ID NO 13
<211> LENGTH: 1299
<212> TYPE: PRT
<213> ORGANISM: Pongo abelii

<400> SEQUENCE: 13

```
Met Gly His Ser Lys Gln Ile Arg Ile Leu Leu Leu Asn Glu Met Glu
1               5                   10                  15

Lys Leu Glu Lys Thr Leu Phe Arg Leu Glu Gln Gly Tyr Glu Leu Gln
            20                  25                  30

Phe Arg Leu Gly Pro Thr Leu Gln Gly Lys Ala Val Thr Val Tyr Thr
        35                  40                  45

Asn Tyr Pro Phe Pro Gly Glu Thr Phe Asn Arg Glu Lys Phe Arg Ser
    50                  55                  60

Leu Asp Trp Glu Asn Pro Thr Glu Arg Glu Asp Asp Ser Asp Lys Tyr
65                  70                  75                  80

Cys Lys Leu Asn Leu Gln Gln Ser Gly Ser Phe Gln Tyr Tyr Phe Leu
                85                  90                  95

Gln Gly Asn Glu Lys Ser Gly Gly Gly Tyr Ile Val Val Asp Pro Ile
            100                 105                 110

Leu Arg Val Gly Ala Asp Asn His Val Leu Pro Leu Asp Cys Val Thr
        115                 120                 125

Leu Gln Thr Phe Leu Ala Lys Cys Leu Gly Pro Phe Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Leu Ser Arg Ser Cys Tyr Ser Leu Ala
                165                 170                 175

Asn Gln Leu Glu Leu Asn Pro Asp Phe Ser Arg Pro Asn Arg Lys Tyr
            180                 185                 190

Thr Trp Asn Asp Val Gly Gln Leu Val Glu Lys Leu Lys Lys Glu Trp
        195                 200                 205

Asn Val Ile Cys Ile Thr Asp Val Val Tyr Asn His Thr Ala Ala Asn
    210                 215                 220

Ser Lys Trp Ile Gln Glu His Pro Glu Cys Ala Tyr Asn Leu Val Asn
225                 230                 235                 240

Ser Pro His Leu Lys Pro Ala Trp Val Leu Asp Arg Ala Leu Trp Arg
                245                 250                 255

Phe Ser Cys Asp Val Ala Glu Gly Lys Tyr Lys Glu Lys Gly Ile Pro
            260                 265                 270

Ala Leu Ile Glu Asn Asp His His Met Asn Ser Ile Arg Lys Ile Ile
        275                 280                 285

Trp Glu Asp Ile Phe Pro Lys Leu Lys Leu Trp Glu Phe Phe Glu Val
    290                 295                 300

Asp Val Asn Lys Ala Val Glu Gln Phe Arg Arg Leu Leu Thr Gln Glu
305                 310                 315                 320

Asn Arg Arg Val Thr Lys Ser Asp Pro Asn Gln His Leu Thr Ile Ile
                325                 330                 335

Gln Asp Pro Glu Tyr Arg Arg Phe Gly Cys Thr Val Asp Met Asn Ile
            340                 345                 350

Ala Leu Thr Thr Phe Ile Pro His Asp Asn Gly Pro Ala Ala Ile Glu
        355                 360                 365

Glu Cys Cys Asn Trp Phe Arg Lys Arg Ile Glu Glu Leu Asn Ser Glu
    370                 375                 380
```

-continued

```
Lys His Gln Leu Ile Asn Tyr His Gln Glu Gln Ala Val Asn Cys Leu
385                 390                 395                 400

Leu Gly Asn Val Phe Tyr Glu Arg Leu Ala Gly His Gly Pro Lys Leu
                405                 410                 415

Gly Pro Val Thr Arg Lys His Pro Leu Val Thr Arg Tyr Phe Thr Phe
            420                 425                 430

Pro Phe Glu Glu Met Asp Phe Ser Met Glu Glu Ser Met Ile His Leu
        435                 440                 445

Pro Asn Lys Ala Cys Leu Leu Met Ala His Asn Gly Trp Val Met Gly
    450                 455                 460

Asp Asp Pro Leu Arg Asn Phe Ala Glu Pro Gly Ser Glu Val Tyr Leu
465                 470                 475                 480

Arg Arg Glu Leu Ile Cys Trp Gly Asp Ser Val Lys Leu Arg Tyr Gly
                485                 490                 495

Asn Lys Pro Glu Asp Cys Pro Tyr Leu Trp Ala His Met Lys Lys Tyr
            500                 505                 510

Thr Glu Ile Thr Ala Thr Tyr Phe Gln Gly Val Arg Leu Asp Asn Cys
        515                 520                 525

His Ser Thr Pro Leu His Val Ala Glu Tyr Met Leu Asp Ala Ala Arg
    530                 535                 540

Asn Leu Gln Pro Asn Leu Tyr Val Val Ala Glu Leu Phe Thr Gly Ser
545                 550                 555                 560

Glu Asp Leu Asp Asn Val Phe Val Thr Arg Leu Gly Ile Ser Ser Leu
                565                 570                 575

Ile Arg Glu Ala Met Ser Ala Tyr Asp Ser His Glu Glu Gly Arg Leu
            580                 585                 590

Val Tyr Arg Tyr Gly Gly Glu Pro Val Gly Ser Phe Val Gln Pro Cys
        595                 600                 605

Leu Arg Pro Leu Met Pro Ala Ile Ala His Ala Leu Phe Met Asp Ile
    610                 615                 620

Thr His Asp Asn Glu Cys Pro Ile Val His Arg Ser Ala Tyr Asp Ala
625                 630                 635                 640

Leu Pro Ser Thr Thr Ile Val Ser Met Ala Cys Cys Ala Ser Gly Ser
                645                 650                 655

Thr Arg Gly Tyr Asp Glu Leu Val Pro His Gln Ile Ser Val Val Ser
            660                 665                 670

Glu Glu Arg Phe Tyr Thr Lys Trp Asn Pro Glu Ala Leu Pro Ser Asn
        675                 680                 685

Thr Gly Glu Val Asn Phe Gln Ser Gly Ile Ile Ala Ala Arg Cys Ala
    690                 695                 700

Ile Asn Lys Leu His Gln Glu Leu Gly Ala Lys Gly Phe Ile Gln Val
705                 710                 715                 720

Tyr Val Asp Gln Val Asp Glu Asp Ile Val Ala Val Thr Arg His Ser
                725                 730                 735

Pro Ser Ile His Gln Ser Val Val Ala Val Ser Arg Thr Ala Phe Arg
            740                 745                 750

Asn Pro Lys Thr Ser Phe Tyr Ser Lys Glu Val Pro Gln Met Cys Ile
        755                 760                 765

Pro Gly Lys Ile Glu Glu Val Val Leu Glu Ala Arg Thr Ile Glu Arg
    770                 775                 780

Asn Thr Lys Pro Tyr Arg Lys Asp Glu Asn Ser Ile Asn Gly Thr Pro
785                 790                 795                 800
```

```
Asp Ile Thr Val Glu Ile Arg Glu His Ile Gln Leu Asn Glu Ser Lys
                805                 810                 815

Ile Val Lys Gln Ala Gly Val Ala Thr Lys Gly Pro Asn Glu Phe Ile
            820                 825                 830

Gln Glu Ile Glu Phe Glu Asn Leu Ser Pro Gly Ser Val Ile Ile Phe
        835                 840                 845

Arg Val Ser Leu Asp Pro His Ala Gln Val Ala Val Gly Ile Leu Arg
    850                 855                 860

Asn His Leu Thr Gln Phe Ser Pro His Phe Lys Ser Gly Ser Leu Ala
865                 870                 875                 880

Val Asp Asn Ala Asp Pro Ile Leu Lys Ile Pro Phe Ala Leu Pro His
                885                 890                 895

Phe Ser Ser Gly Ile Phe Arg Cys Trp Gly Arg Asp Thr Phe Ile Ala
            900                 905                 910

Leu Arg Gly Met Leu Leu Ile Thr Gly Arg Tyr Val Glu Ala Arg Asn
        915                 920                 925

Ile Ile Leu Ala Phe Ala Gly Thr Leu Arg His Gly Leu Ile Pro Asn
    930                 935                 940

Leu Leu Gly Glu Gly Thr Tyr Ala Arg Tyr Asn Cys Arg Asp Ala Val
945                 950                 955                 960

Trp Trp Trp Leu Gln Cys Ile Gln Asp Tyr Cys Lys Val Val Pro Asn
                965                 970                 975

Gly Leu Asp Ile Leu Lys Cys Pro Val Ser Arg Met Tyr Pro Thr Asp
            980                 985                 990

Asp Ser Ala Pro Leu Pro Ala Gly  Ala Leu Phe Asn Ile  Thr Ala Gly
        995                 1000                1005

Val Asp  Glu Glu Thr Gly Phe  Val Tyr Gly Gly Asn  Arg Phe Asn
    1010                 1015                 1020

Cys Gly  Thr Trp Met Asp Lys  Met Gly Glu Ser Asp  Arg Ala Arg
    1025                 1030                 1035

Asn Arg  Gly Ile Pro Ala Thr  Pro Arg Asp Gly Ser  Ala Val Glu
    1040                 1045                 1050

Ile Val  Gly Leu Ser Lys Ser  Ala Val Arg Trp Leu  Leu Glu Leu
    1055                 1060                 1065

Ser Lys  Lys Asn Ile Phe Pro  Tyr His Glu Val Thr  Val Lys His
    1070                 1075                 1080

Gly Lys  Ala Ile Lys Val Ser  Tyr Asp Glu Trp Asn  Arg Lys Ile
    1085                 1090                 1095

Gln Asp  Asn Phe Glu Lys Leu  Phe His Val Ser Glu  Asp Pro Ser
    1100                 1105                 1110

Asp Leu  Asn Glu Lys His Pro  Asn Leu Val His Lys  Arg Gly Ile
    1115                 1120                 1125

Tyr Lys  Asp Ser Tyr Gly Ala  Ser Ser Pro Trp Cys  Asp Tyr Gln
    1130                 1135                 1140

Leu Arg  Pro Asn Phe Thr Ile  Ala Met Val Val Ala  Pro Glu Leu
    1145                 1150                 1155

Phe Thr  Thr Glu Lys Ala Trp  Lys Ala Leu Glu Ile  Ala Glu Lys
    1160                 1165                 1170

Lys Leu  Leu Gly Pro Leu Gly  Met Lys Thr Leu Asp  Pro Asp Asp
    1175                 1180                 1185

Met Val  Tyr Cys Gly Ile Tyr  Asp Asn Ala Leu Asp  Asn Asp Asn
    1190                 1195                 1200

Tyr Asn  Leu Ala Lys Gly Phe  Asn Tyr His Gln Gly  Pro Glu Trp
```

```
    1205                1210                1215

Leu Trp  Pro Ile Gly Tyr Phe  Leu Arg Ala Lys Leu  Tyr Phe Ser
    1220                1225                1230

Arg Leu  Met Gly Pro Glu Thr  Thr Ala Lys Thr Ile  Val Leu Val
    1235                1240                1245

Lys Asn  Val Leu Ser Arg His  Tyr Val His Leu Glu  Arg Ser Pro
    1250                1255                1260

Trp Lys  Gly Leu Pro Glu Leu  Thr Asn Glu Asn Ala  Gln Tyr Cys
    1265                1270                1275

Pro Phe  Ser Cys Glu Thr Gln  Ala Trp Ser Val Ala  Thr Ile Leu
    1280                1285                1290

Glu Thr  Leu Tyr Asp Leu
    1295


<210> SEQ ID NO 14
<211> LENGTH: 1390
<212> TYPE: PRT
<213> ORGANISM: Pteropus alecto

<400> SEQUENCE: 14

Met Gly His Gly Lys Gln Ile Arg Ile Leu Leu Leu Asn Glu Met Glu
1               5                   10                  15

Lys Leu Glu Lys Thr Leu Phe Arg Leu Glu Gln Gly Phe Glu Leu Gln
            20                  25                  30

Phe Arg Leu Gly Pro Thr Leu Gln Gly Lys Thr Val Thr Val His Thr
        35                  40                  45

Asn Tyr Pro Tyr Pro Gly Glu Thr Phe Asn Arg Glu Lys Phe Arg Ser
    50                  55                  60

Leu Glu Trp Glu Asn Pro Ser Glu Arg Glu Asp Asp Ser Asp Lys Tyr
65                  70                  75                  80

Cys Lys Leu Asn Leu Gln Gln Ala Gly Ser Phe Gln Tyr Tyr Phe Leu
                85                  90                  95

Arg Gly Asn Glu Lys Ser Gly Gly Gly Tyr Ile Val Val Asp Pro Val
            100                 105                 110

Leu Arg Val Gly Thr Asp Asn His Val Leu Pro Leu Asp Cys Val Thr
        115                 120                 125

Leu Gln Thr Phe Leu Ala Lys Cys Leu Gly Pro Leu Asp Glu Trp Glu
    130                 135                 140

Ser Arg Leu Arg Val Ala Lys Glu Ser Gly Tyr Asn Met Ile His Phe
145                 150                 155                 160

Thr Pro Leu Gln Thr Leu Gly Gln Ser Arg Ser Cys Tyr Ser Leu Ala
                165                 170                 175

Asp Gln Leu Glu Leu Asn Pro Asp Phe Ser Arg Pro Asn Lys Lys Cys
            180                 185                 190

Thr Trp Asp Asp Val Gly Gln Leu Val Glu Lys Leu Lys Lys Glu Trp
        195                 200                 205

Asn Ile Leu Cys Ile Thr Asp Val Val Tyr Asn His Thr Gly Asn Arg
    210                 215                 220

Lys Ile Thr Lys Pro Asp Pro Lys Glu His Leu Lys Ile Ile Gln Asp
225                 230                 235                 240

Pro Glu Tyr Arg Arg Leu Gly Cys Thr Val Asp Met Asn Ile Ala Leu
                245                 250                 255

Ala Thr Phe Ile Pro Asn Glu Tyr Phe Thr Phe Pro Phe Glu Glu Met
            260                 265                 270
```

```
Thr Leu Ser Thr Glu Glu Ser Met Ile His Leu Pro Asn Lys Ala Cys
        275                 280                 285

Phe Leu Met Ala His Asn Gly Trp Val Met Gly Asp Asp Pro Leu Arg
    290                 295                 300

Asn Phe Ala Glu Pro Gly Ser Asp Val Tyr Leu Arg Arg Glu Leu Ile
305                 310                 315                 320

Cys Trp Gly Asp Ser Val Lys Leu Arg Tyr Gly Asn Lys Pro Glu Asp
                325                 330                 335

Cys Pro Tyr Leu Trp Ala His Met Lys Lys Tyr Thr Glu Ile Thr Ala
            340                 345                 350

Thr Tyr Phe Gln Gly Val Arg Leu Asp Asn Cys His Ser Thr Pro Leu
        355                 360                 365

His Val Ala Glu Tyr Met Leu Asp Ala Ala Arg Lys Leu Gln Pro Asn
    370                 375                 380

Leu Tyr Ile Val Ala Glu Leu Phe Thr Gly Ser Glu Asp Leu Asp Asn
385                 390                 395                 400

Val Phe Val Thr Arg Leu Gly Ile Ser Ser Leu Ile Arg Glu Ala Met
                405                 410                 415

Ser Ala His Asp Ser His Glu Glu Gly Arg Leu Val Tyr Arg Tyr Gly
            420                 425                 430

Gly Glu Pro Val Gly Ser Phe Val Gln Pro Cys Leu Arg Pro Leu Met
        435                 440                 445

Pro Ala Ile Ala His Ala Leu Phe Met Asp Ile Thr His Asp Asn Glu
    450                 455                 460

Cys Pro Ile Val His Arg Ser Ala Tyr Asp Ala Leu Pro Ser Ser Met
465                 470                 475                 480

Ile Val Ser Met Ala Cys Cys Ala Ser Gly Ser Thr Lys Gly Tyr Asp
                485                 490                 495

Glu Leu Val Pro His Gln Val Tyr Val Asp Gln Val Asp Glu Asp Ile
            500                 505                 510

Val Ala Val Thr Arg His Ser Pro Ser Ile His Gln Ser Val Val Ala
        515                 520                 525

Val Ser Arg Thr Ala Phe Lys Asn Pro Lys Thr Ser Phe Tyr Ser Lys
    530                 535                 540

Glu Val Pro Gln Met Cys Ile Pro Gly Lys Ile Glu Glu Val Val Leu
545                 550                 555                 560

Glu Ala Arg Thr Ile Glu Arg Asn Thr Lys Pro Tyr Lys Arg Asp Glu
                565                 570                 575

Asn Ser Ile Asn Gly Met Pro Asp Ile Thr Ala Glu Ile Arg Glu His
            580                 585                 590

Ile Gln Leu Asn Glu Ser Lys Ile Val Lys Gln Ala Gly Ile Ala Thr
        595                 600                 605

Lys Gly Pro Asn Glu Tyr Ile Gln Glu Ile Glu Phe Glu Asn Leu Ser
    610                 615                 620

Pro Gly Ser Val Ile Val Phe Arg Val Ser Leu Asp Pro His Ala Gln
625                 630                 635                 640

Val Ala Val Gly Ile Leu Arg Asn His Leu Thr Gln Phe Ser Pro His
                645                 650                 655

Phe Lys Ser Gly Ser Leu Ser Ala Asp Ser Ser Asp Pro Ile Leu Lys
            660                 665                 670

Ile Pro Phe Ala Tyr Ile Ala Ser Lys Leu Thr Leu Ala Glu Leu Asn
        675                 680                 685

Gln Ile Leu Tyr Arg Cys Glu Ser Glu Glu Gln Glu Asp Gly Gly Gly
```

```
    690                 695                 700

Cys Tyr Asn Ile Pro Asn Trp Ser Ser Leu Lys Tyr Ala Gly Leu Gln
705                 710                 715                 720

Glu Asn Ser Ser Leu Glu Leu Ala Pro Tyr Val Gly Phe Gly Gly Gly
                725                 730                 735

Cys Gly Ala Ala Pro Ala Gly Leu Asn Arg Gly Gly Gly Val Arg Ser
            740                 745                 750

Asp Gln Ala Ser Leu Glu Arg Phe Leu Thr Thr Leu Leu Ala Thr Val
        755                 760                 765

Asp Tyr Thr Ala Leu Val Ser Thr Ser Val Cys Ser Pro His Ile Thr
    770                 775                 780

Gly His Glu Gln Gln Pro Arg Leu Trp Glu Arg Ile Ala Ser Ala Asn
785                 790                 795                 800

Asn Ile Ala Cys Tyr Phe Tyr Asp Phe Ser Gly Leu Met Ser Val Leu
                805                 810                 815

Ala Glu Met Arg Pro Lys Asn Asp Leu Gly His Pro Phe Cys Asp Asn
            820                 825                 830

Leu Arg Ser Gly Asp Trp Met Ile Asp Tyr Val Ser Asn Arg Leu Ile
        835                 840                 845

Ser Arg Ser Gly Thr Ile Ala Glu Val Gly Arg Trp Leu Gln Ala Met
    850                 855                 860

Phe Phe Tyr Leu Lys Gln Ile Pro Arg Tyr Leu Ile Pro Cys Tyr Phe
865                 870                 875                 880

Asp Ala Val Leu Ile Gly Ala Tyr Thr Thr Leu Leu Asp Thr Ala Trp
                885                 890                 895

Lys Gln Met Ser Ser Phe Val Gln Asn Gly Ser Thr Phe Val Lys His
            900                 905                 910

Leu Ser Leu Gly Ser Val Gln Leu Cys Gly Val Gly Lys Tyr Ala Ser
        915                 920                 925

Leu Pro Leu Leu Ser Pro Ser Leu Met Asp Val Pro Tyr Arg Leu Asn
    930                 935                 940

Glu Ile Thr Lys Glu Lys Glu Gln Cys Cys Val Thr Leu Ala Ala Gly
945                 950                 955                 960

Leu Pro His Phe Ser Ser Gly Ile Phe Arg Cys Trp Gly Arg Asp Thr
                965                 970                 975

Phe Ile Ala Leu Arg Gly Ile Leu Leu Ile Thr Gly Arg Tyr Leu Glu
            980                 985                 990

Ala Arg Asn Ile Ile Leu Ala Phe  Ala Gly Thr Leu Arg  His Gly Leu
        995                 1000                 1005

Ile Pro  Asn Leu Leu Gly Glu  Gly Thr Tyr Ala Arg  Tyr Asn Cys
    1010                 1015                 1020

Arg Asp  Ala Val Trp Trp Trp  Leu Gln Cys Ile Gln  Asp Tyr Cys
    1025                 1030                 1035

Lys Val  Val Pro Asn Gly Leu  Asp Ile Leu Lys Cys  Pro Val Ser
    1040                 1045                 1050

Arg Met  Tyr Pro Thr Asp Asp  Ser Val Pro Leu Ser  Ala Gly Thr
    1055                 1060                 1065

Val Asp  Gln Pro Leu Phe Glu  Val Ile Gln Glu Ala  Met Gln Arg
    1070                 1075                 1080

His Met  Gln Gly Ile Gln Phe  Arg Glu Arg Asn Ala  Gly Pro Gln
    1085                 1090                 1095

Ile Asp  Arg Asn Met Lys Asp  Glu Gly Phe Asn Ile  Thr Val Gly
    1100                 1105                 1110
```

```
Val Asp  Glu Glu Thr Gly Phe  Val Tyr Gly Gly Asn  Arg Phe Asn
    1115                 1120                 1125

Cys Gly  Thr Trp Met Asp Lys  Met Gly Glu Ser Asp  Arg Ala Arg
    1130                 1135                 1140

Asn Arg  Gly Ile Pro Ala Thr  Pro Arg Asp Gly Ser  Ala Val Glu
    1145                 1150                 1155

Ile Val  Gly Leu Ser Lys Ser  Ala Ile Arg Trp Leu  Leu Glu Leu
    1160                 1165                 1170

Ser Lys  Lys Asn Ile Phe Pro  Tyr His Glu Val Thr  Val Lys Arg
    1175                 1180                 1185

Asp Gly  Lys Val Val Thr Val  Ser Tyr Asp Glu Trp  Asn Arg Lys
    1190                 1195                 1200

Ile Gln  Asp Asn Phe Glu Lys  Leu Phe Tyr Val Ser  Glu Asp Pro
    1205                 1210                 1215

Ser Asp  Phe Asn Glu Lys Asn  Pro Asn Leu Val His  Lys Arg Gly
    1220                 1225                 1230

Ile Tyr  Lys Asp Ser Tyr Gly  Ala Ser Ser Pro Trp  Cys Asp Tyr
    1235                 1240                 1245

Gln Leu  Arg Pro Asn Phe Thr  Ile Ala Met Val Val  Ala Pro Glu
    1250                 1255                 1260

Leu Phe  Thr Thr Glu Lys Ala  Trp Lys Ala Leu Gln  Val Ala Glu
    1265                 1270                 1275

Lys Lys  Leu Leu Gly Pro Leu  Gly Met Lys Thr Leu  Asp Pro Asp
    1280                 1285                 1290

Asp Met  Val Tyr Cys Gly Val  Tyr Asp Asn Ala Leu  Asp Asn Asp
    1295                 1300                 1305

Asn Tyr  Asn Leu Ala Lys Gly  Phe Asn Tyr His Gln  Gly Pro Glu
    1310                 1315                 1320

Trp Leu  Trp Leu Ile Gly Tyr  Phe Leu Arg Ala Lys  Leu Tyr Phe
    1325                 1330                 1335

Ser Lys  Leu Met Gly Pro Glu  Thr Asn Ala Lys Thr  Ile Phe Leu
    1340                 1345                 1350

Val Lys  Asn Val Leu Ser Arg  His Tyr Val His Leu  Glu Ser Leu
    1355                 1360                 1365

Ala Cys  Phe Ala Leu Thr Thr  Leu Leu Gln Leu Leu  Asn Lys Ile
    1370                 1375                 1380

Leu Ser  Ala Ser Gln Ile Pro
    1385                 1390


<210> SEQ ID NO 15
<211> LENGTH: 1252
<212> TYPE: PRT
<213> ORGANISM: Cercocebus atys

<400> SEQUENCE: 15

Met Asn Ser Ile Arg Lys Met Ile Trp Glu Asp Ile Phe Pro Lys Leu
1               5                   10                  15

Lys Leu Trp Glu Phe Phe Gln Val Asp Val Asn Lys Lys Lys Lys Lys
            20                  25                  30

Lys Lys Arg Leu Leu Thr Gln Glu Asn Arg Arg Val Thr Lys Ser Asp
        35                  40                  45

Pro His Gln His Leu Lys Ile Ile Gln Asp Pro Glu Tyr Arg Arg Phe
    50                  55                  60

Gly Cys Thr Val Asp Met Asn Ile Ala Leu Thr Thr Phe Ile Pro His
```

-continued

```
65                  70                  75                  80

Asp Asn Gly Pro Ala Ala Ile Glu Glu Cys Cys Asn Trp Phe Arg Lys
                85                  90                  95

Arg Ile Glu Glu Leu Asn Ser Glu Lys His Arg Leu Ile Asn Tyr His
            100                 105                 110

Gln Glu Gln Ala Val Asn Cys Leu Leu Gly Asn Val Phe Tyr Glu Arg
        115                 120                 125

Leu Ala Gly His Gly Pro Lys Leu Gly Pro Val Thr Arg Lys His Pro
    130                 135                 140

Leu Val Thr Arg Tyr Phe Thr Phe Pro Phe Glu Glu Met Asp Phe Ser
145                 150                 155                 160

Val Glu Glu Ser Met Ile His Leu Pro Asn Lys Ala Cys Phe Leu Met
                165                 170                 175

Ala His Asn Gly Trp Val Met Gly Asp Asp Pro Leu Arg Asn Phe Ala
            180                 185                 190

Glu Pro Gly Ser Glu Val Tyr Leu Arg Arg Glu Leu Ile Cys Trp Gly
        195                 200                 205

Asp Ser Val Lys Leu Arg Tyr Gly Asn Lys Pro Glu Asp Cys Pro Phe
    210                 215                 220

Leu Trp Ala His Met Lys Lys Tyr Thr Glu Ile Thr Ala Thr Tyr Phe
225                 230                 235                 240

Gln Gly Val Arg Leu Asp Asn Cys His Ser Thr Pro Leu His Val Ala
                245                 250                 255

Glu Tyr Met Leu Asp Ala Ala Arg Asn Leu Gln Pro Asn Leu Tyr Val
            260                 265                 270

Val Ala Glu Leu Phe Thr Gly Ser Glu Asp Leu Asp Asn Ile Phe Val
        275                 280                 285

Thr Arg Leu Gly Ile Ser Ser Leu Ile Arg Glu Ala Met Ser Ala Tyr
    290                 295                 300

Asn Ser His Glu Glu Gly Arg Leu Val Tyr Arg Tyr Gly Gly Glu Pro
305                 310                 315                 320

Val Gly Ser Phe Val Gln Pro Cys Leu Arg Pro Leu Met Pro Ala Ile
                325                 330                 335

Ala His Ala Leu Phe Met Asp Ile Thr His Asp Asn Glu Cys Pro Ile
            340                 345                 350

Val His Arg Ser Ala Tyr Asp Ala Leu Pro Ser Thr Thr Ile Val Ser
        355                 360                 365

Met Ala Cys Cys Ala Ser Gly Ser Thr Arg Gly Tyr Asp Glu Leu Val
    370                 375                 380

Pro His Gln Ile Ser Val Val Ser Glu Glu Arg Phe Tyr Thr Lys Trp
385                 390                 395                 400

Asn Pro Gly Ala Leu Pro Ser Asn Thr Gly Glu Val Asn Phe Gln Ser
                405                 410                 415

Gly Ile Ile Ala Ala Arg Cys Ala Ile Asn Lys Leu His Gln Glu Leu
            420                 425                 430

Gly Ala Lys Gly Phe Ile Gln Val Tyr Val Asp Gln Val Asp Glu Asp
        435                 440                 445

Ile Val Ala Val Thr Arg His Ser Pro Ser Ile His Gln Ser Val Val
    450                 455                 460

Ala Val Ser Arg Thr Ala Phe Arg Asn Pro Lys Thr Ser Phe Tyr Ser
465                 470                 475                 480

Lys Glu Val Pro Gln Met Cys Ile Pro Gly Lys Ile Glu Glu Val Val
                485                 490                 495
```

```
Leu Glu Ala Arg Thr Ile Glu Arg Asn Thr Lys Pro Tyr Arg Lys Asp
            500                 505                 510

Glu Asn Ser Ile Asn Gly Met Pro Asp Ile Thr Val Glu Ile Arg Glu
        515                 520                 525

His Ile Gln Leu Asn Glu Ser Lys Ile Val Lys Gln Ala Gly Val Ala
    530                 535                 540

Thr Lys Gly Pro Asn Glu Tyr Ile Gln Glu Ile Glu Phe Glu Asn Leu
545                 550                 555                 560

Ser Pro Gly Ser Val Ile Ile Phe Arg Val Ser Leu Asp Pro His Ala
                565                 570                 575

Gln Val Ala Val Gly Ile Leu Arg Asn His Leu Thr Gln Phe Ser Pro
            580                 585                 590

His Phe Lys Ser Gly Ser Leu Ala Val Asp Asn Ser Asp Pro Ile Leu
        595                 600                 605

Lys Ile Pro Phe Ala Ser Ile Ala Ser Lys Leu Thr Leu Ala Glu Leu
    610                 615                 620

Asn Gln Ile Leu Tyr Arg Cys Glu Ser Glu Glu Lys Glu Asp Gly Gly
625                 630                 635                 640

Gly Cys Tyr Asp Ile Pro Asn Trp Ser Ala Leu Lys Tyr Ala Gly Leu
                645                 650                 655

Gln Gly Leu Met Ser Val Leu Ala Glu Ile Arg Pro Lys Asn Asp Leu
            660                 665                 670

Gly His Pro Phe Cys Asn Asn Leu Arg Ser Gly Asp Trp Met Ile Asp
        675                 680                 685

Tyr Val Ser Asn Arg Leu Ile Ser Arg Ser Gly Thr Ile Ala Glu Val
    690                 695                 700

Gly Lys Trp Leu Gln Ala Met Phe Phe Tyr Leu Lys Gln Ile Pro Arg
705                 710                 715                 720

Tyr Leu Ile Pro Cys Tyr Phe Asp Ala Ile Leu Ile Gly Ala Tyr Thr
                725                 730                 735

Thr Leu Leu Asp Ile Ala Trp Lys Gln Met Ser Ser Phe Val Gln Asn
            740                 745                 750

Gly Ser Thr Phe Val Lys His Leu Ser Leu Gly Ser Val Gln Leu Cys
        755                 760                 765

Gly Val Gly Lys Phe Pro Ser Leu Pro Ile Leu Ser Pro Ala Leu Thr
    770                 775                 780

Gly Val Pro Tyr Arg Leu Asn Glu Ile Thr Lys Glu Lys Glu Gln Cys
785                 790                 795                 800

Cys Val Ser Leu Ala Ala Gly Leu Pro His Phe Ser Ser Gly Ile Phe
                805                 810                 815

Arg Cys Trp Gly Arg Asp Thr Phe Ile Ala Leu Arg Gly Ile Leu Leu
            820                 825                 830

Ile Thr Gly Arg Tyr Val Glu Ala Arg Asn Ile Ile Leu Ala Phe Ala
        835                 840                 845

Gly Thr Leu Arg His Gly Leu Ile Pro Asn Leu Leu Gly Glu Gly Thr
    850                 855                 860

Tyr Ala Arg Tyr Asn Cys Arg Asp Ala Val Trp Trp Trp Leu Gln Cys
865                 870                 875                 880

Ile Gln Asp Tyr Cys Lys Met Val Pro Asn Gly Leu Asp Ile Leu Lys
                885                 890                 895

Cys Pro Val Ser Arg Met Tyr Pro Thr Asp Asp Ser Ala Pro Leu Pro
            900                 905                 910
```

```
Ala Gly Thr Leu Asp Gln Pro Leu Phe Glu Val Ile Gln Glu Ala Met
        915                 920                 925

Gln Arg His Met Gln Gly Ile Gln Phe Arg Glu Arg Asn Ala Gly Pro
    930                 935                 940

Lys Ile Asp Arg Asn Met Lys Asp Glu Gly Phe Asn Val Thr Ala Gly
945                 950                 955                 960

Val Asp Glu Glu Thr Gly Phe Val Tyr Gly Gly Asn Arg Phe Asn Cys
                965                 970                 975

Gly Thr Trp Met Asp Lys Met Gly Glu Ser Asp Arg Ala Arg Asn Thr
            980                 985                 990

Gly Ile Pro Ala Thr Pro Arg Asp  Gly Ser Ala Val Glu  Ile Val Gly
        995                 1000                1005

Leu Ser  Lys Ser Ala Val Arg  Trp Leu Leu Glu Leu  Ser Lys Lys
    1010                1015                1020

Asn Ile  Phe Pro Tyr His Glu  Val Thr Val Lys Arg  His Gly Lys
    1025                1030                1035

Val Val  Lys Val Ser Tyr Asp  Glu Trp Asn Arg Lys  Ile Gln Asp
    1040                1045                1050

Asn Phe  Glu Lys Leu Phe His  Val Ser Glu Asp Pro  Ser Asp Leu
    1055                1060                1065

Asn Glu  Lys His Pro Asn Leu  Val His Lys Arg Gly  Ile Tyr Lys
    1070                1075                1080

Asp Ser  Tyr Gly Ala Ser Ser  Pro Trp Cys Asp Tyr  Gln Leu Arg
    1085                1090                1095

Pro Asn  Phe Thr Ile Ala Met  Val Val Ala Pro Glu  Leu Phe Thr
    1100                1105                1110

Thr Ala  Lys Ala Trp Lys Ala  Leu Glu Ile Ala Glu  Lys Lys Leu
    1115                1120                1125

Leu Gly  Pro Leu Gly Met Lys  Thr Leu Asp Pro Asp  Asp Met Val
    1130                1135                1140

Tyr Cys  Gly Ile Tyr Asp Asn  Ala Leu Asp Asn Asp  Asn Tyr Asn
    1145                1150                1155

Leu Ala  Lys Gly Phe Asn Tyr  His Gln Gly Pro Glu  Trp Leu Trp
    1160                1165                1170

Pro Ile  Gly Tyr Phe Leu Arg  Ala Lys Leu Tyr Phe  Ser Arg Leu
    1175                1180                1185

Met Gly  Pro Glu Thr Thr Ala  Lys Thr Ile Val Leu  Val Lys Asn
    1190                1195                1200

Val Leu  Ser Arg His Tyr Val  His Leu Glu Arg Ser  Pro Trp Lys
    1205                1210                1215

Gly Leu  Pro Glu Leu Thr Asn  Glu Asn Ala Gln Tyr  Cys Pro Phe
    1220                1225                1230

Ser Cys  Glu Thr Gln Ala Trp  Ser Ile Ser Thr Ile  Leu Glu Thr
    1235                1240                1245

Leu Tyr  Asp Leu
    1250


<210> SEQ ID NO 16
<211> LENGTH: 1116
<212> TYPE: PRT
<213> ORGANISM: Ornithorhynchus anatinus

<400> SEQUENCE: 16

Met Phe Glu Gly Arg Ala Glu Gly Val Val Gly Glu Tyr Phe Thr Phe
1               5                   10                  15
```

```
Pro Tyr Gly Glu Met Thr Ser Val Glu Glu Glu Ser Leu Met His Gln
            20                  25                  30

Pro Glu Lys Ala Cys Phe Phe Met Ala His Asn Gly Trp Val Met Gly
        35                  40                  45

Asp Asp Pro Leu Arg Asn Phe Ala Glu Pro Gly Ser Asp Val Tyr Leu
    50                  55                  60

Arg Arg Glu Leu Val Cys Trp Gly Asp Ser Val Lys Leu Arg Tyr Gly
65                  70                  75                  80

Asn Lys Pro Glu Asp Cys Pro Tyr Leu Trp Ala His Met Lys Lys Tyr
                85                  90                  95

Thr Glu Ile Thr Ala Lys Tyr Phe Gln Gly Val Arg Leu Asp Asn Cys
            100                 105                 110

His Ser Thr Pro Leu His Val Ala Glu Tyr Met Leu Asp Ala Ala Arg
        115                 120                 125

Lys Leu Gln Pro Asn Leu Tyr Val Val Ala Glu Leu Phe Thr Gly Ser
    130                 135                 140

Glu Glu Leu Asp Asn Ile Phe Val Thr Arg Leu Gly Ile Ser Ser Leu
145                 150                 155                 160

Ile Arg Glu Ala Met Ser Ala Tyr Asn Ser His Glu Glu Gly Arg Leu
                165                 170                 175

Val Tyr Arg Phe Gly Gly Glu Pro Val Gly Ser Phe Val Gln Pro Cys
            180                 185                 190

Leu Arg Pro Leu Met Pro Ala Ile Ala His Ala Leu Phe Met Asp Ile
        195                 200                 205

Thr His Asp Asn Glu Cys Pro Ile Val His Arg Ser Ala Tyr Asp Ala
    210                 215                 220

Leu Pro Ser Ser Thr Ile Val Ser Met Ala Cys Cys Ala Ser Gly Ser
225                 230                 235                 240

Thr Arg Gly Tyr Asp Glu Leu Val Pro His Gln Ile Ser Val Val Ser
                245                 250                 255

Glu Glu Arg Phe Tyr Thr Lys Trp Asn Pro Ala Ala Thr Leu Ser Asn
            260                 265                 270

Pro Ser Glu Val Asn Leu Gln Thr Gly Ile Ile Ala Gly Arg Arg Ala
        275                 280                 285

Ile Asn Lys Leu His Gln Glu Leu Gly Ala Lys Gly Phe Ile Gln Val
    290                 295                 300

Tyr Val Asp Gln Val Asp Glu Asp Ile Val Ala Val Thr Arg His Cys
305                 310                 315                 320

Pro Ser Ser His Gln Ser Val Val Ala Val Ser Arg Thr Ala Phe Arg
                325                 330                 335

Asn Pro Lys Thr Ser Ala Tyr Ser Lys Glu Val Pro Gln Met Cys Ile
            340                 345                 350

Pro Gly Lys Ile Glu Glu Val Val Leu Glu Ala Arg Thr Val Glu Arg
        355                 360                 365

Asn Val Gly Ser Tyr Val Lys Asp Ala Lys Ser Ile Asn Gly Met Pro
    370                 375                 380

Asp Ile Thr Val Glu Ile Arg Glu His Ile Gln Leu Asn Glu Ser Lys
385                 390                 395                 400

Ile Val Lys Gln Ala Gly Val Ala Thr Lys Gly Leu His Glu Tyr Val
                405                 410                 415

Gln Glu Ile Glu Phe Glu Asn Leu Thr Pro Gly Ser Val Ile Ile Phe
            420                 425                 430
```

```
Arg Val Ser Leu Asp Pro His Ala Gln Val Ala Val Gly Ile Leu Arg
        435                 440                 445

Asn His Leu Thr Gln Phe Ser Pro Asn Phe Lys Ile Gly Ser Leu Pro
    450                 455                 460

Val Asp Asn Ser Asp Pro Ile Leu Lys Ile Pro Phe Ala Ser Ile Ser
465                 470                 475                 480

Ser Lys Leu Thr Leu Ala Asp Leu Asn Gln Leu Leu Tyr Arg Cys Glu
                485                 490                 495

Ser Glu Glu Gln Glu Asp Gly Gly Gly Cys Tyr Asp Val Pro Asn Trp
            500                 505                 510

Ser Pro Leu Lys Tyr Gly Gly Leu Gln Gly Leu Met Ser Val Met Ala
        515                 520                 525

Glu Ile Arg Pro Lys Asn Asp Leu Gly His Pro Phe Cys Asn Asn Leu
    530                 535                 540

Arg Ser Gly Asp Trp Met Ile Asp Tyr Val Ser Asn Arg Leu Ile Ser
545                 550                 555                 560

Arg Ser Gly Ser Ile Ala Glu Val Gly Lys Trp Phe Gln Ala Met Phe
                565                 570                 575

Phe Tyr Leu Lys Gln Ile Pro Arg Tyr Leu Ile Pro Cys Tyr Phe Asp
            580                 585                 590

Ala Ile Leu Ile Gly Ala Tyr Thr Thr Leu Leu Asp Ile Ala Trp Lys
        595                 600                 605

Gln Met Ser Ser Phe Val Gln Asn Gly Ser Thr Phe Val Lys His Leu
    610                 615                 620

Ser Leu Gly Ser Val Gln Met Cys Gly Ile Gly Lys Phe Pro Ser Leu
625                 630                 635                 640

Pro Phe Leu Ser Pro Ser Leu Gly Asp Val Pro Tyr Arg Leu Asn Glu
                645                 650                 655

Ile Thr Gln Glu Lys Glu Gln Cys Cys Val Ser Leu Ala Ala Gly Leu
            660                 665                 670

Pro His Phe Ser Ser Gly Ile Phe Arg Cys Trp Gly Arg Asp Thr Phe
        675                 680                 685

Ile Ala Leu Arg Gly Leu Leu Leu Ile Thr Gly Arg Phe Leu Glu Ala
    690                 695                 700

Arg Asn Ile Ile Leu Ala Phe Ala Gly Thr Leu Arg His Gly Leu Ile
705                 710                 715                 720

Pro Asn Leu Leu Gly Gln Gly Thr Tyr Ala Arg Phe Asn Cys Arg Asp
                725                 730                 735

Ala Val Trp Trp Trp Leu Gln Cys Ile Gln Asp Tyr Cys Lys Ile Val
            740                 745                 750

Pro Lys Gly Thr Asp Ile Leu Lys Cys Pro Val Ser Arg Met Tyr Pro
        755                 760                 765

Ser Asp Asp Ser Ser Ala Leu Pro Ala Gly Thr Leu Asp Gln Pro Leu
    770                 775                 780

Tyr Glu Val Ile Gln Glu Ala Met Gln Arg His Met Gln Gly Ile Gln
785                 790                 795                 800

Phe Arg Glu Lys Asn Ala Gly Pro Gln Ile Asp Arg Asn Met Lys Asp
                805                 810                 815

Glu Gly Phe Asn Val Thr Ala Gly Val Asp Asp Glu Ser Gly Phe Val
            820                 825                 830

Tyr Gly Gly Asn His Phe Asn Cys Gly Thr Trp Met Asp Lys Met Gly
        835                 840                 845

Glu Ser Asp Arg Gly Arg Asn Arg Gly Ile Pro Ala Thr Pro Arg Asp
```

```
    850                 855                 860

Gly Ser Ala Val Glu Ile Val Gly Leu Ser Lys Ser Thr Val Arg Trp
865                 870                 875                 880

Leu Val Glu Leu Ser Lys Lys Asn Val Phe Pro Tyr His Gly Val Thr
                885                 890                 895

Val Lys Arg Asn Glu Lys Glu Val Leu Ile Thr Tyr Asp Glu Trp Asn
            900                 905                 910

Arg Lys Ile Gln Asp His Phe Glu Lys Leu Phe Tyr Val Ser Glu Asp
        915                 920                 925

Pro Ser Asp Thr Asn Glu Lys His Pro Asn Leu Val His Lys Arg Gly
    930                 935                 940

Ile Tyr Lys Asp Ser Tyr Gly Ala Ser Ser Pro Trp Cys Asp Tyr Gln
945                 950                 955                 960

Leu Arg Pro Asn Phe Thr Ile Ala Met Val Val Ala Pro Glu Leu Phe
                965                 970                 975

Thr Pro Gln Lys Ala Trp Lys Ala Leu Glu Ile Ala Glu Lys Lys Leu
            980                 985                 990

Leu Gly Pro Leu Gly Met Lys Thr  Leu Asp Pro Asp Asp  Met Val Tyr
        995                 1000                1005

Cys Gly  Val Tyr Asp Asn Ala  Leu Asp Asn Asp Asn  Tyr Asn Leu
    1010                1015                1020

Ala Lys  Gly Phe Asn Tyr His  Gln Gly Pro Glu Trp  Leu Trp Pro
    1025                1030                1035

Val Gly  Tyr Phe Leu Arg Ala  Lys Leu Tyr Phe Ser  Lys Leu Met
    1040                1045                1050

Gly Gln  Glu Thr Tyr Thr Lys  Thr Val Phe Leu Ile  Lys Asn Val
    1055                1060                1065

Leu Ser  Arg His Tyr Val His  Leu Glu Arg Ser Pro  Trp Lys Gly
    1070                1075                1080

Leu Pro  Glu Leu Thr Asn Glu  Asn Gly Gln Tyr Cys  Ser Phe Ser
    1085                1090                1095

Cys Glu  Thr Gln Ala Trp Ser  Ile Ala Val Ile Leu  Glu Thr Leu
    1100                1105                1110

Tyr Asp  Leu
    1115


<210> SEQ ID NO 17
<211> LENGTH: 1304
<212> TYPE: PRT
<213> ORGANISM: Anas platyrhynchos

<400> SEQUENCE: 17

Met His Pro Glu Cys Gly Tyr Asn Leu Val Asn Ser Pro His Leu Lys
1               5                   10                  15

Pro Ala Trp Val Leu Asp Arg Ala Leu Trp His Leu Thr Cys Met Val
            20                  25                  30

Ala Asp Gly Lys Cys Ile Asp Lys Gly Val Pro Pro Leu Ile Glu Asn
        35                  40                  45

Asp His His Leu Asn Cys Val Arg Lys Ile Ile Trp Glu Glu Ile Tyr
    50                  55                  60

Pro Lys Ile Lys Leu Trp Glu Phe Phe Gln Val Asp Val Asn Lys Ala
65                  70                  75                  80

Val Glu Gln Phe Arg Thr Leu Leu Thr Gln Gly Lys Glu Ser Lys Met
                85                  90                  95
```

```
Ser Thr Lys Ser Asp Pro Asn Gln His Leu Gln Ile Val Gln Asp Pro
            100                 105                 110

Glu Tyr Arg Arg Phe Gly Cys Thr Val Asp Met Asn Ile Ala Leu Ala
        115                 120                 125

Thr Phe Ile Pro His Ser Asn Gly Pro Gly Ala Ile Glu Glu Cys Cys
    130                 135                 140

Asn Trp Phe Arg Lys Arg Ile Glu Glu Leu Asn Ala Glu Gln His Arg
145                 150                 155                 160

Gln Ile His His His Gln Glu Gln Ala Val Asn Cys Leu Ala Gly Thr
                165                 170                 175

Val Val Tyr Glu Arg Leu Ala Gly His Gly Pro Lys Leu Gly Pro Ile
            180                 185                 190

Ser Arg Lys Tyr Pro Leu Val Thr Arg Tyr Phe Thr Tyr Pro Phe Lys
        195                 200                 205

Asp Met Thr Val Glu Glu Glu Glu Ala Met Ile His Arg Pro Asp Lys
    210                 215                 220

Ala Cys Tyr Phe Met Ala His Asn Gly Trp Val Met Gly Asp Asp Pro
225                 230                 235                 240

Leu Arg Asn Phe Ala Glu Pro Gly Ser Asn Val Tyr Leu Arg Arg Glu
                245                 250                 255

Leu Ile Cys Trp Gly Asp Ser Val Lys Leu Arg Tyr Gly Asn Lys Pro
            260                 265                 270

Glu Asp Cys Pro Tyr Leu Trp Ala His Met Lys Lys Tyr Thr Glu Ile
        275                 280                 285

Thr Ala Lys Tyr Phe His Gly Val Arg Leu Asp Asn Cys His Ser Thr
    290                 295                 300

Pro Ile His Val Ala Glu Tyr Met Leu Asp Thr Ala Arg Lys Leu Arg
305                 310                 315                 320

Ala Asp Leu Phe Val Val Ala Glu Leu Phe Thr Gly Asn Glu Glu Leu
                325                 330                 335

Asp Asn Ile Phe Val Asn Arg Leu Gly Ile Thr Ser Leu Ile Arg Glu
            340                 345                 350

Ala Met Thr Ala Tyr Asn Ser His Glu Glu Gly Arg Leu Val Tyr Arg
        355                 360                 365

Phe Gly Gly Glu Pro Val Gly Ser Phe Val Gln Pro Arg Leu Arg Pro
    370                 375                 380

Leu Met Pro Ala Ile Ala His Ala Leu Phe Met Asp Ile Thr His Asp
385                 390                 395                 400

Asn Glu Cys Pro Ile Gln His Arg Ser Ala Tyr Asp Ala Leu Pro Ser
                405                 410                 415

Ala Met Ile Val Ser Met Ala Cys Cys Ala Thr Gly Ser Thr Lys Gly
            420                 425                 430

Tyr Asp Glu Leu Val Pro His Gln Ile Ser Val Val Ser Glu Glu Arg
        435                 440                 445

Phe Tyr Ser Thr Trp Asn Pro Ala Ala His Leu Thr Ser Gly Glu Val
    450                 455                 460

Asn Phe Gln Thr Gly Ile Leu Ala Gly Arg Leu Ala Ile Asn Arg Leu
465                 470                 475                 480

His Gln Glu Leu Gly Ala Lys Gly Phe Asn Gln Val Tyr Val Asp Gln
                485                 490                 495

Val Asp Glu Asp Ile Val Ala Val Thr Arg His Cys Pro Asn Thr His
            500                 505                 510

Gln Ser Val Val Ala Val Ser Arg Thr Ala Phe Arg Asp Pro Lys Thr
```

-continued

```
        515                 520                 525

Ser Phe Tyr Ser Lys Glu Val Pro Glu Met Cys Ile Pro Gly Lys Ile
    530                 535                 540

Glu Glu Val Val Leu Glu Ala Arg Thr Ile Glu Arg Asn Thr Asn Pro
545                 550                 555                 560

Tyr Lys Lys Asp Glu Arg Phe Ile Asn Gly Leu Pro Asn Phe Thr Val
                565                 570                 575

Glu Leu Arg Glu His Ile Gln Ile Lys Asp Ser Lys Ile Ile Lys Gln
            580                 585                 590

Ala Gly Thr Ala Ile Lys Gly Pro Asn Glu Phe Val Gln Glu Ile Glu
        595                 600                 605

Phe Glu Asn Leu Thr Pro Gly Ser Val Ile Val Phe Arg Val Ser Leu
    610                 615                 620

Asp Pro Lys Ala Gln Glu Ala Val Gly Val Leu Arg Ser His Leu Ile
625                 630                 635                 640

Gln Phe Ser Pro His Phe Lys Ser Gly Ser Leu Pro Asp Asp His Ser
                645                 650                 655

Ala Pro Ile Leu Lys Thr Leu Phe Ser Ser Ile Ala Ser Lys Leu Ser
            660                 665                 670

Leu Ala Asp Leu Asn Gln Val Leu Tyr Arg Cys Glu Ala Glu Glu Gln
        675                 680                 685

Glu Asp Gly Gly Gly Cys Tyr Asn Ile Pro Asn Trp Ser Pro Leu Lys
    690                 695                 700

Tyr Ala Gly Leu Gln Gly Leu Met Ser Val Met Ala Asp Ile Arg Pro
705                 710                 715                 720

Lys Asn Asp Leu Gly His Pro Phe Cys Asp Asn Leu Arg Ser Gly Asp
                725                 730                 735

Trp Met Ile Asp Tyr Val Ser Asn Arg Leu Ile Ser Arg Thr Gly Ala
            740                 745                 750

Cys Ala Glu Val Gly Lys Trp Leu Lys Ala Met Phe Ile Tyr Leu Lys
        755                 760                 765

Lys Ile Pro Arg Tyr Leu Ile Pro Cys Tyr Phe Asp Ala Ile Leu Val
    770                 775                 780

Gly Ala Tyr Thr Thr Leu Leu Asp Val Gly Trp His Gln Met Ser Ser
785                 790                 795                 800

Phe Val Gln Asn Gly Ser Thr Phe Val Lys His Leu Ser Leu Gly Ser
                805                 810                 815

Ile Gln Met Cys Gly Ile Gly Lys Tyr Ser Cys Leu Pro Asp Leu Ser
            820                 825                 830

Pro Ser Leu His Asp Val Pro Tyr Arg Leu Asn Glu Ile Thr Asn Glu
        835                 840                 845

Lys Glu Gln Cys Cys Val Ser Leu Ala Ala Gly Leu Pro His Phe Ser
    850                 855                 860

Ser Gly Ile Phe Arg Ser Trp Gly Arg Asp Thr Phe Ile Ala Leu Arg
865                 870                 875                 880

Gly Leu Met Leu Val Thr Gly Arg Tyr Leu Glu Ala Arg Asn Ile Ile
                885                 890                 895

Leu Ala Phe Gly Gly Thr Leu Arg His Gly Leu Ile Pro Asn Leu Leu
            900                 905                 910

Gly Gln Gly Thr His Ala Arg Tyr Asn Cys Arg Asp Ala Val Trp Trp
        915                 920                 925

Trp Leu Gln Cys Ile Gln Asp Tyr Cys Lys Ile Val Pro Asn Gly Leu
    930                 935                 940
```

```
Asp Ile Leu Arg Cys Pro Val Ser Arg Met Tyr Pro Arg Asp Asp Ser
945                 950                 955                 960

Ser Pro Gln Pro Ala Gly Ser Val Asp Gln Pro Leu Tyr Glu Val Ile
                965                 970                 975

Gln Glu Ala Met Gln Arg His Met Glu Gly Ile Asn Phe Arg Glu Arg
            980                 985                 990

Asn Ala Gly Pro Gln Ile Asp Gln  Asn Met Arg Asp Glu  Gly Phe Asn
        995                 1000                 1005

Val Thr  Ala Gly Val Asp Arg  Glu Thr Gly Phe Val  Phe Gly Gly
    1010                 1015                 1020

Asn Arg  Phe Asn Cys Gly Thr  Trp Met Asp Lys Met  Gly Glu Ser
    1025                 1030                 1035

Asp Arg  Ala Arg Asn Arg Gly  Ile Pro Ala Thr Pro  Arg Asp Gly
    1040                 1045                 1050

Ser Ala  Val Glu Ile Val Gly  Leu Cys Lys Ser Thr  Val Arg Trp
    1055                 1060                 1065

Leu Leu  Asp Leu Ser Arg Lys  Asn Glu Phe Pro Phe  His Gly Val
    1070                 1075                 1080

Thr Ile  Lys Arg His Gly Lys  Glu Glu Thr Ile Thr  Tyr Asp Glu
    1085                 1090                 1095

Trp Asp  Arg Lys Ile Gln Ala  His Phe Glu Lys Leu  Phe Phe Val
    1100                 1105                 1110

Ser Glu  Asn Pro Ala Asp Pro  Asn Glu Lys His Pro  Asn Leu Val
    1115                 1120                 1125

His Lys  Arg Gly Ile Tyr Lys  Asp Ser Tyr Gly Ala  Ser Ser Pro
    1130                 1135                 1140

Trp Cys  Asp Tyr Gln Leu Arg  Pro Asn Phe Thr Ile  Ala Met Val
    1145                 1150                 1155

Val Ala  Pro Glu Leu Phe Thr  Pro Glu Arg Ala Trp  Lys Ala Leu
    1160                 1165                 1170

Gln Ile  Ala Glu Glu Lys Leu  Leu Gly Pro Leu Gly  Met Lys Thr
    1175                 1180                 1185

Leu Asp  Pro Asp Asp Met Val  Tyr Cys Gly Val Tyr  Asp Asn Ala
    1190                 1195                 1200

Leu Asp  Asn Asp Asn Tyr Asn  Val Ala Arg Gly Phe  Asn Tyr His
    1205                 1210                 1215

Gln Gly  Pro Glu Trp Leu Trp  Pro Ile Gly Tyr Phe  Leu Arg Ala
    1220                 1225                 1230

Lys Leu  Tyr Phe Ser Lys Leu  Ile Gly Pro Gln Ile  Tyr Ala Lys
    1235                 1240                 1245

Thr Val  Val Met Ile Lys Asn  Val Leu Ser Arg His  Tyr Val His
    1250                 1255                 1260

Leu Glu  Arg Ser Ser Trp Lys  Gly Leu Pro Glu Leu  Thr Asn Glu
    1265                 1270                 1275

Asn Gly  Gln Tyr Cys Pro Phe  Ser Cys Glu Thr Gln  Ala Trp Ser
    1280                 1285                 1290

Ile Ser  Val Ile Leu Glu Ile  Leu Tyr Asp Leu
    1295                 1300
```

<210> SEQ ID NO 18
<211> LENGTH: 4131
<212> TYPE: DNA
<213> ORGANISM: artificial
<220> FEATURE:

<223> OTHER INFORMATION: Nucleic acid sequence encoding D1 hGDEWT

<400> SEQUENCE: 18

```
atgattcatt ttaccccatt gcagactctt ggactatcta ggtcatgcta ctcccttgcc     60
aatcagttag aattaaatcc tgacttttca agacctaata gaaagtatac ctggaatgat    120
gttggacagc tagtggaaaa attaaaaaag gaatggaatg ttatttgtat tactgatgtt    180
gtctacaatc atactgctgc taatagtaaa tggatccagg aacatccaga atgtgcctat    240
aatcttgtaa attctccaca cttaaaacct gcctgggtct tagacagagc actttggcgt    300
ttctcctgtg atgttgcaga agggaaatac aaagaaaagg gaatacctgc tttgattgaa    360
aatgatcacc atatgaactc catccgaaaa ataatttggg aggatatttt tccaaagctt    420
aaactctggg aatttttcca agtagatgtc aacaaagcgg ttgagcaatt tagaagactt    480
cttacacaag aaaataggcg agtaaccaag tctgatccaa accaacacct tacgattatt    540
caagatcctg aatacagacg gtttggctgt actgtagata tgaacattgc actaacgact    600
ttcataccac atgacaaggg gccagcagca attgaagaat gctgtaattg gtttcataaa    660
agaatggagg aattaaattc agagaagcat cgactcatta actatcatca ggaacaggca    720
gttaattgcc ttttgggaaa tgtgttttat gaacgactgg ctggccatgg tccaaaacta    780
ggacctgtca ctagaaagca tcctttagtt accaggtatt ttactttccc atttgaagag    840
atagacttct ccatggaaga atctatgatt catctgccaa ataaagcttg ttttctgatg    900
gcacacaatg gatgggtaat gggagatgat cctcttcgaa actttgctga accgggttca    960
gaagtttacc taaggagaga acttatttgc tggggagaca gtgttaaatt acgctatggg   1020
aataaaccag aggactgtcc ttatctctgg gcacacatga aaaaatacac tgaaataact   1080
gcaacttatt tccagggagt acgtcttgat aactgccact caacacctct tcacgtagct   1140
gagtacatgt tggatgctgc taggaatttg caacccaatt tatatgtagt agctgaactg   1200
ttcacaggaa gtgaggacct agacaatgtc tttgttacta gactgggcat tagttcctta   1260
ataagagagg caatgagtgc atataatagt catgaagagg gcagattagt ttaccgatat   1320
ggaggagaac ctgttggatc ctttgttcag ccctgtttga ggcctttaat gccagctatt   1380
gcacatgccc tgtttatgga tattacgcat gataatgagt gtcctattgt gcatagatca   1440
gcgtatgatg ctcttccaag tactacaatt gtttctatgg catgttgtgc tagtggaagt   1500
acaagaggct atgatgaatt agtgcctcat cagatttcag tggtttctga agaacggttt   1560
tacactaagt ggaatcctga agcattgcct tcaaacacag gtgaagttaa tttccaaagc   1620
ggcattattg cagccaggtg tgctatcagt aaacttcatc aggagcttgg agccaagggt   1680
tttattcagg tgtatgtgga tcaagttgat gaagacatag tggcagtaac aagacactca   1740
cctagcatcc atcagtctgt tgtggctgta actagaactg ctttcaggaa tcccaagact   1800
tcattttaca gcaaggaagt gcctcaaatg tgcatccctg gcaaaattga agaagtagtt   1860
cttgaagcta gaactattga gagaaacacg aaaccttata ggaaggatga aaattcaatc   1920
aatggaacac cagatatcac agtagaaatt agagaacata ttcagcttaa tgaaagtaaa   1980
attgttaaac aagctggagt tgccacaaaa gggcccaatg aatatattca agaaatagaa   2040
tttgaaaact tgtctccagg aagtgttatt atattcagag ttagtcttga tccacatgca   2100
caagtcgctg ttggcattct tcgaaatcat ctgacacaat tcagtcctca ctttaaatct   2160
ggcagcctag ctgttgacaa tgcagatcct atattaaaaa ttccttttgc ttctcttgcc   2220
tatagattaa ctttggctga gctaaatcag atcctttacc gatgtgaatc agaagaaaag   2280
```

```
gaagatggtg gagggtgcta tgacatacca aactggtcag cccttaaata tgcaggtctt   2340

caaggtttaa tgtctgtatt ggcagaaata agaccaaaga atgacttggg gcatcctttt   2400

tgtaataatt tgaggtctgg agattggatg attgactatg tcagtaaccg gcttatttca   2460

cgatcaggaa ctattgctga agttggtaaa tggttgcagg ctatgttctt ctacctgaag   2520

cagatcccac gttaccttat cccatgttac tttgatgcta tattaattgg tgcatatacc   2580

actcttctgg atacagcatg gaagcagatg tcaagctttg ttcagaatgg ttcaaccttt   2640

gtgaaacacc tttcattggg ttcagttcaa ctgtgtggag taggaaaatt cccttccctg   2700

ccaattcttt cacctgccct aatggatgta ccttataggt taaatgagat cacaaaagaa   2760

aaggagcaat gttgtgtttc tctagctgca ggcttacctc atttttcttc tggtattttc   2820

cgctgctggg gaagggatac ttttattgca cttagaggta tactgctgat tactggacgc   2880

tatgtagaag ccaggaatat tattttagca tttgcgggta ccctgaggca tggtctcatt   2940

cctaatctac tgggtgaagg aatttatgcc agatacaatt gtcgggatgc tgtgtggtgg   3000

tggctgcagt gtatccagga ttactgtaaa atggttccaa atggactaga cattctcaag   3060

tgcccagttt ccagaatgta tcctacagat gattctgctc ctttgcctgc tggcacactg   3120

gatcagccat tgtttgaagt catacaggaa gcaatgcaaa aacacatgca gggcatacag   3180

ttccgagaaa ggaatgctgg tccccagata gatcgaaaca tgaaggacga aggttttaat   3240

ataactgcag gagttgatga agaaacagga tttgtttatg gaggaaatcg tttcaattgt   3300

ggcacatgga tggataaaat gggagaaagt gacagagcta gaaacagagg aatcccagcc   3360

acaccaagag atgggtctgc tgtggaaatt gtgggcctga gtaaatctgc tgttcgctgg   3420

ttgctggaat tatccaaaaa aaatattttc ccttatcatg aagtcacagt aaaaagacat   3480

ggaaaggcta taaaggtctc atatgatgag tggaacagaa aaatacaaga caactttgaa   3540

aagctatttc atgtttccga agacccttca gatttaaatg aaaagcatcc aaatctggtt   3600

cacaaacgtg gcatatacaa agatagttat ggagcttcaa gtccttggtg tgactatcag   3660

ctcaggccta attttaccat agcaatggtt gtggcccctg agctctttac tacagaaaaa   3720

gcatggaaag ctttggagat tgcagaaaaa aaattgcttg gtccccttgg catgaaaact   3780

ttagatccag atgatatggt ttactgtgga atttatgaca acgcattaga caatgacaac   3840

tacaatcttg ctaaaggttt caattatcac caaggacctg agtggctgtg gcctattggg   3900

tattttcttc gtgcaaaatt atatttttcc agattgatgg gcccggagac tactgcaaag   3960

actatagttt tggttaaaaa tgttctttcc cgacattatg ttcatcttga gagatcccct   4020

tggaaaggac ttccagaact gaccaatgag aatgcccagt actgtccttt cagctgtgaa   4080

acacaagcct ggtcaattgc tactattctt gagacacttt atgatttata g            4131
```

<210> SEQ ID NO 19
<211> LENGTH: 4131
<212> TYPE: DNA
<213> ORGANISM: artificial
<220> FEATURE:
<223> OTHER INFORMATION: Nucleic acid sequence encoding D1 hGDE co2

<400> SEQUENCE: 19

```
atgatccact tcacccctct gcagaccctg ggcctgagca gaagctgtta cagcctggcc     60

aaccagctgg aactgaaccc cgacttcagc agacccaacc ggaagtacac ctggaacgat    120

gtgggccagc tggtggaaaa actgaagaaa gaatggaacg tgatctgcat caccgacgtg    180
```

```
gtgtacaacc acaccgccgc caacagcaag tggatccaag agcaccctga gtgcgcctac    240
aacctggtca acagccctca cctgaaacct gcctgggtgc tcgatagagc cctgtggcgg    300
tttagctgtg atgtggccga gggcaagtac aaagagaagg gcatccccgc tctgatcgag    360
aacgaccacc acatgaacag catccggaag atcatctggg aagatatttt ccccaagctg    420
aagctgtggg agttcttcca ggtggacgtg aacaaggccg tggaacagtt cagacggctg    480
ctgacccaag agaacagaag agtgaccaag agcgaccccca accagcacct gaccatcatt    540
caggaccccg agtatcggag attcggctgc accgtggaca tgaatatcgc cctgaccacc    600
ttcattcccc acgacaaagg acctgccgcc atcgaggaat gctgcaactg gttccacaag    660
cggatggaag aattgaacag cgagaagcac cggctgatca actaccacca agagcaggcc    720
gtgaactgcc tgctgggcaa cgtgttctat gagagactgg ccggacacgg ccctaagctg    780
ggacctgtga caagaaagca ccctctggtt acccggtact tcacctttcc attcgaagag    840
atcgacttct ccatggaaga gagcatgatc catctgccta acaaggcctg cttcctgatg    900
gctcacaacg gctgggttat gggcgacgac cctctgagaa atttcgccga gcctggcagc    960
gaggtgtacc tgagaagaga actgatctgt tggggcgaca gcgtgaagct gagatacggc   1020
aacaagcccg aggactgccc ttacctgtgg gcccatatga agaagtacac agagatcacc   1080
gccacctact ttcagggcgt cagactggac aactgccaca gcacacctct gcacgtggcc   1140
gagtacatgc tggacgccgc tagaaatctg cagcccaacc tgtatgtggt ggccgagctg   1200
tttaccggct ccgaggacct ggacaatgtg ttcgtgacca gactgggcat cagcagcctg   1260
atcagagaag ccatgtccgc ctacaatagc cacgaagagg gcagactggt gtacagatat   1320
ggcggcgagc ctgtgggcag cttcgttcag ccttgtctga ggcctctgat gcccgccatt   1380
gctcacgccc tgttcatgga catcacccac gataacgagt gccccatcgt gcacagaagc   1440
gcctacgacg ctctgcctag caccaccatt gtgtccatgg cctgttgtgc cagcggcagc   1500
acaagaggct atgacgaact ggtgccccac cagatttccg tggtgtccga ggaacggttc   1560
tacaccaagt ggaaccccga ggctctgccc agcaataccg gcgaagtgaa tttccagagc   1620
ggcatcattg ccgccagatg cgccatcagc aagctgcacc aagaactggg cgccaagggc   1680
ttcattcagg tgtacgtgga ccaggtcgac gaggacattg tggccgtgac aagacacagc   1740
cccagcatcc atcagagcgt ggtggctgtg accagaaccg ccttcagaaa ccccaagacc   1800
agcttctaca gcaaagaggt gccccagatg tgcatccccg gcaagattga ggaagtggtg   1860
ctcgaggccc ggaccatcga gagaaacacc aagccttacc ggaaggacga gaactccatc   1920
aacggcaccc ctgacatcac cgtggaaatc agagagcaca tccagctcaa cgagagcaag   1980
atcgtgaaac aggccggcgt ggccacaaag ggccccaacg agtatatcca agagattgag   2040
ttcgagaatc tgagccccgg cagcgtgatc atcttcagag tgtccctgga tcctcacgct   2100
caggtggccg tgggcatcct gagaaatcac ctgacacagt tcagcccaca cttcaagagc   2160
ggaagcctgg ccgtggacaa cgccgatcct atcctgaaga tccccttcgc ctctctggcc   2220
tacagactga cactggctga gctgaaccag atcctgtaca gatgcgagtc cgaagagaaa   2280
gaggatggcg gaggctgcta cgacatcccc aattggagcg ccctgaagta tgccggactg   2340
cagggactga tgtctgtgct ggccgagatc agacccaaga acgacctggg acaccccttc   2400
tgcaacaacc tgagatccgg cgactggatg atcgactacg tgtccaacag actgatcagc   2460
agatccggca caatcgccga agtcggcaaa tggctgcagg ccatgttctt ctacctgaag   2520
cagatccctc ggtatctgat cccctgctac ttcgacgcca tcctgatcgg cgcctacacc   2580
```

```
acactgctgg ataccgcctg gaagcagatg tccagcttcg tgcagaacgg cagcaccttc   2640

gtgaagcacc tgtctctggg aagcgtgcag ctgtgtggcg tgggcaaatt tcccagcctg   2700

cctatcctgt ctcctgcact gatggacgtg ccctaccggc tgaatgagat caccaaagaa   2760

aaagagcagt gctgcgtcag cctggctgct ggcctgcctc atttttccag cggcatcttc   2820

cggtgttggg gcagagacac ctttattgcc ctgagaggca tcctgctgat taccggcaga   2880

tacgtggaag cccggaacat catcctggcc tttgccggca cactgcggca cggactgatt   2940

cctaatctgc tcggcgaggg catctacgcc agatacaact gcagagatgc cgtgtggtgg   3000

tggctccagt gcatccagga ctactgcaag atggtgccca acggcctgga catcctgaag   3060

tgccctgtgt ccagaatgta ccctaccgac gatagcgccc ctctgcctgc cggaacactt   3120

gaccagcctc tgttcgaagt gattcaagag gccatgcaga aacacatgca gggaatccag   3180

tttcgcgagc ggaatgccgg acctcagatc gacagaaaca tgaaggatga gggcttcaac   3240

atcaccgctg gcgtggacga agagacaggc tttgtgtacg gcggcaaccg gttcaattgc   3300

ggcacctgga tggacaagat gggcgagtct gaccgggcca gaaacagagg aattcccgcc   3360

acacctagag atggcagcgc tgtggaaatc gtgggcctgt ctaagtctgc tgtgcggtgg   3420

ctgctcgaac tgagcaagaa gaatatcttt ccgtaccacg aagtgaccgt gaagcggcac   3480

ggcaaggcca tcaaggtgtc ctacgacgag tggaacagaa agatccagga caacttcgaa   3540

aagctgttcc atgtgtctga ggaccccagc gacctgaacg aaaagcaccc caacctggtg   3600

cacaagcgcg gcatctacaa ggacagctac ggcgcctctt ctccttggtg cgattaccag   3660

ctgcggccca acttcaccat tgccatggtg gttgcccctg agctgttcac cacagagaag   3720

gcctggaagg ccctggaaat cgccgagaag aaactgctgg gccctctggg catgaagaca   3780

ctggaccccg acgacatggt gtactgcgga atctacgaca acgccctgga taacgacaac   3840

tacaatctgg ccaaggggtt caattaccat cagggacccg agtggctgtg gcctatcggc   3900

tatttcctgc gggccaagct gtacttctcc agactgatgg gccctgagac aaccgccaag   3960

acaatcgtgc tcgtgaagaa cgtgctgagc cggcactatg tgcacctgga aagaagcccc   4020

tggaagggac tgcccgagct gaccaatgag aacgcccagt actgcccctt cagctgcgaa   4080

acacaggcct ggtctatcgc caccatcctg gaaaccctgt acgacctgtg a            4131
```

<210> SEQ ID NO 20
<211> LENGTH: 4395
<212> TYPE: DNA
<213> ORGANISM: artificial
<220> FEATURE:
<223> OTHER INFORMATION: Nucleic acid sequence encoding D2 hGDE

<400> SEQUENCE: 20

```
atgggacaca gtaaacagat tcgaatttta cttctgaacg aaatggagaa actggaaaag     60

accctcttca gacttgaaca agggtatgag ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420

gatgaatggg aaagcagact tagggttgca aaagaatcag gctacaacat gattcatttt    480
```

-continued

```
accccattgc agactcttgg actatctagg tcatgctact cccttgccaa tcagttagaa    540
ttaaatcctg acttttcaag acctaataga aagtatacct ggaatgatgt tggacagcta    600
gtggaaaaat taaaaaagga atggaatgtt atttgtatta ctgatgttgt ctacaatcat    660
actgctgcta atagtaaatg gatccaggaa catccagaat gtgcctataa tcttgtaaat    720
tctccacact taaaacctgc ctgggtctta gacagagcac tttggcgttt ctcctgtgat    780
gttgcagaag ggaaatacaa agaaaaggga atacctgctt tgattgaaaa tgatcaccat    840
atgaactcca tccgaaaaat aatttgggag gatatttttc caaagcttaa actctgggaa    900
tttttccaag tagatgtcaa caaagcggtt gagcaattta gaagacttct tacacaagaa    960
aataggcgag taaccaagtc tgatccaaac caacacctta cgattattca agatcctgaa   1020
tacagacggt ttggctgtac tgtagatatg aacattgcac taacgacttt cataccacat   1080
tattttactt tcccatttga agagatagac ttctccatgg aagaatctat gattcatctg   1140
ccaaataaag cttgttttct gatggcacac aatggatggg taatgggaga tgatcctctt   1200
cgaaactttg ctgaaccggg ttcagaagtt tacctaagga gagaacttat ttgctgggga   1260
gacagtgtta aattacgcta tgggaataaa ccagaggact gtccttatct ctgggcacac   1320
atgaaaaaat acactgaaat aactgcaact tatttccagg gagtacgtct tgataactgc   1380
cactcaacac ctcttcacgt agctgagtac atgttggatg ctgctaggaa tttgcaaccc   1440
aatttatatg tagtagctga actgttcaca ggaagtgagg acctagacaa tgtctttgtt   1500
actagactgg gcattagttc cttaataaga gaggcaatga gtgcatataa tagtcatgaa   1560
gagggcagat tagtttaccg atatggagga gaacctgttg gatcctttgt tcagccctgt   1620
ttgaggcctt taatgccagc tattgcacat gccctgttta tggatattac gcatgataat   1680
gagtgtccta ttgtgcatag atcagcgtat gatgctcttc caagtactac aattgtttct   1740
atggcatgtt gtgctagtgg aagtacaaga ggctatgatg aattagtgcc tcatcagatt   1800
tcagtggttt ctgaagaacg gttttacact aagtggaatc ctgaagcatt gccttcaaac   1860
acaggtgaag ttaatttcca aagcggcatt attgcagcca ggtgtgctat cagtaaactt   1920
catcaggagc ttggagccaa gggttttatt caggtgtatg tggatcaagt tgatgaagac   1980
atagtggcag taacaagaca ctcacctagc atccatcagt ctgttgtggc tgtaactaga   2040
actgctttca ggaatcccaa gacttcattt tacagcaagg aagtgcctca aatgtgcatc   2100
cctggcaaaa ttgaagaagt agttcttgaa gctagaacta ttgagagaaa cacgaaacct   2160
tataggaagg atgaaaattc aatcaatgga acaccagata tcacagtaga aattagagaa   2220
catattcagc ttaatgaaag taaaattgtt aaacaagctg gagttgccac aaaagggccc   2280
aatgaatata ttcaagaaat agaatttgaa aacttgtctc caggaagtgt tattatattc   2340
agagttagtc ttgatccaca tgcacaagtc gctgttggca ttcttcgaaa tcatctgaca   2400
caattcagtc ctcactttaa atctggcagc ctagctgttg acaatgcaga tcctatatta   2460
aaaattcctt ttgcttctct tgcctataga ttaactttgg ctgagctaaa tcagatcctt   2520
taccgatgtg aatcagaaga aaaggaagat ggtggagggt gctatgacat accaaactgg   2580
tcagccctta aatatgcagg tcttcaaggt ttaatgtctg tattggcaga aataagacca   2640
aagaatgact tggggcatcc tttttgtaat aatttgaggt ctggagattg gatgattgac   2700
tatgtcagta accggcttat ttcacgatca ggaactattg ctgaagttgg taaatggttg   2760
caggctatgt tcttctacct gaagcagatc ccacgttacc ttatcccatg ttactttgat   2820
gctatattaa ttggtgcata taccactctt ctggatacag catggaagca gatgtcaagc   2880
```

```
tttgttcaga atggttcaac ctttgtgaaa cacctttcat tgggttcagt tcaactgtgt   2940

ggagtaggaa aattcccttc cctgccaatt ctttcacctg ccctaatgga tgtaccttat   3000

aggttaaatg agatcacaaa agaaaaggag caatgttgtg tttctctagc tgcaggctta   3060

cctcattttt cttctggtat tttccgctgc tggggaaggg atacttttat tgcacttaga   3120

ggtatactgc tgattactgg acgctatgta gaagccagga atattatttt agcatttgcg   3180

ggtaccctga ggcatggtct cattcctaat ctactgggtg aaggaattta tgccagatac   3240

aattgtcggg atgctgtgtg gtggtggctg cagtgtatcc aggattactg taaaatggtt   3300

ccaaatggac tagacattct caagtgccca gtttccagaa tgtatcctac agatgattct   3360

gctcctttgc ctgctggcac actggatcag ccattgtttg aagtcataca ggaagcaatg   3420

caaaaacaca tgcagggcat acagttccga gaaaggaatg ctggtcccca gatagatcga   3480

aacatgaagg acgaaggttt taatataact gcaggagttg atgaagaaac aggatttgtt   3540

tatggaggaa atcgtttcaa ttgtggcaca tggatggata aaatgggaga aagtgacaga   3600

gctagaaaca gaggaatccc agccacacca agagatgggt ctgctgtgga aattgtgggc   3660

ctgagtaaat ctgctgttcg ctggttgctg gaattatcca aaaaaaatat tttcccttat   3720

catgaagtca cagtaaaaag acatggaaag gctataaagg tctcatatga tgagtggaac   3780

agaaaaatac aagacaactt tgaaaagcta tttcatgttt ccgaagaccc ttcagattta   3840

aatgaaaagc atccaaatct ggttcacaaa cgtggcatat acaaagatag ttatggagct   3900

tcaagtcctt ggtgtgacta tcagctcagg cctaatttta ccatagcaat ggttgtggcc   3960

cctgagctct ttactacaga aaaagcatgg aaagctttgg agattgcaga aaaaaaattg   4020

cttggtcccc ttggcatgaa aactttagat ccagatgata tggtttactg tggaatttat   4080

gacaacgcat tagacaatga caactacaat cttgctaaag gtttcaatta tcaccaagga   4140

cctgagtggc tgtggcctat tgggtatttt cttcgtgcaa aattatattt ttccagattg   4200

atgggcccgg agactactgc aaagactata gttttggtta aaaatgttct ttcccgacat   4260

tatgttcatc ttgagagatc cccttggaaa ggacttccag aactgaccaa tgagaatgcc   4320

cagtactgtc ctttcagctg tgaaacacaa gcctggtcaa ttgctactat tcttgagaca   4380

ctttatgatt tatag                                                    4395
```

<210> SEQ ID NO 21
<211> LENGTH: 4293
<212> TYPE: DNA
<213> ORGANISM: artificial
<220> FEATURE:
<223> OTHER INFORMATION: Nucleic acid sequence encoding D3 hGDE

<400> SEQUENCE: 21

```
atgggacaca gtaaacagat tcgaatttta cttctgaacg aaatggagaa actggaaaag     60

accctcttca gacttgaaca agggtatgag ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420

gatgaatggg aaagcagact tagggttgca aaagaatcag gctacaacat gattcatttt    480
```

```
accccattgc agactcttgg actatctagg tcatgctact cccttgccaa tcagttagaa    540

ttaaatcctg acttttcaag acctaataga aagtatacct ggaatgatgt tggacagcta    600

gtggaaaaat taaaaaagga atggaatgtt atttgtatta ctgatgttgt ctacaatcat    660

actgctgcta atagtaaatg gatccaggaa catccagaat gtgcctataa tcttgtaaat    720

tctccacact taaaacctgc ctgggtctta gacagagcac tttggcgttt ctcctgtgat    780

gttgcagaag ggaaatacaa agaaaaggga atacctgctt tgattgaaaa tgatcaccat    840

atgaactcca tccgaaaaat aatttgggag gatatttttc caaagcttaa actctgggaa    900

tttttccaag tagatgtcaa caaagcggtt gagcaattta gaagacttct tacacaagaa    960

aataggcgag taaccaagtc tgatccaaac caacacctta cgattattca agatcctgaa   1020

tacagacggt ttggctgtac tgtagatatg aacattgcac taacgacttt cataccacat   1080

gacaaggggc cagcagcaat tgaagaatgc tgtaattggt ttcataaaag aatggaggaa   1140

ttaaattcag agaagcatcg actcattaac tatcatcagg aacaggcagt taattgcctt   1200

ttgggaaatg tgttttatga acgactggct ggccatggtc caaaactagg acctgtcact   1260

agaaagcatc ctttagttac caggtatttt actttcccat ttgaagagat agacttctcc   1320

atggaagaat ctatgattca tctgccaaat aaagcttgtt ttctgatggc acacaatgga   1380

tgggtaatgg gagatgatcc tcttcgaaac tttgctgaac cgggttcaga agtttaccta   1440

aggagagaac ttatttgctg gggagacagt gttaaattac gctatgggaa taaaccagag   1500

gactgtcctt atctctgggc acacatgaaa aaatacactg aaataactgc aacttatttc   1560

cagggagtac gtcttgataa ctgccactca acacctcttc acgtagctga gtacatgttg   1620

gatgctgcta ggaatttgca acccaattta tatgtagtag ctgaactgtt cacaggaagt   1680

gaggacctag acaatgtctt tgttactaga ctgggcatta gttccttaat aagagaggca   1740

atgagtgcat ataatagtca tgaagagggc agattagttt accgatatgg aggagaacct   1800

gttggatcct ttgttcagcc ctgtttgagg cctttaatgc cagctattgc acatgccctg   1860

tttatggata ttacgcatga taatgagtgt cctattgtgc atagatcagc gtatgatgct   1920

cttccaagta ctacaattgt ttctatggca tgttgtgcta gtggaagtac aagaggctat   1980

gatgaattag tgcctcatca gggcaaaatt gaagaagtag ttcttgaagc tagaactatt   2040

gagagaaaca cgaaacctta taggaaggat gaaaattcaa tcaatggaac accagatatc   2100

acagtagaaa ttagagaaca tattcagctt aatgaaagta aaattgttaa acaagctgga   2160

gttgccacaa aagggcccaa tgaatatatt caagaaatag aatttgaaaa cttgtctcca   2220

ggaagtgtta ttatattcag agttagtctt gatccacatg cacaagtcgc tgttggcatt   2280

cttcgaaatc atctgacaca attcagtcct cactttaaat ctggcagcct agctgttgac   2340

aatgcagatc ctatattaaa aattcctttt gcttctcttg cctatagatt aactttggct   2400

gagctaaatc agatccttta ccgatgtgaa tcagaagaaa aggaagatgg tggagggtgc   2460

tatgacatac caaactggtc agcccttaaa tatgcaggtc ttcaaggttt aatgtctgta   2520

ttggcagaaa taagaccaaa gaatgacttg gggcatcctt tttgtaataa tttgaggtct   2580

ggagattgga tgattgacta tgtcagtaac cggcttattt cacgatcagg aactattgct   2640

gaagttggta aatggttgca ggctatgttc ttctacctga agcagatccc acgttacctt   2700

atcccatgtt actttgatgc tatattaatt ggtgcatata ccactcttct ggatacagca   2760

tggaagcaga tgtcaagctt tgttcagaat ggttcaacct ttgtgaaaca cctttcattg   2820

ggttcagttc aactgtgtgg agtaggaaaa ttcccttccc tgccaattct ttcacctgcc   2880
```

```
ctaatggatg taccttatag gttaaatgag atcacaaaag aaaaggagca atgttgtgtt   2940

tctctagctg caggcttacc tcatttttct tctggtattt tccgctgctg gggaagggat   3000

acttttattg cacttagagg tatactgctg attactggac gctatgtaga agccaggaat   3060

attattttag catttgcggg taccctgagg catggtctca ttcctaatct actgggtgaa   3120

ggaatttatg ccagatacaa ttgtcgggat gctgtgtggt ggtggctgca gtgtatccag   3180

gattactgta aaatggttcc aaatggacta gacattctca agtgcccagt ttccagaatg   3240

tatcctacag atgattctgc tcctttgcct gctggcacac tggatcagcc attgtttgaa   3300

gtcatacagg aagcaatgca aaaacacatg cagggcatac agttccgaga aaggaatgct   3360

ggtccccaga tagatcgaaa catgaaggac gaaggtttta atataactgc aggagttgat   3420

gaagaaacag gatttgttta tggaggaaat cgtttcaatt gtggcacatg gatggataaa   3480

atgggagaaa gtgacagagc tagaaacaga ggaatcccag ccacaccaag agatgggtct   3540

gctgtggaaa ttgtgggcct gagtaaatct gctgttcgct ggttgctgga attatccaaa   3600

aaaaatattt tcccttatca tgaagtcaca gtaaaaagac atggaaaggc tataaaggtc   3660

tcatatgatg agtggaacag aaaaatacaa gacaactttg aaaagctatt tcatgtttcc   3720

gaagaccctt cagatttaaa tgaaaagcat ccaaatctgg ttcacaaacg tggcatatac   3780

aaagatagtt atggagcttc aagtccttgg tgtgactatc agctcaggcc taattttacc   3840

atagcaatgg ttgtggcccc tgagctcttt actacagaaa aagcatggaa agctttggag   3900

attgcagaaa aaaaattgct tggtcccctt ggcatgaaaa ctttagatcc agatgatatg   3960

gtttactgtg gaatttatga caacgcatta gacaatgaca actacaatct tgctaaaggt   4020

ttcaattatc accaaggacc tgagtggctg tggcctattg ggtattttct tcgtgcaaaa   4080

ttatattttt ccagattgat gggcccggag actactgcaa agactatagt tttggttaaa   4140

aatgttcttt cccgacatta tgttcatctt gagagatccc cttggaaagg acttccagaa   4200

ctgaccaatg agaatgccca gtactgtcct ttcagctgtg aaacacaagc ctggtcaatt   4260

gctactattc ttgagacact ttatgattta tag                                4293
```

<210> SEQ ID NO 22
<211> LENGTH: 4089
<212> TYPE: DNA
<213> ORGANISM: artificial
<220> FEATURE:
<223> OTHER INFORMATION: Nucleic acid sequence encoding D2,3 hGDE WT

<400> SEQUENCE: 22

```
atgggacaca gtaaacagat tcgaatttta cttctgaacg aaatggagaa actggaaaag     60

accctcttca gacttgaaca agggtatgag ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420

gatgaatggg aaagcagact tagggttgca aaagaatcag gctacaacat gattcatttt    480

accccattgc agactcttgg actatctagg tcatgctact cccttgccaa tcagttagaa    540

ttaaatcctg acttttcaag acctaataga aagtatacct ggaatgatgt tggacagcta    600
```

```
gtggaaaaat taaaaaagga atggaatgtt atttgtatta ctgatgttgt ctacaatcat    660
actgctgcta atagtaaatg gatccaggaa catccagaat gtgcctataa tcttgtaaat    720
tctccacact taaaacctgc ctgggtctta gacagagcac tttggcgttt ctcctgtgat    780
gttgcagaag ggaaatacaa agaaaaggga atacctgctt tgattgaaaa tgatcaccat    840
atgaactcca tccgaaaaat aatttgggag gatatttttc caaagcttaa actctgggaa    900
tttttccaag tagatgtcaa caaagcggtt gagcaattta gaagacttct tacacaagaa    960
aataggcgag taaccaagtc tgatccaaac caacacctta cgattattca agatcctgaa   1020
tacagacggt ttggctgtac tgtagatatg aacattgcac taacgacttt cataccacat   1080
tattttactt tcccatttga agagatagac ttctccatgg aagaatctat gattcatctg   1140
ccaaataaag cttgttttct gatggcacac aatggatggg taatgggaga tgatcctctt   1200
cgaaactttg ctgaaccggg ttcagaagtt tacctaagga gagaacttat ttgctgggga   1260
gacagtgtta aattacgcta tggaataaa ccagaggact gtccttatct ctgggcacac   1320
atgaaaaaat acactgaaat aactgcaact tatttccagg gagtacgtct tgataactgc   1380
cactcaacac ctcttcacgt agctgagtac atgttggatg ctgctaggaa tttgcaaccc   1440
aatttatatg tagtagctga actgttcaca ggaagtgagg acctagacaa tgtctttgtt   1500
actagactgg gcattagttc cttaataaga gaggcaatga gtgcatataa tagtcatgaa   1560
gagggcagat tagtttaccg atatggagga gaacctgttg gatcctttgt tcagccctgt   1620
ttgaggcctt taatgccagc tattgcacat gccctgttta tggatattac gcatgataat   1680
gagtgtccta ttgtgcatag atcagcgtat gatgctcttc caagtactac aattgtttct   1740
atggcatgtt gtgctagtgg aagtacaaga ggctatgatg aattagtgcc tcatcagggc   1800
aaaattgaag aagtagttct tgaagctaga actattgaga gaaacacgaa accttatagg   1860
aaggatgaaa attcaatcaa tggaacacca gatatcacag tagaaattag agaacatatt   1920
cagcttaatg aaagtaaaat tgttaaacaa gctggagttg ccacaaaagg gcccaatgaa   1980
tatattcaag aaatagaatt tgaaaacttg tctccaggaa gtgttattat attcagagtt   2040
agtcttgatc cacatgcaca agtcgctgtt ggcattcttc gaaatcatct gacacaattc   2100
agtcctcact ttaaatctgg cagcctagct gttgacaatg cagatcctat attaaaaatt   2160
ccttttgctt ctcttgccta tagattaact ttggctgagc taaatcagat cctttaccga   2220
tgtgaatcag aagaaaagga agatggtgga gggtgctatg acataccaaa ctggtcagcc   2280
cttaaatatg caggtcttca aggtttaatg tctgtattgg cagaaataag accaaagaat   2340
gacttggggc atcctttttg taataatttg aggtctggag attggatgat tgactatgtc   2400
agtaaccggc ttatttcacg atcaggaact attgctgaag ttggtaaatg gttgcaggct   2460
atgttcttct acctgaagca gatcccacgt taccttatcc catgttactt tgatgctata   2520
ttaattggtg catataccac tcttctggat acagcatgga agcagatgtc aagctttgtt   2580
cagaatggtt caacctttgt gaaacacctt tcattgggtt cagttcaact gtgtggagta   2640
ggaaaattcc cttccctgcc aattctttca cctgccctaa tggatgtacc ttataggtta   2700
aatgagatca caaaagaaaa ggagcaatgt tgtgtttctc tagctgcagg cttacctcat   2760
ttttcttctg gtattttccg ctgctgggga agggatactt ttattgcact tagaggtata   2820
ctgctgatta ctggacgcta tgtagaagcc aggaatatta ttttagcatt tgcgggtacc   2880
ctgaggcatg gtctcattcc taatctactg ggtgaaggaa tttatgccag atacaattgt   2940
cgggatgctg tgtggtggtg gctgcagtgt atccaggatt actgtaaaat ggttccaaat   3000
```

```
ggactagaca ttctcaagtg cccagtttcc agaatgtatc ctacagatga ttctgctcct   3060

ttgcctgctg gcacactgga tcagccattg tttgaagtca tacaggaagc aatgcaaaaa   3120

cacatgcagg gcatacagtt ccgagaaagg aatgctggtc cccagataga tcgaaacatg   3180

aaggacgaag gttttaatat aactgcagga gttgatgaag aaacaggatt tgtttatgga   3240

ggaaatcgtt tcaattgtgg cacatggatg gataaaatgg gagaaagtga cagagctaga   3300

aacagaggaa tcccagccac accaagagat gggtctgctg tggaaattgt gggcctgagt   3360

aaatctgctg ttcgctggtt gctggaatta tccaaaaaaa atattttccc ttatcatgaa   3420

gtcacagtaa aaagacatgg aaaggctata aaggtctcat atgatgagtg gaacagaaaa   3480

atacaagaca actttgaaaa gctatttcat gtttccgaag acccttcaga tttaaatgaa   3540

aagcatccaa atctggttca caaacgtggc atatacaaag atagttatgg agcttcaagt   3600

ccttggtgtg actatcagct caggcctaat tttaccatag caatggttgt ggcccctgag   3660

ctctttacta cagaaaaagc atggaaagct ttggagattg cagaaaaaaa attgcttggt   3720

ccccttggca tgaaaacttt agatccagat gatatggttt actgtggaat ttatgacaac   3780

gcattagaca atgacaacta caatcttgct aaaggtttca attatcacca aggacctgag   3840

tggctgtggc ctattgggta ttttcttcgt gcaaaattat atttttccag attgatgggc   3900

ccggagacta ctgcaaagac tatagttttg gttaaaaatg ttctttcccg acattatgtt   3960

catcttgaga gatccccttg gaaaggactt ccagaactga ccaatgagaa tgcccagtac   4020

tgtcctttca gctgtgaaac acaagcctgg tcaattgcta ctattcttga gacactttat   4080

gatttatag                                                            4089
```

<210> SEQ ID NO 23
<211> LENGTH: 4089
<212> TYPE: DNA
<213> ORGANISM: artificial
<220> FEATURE:
<223> OTHER INFORMATION: Nucleic acid sequence encoding D2,3 hGDE co2

<400> SEQUENCE: 23

```
atgggccaca gcaagcagat cagaatcctg ctgctgaacg agatggaaaa gctggaaaag     60

accctgttcc ggctcgagca gggctacgag ctgcagttta gactgggccc tacactgcag    120

ggcaaagccg tgaccgtgta cacaaactac cccttccctg gcgaaacctt caaccgcgag    180

aagttcagaa gcctggactg ggagaacccc accgagagag aggacgacag cgacaagtac    240

tgcaagctga acctgcagca gagcggctcc ttccagtact acttcctgca aggcaacgag    300

aagtccggcg gaggctacat cgtggtggac cctattctga gagtgggcgc cgacaatcac    360

gtgctgcctc tggattgtgt gaccctgcag accttcctgg ccaagtgtct gggccctttc    420

gatgagtggg agagcagact gcgcgtggcc aaagaaagcg gctacaacat gatccacttc    480

acccctctgc agaccctggg cctgagcaga agctgttaca gcctggccaa ccagctggaa    540

ctgaaccccg acttcagcag acccaaccgg aagtacacct ggaacgatgt gggccagctg    600

gtggaaaaac tgaagaaaga atggaacgtg atctgcatca ccgacgtggt gtacaaccac    660

accgccgcca acagcaagtg gatccaagag caccctgagt gcgcctacaa cctggtcaac    720

agccctcacc tgaaacctgc ctgggtgctc gatagagccc tgtggcggtt tagctgtgat    780

gtggccgagg gcaagtacaa agagaagggc atccccgctc tgatcgagaa cgaccaccac    840

atgaacagca tccggaagat catctgggaa gatattttcc ccaagctgaa gctgtgggag    900
```

-continued

```
ttcttccagg tggacgtgaa caaggccgtg gaacagttca gacggctgct gacccaagag    960
aacagaagag tgaccaagag cgaccccaac cagcacctga ccatcattca ggaccccgag   1020
tatcggagat tcggctgcac cgtggacatg aatatcgccc tgaccacctt cattccccac   1080
tacttcacct ttccattcga agagatcgac ttctccatgg aagagagcat gatccatctg   1140
cctaacaagg cctgcttcct gatggctcac aacggctggg ttatgggcga cgaccctctg   1200
agaaatttcg ccgagcctgg cagcgaggtg tacctgagaa gagaactgat ctgttggggc   1260
gacagcgtga agctgagata cggcaacaag cccgaggact gcccttacct gtgggcccat   1320
atgaagaagt acacagagat caccgccacc tactttcagg gcgtcagact ggacaactgc   1380
cacagcacac ctctgcacgt ggccgagtac atgctggacg ccgctagaaa tctgcagccc   1440
aacctgtatg tggtggccga gctgtttacc ggctccgagg acctggacaa tgtgttcgtg   1500
accagactgg gcatcagcag cctgatcaga gaagccatgt ccgcctacaa tagccacgaa   1560
gagggcagac tggtgtacag atatggcggc gagcctgtgg gcagcttcgt tcagccttgt   1620
ctgaggcctc tgatgcccgc cattgctcac gccctgttca tggacatcac ccacgataac   1680
gagtgcccca tcgtgcacag aagcgcctac gacgctctgc ctagcaccac cattgtgtcc   1740
atggcctgtt gtgccagcgg cagcacaaga ggctatgacg aactggtgcc ccaccagggc   1800
aagattgagg aagtggtgct cgaggcccgg accatcgaga gaaacaccaa gccttaccgg   1860
aaggacgaga actccatcaa cggcacccct gacatcaccg tggaaatcag agagcacatc   1920
cagctcaacg agagcaagat cgtgaaacag gccggcgtgg ccacaaaggg ccccaacgag   1980
tatatccaag agattgagtt cgagaatctg agccccggca gcgtgatcat cttcagagtg   2040
tccctggatc ctcacgctca ggtggccgtg ggcatcctga gaaatcacct gacacagttc   2100
agcccacact tcaagagcgg aagcctggcc gtggacaacg ccgatcctat cctgaagatc   2160
cccttcgcct ctctggccta cagactgaca ctggctgagc tgaaccagat cctgtacaga   2220
tgcgagtccg aagagaaaga ggatggcgga ggctgctacg acatccccaa ttggagcgcc   2280
ctgaagtatg ccggactgca gggactgatg tctgtgctgg ccgagatcag acccaagaac   2340
gacctgggac accccttctg caacaacctg agatccggcg actggatgat cgactacgtg   2400
tccaacagac tgatcagcag atccggcaca atcgccgaag tcggcaaatg gctgcaggcc   2460
atgttcttct acctgaagca gatccctcgg tatctgatcc cctgctactt cgacgccatc   2520
ctgatcggcg cctacaccac actgctggat accgcctgga agcagatgtc cagcttcgtg   2580
cagaacggca gcaccttcgt gaagcacctg tctctgggaa gcgtgcagct gtgtggcgtg   2640
ggcaaatttc ccagcctgcc tatcctgtct cctgcactga tggacgtgcc ctaccggctg   2700
aatgagatca ccaaagaaaa agagcagtgc tgcgtcagcc tggctgctgg cctgcctcat   2760
ttttccagcg gcatcttccg gtgttggggc agagacacct ttattgccct gagaggcatc   2820
ctgctgatta ccggcagata cgtggaagcc cggaacatca tcctggcctt tgccggcaca   2880
ctgcggcacg gactgattcc taatctgctc ggcgagggca tctacgccag atacaactgc   2940
agagatgccg tgtggtggtg gctccagtgc atccaggact actgcaagat ggtgcccaac   3000
ggcctggaca tcctgaagtg ccctgtgtcc agaatgtacc ctaccgacga tagcgcccct   3060
ctgcctgccg gaacacttga ccagcctctg ttcgaagtga ttcaagaggc catgcagaaa   3120
cacatgcagg gaatccagtt tcgcgagcgg aatgccggac ctcagatcga cagaaacatg   3180
aaggatgagg gcttcaacat caccgctggc gtggacgaag agacaggctt tgtgtacggc   3240
ggcaaccggt tcaattgcgg cacctggatg gacaagatgg gcgagtctga ccgggccaga   3300
```

```
aacagaggaa ttcccgccac acctagagat ggcagcgctg tggaaatcgt gggcctgtct   3360

aagtctgctg tgcggtggct gctcgaactg agcaagaaga atatctttcc gtaccacgaa   3420

gtgaccgtga agcggcacgg caaggccatc aaggtgtcct acgacgagtg gaacagaaag   3480

atccaggaca acttcgaaaa gctgttccat gtgtctgagg accccagcga cctgaacgaa   3540

aagcacccca acctggtgca caagcgcggc atctacaagg acagctacgg cgcctcttct   3600

ccttggtgcg attaccagct gcggcccaac ttcaccattg ccatggtggt tgcccctgag   3660

ctgttcacca cagagaaggc ctggaaggcc ctggaaatcg ccgagaagaa actgctgggc   3720

cctctgggca tgaagacact ggaccccgac gacatggtgt actgcggaat ctacgacaac   3780

gccctggata acgacaacta caatctggcc aaggggttca attaccatca gggacccgag   3840

tggctgtggc ctatcggcta tttcctgcgg gccaagctgt acttctccag actgatgggc   3900

cctgagacaa ccgccaagac aatcgtgctc gtgaagaacg tgctgagccg gcactatgtg   3960

cacctggaaa gaagcccctg gaagggactg cccgagctga ccaatgagaa cgcccagtac   4020

tgccccttca gctgcgaaac acaggcctgg tctatcgcca ccatcctgga aaccctgtac   4080

gacctgtga                                                           4089
```

<210> SEQ ID NO 24
<211> LENGTH: 4020
<212> TYPE: DNA
<213> ORGANISM: artificial
<220> FEATURE:
<223> OTHER INFORMATION: Nucleic acid sequence encoding D4 hGDE WT

<400> SEQUENCE: 24

```
atgggacaca gtaaacagat tcgaatttta cttctgaacg aaatggagaa actggaaaag     60

accctcttca gacttgaaca agggtatgag ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420

gatgaatggg aaagcagact tagggttgca aaagaatcag gctacaacat gattcatttt    480

accccattgc agactcttgg actatctagg tcatgctact cccttgccaa tcagttagaa    540

ttaaatcctg acttttcaag acctaataga aagtatacct ggaatgatgt tggacagcta    600

gtggaaaaat taaaaaagga atggaatgtt atttgtatta ctgatgttgt ctacaatcat    660

actgctgcta atagtaaatg gatccaggaa catccagaat gtgcctataa tcttgtaaat    720

tctccacact taaaacctgc ctgggtctta gacagagcac tttggcgttt ctcctgtgat    780

gttgcagaag ggaaatacaa agaaaaggga atacctgctt tgattgaaaa tgatcaccat    840

atgaactcca tccgaaaaat aatttgggag gatatttttc caaagcttaa actctgggaa    900

tttttccaag tagatgtcaa caaagcggtt gagcaattta gaagacttct tacacaagaa    960

aataggcgag taaccaagtc tgatccaaac caacacctta cgattattca agatcctgaa   1020

tacagacggt ttggctgtac tgtagatatg aacattgcac taacgacttt cataccacat   1080

gacaaggggc cagcagcaat tgaagaatgc tgtaattggt ttcataaaag aatggaggaa   1140

ttaaattcag agaagcatcg actcattaac tatcatcagg aacaggcagt taattgcctt   1200
```

```
ttgggaaatg tgttttatga acgactggct ggccatggtc caaaactagg acctgtcact   1260
agaaagcatc ctttagttac caggtatttt actttcccat ttgaagagat agacttctcc   1320
atggaagaat ctatgattca tctgccaaat aaagcttgtt ttctgatggc acacaatgga   1380
tgggtaatgg gagatgatcc tcttcgaaac tttgctgaac cgggttcaga agtttaccta   1440
aggagagaac ttatttgctg gggagacagt gttaaattac gctatgggaa taaaccagag   1500
gactgtcctt atctctgggc acacatgaaa aaatacactg aaataactgc aacttatttc   1560
cagggagtac gtcttgataa ctgccactca acacctcttc acgtagctga gtacatgttg   1620
gatgctgcta ggaatttgca acccaattta tatgtagtag ctgaactgtt cacaggaagt   1680
gaggacctag acaatgtctt tgttactaga ctgggcatta gttccttaat aagagaggca   1740
atgagtgcat ataatagtca tgaagagggc agattagttt accgatatgg aggagaacct   1800
gttggatcct ttgttcagcc ctgtttgagg cctttaatgc cagctattgc acatgccctg   1860
tttatggata ttacgcatga taatgagtgt cctattgtgc atagatcagc gtatgatgct   1920
cttccaagta ctacaattgt ttctatggca tgttgtgcta gtggaagtac aagaggctat   1980
gatgaattag tgcctcatca gatttcagtg gtttctgaag aacggtttta cactaagtgg   2040
aatcctgaag cattgccttc aaacacaggt gaagttaatt tccaaagcgg cattattgca   2100
gccaggtgtg ctatcagtaa acttcatcag gagcttggag ccaagggttt tattcaggtg   2160
tatgtggatc aagttgatga agacatagtg gcagtaacaa gacactcacc tagcatccat   2220
cagtctgttg tggctgtaac tagaactgct ttcaggaatc ccaagacttc attttacagc   2280
aaggaagtgc ctcaaatgtg catccctggc aaaattgaag aagtagttct tgaagctaga   2340
actattgaga gaaacacgaa accttatagg aaggatgaaa attcaatcaa tggaacacca   2400
gatatcacag tagaaattag agaacatatt cagcttaatg aaagtaaaat tgttaaacaa   2460
gctggagttg ccacaaaagg gcccaatgaa tatattcaag aaatagaatt tgaaaacttg   2520
tctccaggaa gtgttattat attcagagtt agtcttgatc cacatgcaca agtcgctgtt   2580
ggcattcttc gaaatcatct gacacaattc agtcctcact ttaaatctgg cagcctagct   2640
gttgacaatg cagatcctat attaaaaatt ccttttgctt ctttacctca tttttcttct   2700
ggtattttcc gctgctgggg aagggatact tttattgcac ttagaggtat actgctgatt   2760
actggacgct atgtagaagc caggaatatt attttagcat ttgcgggtac cctgaggcat   2820
ggtctcattc ctaatctact gggtgaagga atttatgcca gatacaattg tcgggatgct   2880
gtgtggtggt ggctgcagtg tatccaggat tactgtaaaa tggttccaaa tggactagac   2940
attctcaagt gcccagtttc cagaatgtat cctacagatg attctgctcc tttgcctgct   3000
ggcacactgg atcagccatt gtttgaagtc atacaggaag caatgcaaaa acacatgcag   3060
ggcatacagt tccgagaaag gaatgctggt ccccagatag atcgaaacat gaaggacgaa   3120
ggttttaata taactgcagg agttgatgaa gaaacaggat ttgtttatgg aggaaatcgt   3180
ttcaattgtg gcacatggat ggataaaatg ggagagaaag tgacagagctag aaacagagga   3240
atcccagcca caccaagaga tgggtctgct gtggaaattg tgggcctgag taaatctgct   3300
gttcgctggt tgctggaatt atccaaaaaa aatattttcc cttatcatga agtcacagta   3360
aaaagacatg gaaaggctat aaaggtctca tatgatgagt ggaacagaaa aatacaagac   3420
aactttgaaa agctatttca tgtttccgaa gacccttcag atttaaatga aaagcatcca   3480
aatctggttc acaaacgtgg catatacaaa gatagttatg gagcttcaag tccttggtgt   3540
gactatcagc tcaggcctaa ttttaccata gcaatggttg tggcccctga gctctttact   3600
```

```
acagaaaaag catggaaagc tttggagatt gcagaaaaaa aattgcttgg tccccttggc   3660

atgaaaactt tagatccaga tgatatggtt tactgtggaa tttatgacaa cgcattagac   3720

aatgacaact acaatcttgc taaaggtttc aattatcacc aaggacctga gtggctgtgg   3780

cctattgggt attttcttcg tgcaaaatta tatttttcca gattgatggg cccggagact   3840

actgcaaaga ctatagtttt ggttaaaaat gttctttccc gacattatgt tcatcttgag   3900

agatcccctt ggaaaggact tccagaactg accaatgaga atgcccagta ctgtcctttc   3960

agctgtgaaa cacaagcctg gtcaattgct actattcttg agacacttta tgatttatag   4020
```

<210> SEQ ID NO 25
<211> LENGTH: 4020
<212> TYPE: DNA
<213> ORGANISM: artificial
<220> FEATURE:
<223> OTHER INFORMATION: Nucleic acid sequence encoding D4 hGDE co2

<400> SEQUENCE: 25

```
atgggccaca gcaagcagat cagaatcctg ctgctgaacg agatggaaaa gctggaaaag     60

accctgttcc ggctcgagca gggctacgag ctgcagttta gactgggccc tacactgcag    120

ggcaaagccg tgaccgtgta cacaaactac cccttccctg gcgaaacctt caaccgcgag    180

aagttcagaa gcctggactg ggagaacccc accgagagag aggacgacag cgacaagtac    240

tgcaagctga acctgcagca gagcggctcc ttccagtact acttcctgca aggcaacgag    300

aagtccggcg gaggctacat cgtggtggac cctattctga gagtgggcgc cgacaatcac    360

gtgctgcctc tggattgtgt gaccctgcag accttcctgg ccaagtgtct gggccctttc    420

gatgagtggg agagcagact gcgcgtggcc aaagaaagcg gctacaacat gatccacttc    480

acccctctgc agaccctggg cctgagcaga agctgttaca gcctggccaa ccagctggaa    540

ctgaaccccg acttcagcag acccaaccgg aagtacacct ggaacgatgt gggccagctg    600

gtggaaaaac tgaagaaaga atggaacgtg atctgcatca ccgacgtggt gtacaaccac    660

accgccgcca acagcaagtg gatccaagag caccctgagt gcgcctacaa cctggtcaac    720

agccctcacc tgaaacctgc ctgggtgctc gatagagccc tgtggcggtt tagctgtgat    780

gtggccgagg gcaagtacaa agagaagggc atccccgctc tgatcgagaa cgaccaccac    840

atgaacagca tccggaagat catctgggaa gatattttcc ccaagctgaa gctgtgggag    900

ttcttccagg tggacgtgaa caaggccgtg gaacagttca gacggctgct gacccaagag    960

aacagaagag tgaccaagag cgaccccaac cagcacctga ccatcattca ggaccccgag   1020

tatcggagat tcggctgcac cgtggacatg aatatcgccc tgaccacctt cattccccac   1080

gacaaaggac ctgccgccat cgaggaatgc tgcaactggt tccacaagcg gatggaagaa   1140

ttgaacagcg agaagcaccg gctgatcaac taccaccaag agcaggccgt gaactgcctg   1200

ctgggcaacg tgttctatga gagactggcc ggacacggcc ctaagctggg acctgtgaca   1260

agaaagcacc ctctggttac ccggtacttc acctttccat tcgaagagat cgacttctcc   1320

atggaagaga gcatgatcca tctgcctaac aaggcctgct tcctgatggc tcacaacggc   1380

tgggttatgg gcgacgaccc tctgagaaat ttcgccgagc ctggcagcga ggtgtacctg   1440

agaagagaac tgatctgttg ggcgacagc gtgaagctga gatacggcaa caagcccgag    1500

gactgccctt acctgtgggc ccatatgaag aagtacacag agatcaccgc cacctacttt   1560

cagggcgtca gactggacaa ctgccacagc acacctctgc acgtggccga gtacatgctg   1620
```

-continued

```
gacgccgcta gaaatctgca gcccaacctg tatgtggtgg ccgagctgtt taccggctcc   1680
gaggacctgg acaatgtgtt cgtgaccaga ctgggcatca gcagcctgat cagagaagcc   1740
atgtccgcct acaatagcca cgaagagggc agactggtgt acagatatgg cggcgagcct   1800
gtgggcagct tcgttcagcc ttgtctgagg cctctgatgc ccgccattgc tcacgccctg   1860
ttcatggaca tcacccacga taacgagtgc cccatcgtgc acagaagcgc ctacgacgct   1920
ctgcctagca ccaccattgt gtccatggcc tgttgtgcca gcggcagcac aagaggctat   1980
gacgaactgg tgccccacca gatttccgtg gtgtccgagg aacggttcta caccaagtgg   2040
aaccccgagg ctctgcccag caataccggc gaagtgaatt tccagagcgg catcattgcc   2100
gccagatgcg ccatcagcaa gctgcaccaa gaactgggcg ccaagggctt cattcaggtg   2160
tacgtggacc aggtcgacga ggacattgtg gccgtgacaa gacacagccc cagcatccat   2220
cagagcgtgg tggctgtgac cagaaccgcc ttcagaaacc ccaagaccag cttctacagc   2280
aaagaggtgc cccagatgtg catccccggc aagattgagg aagtggtgct cgaggcccgg   2340
accatcgaga gaaacaccaa gccttaccgg aaggacgaga actccatcaa cggcacccct   2400
gacatcaccg tggaaatcag agagcacatc cagctcaacg agagcaagat cgtgaaacag   2460
gccggcgtgg ccacaaaggg ccccaacgag tatatccaag agattgagtt cgagaatctg   2520
agccccggca gcgtgatcat cttcagagtg tccctggatc ctcacgctca ggtggccgtg   2580
ggcatcctga gaaatcacct gacacagttc agcccacact tcaagagcgg aagcctggcc   2640
gtggacaacg ccgatcctat cctgaagatc cccttcgcct ctctgcctca tttttccagc   2700
ggcatcttcc ggtgttgggg cagagacacc tttattgccc tgagaggcat cctgctgatt   2760
accggcagat acgtggaagc ccggaacatc atcctggcct ttgccggcac actgcggcac   2820
ggactgattc ctaatctgct cggcgagggc atctacgcca gatacaactg cagagatgcc   2880
gtgtggtggt ggctccagtg catccaggac tactgcaaga tggtgcccaa cggcctggac   2940
atcctgaagt gccctgtgtc cagaatgtac cctaccgacg atagcgcccc tctgcctgcc   3000
ggaacacttg accagcctct gttcgaagtg attcaagagg ccatgcagaa acacatgcag   3060
ggaatccagt ttcgcgagcg gaatgccgga cctcagatcg acagaaacat gaaggatgag   3120
ggcttcaaca tcaccgctgg cgtggacgaa gagacaggct ttgtgtacgg cggcaaccgg   3180
ttcaattgcg gcacctggat ggacaagatg ggcgagtctg accgggccag aaacagagga   3240
attcccgcca cacctagaga tggcagcgct gtggaaatcg tgggcctgtc taagtctgct   3300
gtgcggtggc tgctcgaact gagcaagaag aatatctttc cgtaccacga agtgaccgtg   3360
aagcggcacg gcaaggccat caaggtgtcc tacgacgagt ggaacagaaa gatccaggac   3420
aacttcgaaa agctgttcca tgtgtctgag gaccccagcg acctgaacga aaagcacccc   3480
aacctggtgc acaagcgcgg catctacaag gacagctacg gcgcctcttc tccttggtgc   3540
gattaccagc tgcggcccaa cttcaccatt gccatggtgg ttgcccctga gctgttcacc   3600
acagagaagg cctggaaggc cctggaaatc gccgagaaga aactgctggg ccctctgggc   3660
atgaagacac tggaccccga cgacatggtg tactgcggaa tctacgacaa cgccctggat   3720
aacgacaact acaatctggc caaggggttc aattaccatc agggacccga gtggctgtgg   3780
cctatcggct atttcctgcg ggccaagctg tacttctcca gactgatggg ccctgagaca   3840
accgccaaga caatcgtgct cgtgaagaac gtgctgagcc ggcactatgt gcacctggaa   3900
agaagcccct ggaagggact gcccgagctg accaatgaga acgcccagta ctgccccttc   3960
agctgcgaaa cacaggcctg gtctatcgcc accatcctgg aaaccctgta cgacctgtga   4020
```

<210> SEQ ID NO 26
<211> LENGTH: 3942
<212> TYPE: DNA
<213> ORGANISM: artificial
<220> FEATURE:
<223> OTHER INFORMATION: Nucleic acid sequence encoding D5 hGDE

<400> SEQUENCE: 26
atgggacaca gtaaacagat tcgaatttta cttctgaacg aaatggagaa actggaaaag 60
accctcttca gacttgaaca agggtatgag ctacagttcc gattaggccc aactttacag 120
ggaaaagcag ttaccgtgta tacaaattac ccatttcctg gagaaacatt taatagagaa 180
aaattccgtt ctctggattg ggaaaatcca acagaaagag aagatgattc tgataaatac 240
tgtaaactta atctgcaaca atctggttca tttcagtatt atttccttca aggaaatgag 300
aaaagtggtg gaggttacat agttgtggac cccattttac gtgttggtgc tgataatcat 360
gtgctaccct tggactgtgt tactcttcag acatttttag ctaagtgttt gggacctttt 420
gatgaatggg aaagcagact tagggttgca aaagaatcag gctacaacat gattcatttt 480
accccattgc agactcttgg actatctagg tcatgctact cccttgccaa tcagttagaa 540
ttaaatcctg acttttcaag acctaataga aagtatacct ggaatgatgt tggacagcta 600
gtggaaaaat taaaaaagga atggaatgtt atttgtatta ctgatgttgt ctacaatcat 660
actgctaata ggcgagtaac caagtctgat ccaaaccaac accttacgat tattcaagat 720
cctgaataca gacggtttgg ctgtactgta gatatgaaca ttgcactaac gactttcata 780
ccatatttta ctttcccatt tgaagagata gacttctcca tggaagaatc tatgattcat 840
ctgccaaata aagcttgttt tctgatggca cacaatggat gggtaatggg agatgatcct 900
cttcgaaact ttgctgaacc gggttcagaa gtttacctaa ggagagaact tatttgctgg 960
ggagacagtg ttaaattacg ctatgggaat aaaccagagg actgtcctta tctctgggca 1020
cacatgaaaa aatacactga aataactgca acttatttcc agggagtacg tcttgataac 1080
tgccactcaa cacctcttca cgtagctgag tacatgttgg atgctgctag gaatttgcaa 1140
cccaatttat atgtagtagc tgaactgttc acaggaagtg aggacctaga caatgtcttt 1200
gttactagac tgggcattag ttccttaata agagaggcaa tgagtgcata taatagtcat 1260
gaagagggca gattagttta ccgatatgga ggagaacctg ttggatcctt tgttcagccc 1320
tgtttgaggc ctttaatgcc agctattgca catgccctgt ttatggatat tacgcatgat 1380
aatgagtgtc ctattgtgca tagatcagcg tatgatgctc ttccaagtac tacaattgtt 1440
tctatggcat gttgtgctag tggaagtaca agaggctatg atgaattagt gcctcatcag 1500
atttatgtgg atcaagttga tgaagacata gtggcagtaa caagacactc acctagcatc 1560
catcagtctg ttgtggctgt aactagaact gctttcagga atcccaagac ttcattttac 1620
agcaaggaag tgcctcaaat gtgcatccct ggcaaaattg aagaagtagt tcttgaagct 1680
agaactattg agagaaacac gaaaccttat aggaaggatg aaaattcaat caatggaaca 1740
ccagatatca cagtagaaat tagagaacat attcagctta atgaaagtaa aattgttaaa 1800
caagctggag ttgccacaaa agggcccaat gaatatattc aagaaataga atttgaaaac 1860
ttgtctccag gaagtgttat tatattcaga gttagtcttg atccacatgc acaagtcgct 1920
gttggcattc ttcgaaatca tctgacacaa ttcagtcctc actttaaatc tggcagccta 1980
gctgttgaca atgcagatcc tatattaaaa attccttttg cttctcttgc ctatagatta 2040

```
actttggctg agctaaatca gatcctttac cgatgtgaat cagaagaaaa ggaagatggt   2100

ggagggtgct atgacatacc aaactggtca gcccttaaat atgcaggtct tcaaggttta   2160

atgtctgtat tggcagaaat aagaccaaag aatgacttgg ggcatccttt ttgtaataat   2220

ttgaggtctg gagattggat gattgactat gtcagtaacc ggcttatttc acgatcagga   2280

actattgctg aagttggtaa atggttgcag gctatgttct tctacctgaa gcagatccca   2340

cgttacctta tcccatgtta ctttgatgct atattaattg gtgcatatac cactcttctg   2400

gatacagcat ggaagcagat gtcaagcttt gttcagaatg gttcaacctt tgtgaaacac   2460

ctttcattgg gttcagttca actgtgtgga gtaggaaaat tcccttccct gccaattctt   2520

tcacctgccc taatggatgt accttatagg ttaaatgaga tcacaaaaga aaaggagcaa   2580

tgttgtgttt ctctagctgc aggcttacct catttttctt ctggtatttt ccgctgctgg   2640

ggaagggata cttttattgc acttagaggt atactgctga ttactggacg ctatgtagaa   2700

gccaggaata ttattttagc atttgcgggt accctgaggc atggtctcat tcctaatcta   2760

ctgggtgaag gaatttatgc cagatacaat tgtcgggatg ctgtgtggtg gtggctgcag   2820

tgtatccagg attactgtaa aatggttcca aatggactag acattctcaa gtgcccagtt   2880

tccagaatgt atcctacaga tgattctgct cctttgcctg ctggcacact ggatcagcca   2940

ttgtttgaag tcatacagga agcaatgcaa aaacacatgc agggcataca gttccgagaa   3000

aggaatgctg gtccccagat agatcgaaac atgaaggacg aaggttttaa tataactgca   3060

ggagttgatg aagaaacagg atttgtttat ggaggaaatc gtttcaattg tggcacatgg   3120

atggataaaa tgggagaaag tgacagagct agaaacagag gaatcccagc cacaccaaga   3180

gatgggtctg ctgtggaaat tgtgggcctg agtaaatctg ctgttcgctg gttgctggaa   3240

ttatccaaaa aaaatatttt cccttatcat gaagtcacag taaaaagaca tggaaaggct   3300

ataaaggtct catatgatga gtggaacaga aaaatacaag acaactttga aaagctattt   3360

catgtttccg aagacccttc agatttaaat gaaaagcatc caaatctggt tcacaaacgt   3420

ggcatataca aagatagtta tggagcttca agtccttggt gtgactatca gctcaggcct   3480

aattttacca tagcaatggt tgtggcccct gagctcttta ctacagaaaa agcatggaaa   3540

gctttggaga ttgcagaaaa aaaattgctt ggtccccttg gcatgaaaac tttagatcca   3600

gatgatatgg tttactgtgg aatttatgac aacgcattag acaatgacaa ctacaatctt   3660

gctaaaggtt tcaattatca ccaaggacct gagtggctgt ggcctattgg gtattttctt   3720

cgtgcaaaat tatatttttc cagattgatg ggcccggaga ctactgcaaa gactatagtt   3780

ttggttaaaa atgttctttc ccgacattat gttcatcttg agagatcccc ttggaaagga   3840

cttccagaac tgaccaatga gaatgcccag tactgtcctt tcagctgtga aacacaagcc   3900

tggtcaattg ctactattct tgagacactt tatgatttat ag                      3942
```

```
<210> SEQ ID NO 27
<211> LENGTH: 3759
<212> TYPE: DNA
<213> ORGANISM: artificial
<220> FEATURE:
<223> OTHER INFORMATION: Nucleic acid sequence encoding D6 hGDE

<400> SEQUENCE: 27
```

```
atgaactcca tccgaaaaat aatttgggag gatatttttc caaagcttaa actctgggaa     60

tttttccaag tagatgtcaa caaagcggtt gagcaattta gaagacttct tacacaagaa    120

aataggcgag taaccaagtc tgatccaaac caacacctta cgattattca agatcctgaa    180
```

```
tacagacggt ttggctgtac tgtagatatg aacattgcac taacgacttt cataccacat    240
gacaaggggc cagcagcaat tgaagaatgc tgtaattggt ttcataaaag aatggaggaa    300
ttaaattcag agaagcatcg actcattaac tatcatcagg aacaggcagt taattgcctt    360
ttgggaaatg tgttttatga acgactggct ggccatggtc caaaactagg acctgtcact    420
agaaagcatc ctttagttac caggtatttt actttcccat ttgaagagat agacttctcc    480
atggaagaat ctatgattca tctgccaaat aaagcttgtt ttctgatggc acacaatgga    540
tgggtaatgg gagatgatcc tcttcgaaac tttgctgaac cgggttcaga agtttaccta    600
aggagagaac ttatttgctg gggagacagt gttaaattac gctatgggaa taaaccagag    660
gactgtcctt atctctgggc acacatgaaa aaatacactg aaataactgc aacttatttc    720
cagggagtac gtcttgataa ctgccactca acacctcttc acgtagctga gtacatgttg    780
gatgctgcta ggaatttgca acccaattta tatgtagtag ctgaactgtt cacaggaagt    840
gaggacctag acaatgtctt tgttactaga ctgggcatta gttccttaat aagagaggca    900
atgagtgcat ataatagtca tgaagagggc agattagttt accgatatgg aggagaacct    960
gttggatcct ttgttcagcc ctgtttgagg cctttaatgc cagctattgc acatgccctg   1020
tttatggata ttacgcatga taatgagtgt cctattgtgc atagatcagc gtatgatgct   1080
cttccaagta ctacaattgt ttctatggca tgttgtgcta gtggaagtac aagaggctat   1140
gatgaattag tgcctcatca gatttcagtg gtttctgaag aacggtttta cactaagtgg   1200
aatcctgaag cattgccttc aaacacaggt gaagttaatt tccaaagcgg cattattgca   1260
gccaggtgtg ctatcagtaa acttcatcag gagcttggag ccaagggttt tattcaggtg   1320
tatgtggatc aagttgatga agacatagtg gcagtaacaa gacactcacc tagcatccat   1380
cagtctgttg tggctgtaac tagaactgct ttcaggaatc ccaagacttc attttacagc   1440
aaggaagtgc ctcaaatgtg catccctggc aaaattgaag aagtagttct tgaagctaga   1500
actattgaga gaaacacgaa accttatagg aaggatgaaa attcaatcaa tggaacacca   1560
gatatcacag tagaaattag agaacatatt cagcttaatg aaagtaaaat tgttaaacaa   1620
gctggagttg ccacaaaagg gcccaatgaa tatattcaag aaatagaatt tgaaaacttg   1680
tctccaggaa gtgttattat attcagagtt agtcttgatc cacatgcaca agtcgctgtt   1740
ggcattcttc gaaatcatct gacacaattc agtcctcact ttaaatctgg cagcctagct   1800
gttgacaatg cagatcctat attaaaaatt ccttttgctt ctcttgccta tagattaact   1860
ttggctgagc taaatcagat cctttaccga tgtgaatcag aagaaaagga agatggtgga   1920
gggtgctatg acataccaaa ctggtcagcc cttaaatatg caggtcttca aggtttaatg   1980
tctgtattgg cagaaataag accaaagaat gacttggggc atcctttttg taataatttg   2040
aggtctggag attggatgat tgactatgtc agtaaccggc ttatttcacg atcaggaact   2100
attgctgaag ttggtaaatg gttgcaggct atgttcttct acctgaagca gatcccacgt   2160
taccttatcc catgttactt tgatgctata ttaattggtg catataccac tcttctggat   2220
acagcatgga agcagatgtc aagctttgtt cagaatggtt caacctttgt gaaacacctt   2280
tcattgggtt cagttcaact gtgtggagta ggaaaattcc cttccctgcc aattctttca   2340
cctgccctaa tggatgtacc ttataggtta aatgagatca caaaagaaaa ggagcaatgt   2400
tgtgtttctc tagctgcagg cttacctcat ttttcttctg gtattttccg ctgctgggga   2460
agggatactt ttattgcact tagaggtata ctgctgatta ctggacgcta tgtagaagcc   2520
```

```
aggaatatta ttttagcatt tgcgggtacc ctgaggcatg gtctcattcc taatctactg   2580

ggtgaaggaa tttatgccag atacaattgt cgggatgctg tgtggtggtg gctgcagtgt   2640

atccaggatt actgtaaaat ggttccaaat ggactagaca ttctcaagtg cccagtttcc   2700

agaatgtatc ctacagatga ttctgctcct ttgcctgctg gcacactgga tcagccattg   2760

tttgaagtca tacaggaagc aatgcaaaaa cacatgcagg gcatacagtt ccgagaaagg   2820

aatgctggtc cccagataga tcgaaacatg aaggacgaag gttttaatat aactgcagga   2880

gttgatgaag aaacaggatt tgtttatgga ggaaatcgtt tcaattgtgg cacatggatg   2940

gataaaatgg gagaaagtga cagagctaga aacagaggaa tcccagccac accaagagat   3000

gggtctgctg tggaaattgt gggcctgagt aaatctgctg ttcgctggtt gctggaatta   3060

tccaaaaaaa atattttccc ttatcatgaa gtcacagtaa aaagacatgg aaaggctata   3120

aaggtctcat atgatgagtg gaacagaaaa atacaagaca actttgaaaa gctatttcat   3180

gtttccgaag acccttcaga tttaaatgaa aagcatccaa atctggttca caaacgtggc   3240

atatacaaag atagttatgg agcttcaagt ccttggtgtg actatcagct caggcctaat   3300

tttaccatag caatggttgt ggcccctgag ctctttacta cagaaaaagc atggaaagct   3360

ttggagattg cagaaaaaaa attgcttggt ccccttggca tgaaaacttt agatccagat   3420

gatatggttt actgtggaat ttatgacaac gcattagaca atgacaacta caatcttgct   3480

aaaggtttca attatcacca aggacctgag tggctgtggc ctattgggta ttttcttcgt   3540

gcaaaattat atttttccag attgatgggc ccggagacta ctgcaaagac tatagttttg   3600

gttaaaaatg ttctttcccg acattatgtt catcttgaga gatccccttg gaaaggactt   3660

ccagaactga ccaatgagaa tgcccagtac tgtcctttca gctgtgaaac acaagcctgg   3720

tcaattgcta ctattcttga gacactttat gatttatag                          3759
```

<210> SEQ ID NO 28
<211> LENGTH: 3327
<212> TYPE: DNA
<213> ORGANISM: artificial
<220> FEATURE:
<223> OTHER INFORMATION: Nucleic acid sequence encoding D7 hGDE

<400> SEQUENCE: 28

```
atggttacca ggtattttac tttcccattt gaagagatag acttctccat ggaagaatct     60

atgattcatc tgccaaataa agcttgtttt ctgatggcac acaatggatg ggtaatggga    120

gatgatcctc ttcgaaactt tgctgaaccg ggttcagaag tttacctaag gagagaactt    180

atttgctggg gagacagtgt taaattacgc tatgggaata aaccagagga ctgtccttat    240

ctctgggcac acatgaaaaa atacactgaa ataactgcaa cttatttcca gggagtacgt    300

cttgataact gccactcaac acctcttcac gtagctgagt acatgttgga tgctgctagg    360

aatttgcaac ccaatttata tgtagtagct gaactgttca caggaagtga ggacctagac    420

aatgtctttg ttactagact gggcattagt tccttaataa gagaggcaat gagtgcatat    480

aatagtcatg aagagggcag attagtttac cgatatggag gagaacctgt tggatccttt    540

gttcagccct gtttgaggcc tttaatgcca gctattgcac atgccctgtt tatggatatt    600

acgcatgata atgagtgtcc tattgtgcat agatcagcgt atgatgctct tccaagtact    660

acaattgttt ctatggcatg ttgtgctagt ggaagtacaa gaggctatga tgaattagtg    720

cctcatcaga tttcagtggt ttctgaagaa cggttttaca ctaagtggaa tcctgaagca    780

ttgccttcaa acacaggtga agttaatttc caaagcggca ttattgcagc caggtgtgct    840
```

```
atcagtaaac ttcatcagga gcttggagcc aagggtttta ttcaggtgta tgtggatcaa    900
gttgatgaag acatagtggc agtaacaaga cactcaccta gcatccatca gtctgttgtg    960
gctgtaacta gaactgcttt caggaatccc aagacttcat tttacagcaa ggaagtgcct   1020
caaatgtgca tccctggcaa aattgaagaa gtagttcttg aagctagaac tattgagaga   1080
aacacgaaac cttataggaa ggatgaaaat tcaatcaatg gaacaccaga tatcacagta   1140
gaaattagag aacatattca gcttaatgaa agtaaaattg ttaaacaagc tggagttgcc   1200
acaaaagggc ccaatgaata tattcaagaa atagaatttg aaaacttgtc tccaggaagt   1260
gttattatat tcagagttag tcttgatcca catgcacaag tcgctgttgg cattcttcga   1320
aatcatctga cacaattcag tcctcacttt aaatctggca gcctagctgt tgacaatgca   1380
gatcctatat taaaaattcc ttttgcttct cttgcctata gattaacttt ggctgagcta   1440
aatcagatcc tttaccgatg tgaatcagaa gaaaaggaag atggtggagg gtgctatgac   1500
ataccaaact ggtcagccct taaatatgca ggtcttcaag gtttaatgtc tgtattggca   1560
gaaataagac caaagaatga cttggggcat cctttttgta ataatttgag gtctggagat   1620
tggatgattg actatgtcag taaccggctt atttcacgat caggaactat tgctgaagtt   1680
ggtaaatggt tgcaggctat gttcttctac ctgaagcaga tcccacgtta ccttatccca   1740
tgttactttg atgctatatt aattggtgca tataccactc ttctggatac agcatggaag   1800
cagatgtcaa gctttgttca gaatggttca acctttgtga aacacctttc attgggttca   1860
gttcaactgt gtggagtagg aaaattccct tccctgccaa ttctttcacc tgccctaatg   1920
gatgtacctt ataggttaaa tgagatcaca aaagaaaagg agcaatgttg tgtttctcta   1980
gctgcaggct tacctcattt ttcttctggt attttccgct gctggggaag ggatactttt   2040
attgcactta gaggtatact gctgattact ggacgctatg tagaagccag gaatattatt   2100
ttagcatttg cgggtaccct gaggcatggt ctcattccta atctactggg tgaaggaatt   2160
tatgccagat acaattgtcg ggatgctgtg tggtggtggc tgcagtgtat ccaggattac   2220
tgtaaaatgg ttccaaatgg actagacatt ctcaagtgcc cagtttccag aatgtatcct   2280
acagatgatt ctgctccttt gcctgctggc acactggatc agccattgtt tgaagtcata   2340
caggaagcaa tgcaaaaaca catgcagggc atacagttcc gagaaaggaa tgctggtccc   2400
cagatagatc gaaacatgaa ggacgaaggt tttaatataa ctgcaggagt tgatgaagaa   2460
acaggatttg tttatggagg aaatcgtttc aattgtggca catggatgga taaaatggga   2520
gaaagtgaca gagctagaaa cagaggaatc ccagccacac caagagatgg gtctgctgtg   2580
gaaattgtgg gcctgagtaa atctgctgtt cgctggttgc tggaattatc caaaaaaaat   2640
attttccctt atcatgaagt cacagtaaaa agacatggaa aggctataaa ggtctcatat   2700
gatgagtgga acagaaaaat acaagacaac tttgaaaagc tatttcatgt ttccgaagac   2760
ccttcagatt taaatgaaaa gcatccaaat ctggttcaca aacgtggcat atacaaagat   2820
agttatggag cttcaagtcc ttggtgtgac tatcagctca ggcctaattt taccatagca   2880
atggttgtgg cccctgagct ctttactaca gaaaaagcat ggaaagcttt ggagattgca   2940
gaaaaaaaat tgcttggtcc ccttggcatg aaaactttag atccagatga tatggtttac   3000
tgtggaattt atgacaacgc attagacaat gacaactaca atcttgctaa aggtttcaat   3060
tatcaccaag gacctgagtg gctgtggcct attgggtatt ttcttcgtgc aaaattatat   3120
ttttccagat tgatgggccc ggagactact gcaaagacta tagttttggt taaaaatgtt   3180
```

```
ctttcccgac attatgttca tcttgagaga tccccttgga aaggacttcc agaactgacc   3240

aatgagaatg cccagtactg tcctttcagc tgtgaaacac aagcctggtc aattgctact   3300

attcttgaga cactttatga tttatag                                       3327


<210> SEQ ID NO 29
<211> LENGTH: 3912
<212> TYPE: DNA
<213> ORGANISM: artificial
<220> FEATURE:
<223> OTHER INFORMATION: Nucleic acid sequence encoding D8 hGDE

<400> SEQUENCE: 29

atgcatccag aatgtgccta taatcttgta aattctccac acttaaaacc tgcctgggtc     60

ttagacagag cactttggcg tttctcctgt gatgttgcag aagggaaata caaagaaaag    120

ggaatacctg ctttgattga aaatgatcac catatgaact ccatccgaaa aataatttgg    180

gaggatattt ttccaaagct taaactctgg gaatttttcc aagtagatgt caacaaagcg    240

gttgagcaat ttagaagact tcttacacaa gaaaataggc gagtaaccaa gtctgatcca    300

aaccaacacc ttacgattat tcaagatcct gaatacagac ggtttggctg tactgtagat    360

atgaacattg cactaacgac tttcatacca catgacaagg ggccagcagc aattgaagaa    420

tgctgtaatt ggtttcataa aagaatggag gaattaaatt cagagaagca tcgactcatt    480

aactatcatc aggaacaggc agttaattgc cttttgggaa atgtgtttta tgaacgactg    540

gctggccatg gtccaaaact aggacctgtc actagaaagc atcctttagt taccaggtat    600

tttactttcc catttgaaga gatagacttc tccatggaag aatctatgat tcatctgcca    660

aataaagctt gttttctgat ggcacacaat ggatgggtaa tgggagatga tcctcttcga    720

aactttgctg aaccgggttc agaagtttac ctaaggagag aacttatttg ctggggagac    780

agtgttaaat tacgctatgg gaataaacca gaggactgtc cttatctctg ggcacacatg    840

aaaaaataca ctgaaataac tgcaacttat ttccagggag tacgtcttga taactgccac    900

tcaacacctc ttcacgtagc tgagtacatg ttggatgctg ctaggaattt gcaacccaat    960

ttatatgtag tagctgaact gttcacagga agtgaggacc tagacaatgt ctttgttact   1020

agactgggca ttagttcctt aataagagag gcaatgagtg catataatag tcatgaagag   1080

ggcagattag tttaccgata tggaggagaa cctgttggat cctttgttca gccctgtttg   1140

aggcctttaa tgccagctat tgcacatgcc ctgtttatgg atattacgca tgataatgag   1200

tgtcctattg tgcatagatc agcgtatgat gctcttccaa gtactacaat tgtttctatg   1260

gcatgttgtg ctagtggaag tacaagaggc tatgatgaat tagtgcctca tcagatttca   1320

gtggtttctg aagaacggtt ttacactaag tggaatcctg aagcattgcc ttcaaacaca   1380

ggtgaagtta atttccaaag cggcattatt gcagccaggt gtgctatcag taaacttcat   1440

caggagcttg gagccaaggg ttttattcag gtgtatgtgg atcaagttga tgaagacata   1500

gtggcagtaa caagacactc acctagcatc catcagtctg ttgtggctgt aactagaact   1560

gctttcagga atcccaagac ttcattttac agcaaggaag tgcctcaaat gtgcatccct   1620

ggcaaaattg aagaagtagt tcttgaagct agaactattg agagaaacac gaaaccttat   1680

aggaaggatg aaaattcaat caatggaaca ccagatatca cagtagaaat tagagaacat   1740

attcagctta atgaaagtaa aattgttaaa caagctggag ttgccacaaa agggcccaat   1800

gaatatattc aagaaataga atttgaaaac ttgtctccag gaagtgttat tatattcaga   1860

gttagtcttg atccacatgc acaagtcgct gttggcattc ttcgaaatca tctgacacaa   1920
```

ttcagtcctc actttaaatc tggcagccta gctgttgaca atgcagatcc tatattaaaa 1980
attccttttg cttctcttgc ctatagatta actttggctg agctaaatca gatcctttac 2040
cgatgtgaat cagaagaaaa ggaagatggt ggagggtgct atgacatacc aaactggtca 2100
gcccttaaat atgcaggtct tcaaggttta atgtctgtat tggcagaaat aagaccaaag 2160
aatgacttgg ggcatccttt ttgtaataat ttgaggtctg gagattggat gattgactat 2220
gtcagtaacc ggcttatttc acgatcagga actattgctg aagttggtaa atggttgcag 2280
gctatgttct tctacctgaa gcagatccca cgttacctta tcccatgtta ctttgatgct 2340
atattaattg gtgcatatac cactcttctg gatacagcat ggaagcagat gtcaagcttt 2400
gttcagaatg gttcaacctt tgtgaaacac ctttcattgg gttcagttca actgtgtgga 2460
gtaggaaaat tcccttccct gccaattctt tcacctgccc taatggatgt accttatagg 2520
ttaaatgaga tcacaaaaga aaaggagcaa tgttgtgttt ctctagctgc aggcttacct 2580
catttttctt ctggtatttt ccgctgctgg ggaagggata cttttattgc acttagaggt 2640
atactgctga ttactggacg ctatgtagaa gccaggaata ttattttagc atttgcgggt 2700
accctgaggc atggtctcat tcctaatcta ctgggtgaag gaatttatgc cagatacaat 2760
tgtcgggatg ctgtgtggtg gtggctgcag tgtatccagg attactgtaa aatggttcca 2820
aatggactag acattctcaa gtgcccagtt tccagaatgt atcctacaga tgattctgct 2880
cctttgcctg ctggcacact ggatcagcca ttgtttgaag tcatacagga agcaatgcaa 2940
aaacacatgc agggcataca gttccgagaa aggaatgctg gtccccagat agatcgaaac 3000
atgaaggacg aaggttttaa tataactgca ggagttgatg aagaaacagg atttgtttat 3060
ggaggaaatc gtttcaattg tggcacatgg atggataaaa tgggagaaag tgacagagct 3120
agaaacagag gaatcccagc cacaccaaga gatgggtctg ctgtggaaat tgtgggcctg 3180
agtaaatctg ctgttcgctg gttgctggaa ttatccaaaa aaaatatttt cccttatcat 3240
gaagtcacag taaaaagaca tggaaaggct ataaaggtct catatgatga gtggaacaga 3300
aaaatacaag acaactttga aaagctattt catgtttccg aagacccttc agatttaaat 3360
gaaaagcatc caaatctggt tcacaaacgt ggcatataca aagatagtta tggagcttca 3420
agtccttggt gtgactatca gctcaggcct aattttacca tagcaatggt tgtggcccct 3480
gagctcttta ctacagaaaa agcatggaaa gctttggaga ttgcagaaaa aaaattgctt 3540
ggtccccttg gcatgaaaac tttagatcca gatgatatgg tttactgtgg aatttatgac 3600
aacgcattag acaatgacaa ctacaatctt gctaaaggtt tcaattatca ccaaggacct 3660
gagtggctgt ggcctattgg gtattttctt cgtgcaaaat tatatttttc cagattgatg 3720
ggcccggaga ctactgcaaa gactatagtt ttggttaaaa atgttctttc ccgacattat 3780
gttcatcttg agagatcccc ttggaaagga cttccagaac tgaccaatga gaatgcccag 3840
tactgtcctt tcagctgtga aacacaagcc tggtcaattg ctactattct tgagacactt 3900
tatgatttat ag 3912

<210> SEQ ID NO 30
<211> LENGTH: 4134
<212> TYPE: DNA
<213> ORGANISM: Equus caballus

<400> SEQUENCE: 30
atgattcatt ttacaccatt gcagactctt ggactatcta ggtcatccta ctcccttgct 60

```
gaccagttag aattaaatcc tgacttttca agacctaata aaaagtatac ctggcatgat    120
gttggacagc tagtggaaaa attgaaaaag gaatgggata ttctttgtat tactgatgtt    180
gtctacaatc atactgctgc taatagtaaa tggatccatg aacatccaga aagtgcatat    240
aaccttgtga attctccaca cttaaaacct gcctgggtct tagacagagc actttggcat    300
ttatcctgtg atgtggcaga agggaaatac agagaaaaag gagtacctgc tctgattgaa    360
aatgatcatc aaatgaattg cattcgaaaa ataatttggg aggatattta tccaaagatt    420
cacctctggg aatttttcca agtagacgtt cacaaagcag ttgagcaatt tagaggactt    480
cttacacaag aaaataggaa aataatatct cagcctgatc caaagcaaca ccttaagatt    540
attcaggatc ctgaatacag acggcttggc tgtactgtag atatgaacat tgcactagca    600
actttcatac cacatgataa tggccagct gcaattgatg aatgctgtaa ttggttccgt    660
aagagaattg aggaattaaa cgcagagaag catcaacttg tgaactatca tcaggagcag    720
gcagttaatt gccttttggg aaatgtattt tatgaacgac tggctggcca tggtcctaaa    780
ctaggacctg tcaccagaaa acatcctta gttaccagat attttacttt cccatttgaa    840
gaaatgaccc catccacaga agaatctatg attcatctcc caaataaagc ttgttttctg    900
atggcgcata atggatgggt aatgggagat gatccccttc ggaactttgc tgaaccaggt    960
tcagacgttt atctaaggag agaacttatc tgctggggag acagtgttaa attacgctat   1020
gggaataagc cagaggactg tccttacctc tgggcgcaca tgaaaaaata cactgaaata   1080
actgcaactc atttccaggg agtacgtctt gataactgcc actcaacacc aattcatgta   1140
gccgagtaca tgttggatgc cgctaggaaa ttgcaaccca atttatatgt agtagctgaa   1200
ctgttcacag gaagcgaaga cctggacaat atctttgtta ctagactggg cattagttcc   1260
ttaataagag aggcaatgag tgcagctgat agccatgagg agggcagatt agtttaccga   1320
tatggaggag agcctgttgg gtcctttgtt cagccctgtt tgaggccttt aatgccagct   1380
attgcacatg ccctgtttat ggatatcacc catgataatg agtgtcctat tgtgcatagg   1440
tcagcatatg atgctctccc gagttccacg attgtttcta tggcatcttg tgctagtgga   1500
agtactaaag gctatgatga attagtgcct catcagattt cagtggtttc tgaagaacga   1560
ttttatacta agtggaatcc tgaagcattg ccatcaaata caggtgaagt caatttccaa   1620
agcggaatta ttgcagccag gcgtgctatc aataaacttc atcaagagct tggggccaag   1680
ggtttcattc aggtgtatgt ggatcaggtt gatcaagata tagtggcggt aacaaggcac   1740
tcacctagca tccatcagtc tgttgtgtct gtgtcgagaa ctgctttcag gaatcccaag   1800
acgtcatttt acagcaagga agtgcctcat atgtacatcc ctggcaaaat tgaagaagta   1860
gttcttgaag ctagaactat tgagagacat acaatacctt ataagaagga tgaaaactca   1920
atcaatggaa tgccagatat cacagtagaa attagagaac atattcagct taatgaaagt   1980
aaaattgtta aacatgctgg aattgtcaca aaaggaccca atgaatttgt tcaagaaata   2040
gagtttgaaa acttgactcc aggaagtgtt attatattca gagttagtct tgatccacat   2100
gcacaagttg ctgttggaat tcttcgaaat catctgacac aattcagtcc tcactttaaa   2160
tctgggagcc ttgctgttga caacgcagat cctatattga aaattccttt tgcttctatt   2220
gcctctaaat taactttggc tgagctaaat caggtccttt atcgatgtga atcagaagaa   2280
caagaagatg gtggagggtg ttataacata ccaaactggt cgtctcttaa atatgcaggt   2340
cttcaaggat taatgtccat attggcagaa ataagaccaa ggaatgactt ggggcatccc   2400
ttttgtgaca atttgagatc tggagattgg atgattgact atgtcagtag ccggcttatt   2460
```

```
tcacgatcag gaactattgc tgaagttggt aaatggttgc aggctatgtt cctctacctg   2520

aagcagatcc cccgttatct tattccatgt tactttgatg ctatattaat tggtgcatac   2580

accactctcc tggatatagc atggaagcag atgtcaagct ttgttcagaa tggttctacc   2640

tttgtgaaac acctttctct gggttcagtc caaatgtgtg gagtaggaaa attcccttct   2700

ctgccacttc tttcaccttc ccttacggat ctaccatata gagtaaatga gatcacaaaa   2760

gaaaaggagc agtgttgtgg gtctctagct gcaggcttac ctcatttttc tgctggcatt   2820

ttccgctgct ggggaaggga taccttcatt gcgctcagag gtctgctgct ggttacggga   2880

cgctatttgg aggccaggaa tattatttta gcatttgctg gcaccctgag acacggtctc   2940

attcctaatc tcctgggtga aggaactcac gccagataca attgccggga tgctgtgtgg   3000

tggtggctac agtgtattca ggattactgt aaaattgttc caaatggcct ggacatcctc   3060

aggtgcccgg tttccagaat gtatcctaca gatgattctg ttcctttgtc tgctggcaca   3120

gtggatcaac cattgtttga agtaatacag gaagctatgc aaagacatgt gcagggcata   3180

cagttccgag aaaggaatgc tggtccacag atagatcgaa acatgaagga tgaaggtttt   3240

aatataactg caggagttga tgaagaaacg ggatttgttt atggaggaaa tcgcttcaat   3300

tgcggcacat ggatggataa aatgggagaa agtgacagag ctagaaacag aggaatcccg   3360

gccactccaa gagatgggtc tgctgtggaa attgtgggcc tgagtaaatc tgccgttcgt   3420

tggttgctgg aattatcccg aaaaaatatt ttcccttatc atgaagtccg agtaaaaaga   3480

catggaaagt ttgtgacagt ctcatatgat gagtggaaca gaaaaataca agacaacttt   3540

gaaaagctat ttcatgtgtc agaagaccct tcagatttta acgaaaagca tcctgagctg   3600

gttcacaaac gtggcatata caaagatagt tatggagcat caagcccttg gtgtgactac   3660

cagctcaggc ctaattttac catagcaatg gtcgtagccc ctgagctgtt taccccagaa   3720

aaagcatgga aagctttgga gattgcagaa aaaaaattgc ttggtcccct tggcatgaaa   3780

actttggatc cagatgatat ggtttactgt ggaatttatg acaatgcctt agacaatgac   3840

aactacaatc ttgctaaagg tttcaattat caccaaggac ctgagtggct gtggcccact   3900

ggatattttc ttcgtgcaaa attgtatttt tccaaattaa tgggtccaga gactaatgca   3960

aagactatgt ttttggttaa aaacgtcctt tccagacatt atgttcatct tgagagatcc   4020

ccttggaaag gacttccaga actgactaat gagaatggcc aatactgtcc tttcagctgt   4080

gaaacacaag cctggtcaat tgctactgtt cttgaaacac tctatgactt atag         4134
```

<210> SEQ ID NO 31
<211> LENGTH: 4098
<212> TYPE: DNA
<213> ORGANISM: Gorilla gorilla

<400> SEQUENCE: 31

```
atgggacaca gtaaacagat tcgaatttta cttctgaacg aaatggagaa actggaaaag     60

accctcttca gacttgaaca agggtatgaa ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420
```

```
gatgaatggg aaagcagact tagggttgca aaagaatcag gctacaacat gattcatttt    480
accccattgc agactcttgg actatctagg tcatgctact cccttgccaa tcagttagaa    540
ttaaatcctg acttttcaag acctaataga aagtatacct ggaatgatgt tggacagcta    600
gtggaaaaat taaaaaagga atggaatgtt atttgtatta ctgatgttgt ctacaatcat    660
actgctgcta atagtaaatg gatccaggaa catccagaat gtgcctataa tcttgtgaat    720
tctccacact taaaacctgc ctgggtctta gacagagcac tttggcgttt ctcctgtgat    780
gttgcagaag ggaaatacaa agaaaaggga atacctgctt tgattgaaaa tgatcaccat    840
atgaattcca tccgaaaaat aatttgggag gatatttttc caaagcttaa actctgggaa    900
tttttccaag tagatgtcaa caaagcggtt gagcaattta gaagacttct tacacaagaa    960
aataggcgag taaccaagtc tgatccaaac caacatctta cgattattca agatcctgaa   1020
tacagacggt ttggctgtac tgtagatatg aacattgcac taacgacttt cataccacat   1080
gagtatttta ctttcccatt tgaagagata gacttctcca tggaagaatc tatgattcat   1140
ctcccaaata aagcttgttt tctgatggca cacaatggat gggtaatggg agatgatcct   1200
cttcgaaact ttgctgaacc gggttcagaa gtttacctaa ggagagaact tatttgctgg   1260
ggagacagtg ttaaattacg ctatgggaat aaaccagagg actgtcctta tctctgggca   1320
cacatgaaaa aatacactga aataactgca acttatttcc agggagtacg tcttgataac   1380
tgccactcaa cacctcttca cgtagctgag tacatgttgg atgctgctag gaatttgcaa   1440
cccaatttat atgtagtagc tgaactgttc acaggaagtg aagatctgga caatgtcttt   1500
gttactagac tgggcattag ttccttaata agagaggcaa tgagtgcata taatagtcat   1560
gaagagggca gattagttta ccgatatgga ggagaacctg ttggatcctt tgttcagccc   1620
tgtttgaggc ctttaatgcc agctattgca catgccctgt ttatggatat tacgcatgat   1680
aatgagtgtc ctattgtgca tagatcagcg tatgatgctc ttccaagtac tacaattgtc   1740
tctatggcgt gttgtgctag tggaagtaca agaggctatg atgaattagt gcctcatcag   1800
ttcctaggca aaattgaaga agtagttctt gaagctagaa ctattgagag aaacatgaaa   1860
ccttatagga aggatgagaa ttcaatcaat ggaacgccag atatcacagt agaaattaga   1920
gaacatattc agcttaatga aagtaaaatt gttaaacaag ctggagttgc cacaaaaggg   1980
cccaatgaat atattcaaga aatagaattt gaaaacttgt ctccaggaag tgttattata   2040
ttcagagtta gtcttgatcc acatgcacaa gtcgctgttg gaattcttcg aaatcatctg   2100
acacaattca gtcctcactt taaatctggc agcctagctg ttgacaatgc agatcctata   2160
ttaaaaattc cttttgcttc tattgcctcc agattaactt tggctgagct aaatcagatc   2220
ctttaccgat gtgaatcaga agaaaaggaa gatggtggag ggtgctatga cataccaaac   2280
tggtcagccc ttaaatatgc aggtcttcaa ggtttaatgt ctgtattggc agaaataaga   2340
ccaaagaatg acttggggca tcctttttgt aataatttga gatctggaga ttggatgatt   2400
gactatgtca gtaaccggct tatttcacga tcaggaacta ttgctgaagt tggtaaatgg   2460
ttgcaggcta tgttcttcta cctgaagcag atcccacgtt accttatccc atgttacttt   2520
gatgctatat taattggtgc atataccact cttctggata cagcatggaa gcagatgtca   2580
agctttgttc agaatggttc aacctttgtg aaacaccttt cattgggttc agttcaactg   2640
tgtggagtag gaaaattccc ttccctgcca attctttcac ctgccctaat ggatgtacct   2700
tataggttaa atgagatcac aaaagaaaag gagcaatgtt gtgtttctct agctgcaggc   2760
ttacctcatt tttcttctgg tattttccgc tgctggggaa gggatacttt tattgcactt   2820
```

```
agaggtatac tgctgattac tggacgctat gtagaagcca ggaatattat tttagcattt   2880
gcgggtaccc tgaggcatgg tctcattcct aatctactgg gtgaaggaat ttatgccaga   2940
tacaattgtc gggatgctgt gtggtggtgg ctgcagtgta tccaggatta ctgtaaaatg   3000
gttccaaatg gtgtagacat tctcaagtgc ccagtttcca gaatgtatcc tacagatgat   3060
tctgctcctt tgcctgctgg cacactggat cagccattgt ttgaagtcat acaggaagca   3120
atgcaaaaac acatgcaggg catacagttc cgagaaagga atgctggtcc ccagatagat   3180
cgaaacatga aggacgaagg ttttaatata actgcaggag ttgatgaaga aacaggattt   3240
gtttatggag gaaatcgttt caattgtggc acatggatgg ataaaatggg agaaagtgac   3300
agagctagaa acagaggaat cccagccaca ccaagagatg ggtctgctgt ggaaattgtg   3360
ggcctgagta aatctgctgt tcgctggttg ctggaattat ccaaaaaaaa tattttccct   3420
tatcatgaag tcacagtaaa aagacatgga aaggctataa aggtctcata tgatgagtgg   3480
aacagaaaaa tacaagacaa ctttgaaaag ctatttcatg tttcagaaga cccttcagat   3540
ttaaatgaaa agcatccaaa tctggttcac aaacgtggca tatacaaaga tagttatgga   3600
gcgtcaagtc cttggtgtga ctatcagctc aggcctaatt ttaccatagc aatggttgtg   3660
gcccctgagc tctttactac agaaaaagca tggaaagctt tggagattgc agaaaaaaaa   3720
ttgcttggtc cccttggcat gaaaacttta gatccagatg atatggttta ctgtggaatt   3780
tatgacaatg cattagacaa tgacaactac aatcttgcta aaggtttcaa ttatcaccaa   3840
ggacctgagt ggctgtggcc tattgggtat ttttcttcgtg caaaattata tttttccaga   3900
ttgatgggcc cggagactac tgcaaagact atagttttgg ttaaaaatgt tctttcccga   3960
cattatgttc atcttgagag atccccttgg aaaggacttc cagaactgac caatgagaat   4020
gcccagtact gtcctttcag ctgtgaaaca caagcctggt caattgctac tattcttgag   4080
acactttatg atttgtag                                                 4098
```

<210> SEQ ID NO 32
<211> LENGTH: 3900
<212> TYPE: DNA
<213> ORGANISM: Pongo abelii

<400> SEQUENCE: 32

```
atggggcaca gtaaacagat tcgaatttta cttctgaacg aaatggagaa gctggaaaag     60
accctcttca gacttgaaca agggtatgaa ctacagttcc gattaggccc aactttacag    120
ggaaaagcag ttaccgtgta tacaaattac ccatttcctg gagaaacatt taatagagaa    180
aaattccgtt ctctggattg ggaaaatcca acagaaagag aagatgattc tgataaatac    240
tgcaaactta atctgcaaca atctggttca tttcagtatt atttccttca aggaaatgag    300
aaaagtggtg gaggttacat agttgtggac cccattttac gtgttggtgc cgataatcat    360
gtgctaccct tggactgtgt tactcttcag acatttttag ctaagtgttt gggacctttt    420
gatgaatggg aaagcagact tagggttgca aaagaatcag gctacaacat gattcatttt    480
accccactgc agactcttgg actatctagg tcatgctact cccttgccaa tcagttagaa    540
ttaaatcctg acttttcaag acctaataga aagtatacct ggaatgatgt tggacagcta    600
gtggaaaaat taaaaaagga atggaatgtt atttgtatta ccgatgttgt ctacaatcat    660
actgctgcta atagtaaatg gatccaggaa catccagaat gtgcctataa tcttgtgaat    720
tctccacact taaaacctgc ctgggtctta gacagagcac tttggcgttt ctcctgtgat    780
```

-continued

```
gttgcagaag ggaaatacaa agaaaaggga atacctgctt tgattgaaaa tgatcaccat    840
atgaattcca tccgaaaaat aatttgggag gatatttttc caaagcttaa actctgggaa    900
tttttcgaag tagatgtcaa caaagcggtt gagcaattta gaagacttct tacacaagaa    960
aataggcgag taaccaagtc tgatccaaac caacatctta cgattattca ggatcctgaa   1020
tacagacggt ttggctgtac tgtagatatg aacattgcac taacgacttt cataccacat   1080
gacaatgggc cagcagcaat tgaagagtgc tgtaactggt ttcgtaagag aattgaggaa   1140
ttaaattcag agaagcatca actcattaac tatcatcagg aacaggcagt gaattgcctt   1200
ttgggaaatg tgttttatga acgactggct ggccatggtc caaaactagg acctgtcact   1260
agaaagcatc ctttagttac caggtatttt actttcccat ttgaagagat ggacttctcc   1320
atggaagaat ctatgattca tctcccaaat aaagcttgtt tactgatggc acacaatgga   1380
tgggtaatgg gagatgatcc tcttcgaaac tttgctgaac cgggttcaga agtttaccta   1440
aggagagaac ttatttgctg gggagacagt gttaaattac gctatgggaa taaaccagag   1500
gactgtcctt atctctgggc acacatgaaa aaatacactg aaataactgc aacttatttc   1560
cagggagtac gtcttgataa ctgccactca acacctcttc acgtagctga gtacatgttg   1620
gatgctgcta ggaatttgca acccaattta tatgtagtag ctgaactgtt cacaggaagt   1680
gaagatctgg acaatgtctt tgttactaga ctgggcatta gttccttaat aagagaggca   1740
atgagtgcat atgatagtca tgaagagggc agattagttt accgatatgg aggagaacct   1800
gttggatcct ttgttcagcc ctgtttgagg cctttaatgc cggctattgc acatgccctg   1860
tttatggata ttacacatga taatgagtgt cctattgtgc atagatcagc gtatgatgct   1920
cttccaagta ctacaattgt ttctatggcg tgttgtgcta gtggaagtac aagaggctat   1980
gatgaattag tgcctcatca gatttcggtg gtttctgaag aacggtttta cactaagtgg   2040
aatcctgaag cattgccttc aaatacaggt gaagttaatt tccaaagcgg cattattgca   2100
gccaggtgtg ctatcaataa acttcatcag gagcttggag ccaagggttt tattcaggtg   2160
tatgttgatc aagttgatga agacatagtg gcagtaacaa gacactcacc tagcatccat   2220
cagtctgttg tggctgtatc tagaactgct ttcaggaatc ccaagacttc attttacagc   2280
aaggaagtgc ctcaaatgtg catccctggc aaaattgaag aagtagttct tgaagctaga   2340
actattgaga gaaacacgaa accttatagg aaggatgaga attcaatcaa tggaacgcca   2400
gatatcacag tagaaattag agaacatatt cagcttaatg aaagtaaaat tgttaaacaa   2460
gctggagttg ccacaaaagg gcccaatgaa tttattcaag aaatagaatt tgaaaacttg   2520
tctccaggaa gtgttattat attcagagtt agtcttgatc cacatgcaca agtcgctgtt   2580
ggaattcttc gaaatcatct gacacaattc agtcctcact ttaaatctgg cagcctagct   2640
gttgacaatg cagatcctat attaaaaatt ccttttgctt tacctcattt ttcttctggt   2700
attttccgct gctggggaag ggatactttt attgcactta gaggtatgct gctgattact   2760
ggacgctatg tagaagccag gaatattatt ttagcatttg ctggtaccct gaggcatggt   2820
ctcattccta atctactggg tgaaggaact tatgccagat acaattgtcg ggacgctgtg   2880
tggtggtggc tgcagtgtat ccaggattac tgtaaagtgg ttccaaatgg tctagacatt   2940
ctcaagtgcc cagtttccag aatgtatcct acagatgatt ctgctccttt gcctgctggc   3000
gcactgttta atataactgc aggagttgat gaagaaacag gatttgttta tggaggaaat   3060
cgtttcaatt gtggcacatg gatggataaa atgggagaaa gtgacagagc tagaaacaga   3120
ggaatcccag ccacaccaag agatgggtct gctgtggaaa ttgtgggcct gagtaaatct   3180
```

```
gctgttcgct ggttgctgga attatccaaa aaaaatattt tcccttatca tgaagtcaca   3240

gtaaaacatg gaaaggctat aaaggtctca tatgatgagt ggaacagaaa aatacaggat   3300

aactttgaaa agctgtttca tgtttcagaa gacccttcag atttaaatga aaagcatcca   3360

aatttggttc acaaacgtgg catatacaaa gatagttatg gagcttcaag tccttggtgt   3420

gactatcagc tcaggcctaa ttttaccata gcaatggttg tggcccctga gctctttact   3480

acagaaaaag catggaaagc tttggagatt gcagaaaaaa aattgcttgg tccccttggc   3540

atgaaaactt tagatccaga tgatatggtt tactgtggaa tttatgacaa tgcattagac   3600

aatgacaact acaatcttgc taaaggtttc aattatcacc aaggacctga gtggctgtgg   3660

cctattgggt attttcttcg tgcaaaatta tatttttcca gattgatggg cccggagact   3720

actgcaaaga ctatagtttt ggttaaaaat gttctttccc gacattatgt tcatcttgag   3780

agatcccctt ggaaaggact tccagaactg accaatgaga atgcccagta ctgtcctttc   3840

agctgtgaaa cacaagcctg gtcagttgct actattcttg agacacttta tgatttatag   3900
```

```
<210> SEQ ID NO 33
<211> LENGTH: 4173
<212> TYPE: DNA
<213> ORGANISM: Pteropus alecto

<400> SEQUENCE: 33

atgggtcacg gtaaacagat tagaatttta cttctgaacg aaatggaaaa gcttgaaaag     60

accctcttta gacttgaaca agggtttgaa ctacagttcc gattaggccc aactttacaa    120

ggaaaaacag ttactgtgca tacaaattac ccatatcctg gagaaacatt taatcgagaa    180

aaattccgtt ccctggaatg ggaaaatcca tcagaaagag aagatgattc tgataaatac    240

tgtaaactta atctccaaca agcgggatca tttcagtatt acttccttcg aggaaatgag    300

aagagtggtg ggggttacat agttgtggat cctgtattac gtgttggtac tgataatcat    360

gtgttaccct tagactgtgt tactctccag acatttttag ctaagtgttt gggacccttg    420

gatgaatggg aaagcagact tagggttgca aaagaatcag gttacaacat gattcacttt    480

accccattgc agactcttgg ccagtctagg tcatgctact ctcttgctga tcagttagaa    540

ttaaatcctg acttttccag acctaataaa aagtgtacct gggatgatgt tggacagcta    600

gtggaaaaat tgaaaaagga atggaatatt ctttgtatca ccgatgttgt ctacaatcat    660

accggaaata ggaaaataac caagcctgat ccaaaagaac accttaagat aattcaggat    720

cctgaataca ggaggcttgg ctgtactgta gatatgaaca ttgcactagc gactttcata    780

ccaaatgagt attttacttt cccatttgag gaaatgaccc tctccacaga agaatctatg    840

attcatctcc caaataaagc ttgttttctg atggcacata atggatgggt aatgggagat    900

gatccccttc gaaactttgc tgaaccaggt tcagatgttt atctgaggag agaacttatt    960

tgctggggag acagtgttaa attacgctat gggaataaac cagaggactg tccttatctc   1020

tgggcacaca tgaaaaaata cactgaaata actgcaactt atttccaggg agtacgtctt   1080

gataactgcc actccacacc tcttcatgta gctgagtaca tgttggatgc tgctaggaaa   1140

ttgcaaccca atttatatat agtggcagaa ctgttcacag gaagtgaaga cttggacaat   1200

gtctttgtta ctagactggg aattagttcc ttaataagag aggcaatgag tgcacatgat   1260

agtcatgaag agggcagatt agtttaccga tatggaggag aacccgttgg gtcatttgtt   1320

cagccctgtt tgaggccttt gatgccagct attgcacatg ccctgtttat ggatattacc   1380
```

```
catgataatg agtgtcctat tgtgcataga tcagcatatg atgctctccc aagttccatg   1440
attgtttcta tggcgtgttg tgctagtggt agtactaaag gctatgatga attagtgcct   1500
catcaggtgt atgtggatca ggttgatgaa gacatagtgg cagtaacaag acactcacct   1560
agtatccatc agtctgttgt ggctgtgtct agaactgctt tcaagaatcc caagacttca   1620
ttttacagca aggaagtccc tcaaatgtgc atccctggca aaattgaaga agtagttctt   1680
gaagctagaa ctattgaaag aaatacaaaa ccttataaga gggatgaaaa ttcaatcaat   1740
ggaatgccag atatcacagc agaaattaga gaacatattc agcttaatga aagtaaaatt   1800
gttaaacaag ctggaattgc cacaaaagga cccaatgaat acattcaaga aatagaattt   1860
gaaaacttgt ctccaggaag tgttattgta ttcagagtta gtctcgatcc acatgcacaa   1920
gtcgctgttg gaattcttcg aaatcattta actcagttca gtcctcactt taaatctggg   1980
agcctttctg ccgacagctc agatcctata ttaaaaattc ctttcgctta tattgcctct   2040
aaattaactt tggctgagct aaatcaaata ctttaccggt gtgaatcaga agaacaagaa   2100
gatggtgggg gatgttataa tataccaaac tggtcatctc ttaaatatgc aggtcttcaa   2160
gagaatagtt ctttggagtt agctccttat gtgggctttg gtggaggttg tggggcagca   2220
cctgcaggtc taaatcgggg tgggggtgtt cggtccgacc aggcctcact agagcgattc   2280
ctgactacct tgcttgccac tgtggactat acagcccttg tgtccacttc tgtatgttca   2340
ccccacatca ctggacacga gcagcagccc aggctatggg aacgaattgc ctctgccaat   2400
aatatagcat gctatttcta tgacttttca ggattaatgt ctgtattagc agaaatgaga   2460
ccaaagaatg acttggggca tcctttttgt gataatttga gatctggaga ttggatgatt   2520
gactatgtca gtaatcggct tatttcacga tcgggaacta ttgctgaagt tggcagatgg   2580
ttgcaggcta tgttcttcta cctgaagcag atcccacgct atcttatccc atgttatttc   2640
gatgctgtat taatcggtgc atacaccact cttctggata cggcatggaa acaaatgtca   2700
agctttgttc agaatggttc tacctttgtg aaacaccttt cattgggttc tgtccagctg   2760
tgtggagtag gaaaatacgc ttctcttcca cttctttcac cttcgcttat ggatgtacca   2820
tacaggctaa atgagatcac aaaagaaaag gagcaatgtt gtgtgactct agctgcaggc   2880
ttgcctcatt tttcttctgg tattttccgc tgctggggaa gggatacttt tattgcactt   2940
agaggtatac tgctgattac cgggcgctat ttagaagcca ggaatattat tttagcgttt   3000
gctggtacct tgagacacgg tctcattcct aatctcctgg gtgaaggaac ttatgccaga   3060
tacaactgcc gggatgccgt gtggtggtgg ctgcagtgta ttcaagacta ctgtaaagtg   3120
gttccaaatg gcctagacat tctcaagtgc cctgtctcca gaatgtatcc tacagatgat   3180
tctgttcctt tgtcggccgg cacagtggat cagccattgt ttgaagtaat acaagaagct   3240
atgcagaggc acatgcaggg catacagttc cgagaaagga atgctggtcc acagatagat   3300
cgaaacatga aggatgaagg ttttaatata actgtagggg ttgatgaaga aacaggattt   3360
gtttatggag gaaatcgctt caattgcggc acatggatgg ataaaatggg agaaagtgac   3420
agagctagaa acagaggaat cccagccact ccaagagatg gatctgctgt ggaaattgtg   3480
ggcctaagta aatctgccat tcgctggttg ctggaattat ctaaaaaaaa tatttttcct   3540
tatcatgaag tcacagtaaa aagagatgga aaggttgtga cagtctcata tgatgagtgg   3600
aacagaaaaa tacaagacaa ctttgaaaag ctattttatg tgtccgaaga cccttcagac   3660
tttaatgaaa agaatccaaa tctggttcac aaacgtggta tatacaaaga cagttatgga   3720
gcttcaagcc cttggtgtga ctatcagctc aggcctaatt ttaccatagc aatggttgta   3780
```

```
gcccctgagc tctttactac agaaaaagca tggaaagctt tacaggtggc agaaaaaaaa   3840

ttgcttggtc cccttggcat gaaaactttg gatccagatg atatggttta ctgtggagtt   3900

tatgacaatg ccttagacaa tgacaactac aatcttgcga aggtttcaa ttatcatcaa    3960

ggacctgagt ggctttggct cattgggtat tttcttcgtg caaaattata tttttccaaa   4020

ttaatgggtc cagagacgaa tgcaaagact atttttttgg ttaaaaatgt tctttcccgg   4080

cactatgttc atcttgagag tctggcttgt tttgccctca ccactctgct gcagctgctc   4140

aacaagatcc tttctgcttc ccagatccca tga                                4173
```

<210> SEQ ID NO 34
<211> LENGTH: 3759
<212> TYPE: DNA
<213> ORGANISM: Cercocebus atys

<400> SEQUENCE: 34

```
atgaattcca tccgaaaaat gatttgggag gatatttttc caaagcttaa actctgggaa     60

tttttccaag tagacgtcaa caaaaaaaaa aaaaaaaaaa aaagacttct tacacaagaa    120

aataggagag taaccaagtc tgatccacac caacatctta agattattca agatcctgaa    180

tacagacgat ttggctgtac tgtagatatg aacattgcac taacgacttt cataccacat    240

gacaatgggc cagcagcaat tgaagaatgc tgtaattggt ttcgtaagag aattgaggaa    300

ttaaattcag agaagcatcg actcattaac tatcatcagg aacaggcagt taattgcctt    360

ttgggaaatg tgttttatga acgactggct ggccatggtc caaaactagg acctgtcact    420

agaaagcatc ctttagttac caggtatttt actttcccat ttgaagaaat ggacttctcc    480

gtggaagaat ctatgattca tctcccaaat aaagcttgtt ttctgatggc acacaatgga    540

tgggtaatgg gagatgatcc tcttcgaaac tttgctgaac caggctcaga agtttaccta    600

aggagagaac ttatttgctg gggagacagt gttaaattgc gctatgggaa taaaccagag    660

gactgtcctt ttctctgggc acacatgaaa aaatacactg aaataactgc aacttatttc    720

cagggagtac gtcttgataa ctgccactca acacctcttc atgtagctga gtacatgttg    780

gatgctgcta ggaatttgca acccaattta tatgtagtag ctgaactgtt cacaggaagt    840

gaagatctgg acaatatctt tgttactaga ctgggcatta gttccttaat aagagaggca    900

atgagtgcat ataatagtca tgaagagggc agattagttt accgatatgg aggagaacct    960

gttggatcct ttgttcagcc ctgtttgagg cctttaatgc cagctattgc acatgccttg   1020

tttatggata ttacccatga taatgagtgt cctattgtgc atagatcagc atatgatgct   1080

cttccaagta ctacaattgt ttctatggcg tgttgtgcta gtggaagtac aagaggctat   1140

gatgaattag tgcctcatca gatttcagtg gtttctgagg aacggtttta cactaagtgg   1200

aatcctggag cattgccttc aaatacaggt gaagttaatt tccaaagcgg cattattgca   1260

gccaggtgtg ctatcaataa gcttcatcag gagcttggag ccaagggttt tattcaggtg   1320

tatgtggatc aagttgatga agacatagtg gcagtaacaa gacactcacc tagcatccat   1380

cagtctgttg tggctgtatc tagaactgct ttcaggaatc ccaagacttc attttacagc   1440

aaggaagtgc ctcaaatgtg catccctggc aaaattgaag aagtagttct tgaagctaga   1500

actattgaga gaaatacgaa accttacagg aaggatgaga attcaatcaa tggaatgcca   1560

gatatcacag tagaaattag agaacatatt cagcttaatg aaagtaaaat tgttaaacaa   1620

gctggagttg ccacaaaagg gcccaatgaa tatattcaag aaatagaatt tgaaaacttg   1680
```

```
tctccaggaa gcgttattat attcagagtt agtcttgatc cacacgcaca agtcgctgtt   1740
ggaattcttc gaaatcatct gacccaattc agtcctcact ttaaatctgg gagcctagct   1800
gttgacaatt cagatcctat attaaaaatt ccctttgctt ctattgcctc caaattaact   1860
ttggctgagc taaatcagat cctttaccga tgtgaatcag aagaaaagga agatggtgga   1920
gggtgctatg acataccaaa ctggtcagcc cttaaatatg caggtcttca aggtttaatg   1980
tctgtattgg cagaaataag accaaagaat gacttgggcc atcctttttg taataatttg   2040
agatctggag attggatgat tgactatgtc agtaaccggc ttatttcacg atcaggaact   2100
attgctgaag ttggtaaatg gttgcaggct atgttcttct acctgaagca gatcccacgt   2160
taccttatcc catgttactt tgatgctata ttaattggtg catataccac tcttctggat   2220
atagcatgga agcagatgtc aagctttgtt cagaatggtt caacctttgt gaaacacctt   2280
tcattgggtt cagttcaact gtgtggagta ggaaaattcc cttccctgcc aattctttca   2340
cctgcactaa cgggtgtacc ttatagatta aatgagatca caaaagaaaa ggagcaatgt   2400
tgtgtttctc tagctgcagg cttacctcat ttttcttctg gtattttccg ctgctgggga   2460
agggatactt ttattgcact tagaggcata ctgctgatta ctggacgcta tgtagaagcc   2520
aggaatatta ttttagcatt tgctggtacc ctgaggcatg gtctcattcc taatctactg   2580
ggtgaaggaa cttatgccag atacaattgt cgggatgctg tgtggtggtg gctgcagtgt   2640
atccaggatt actgtaaaat ggttccaaat ggtctagaca ttctcaagtg tccagtttcc   2700
agaatgtatc ctacagatga ttctgctcct ttgcctgctg gcacactgga tcagccattg   2760
tttgaagtca tacaggaagc aatgcaaaga cacatgcagg gcatacagtt ccgagaaagg   2820
aatgctggtc ccaagataga tcgaaacatg aaggatgaag gttttaatgt aactgcagga   2880
gttgatgaag aaacaggatt tgtttatgga ggaaatcgtt tcaattgtgg cacatggatg   2940
gataaaatgg gagaaagtga cagagctaga aacacaggaa tcccagccac accaagagat   3000
gggtctgctg tggaaattgt gggactgagt aaatctgctg ttcgctggtt gctggaatta   3060
tccaaaaaaa atattttccc ttatcatgaa gtcacagtaa aaagacatgg aaaggttgta   3120
aaggtctcat atgatgagtg gaacagaaaa atacaagaca actttgaaaa gctatttcat   3180
gtttcagaag acccttcaga tttaaatgaa aagcatccaa atctggttca caaacgtggc   3240
atatacaaag atagttatgg agcttcaagt ccctggtgtg actatcagct caggcctaat   3300
tttactatag caatggttgt ggcccctgag ctctttacta cagcaaaagc atggaaagct   3360
ttggagattg cagaaaaaaa attgcttggt ccccttggca tgaaaacttt agatccagat   3420
gatatggttt actgtggaat ttatgacaat gcattagaca atgacaacta caatcttgca   3480
aaaggtttca attatcacca aggacctgag tggctgtggc ctattggata ttttcttcgt   3540
gcaaaattat atttttccag attgatgggc ccggagacta ctgcaaagac tatagttttg   3600
gttaaaaatg ttctttcccg acactatgtt catcttgaga gatccccttg gaaaggactt   3660
ccagaactga ccaatgagaa tgcccaatac tgtcctttca gctgtgaaac acaagcctgg   3720
tcaatttcta ctattcttga gacactttat gatttatag                          3759
```

<210> SEQ ID NO 35
<211> LENGTH: 3351
<212> TYPE: DNA
<213> ORGANISM: Ornithorhynchus anatinus

<400> SEQUENCE: 35

```
atgtttgaag gcagagcgga aggagtcgtt ggagagtact ttacttttcc gtatggagaa     60
```

```
atgacttctg tagaagaaga atctttgatg catcaacctg aaaaagcttg ttttttcatg    120
gcccataatg gttgggtcat gggagatgat ccattgagaa attttgctga gccagggtca    180
gatgtttacc tcaggagaga gcttgtttgc tggggagaca gtgttaaatt acgttatgga    240
aataaaccag aagactgccc ttacctctgg gcccacatga aaaaatatac tgaaataact    300
gccaagtatt ttcaaggagt gcgtcttgac aactgccact cgacacctct tcacgtagct    360
gagtatatgc tggatgctgc taggaaattg cagcccaatt tgtatgtagt ggctgagctg    420
ttcacaggaa gtgaggagct ggacaatatc tttgtgacta gactgggcat tagctcctta    480
ataagagaag ctatgagtgc atataatagc catgaagaag gcagattagt gtaccgcttt    540
ggaggagagc cagtgggatc tttcgttcag ccgtgtttga gacctttgat gccagctatt    600
gcacatgctc tgtttatgga tatcactcat gataacgaat gtcctattgt gcatcgatca    660
gcatatgatg ctcttccgag ctccaccata gtttccatgg cttgctgtgc tagtggaagt    720
actaggggct atgatgaatt agtacctcat cagatttctg tagtttctga agaacggttt    780
tataccaagt ggaacccagc agctactcta tcaaacccat ctgaagttaa tctccagact    840
ggaattatag caggaagacg tgccataaat aagctgcacc aagaacttgg agctaaaggt    900
tttattcagg tttatgtgga tcaggttgat gaagacatag tagcagtgac gagacactgt    960
cctagctctc accagtccgt agtggccgtg tctcgcactg cttttagaaa ccccaagact   1020
tctgcttaca gcaaagaagt gccgcagatg tgcatcccag gtaaaattga agaagtagtt   1080
cttgaggcca gaactgttga aagaaatgtt ggttcctacg taaaggatgc aaaatccatc   1140
aatggaatgc ccgacatcac agtagaaatt agagaacaca tccagcttaa tgaaagtaaa   1200
attgtaaaac aagctggagt tgccacaaaa ggtcttcatg aatatgtcca agaaatagaa   1260
tttgaaaatt tgaccccagg aagtgttatt atatttcgag taagccttga tccacacgca   1320
caagtggctg ttggaatact tcggaatcac ctgacacaat tcagtcctaa ttttaaaatt   1380
ggaagccttc ctgttgacaa ttcagatcct atattaaaaa ttccttttgc ttctatttca   1440
tctaaattaa ctttagctga cctaaatcaa ttactctacc gatgtgagtc agaagaacaa   1500
gaagatggtg gaggatgtta tgatgtacca aactggtcac ccctcaaata tgggggcctt   1560
caaggattaa tgtcagtaat ggctgaaatt aggccaaaga atgacttggg acatcctttt   1620
tgcaataatt tgcgatctgg agattggatg attgattatg tcagtaatcg actgatttcg   1680
cgctcaggat ctattgctga agttggtaaa tggttccaag ctatgttctt ctatctaaag   1740
cagattccac gttaccttat cccttgttat tttgatgcta tattaattgg tgcgtacacc   1800
actcttctgg atatagcctg gaagcagatg tcaagctttg tccagaatgg ttcaacattt   1860
gtaaaacacc tgtcattggg ttcagttcaa atgtgcggga taggaaagtt cccatctctg   1920
ccttttcttt ctccatcact tggtgatgtt ccctatagac tgaatgaaat tacacaggaa   1980
aaggaacagt gctgtgtttc tctagctgct gggttacctc atttttcatc tggaattttt   2040
cgctgctggg gaagagatac cttcatagca cttagaggtc tactgctaat tactggtcgc   2100
tttttagagg caaggaacat aattctagca tttgctggta ctctgagaca tggtcttatt   2160
cccaatcttc tcggccaggg gacgtatgcc agattcaatt gtcgagatgc agtgtggtgg   2220
tggcttcagt gtattcagga ttactgtaaa attgttccaa agggcacgga cattctcaag   2280
tgccccgtat ccagaatgta tccatcagat gactcttctg ctctaccagc cggcacattg   2340
gatcagccat tgtatgaagt aatacaggaa gctatgcagc gtcatatgca aggcatacag   2400
```

```
ttccgagaaa agaatgctgg tccacagatt gaccggaata tgaaggatga aggttttaat   2460
gtcactgcag gagttgatga tgaaagtggg tttgtttatg gaggcaatca cttcaactgt   2520
ggaacatgga tggataaaat gggagagagt gacagaggtc gcaacagagg aatcccagct   2580
acacccagag atgggtctgc tgtggaaatt gttggcctga gtaaatcaac tgttcgctgg   2640
ttggtagaat tatcgaaaaa aaatgtgttc ccttatcacg gagttacagt aaagagaaat   2700
gaaaaagagg tattaatcac atacgatgaa tggaacagga aaatccaaga ccactttgaa   2760
aagctattct atgtttcaga ggatccatca gatactaatg aaaagcatcc taatttggtt   2820
cataagcgtg gtatatacaa agatagctat ggagcttcaa gtccttggtg tgactaccag   2880
ctcaggccaa actttaccat agcaatggtt gtggctcctg aactctttac tcctcagaag   2940
gcatggaaag ctttggaaat agcagagaag aaattgcttg gtcccctggg catgaaaact   3000
ctggatccag atgatatggt gtactgtgga gtatatgata atgccctaga caatgacaac   3060
tacaaccttg ctaaaggttt taattaccac caaggacctg aatggttgtg gcctgttgga   3120
tattttcttc gtgcaaagtt atatttttcc aagttaatgg gtcaggaaac ttacacaaag   3180
actgtgtttt tgattaaaaa tgttctttcc cgtcattacg tccatcttga gagatcccct   3240
tggaaagggc ttccagagct gactaatgaa aatggacaat actgttcttt cagctgtgaa   3300
acacaggctt ggtcaattgc cgttattctt gaaactcttt atgatttatg a            3351
```

<210> SEQ ID NO 36
<211> LENGTH: 3915
<212> TYPE: DNA
<213> ORGANISM: Anas platyrhynchos

<400> SEQUENCE: 36

```
atgcatccag aatgtggcta taaccttgta aattcccctc acctgaagcc agcttgggtc     60
ttagatagag ctctgtggca cttgacctgt atggtggctg atggaaagtg tattgataaa    120
ggggtccctc cgttgattga aaatgatcac cacctgaatt gtgtccgtaa aataatttgg    180
gaagagatat atccaaaaat taaactgtgg gaatttttcc aagtggatgt taataaagct    240
gtggaacaat ttagaaccct tctaactcaa ggtaaagaaa gcaaaatgag cactaaatct    300
gatccaaatc aacatcttca gatagttcag gaccctgagt atagacgatt tggctgtact    360
gtagatatga atatagcatt ggcaaccttc ataccgcaca gcaatggacc aggtgcaata    420
gaagagtgtt gtaactggtt tcgcaagagg attgaggaac tgaatgctga gcaacacaga    480
cagattcatc accatcaaga gcaggcagtc aactgtcttg cggggactgt ggtttatgaa    540
cgactggctg gtcatggtcc taaactgggt cctattagta gaaaatatcc tttagttacc    600
aggtatttta cttacccatt caaagacatg actgtggagg aagaagaagc tatgatacat    660
cgcccagata aagcttgcta tttcatggcc cataatggat gggttatggg cgatgatcct    720
cttagaaact ttgcagaacc aggttcaaat gtttacttga gaagggagct tatttgctgg    780
ggagacagtg tgaaactgcg ttatgggaac aaacctgaag actgcccata cctctgggca    840
catatgaaaa aatacacaga aatcacagcc aaatatttcc atggcgttcg tcttgacaac    900
tgtcactcaa cacctattca tgtagctgag tacatgctgg acacagctag aaaattgcga    960
gcagatttgt ttgtagtggc tgaactgttc acaggaaatg aggagctgga caatatcttt   1020
gtgaataggc tgggcattac ctccttaata agagaggcaa tgacagctta taatagccat   1080
gaggagggaa ggttagttta tcgttttgga ggtgaacctg ttggctcttt tgttcagcca   1140
cgtttgagac ccctgatgcc agctattgct catgcactgt tcatggatat tacacatgat   1200
```

```
aatgagtgtc cgatccagca ccgatctgca tatgatgctc ttcccagtgc aatgattgtt   1260

tccatggcat gctgtgctac aggtagcacc aaaggttatg atgaacttgt accacaccag   1320

atatccgtag tatccgaaga gagattttat tcaacatgga atccagcagc acacctgact   1380

tctggtgaag ttaatttcca aacaggaatt ctagcaggaa ggctggccat aaacaggctg   1440

catcaggagc tgggagctaa aggttttaat caggtgtatg tagatcaagt tgatgaagat   1500

atagtggcag tgacaagaca ttgccctaat acacaccagt ctgttgtggc tgtaagtaga   1560

actgctttca gagatccaaa gacttccttc tacagtaaag aagtgcctga aatgtgtatc   1620

ccagggaaaa ttgaagaagt agtacttgag gctagaacca ttgagagaaa tactaatcct   1680

tacaaaaaag atgaacgttt tataaatgga ttgcctaact tcacagtgga actcagagag   1740

cacattcaga ttaaagacag taaaattata aagcaagctg gaactgccat aaaagggcca   1800

aatgaatttg ttcaagaaat agaatttgaa aatttaacac caggaagtgt aatagtattc   1860

agagttagtc ttgatccaaa ggcacaagag gctgttggtg tactccgtag tcatctgatc   1920

cagtttagtc ctcactttaa atctggaagt cttcctgatg atcattcagc acccatatta   1980

aaaacattat tttcttcaat tgcatctaaa ttaagtttgg ctgacctaaa tcaagtgctg   2040

tataggtgtg aggcagaaga acaagaagat ggtggaggct gttacaatat accaaactgg   2100

tcaccgttga agtatgcagg cctccaaggg ttaatgtcag taatggcaga cattagacca   2160

aagaatgatt tgggccaccc gttttgtgat aatttaagat ctggagattg gatgattgat   2220

tatgtcagca atcgtctgat ttcacgtact ggagcctgtg cagaagttgg taaatggttg   2280

aaggccatgt ttatctattt aaagaaaatt ccacgttacc ttatcccatg ttattttgat   2340

gccatattag tgggtgcata cacaacgctt ctggatgtgg gatggcatca gatgtctagc   2400

tttgtgcaga acggatcaac atttgttaaa cacctttcct tgggctcaat ccagatgtgt   2460

gggataggaa aatactcatg tttgcccgat ctgtctcctt ccttacatga tgttccctat   2520

agactgaatg agattacaaa tgagaaagaa cagtgttgtg tttctttggc agctggttta   2580

cctcactttt cttcagggat ttttcgctct tggggaaggg atacctttat tgcactgaga   2640

ggtctgatgt tagttacagg gcgttatcta gaagcaagaa acataatttt agcatttggt   2700

gggactttaa gacatggtct cattcccaac ctgctcggcc aggggacgca tgccagatac   2760

aactgtcgtg atgctgtatg gtggtggctt cagtgtatcc aggactactg taaaattgtt   2820

ccaaatggat tagacattct cagatgtcct gtttccagaa tgtacccaag agatgactct   2880

tctcctcaac ctgcaggcag tgtggatcag ccgctttatg aagtaataca ggaagcaatg   2940

caacgacaca tggaaggcat aaatttccga gaaaggaatg ccggcccaca gatagatcaa   3000

aacatgagag atgaaggttt taatgtaaca gcgggtgttg accgtgaaac tggctttgtc   3060

ttcggaggga accgtttcaa ttgtggcacc tggatggata aaatggggga gagtgacaga   3120

gctcgcaaca gaggaattcc tgctactccg agagatggct ctgctgtgga aattgttggc   3180

ttgtgcaagt caactgtacg ctggcttctg gatttgtcta ggaaaaatga gtttccattc   3240

catggagtca ccataaaaag acacggaaag gaggaaacta tcacatatga tgaatgggac   3300

agaaaaattc aagcacactt tgaaaagctc ttctttgtct ctgagaaccc agcagatcca   3360

aatgaaaaac atccaaatct tgttcacaaa cgtggaatct ataaagacag ctatggagct   3420

tcaagtccat ggtgtgatta ccaactcaga ccaaatttta caatagcaat ggttgtggca   3480

cctgagttgt tcacacctga gagagcttgg aaagctctgc agatagcaga ggaaaaacta   3540
```

```
cttggtccgt taggcatgaa aactttagac ccagatgata tggtgtactg tggagtatat   3600

gataatgctc ttgacaatga caactataat gtagccagag gttttaatta tcaccaagga   3660

cctgaatggc tgtggccaat tggatatttc cttcgtgcca aattgtactt ctcaaagcta   3720

attggtccac agatatacgc aaaaactgta gttatgataa agaatgtgct ttctcgccac   3780

tatgttcacc ttgaaaggtc atcctggaaa gggcttccag agctgaccaa tgaaaatgga   3840

caatattgcc ctttcagctg tgaaactcag gcctggtcaa ttagtgttat ccttgaaatc   3900

ctttatgatt tgtga                                                    3915
```

```
<210> SEQ ID NO 37
<211> LENGTH: 4599
<212> TYPE: DNA
<213> ORGANISM: Homo sapiens

<400> SEQUENCE: 37
```

```
atgggacaca gtaaacagat tcgaatttta cttctgaacg aaatggagaa actggaaaag     60

accctcttca gacttgaaca agggtatgag ctacagttcc gattaggccc aactttacag    120

ggaaaagcag ttaccgtgta tacaaattac ccatttcctg gagaaacatt taatagagaa    180

aaattccgtt ctctggattg ggaaaatcca acagaaagag aagatgattc tgataaatac    240

tgtaaactta atctgcaaca atctggttca tttcagtatt atttccttca aggaaatgag    300

aaaagtggtg gaggttacat agttgtggac cccattttac gtgttggtgc tgataatcat    360

gtgctaccct tggactgtgt tactcttcag acatttttag ctaagtgttt gggacctttt    420

gatgaatggg aaagcagact tagggttgca aaagaatcag gctacaacat gattcatttt    480

accccattgc agactcttgg actatctagg tcatgctact cccttgccaa tcagttagaa    540

ttaaatcctg acttttcaag acctaataga aagtatacct ggaatgatgt tggacagcta    600

gtggaaaaat taaaaaagga atggaatgtt atttgtatta ctgatgttgt ctacaatcat    660

actgctgcta atagtaaatg gatccaggaa catccagaat gtgcctataa tcttgtaaat    720

tctccacact taaaacctgc ctgggtctta gacagagcac tttggcgttt ctcctgtgat    780

gttgcagaag ggaaatacaa agaaaaggga atacctgctt tgattgaaaa tgatcaccat    840

atgaactcca tccgaaaaat aatttgggag gatatttttc caaagcttaa actctgggaa    900

tttttccaag tagatgtcaa caaagcggtt gagcaattta gaagacttct tacacaagaa    960

aataggcgag taaccaagtc tgatccaaac caacacctta cgattattca agatcctgaa   1020

tacagacggt ttggctgtac tgtagatatg aacattgcac taacgacttt cataccacat   1080

gacaaggggc cagcagcaat tgaagaatgc tgtaattggt ttcataaaag aatggaggaa   1140

ttaaattcag agaagcatcg actcattaac tatcatcagg aacaggcagt taattgcctt   1200

ttgggaaatg tgttttatga acgactggct ggccatggtc caaaactagg acctgtcact   1260

agaaagcatc ctttagttac caggtatttt actttcccat ttgaagagat agacttctcc   1320

atggaagaat ctatgattca tctgccaaat aaagcttgtt ttctgatggc acacaatgga   1380

tgggtaatgg gagatgatcc tcttcgaaac tttgctgaac cgggttcaga agtttaccta   1440

aggagagaac ttatttgctg ggagacagt gttaaattac gctatgggaa taaaccagag   1500

gactgtcctt atctctgggc acacatgaaa aaatacactg aaataactgc aacttatttc   1560

cagggagtac gtcttgataa ctgccactca acacctcttc acgtagctga gtacatgttg   1620

gatgctgcta ggaatttgca acccaattta tatgtagtag ctgaactgtt cacaggaagt   1680

gaggacctag acaatgtctt tgttactaga ctgggcatta gttccttaat aagagaggca   1740
```

```
atgagtgcat ataatagtca tgaagagggc agattagttt accgatatgg aggagaacct   1800
gttggatcct ttgttcagcc ctgtttgagg cctttaatgc cagctattgc acatgccctg   1860
tttatggata ttacgcatga taatgagtgt cctattgtgc atagatcagc gtatgatgct   1920
cttccaagta ctacaattgt ttctatggca tgttgtgcta gtggaagtac aagaggctat   1980
gatgaattag tgcctcatca gatttcagtg gtttctgaag aacggtttta cactaagtgg   2040
aatcctgaag cattgccttc aaacacaggt gaagttaatt tccaaagcgg cattattgca   2100
gccaggtgtg ctatcagtaa acttcatcag gagcttggag ccaagggttt tattcaggtg   2160
tatgtggatc aagttgatga agacatagtg gcagtaacaa gacactcacc tagcatccat   2220
cagtctgttg tggctgtaac tagaactgct ttcaggaatc ccaagacttc attttacagc   2280
aaggaagtgc ctcaaatgtg catccctggc aaaattgaag aagtagttct tgaagctaga   2340
actattgaga gaaacacgaa accttatagg aaggatgaaa attcaatcaa tggaacacca   2400
gatatcacag tagaaattag agaacatatt cagcttaatg aaagtaaaat tgttaaacaa   2460
gctggagttg ccacaaaagg gcccaatgaa tatattcaag aaatagaatt tgaaaacttg   2520
tctccaggaa gtgttattat attcagagtt agtcttgatc cacatgcaca agtcgctgtt   2580
ggcattcttc gaaatcatct gacacaattc agtcctcact ttaaatctgg cagcctagct   2640
gttgacaatg cagatcctat attaaaaatt ccttttgctt ctcttgccta tagattaact   2700
ttggctgagc taaatcagat cctttaccga tgtgaatcag aagaaaagga agatggtgga   2760
gggtgctatg acataccaaa ctggtcagcc cttaaatatg caggtcttca aggtttaatg   2820
tctgtattgg cagaaataag accaaagaat gacttggggc atcctttttg taataatttg   2880
aggtctggag attggatgat tgactatgtc agtaaccggc ttatttcacg atcaggaact   2940
attgctgaag ttggtaaatg gttgcaggct atgttcttct acctgaagca gatcccacgt   3000
taccttatcc catgttactt tgatgctata ttaattggtg catataccac tcttctggat   3060
acagcatgga agcagatgtc aagctttgtt cagaatggtt caacctttgt gaaacacctt   3120
tcattgggtt cagttcaact gtgtggagta ggaaaattcc cttccctgcc aattctttca   3180
cctgccctaa tggatgtacc ttataggtta aatgagatca caaaagaaaa ggagcaatgt   3240
tgtgtttctc tagctgcagg cttacctcat ttttcttctg gtattttccg ctgctgggga   3300
agggatactt ttattgcact tagaggtata ctgctgatta ctggacgcta tgtagaagcc   3360
aggaatatta ttttagcatt tgcgggtacc ctgaggcatg gtctcattcc taatctactg   3420
ggtgaaggaa tttatgccag atacaattgt cgggatgctg tgtggtggtg gctgcagtgt   3480
atccaggatt actgtaaaat ggttccaaat ggactagaca ttctcaagtg cccagtttcc   3540
agaatgtatc ctacagatga ttctgctcct ttgcctgctg gcacactgga tcagccattg   3600
tttgaagtca tacaggaagc aatgcaaaaa cacatgcagg gcatacagtt ccgagaaagg   3660
aatgctggtc cccagataga tcgaaacatg aaggacgaag gttttaatat aactgcagga   3720
gttgatgaag aaacaggatt tgtttatgga ggaaatcgtt tcaattgtgg cacatggatg   3780
gataaaatgg gagaaagtga cagagctaga aacagaggaa tcccagccac accaagagat   3840
gggtctgctg tggaaattgt gggcctgagt aaatctgctg ttcgctggtt gctggaatta   3900
tccaaaaaaa atattttccc ttatcatgaa gtcacagtaa aaagacatgg aaaggctata   3960
aaggtctcat atgatgagtg gaacagaaaa atacaagaca actttgaaaa gctatttcat   4020
gtttccgaag acccttcaga tttaaatgaa aagcatccaa atctggttca caaacgtggc   4080
```

```
atatacaaag atagttatgg agcttcaagt ccttggtgtg actatcagct caggcctaat   4140

tttaccatag caatggttgt ggcccctgag ctctttacta cagaaaaagc atggaaagct   4200

ttggagattg cagaaaaaaa attgcttggt ccccttggca tgaaaacttt agatccagat   4260

gatatggttt actgtggaat ttatgacaac gcattagaca atgacaacta caatcttgct   4320

aaaggtttca attatcacca aggacctgag tggctgtggc ctattgggta ttttcttcgt   4380

gcaaaattat atttttccag attgatgggc ccggagacta ctgcaaagac tatagttttg   4440

gttaaaaatg ttctttcccg acattatgtt catcttgaga gatccccttg gaaaggactt   4500

ccagaactga ccaatgagaa tgcccagtac tgtcctttca gctgtgaaac acaagcctgg   4560

tcaattgcta ctattcttga gacactttat gatttatag                         4599
```

```
<210> SEQ ID NO 38
<211> LENGTH: 4599
<212> TYPE: DNA
<213> ORGANISM: artificial
<220> FEATURE:
<223> OTHER INFORMATION: hGDE co1

<400> SEQUENCE: 38

atgggccata gtaaacagat tcgcatactc ctcttgaacg agatggagaa actggagaag     60

acattgtttc ggttggagca ggggtacgag ctccagtttc gcctgggacc gacgctccaa    120

ggcaaagctg tgactgtata cacgaactat ccattcccgg gggagacgtt taacagggag    180

aagtttaggt ccctggactg ggagaaccca accgaacgag aggacgattc cgataaatat    240

tgcaagctca acttgcagca aagtggcagc tttcaatatt actttctcca aggcaatgag    300

aaaagtgggg gggggtatat tgttgtcgat ccaatactgc gcgtaggggc agataatcac    360

gttctcccgc tggattgcgt cactctccag acattcttgg ctaaatgctt ggggccgttt    420

gatgaatggg agtctcgctt gcgagtggcc aaagagtcag gttataacat gattcacttc    480

acaccactcc agacattggg acttagtcgg agctgttact cactcgcaaa tcaattggag    540

cttaacccag acttcagtcg gccaaatcgg aagtacacgt ggaacgacgt tggacaactt    600

gtcgaaaagt tgaagaaaga gtggaatgtg atttgcatca ctgacgtggt gtacaatcac    660

accgcagcca acagcaagtg gattcaggag cacccagagt gtgcgtacaa cctggtgaac    720

tcacctcacc tcaaacccgc ctgggtgctc gatagggctt tgtggcgctt ttcttgcgac    780

gtagcggaag gaaagtataa agagaaagga atacccgccc tcatagaaaa cgatcatcac    840

atgaattcta tacggaaaat catctgggag gatatatttc cgaaacttaa actttgggag    900

ttctttcaag tagatgtaaa caaggcggtg gagcaattca ggaggctcct cacccaagag    960

aatcgccggg ttactaaatc tgacccgaat caacacctta caataatcca agatccggaa   1020

tacaggaggt ttggttgcac tgtcgatatg aatattgcgc ttactacgtt catcccccac   1080

gacaagggcc cggccgcaat agaagaatgc tgcaattggt tccacaagcg gatggaagaa   1140

ctgaactctg aaaagcaccg ccttataaat tatcaccaag agcaggctgt gaactgtctg   1200

ctcggtaacg tttttacga gcgcctggcc ggacacggac ctaaactcgg gccagtcact   1260

cgaaaacacc cactggttac gcgatacttc acattcccgt tcgaggagat cgacttttct   1320

atggaggaat ctatgatcca cctcccaaat aaagcttgtt ttcttatggc gcacaacgga   1380

tgggttatgg gggacgaccc actgcgaaac ttcgcagaac cgggtagtga ggtctacctt   1440

aggcgcgagc tcatttgttg ggcgacagc gtcaagctcc ggtatggaaa taagccagag   1500

gattgccctt acttgtgggc acacatgaag aagtatacgg aaataacagc tacctacttc   1560
```

```
caggggggtac gactggataa ctgccactcc acaccgttgc acgtggccga gtatatgctc   1620
gacgctgcgc gcaatttgca gccaaatctg tacgtcgtgg cagagctttt cactggaagt   1680
gaggacttgg ataacgtctt tgtgactcgc ctgggaatta gtagcttgat aagggaggct   1740
atgtccgcgt acaacagtca cgaggaagga cgattggttt atcgatatgg gggcgagcct   1800
gtaggctcct ttgtgcaacc ctgcttgcgg ccccttatgc ccgctatagc acacgcgctc   1860
ttcatggata tcacgcacga taatgaatgc cccatagtac acagatccgc ctacgacgcc   1920
cttccatcta cgacaatcgt ctctatggcc tgctgcgcct ccggcagcac tagaggctac   1980
gacgaactcg tcccacacca gatttcagtg gtatcagagg aacggtttta cactaaatgg   2040
aaccctgagg cgctcccatc taatactggc gaagtaaatt tccagtccgg aatcattgcg   2100
gcccgctgtg ctatctccaa gttgcatcag gaacttggag ctaaaggttt cattcaagta   2160
tatgtcgatc aggtcgatga agatattgtg gctgtgaccc gacactcccc atcaattcat   2220
caaagtgtag tggctgtaac tcggacggct tttcgcaacc caaagacttc attctactcc   2280
aaagaggttc cacagatgtg tattccggga aagatagaag aagtggtatt ggaagcccgg   2340
accatcgaga ggaacactaa accatatcga aaagacgaga actccattaa cggaacccct   2400
gacatcactg ttgagatccg cgagcatatt cagcttaacg aaagcaaaat cgttaagcag   2460
gccggcgttg ccactaaggg accaaacgaa tatatccaag aaatcgaatt cgaaaacctc   2520
agtcctggct ccgttattat ctttcgcgta tccctcgacc cacacgccca agttgcggta   2580
gggatcttga gaaaccacct cacacagttc agcccacact ttaaatcagg ctccctcgcc   2640
gttgataacg cggacccaat acttaagatc ccctttgcat cccttgcgta tcgacttact   2700
ctcgcagagc ttaatcaaat attgtaccgc tgcgagtccg aagagaagga agacggtggt   2760
ggctgctacg acatccctaa ttggagtgca cttaagtacg cggggctgca gggactgatg   2820
tcagtgcttg cagagataag gccgaagaat gaccttggcc atccattttg taataatctc   2880
cgaagtggtg attggatgat agattacgta tcaaaccgct tgatcagtcg gtctggtacc   2940
atcgcggaag tgggaaagtg gttgcaggca atgttctttt atctcaaaca aatcccacgg   3000
tacttgatac cttgctattt cgacgcaatt ctcatcggtg catacacgac cttgctggac   3060
acggcctgga agcagatgtc tagcttcgtt cagaacggtt ctaccttcgt aaagcacctc   3120
tcattgggtt cagtccaact ctgcggagtc gggaaattcc cttcacttcc tattctctca   3180
cctgccctca tggacgtgcc ctaccggctg aacgaaatta ctaaggagaa ggaacagtgt   3240
tgtgtttctt tggcggcagg cttgccgcac ttttccagtg gaatcttcag atgttgggga   3300
cgggacacat tcattgcgct ccggggtatt ttgttgataa cgggccgata cgttgaggca   3360
cgaaatatta ttctggcatt cgccgggacc ttgcggcacg ggctgatacc caacctgctg   3420
ggcgaaggga tttacgctcg ctataactgc cgagacgcag tttggtggtg gctgcagtgt   3480
attcaggact attgtaagat ggtaccgaac gggctcgaca tcttgaagtg tcccgttagt   3540
cgaatgtatc ccaccgacga ttcagctccc ctgcccgcgg gaacacttga ccaaccactc   3600
tttgaagtga tccaagaggc tatgcagaaa cacatgcagg gaatacagtt ccgagaacga   3660
aacgcagggc cgcagattga tcgaaatatg aaagacgaag gatttaatat cacggcaggg   3720
gtcgacgaag agacggggtt tgtctacggc gggaatagat ttaactgcgg cacctggatg   3780
gataaaatgg gagaaagtga ccgagcacgg aaccggggca taccagcaac cccccgagac   3840
gggagcgctg ttgagatcgt gggtctgtct aagagtgcgg ttcgctggct tctcgagctt   3900
```

```
tcaaaaaaaa atatatttcc ttaccacgag gtcacggtca aaaggcatgg aaaagccata   3960

aaagtgtcat acgacgagtg gaataggaaa atacaagata actttgaaaa gctgtttcac   4020

gttagcgaag atcccagcga tctcaacgaa aaacatccca atctggttca caaacgcggg   4080

atctataaag actcatatgg agctagttct ccttggtgcg attatcaact gagaccgaac   4140

tttacaatcg ccatggtagt tgcgcccgag ctctttacta cagaaaaagc ctggaaggca   4200

cttgagattg cggaaaagaa actgcttggc cctctcggga tgaaaacgct tgatcccgac   4260

gacatggtct attgcgggat ttacgacaac gcattggaca acgacaacta caacttggcg   4320

aaaggattta attatcacca gggtcctgag tggttgtggc ccattggata ctttcttcga   4380

gcgaagctgt atttttcaag gctgatgggg ccggaaacga cagcgaaaac tattgtgctt   4440

gtcaaaaacg tgcttagcag gcattacgtg cacctcgagc gcagcccttg gaaaggactt   4500

ccggagctta cgaacgaaaa cgcccagtat tgtccattta gctgtgagac gcaggcctgg   4560

tctattgcta ccatcctcga gacactctac gacttgtag                          4599
```

```
<210> SEQ ID NO 39
<211> LENGTH: 4599
<212> TYPE: DNA
<213> ORGANISM: artificial
<220> FEATURE:
<223> OTHER INFORMATION: hGDE co2

<400> SEQUENCE: 39
```

```
atgggccaca gcaagcagat cagaatcctg ctgctgaacg agatggaaaa gctggaaaag     60

accctgttcc ggctcgagca gggctacgag ctgcagttta gactgggccc tacactgcag    120

ggcaaagccg tgaccgtgta cacaaactac cccttccctg gcgaaacctt caaccgcgag    180

aagttcagaa gcctggactg ggagaacccc accgagagag aggacgacag cgacaagtac    240

tgcaagctga acctgcagca gagcggctcc ttccagtact acttcctgca aggcaacgag    300

aagtccggcg gaggctacat cgtggtggac cctattctga gagtgggcgc cgacaatcac    360

gtgctgcctc tggattgtgt gaccctgcag accttcctgg ccaagtgtct gggccctttc    420

gatgagtggg agagcagact gcgcgtggcc aaagaaagcg gctacaacat gatccacttc    480

acccctctgc agaccctggg cctgagcaga agctgttaca gcctggccaa ccagctggaa    540

ctgaaccccg acttcagcag acccaaccgg aagtacacct ggaacgatgt gggccagctg    600

gtggaaaaac tgaagaaaga atggaacgtg atctgcatca ccgacgtggt gtacaaccac    660

accgccgcca acagcaagtg gatccaagag caccctgagt gcgcctacaa cctggtcaac    720

agccctcacc tgaaacctgc ctgggtgctc gatagagccc tgtggcggtt tagctgtgat    780

gtggccgagg gcaagtacaa agagaagggc atccccgctc tgatcgagaa cgaccaccac    840

atgaacagca tccggaagat catctgggaa gatattttcc ccaagctgaa gctgtgggag    900

ttcttccagg tggacgtgaa caaggccgtg gaacagttca gacggctgct gacccaagag    960

aacagaagag tgaccaagag cgaccccaac cagcacctga ccatcattca ggacccccgag   1020

tatcggagat tcggctgcac cgtggacatg aatatcgccc tgaccacctt cattccccac   1080

gacaaaggac ctgccgccat cgaggaatgc tgcaactggt tccacaagcg gatggaagaa   1140

ttgaacagcg agaagcaccg gctgatcaac taccaccaag agcaggccgt gaactgcctg   1200

ctgggcaacg tgttctatga gagactggcc ggacacggcc ctaagctggg acctgtgaca   1260

agaaagcacc ctctggttac ccggtacttc acctttccat tcgaagagat cgacttctcc   1320

atggaagaga gcatgatcca tctgcctaac aaggcctgct tcctgatggc tcacaacggc   1380
```

```
tgggttatgg gcgacgaccc tctgagaaat ttcgccgagc ctggcagcga ggtgtacctg   1440
agaagagaac tgatctgttg ggcgacagc  gtgaagctga gatacggcaa caagcccgag   1500
gactgccctt acctgtgggc ccatatgaag aagtacacag agatcaccgc cacctacttt   1560
cagggcgtca gactggacaa ctgccacagc acacctctgc acgtggccga gtacatgctg   1620
gacgccgcta gaaatctgca gcccaacctg tatgtggtgg ccgagctgtt taccggctcc   1680
gaggacctgg acaatgtgtt cgtgaccaga ctgggcatca gcagcctgat cagagaagcc   1740
atgtccgcct acaatagcca cgaagagggc agactggtgt acagatatgg cggcgagcct   1800
gtgggcagct tcgttcagcc ttgtctgagg cctctgatgc ccgccattgc tcacgccctg   1860
ttcatggaca tcacccacga taacgagtgc cccatcgtgc acagaagcgc ctacgacgct   1920
ctgcctagca ccaccattgt gtccatggcc tgttgtgcca gcggcagcac aagaggctat   1980
gacgaactgg tgccccacca gatttccgtg gtgtccgagg aacggttcta caccaagtgg   2040
aaccccgagg ctctgcccag caataccggc gaagtgaatt tccagagcgg catcattgcc   2100
gccagatgcg ccatcagcaa gctgcaccaa gaactgggcg ccaagggctt cattcaggtg   2160
tacgtggacc aggtcgacga ggacattgtg gccgtgacaa gacacagccc cagcatccat   2220
cagagcgtgg tggctgtgac cagaaccgcc ttcagaaacc ccaagaccag cttctacagc   2280
aaagaggtgc cccagatgtg catccccggc aagattgagg aagtggtgct cgaggcccgg   2340
accatcgaga gaaacaccaa gccttaccgg aaggacgaga actccatcaa cggcacccct   2400
gacatcaccg tggaaatcag agagcacatc cagctcaacg agagcaagat cgtgaaacag   2460
gccggcgtgg ccacaaaggg ccccaacgag tatatccaag agattgagtt cgagaatctg   2520
agccccggca gcgtgatcat cttcagagtg tccctggatc ctcacgctca ggtggccgtg   2580
ggcatcctga gaaatcacct gacacagttc agcccacact tcaagagcgg aagcctggcc   2640
gtggacaacg ccgatcctat cctgaagatc cccttcgcct ctctggccta cagactgaca   2700
ctggctgagc tgaaccagat cctgtacaga tgcgagtccg aagagaaaga ggatggcgga   2760
ggctgctacg acatccccaa ttggagcgcc ctgaagtatg ccggactgca gggactgatg   2820
tctgtgctgg ccgagatcag acccaagaac gacctgggac accccttctg caacaacctg   2880
agatccggcg actggatgat cgactacgtg tccaacagac tgatcagcag atccggcaca   2940
atcgccgaag tcggcaaatg gctgcaggcc atgttcttct acctgaagca gatccctcgg   3000
tatctgatcc cctgctactt cgacgccatc ctgatcggcg cctacaccac actgctggat   3060
accgcctgga agcagatgtc cagcttcgtg cagaacggca gcaccttcgt gaagcacctg   3120
tctctgggaa gcgtgcagct gtgtggcgtg ggcaaatttc ccagcctgcc tatcctgtct   3180
cctgcactga tggacgtgcc ctaccggctg aatgagatca ccaaagaaaa agagcagtgc   3240
tgcgtcagcc tggctgctgg cctgcctcat ttttccagcg gcatcttccg gtgttggggc   3300
agagacacct ttattgccct gagaggcatc ctgctgatta ccggcagata cgtggaagcc   3360
cggaacatca tcctggcctt tgccggcaca ctgcggcacg gactgattcc taatctgctc   3420
ggcgagggca tctacgccag atacaactgc agagatgccg tgtggtggtg gctccagtgc   3480
atccaggact actgcaagat ggtgcccaac ggcctggaca tcctgaagtg ccctgtgtcc   3540
agaatgtacc ctaccgacga tagcgcccct ctgcctgccg gaacacttga ccagcctctg   3600
ttcgaagtga ttcaagaggc catgcagaaa cacatgcagg gaatccagtt tcgcgagcgg   3660
aatgccggac ctcagatcga cagaaacatg aaggatgagg gcttcaacat caccgctggc   3720
```

```
gtggacgaag agacaggctt tgtgtacggc ggcaaccggt tcaattgcgg cacctggatg   3780

gacaagatgg gcgagtctga ccgggccaga aacagaggaa ttcccgccac acctagagat   3840

ggcagcgctg tggaaatcgt gggcctgtct aagtctgctg tgcggtggct gctcgaactg   3900

agcaagaaga atatctttcc gtaccacgaa gtgaccgtga agcggcacgg caaggccatc   3960

aaggtgtcct acgacgagtg gaacagaaag atccaggaca acttcgaaaa gctgttccat   4020

gtgtctgagg accccagcga cctgaacgaa aagcacccca acctggtgca caagcgcggc   4080

atctacaagg acagctacgg cgcctcttct ccttggtgcg attaccagct gcggcccaac   4140

ttcaccattg ccatggtggt tgcccctgag ctgttcacca cagagaaggc ctggaaggcc   4200

ctggaaatcg ccgagaagaa actgctgggc cctctgggca tgaagacact ggaccccgac   4260

gacatggtgt actgcggaat ctacgacaac gccctggata acgacaacta caatctggcc   4320

aaggggttca attaccatca gggacccgag tggctgtggc ctatcggcta tttcctgcgg   4380

gccaagctgt acttctccag actgatgggc cctgagacaa ccgccaagac aatcgtgctc   4440

gtgaagaacg tgctgagccg gcactatgtg cacctggaaa gaagcccctg gaagggactg   4500

cccgagctga ccaatgagaa cgcccagtac tgccccttca gctgcgaaac acaggcctgg   4560

tctatcgcca ccatcctgga aaccctgtac gacctgtga                          4599
```

```
<210> SEQ ID NO 40
<211> LENGTH: 1515
<212> TYPE: PRT
<213> ORGANISM: Homo sapiens

<400> SEQUENCE: 40

Met Ser Leu Leu Thr Cys Ala Phe Tyr Leu Gly Tyr Glu Leu Gln Phe
1               5                   10                  15

Arg Leu Gly Pro Thr Leu Gln Gly Lys Ala Val Thr Val Tyr Thr Asn
            20                  25                  30

Tyr Pro Phe Pro Gly Glu Thr Phe Asn Arg Glu Lys Phe Arg Ser Leu
        35                  40                  45

Asp Trp Glu Asn Pro Thr Glu Arg Glu Asp Asp Ser Asp Lys Tyr Cys
    50                  55                  60

Lys Leu Asn Leu Gln Gln Ser Gly Ser Phe Gln Tyr Tyr Phe Leu Gln
65                  70                  75                  80

Gly Asn Glu Lys Ser Gly Gly Gly Tyr Ile Val Val Asp Pro Ile Leu
                85                  90                  95

Arg Val Gly Ala Asp Asn His Val Leu Pro Leu Asp Cys Val Thr Leu
            100                 105                 110

Gln Thr Phe Leu Ala Lys Cys Leu Gly Pro Phe Asp Glu Trp Glu Ser
        115                 120                 125

Arg Leu Arg Val Ala Lys Glu Ser Gly Tyr Asn Met Ile His Phe Thr
    130                 135                 140

Pro Leu Gln Thr Leu Gly Leu Ser Arg Ser Cys Tyr Ser Leu Ala Asn
145                 150                 155                 160

Gln Leu Glu Leu Asn Pro Asp Phe Ser Arg Pro Asn Arg Lys Tyr Thr
                165                 170                 175

Trp Asn Asp Val Gly Gln Leu Val Glu Lys Leu Lys Lys Glu Trp Asn
            180                 185                 190

Val Ile Cys Ile Thr Asp Val Val Tyr Asn His Thr Ala Ala Asn Ser
        195                 200                 205

Lys Trp Ile Gln Glu His Pro Glu Cys Ala Tyr Asn Leu Val Asn Ser
    210                 215                 220
```

```
Pro His Leu Lys Pro Ala Trp Val Leu Asp Arg Ala Leu Trp Arg Phe
225                 230                 235                 240

Ser Cys Asp Val Ala Glu Gly Lys Tyr Lys Glu Lys Gly Ile Pro Ala
                245                 250                 255

Leu Ile Glu Asn Asp His His Met Asn Ser Ile Arg Lys Ile Ile Trp
            260                 265                 270

Glu Asp Ile Phe Pro Lys Leu Lys Leu Trp Glu Phe Phe Gln Val Asp
        275                 280                 285

Val Asn Lys Ala Val Glu Gln Phe Arg Arg Leu Leu Thr Gln Glu Asn
    290                 295                 300

Arg Arg Val Thr Lys Ser Asp Pro Asn Gln His Leu Thr Ile Ile Gln
305                 310                 315                 320

Asp Pro Glu Tyr Arg Arg Phe Gly Cys Thr Val Asp Met Asn Ile Ala
                325                 330                 335

Leu Thr Thr Phe Ile Pro His Asp Lys Gly Pro Ala Ala Ile Glu Glu
            340                 345                 350

Cys Cys Asn Trp Phe His Lys Arg Met Glu Glu Leu Asn Ser Glu Lys
        355                 360                 365

His Arg Leu Ile Asn Tyr His Gln Glu Gln Ala Val Asn Cys Leu Leu
    370                 375                 380

Gly Asn Val Phe Tyr Glu Arg Leu Ala Gly His Gly Pro Lys Leu Gly
385                 390                 395                 400

Pro Val Thr Arg Lys His Pro Leu Val Thr Arg Tyr Phe Thr Phe Pro
                405                 410                 415

Phe Glu Glu Ile Asp Phe Ser Met Glu Glu Ser Met Ile His Leu Pro
            420                 425                 430

Asn Lys Ala Cys Phe Leu Met Ala His Asn Gly Trp Val Met Gly Asp
        435                 440                 445

Asp Pro Leu Arg Asn Phe Ala Glu Pro Gly Ser Glu Val Tyr Leu Arg
    450                 455                 460

Arg Glu Leu Ile Cys Trp Gly Asp Ser Val Lys Leu Arg Tyr Gly Asn
465                 470                 475                 480

Lys Pro Glu Asp Cys Pro Tyr Leu Trp Ala His Met Lys Lys Tyr Thr
                485                 490                 495

Glu Ile Thr Ala Thr Tyr Phe Gln Gly Val Arg Leu Asp Asn Cys His
            500                 505                 510

Ser Thr Pro Leu His Val Ala Glu Tyr Met Leu Asp Ala Ala Arg Asn
        515                 520                 525

Leu Gln Pro Asn Leu Tyr Val Val Ala Glu Leu Phe Thr Gly Ser Glu
    530                 535                 540

Asp Leu Asp Asn Val Phe Val Thr Arg Leu Gly Ile Ser Ser Leu Ile
545                 550                 555                 560

Arg Glu Ala Met Ser Ala Tyr Asn Ser His Glu Glu Gly Arg Leu Val
                565                 570                 575

Tyr Arg Tyr Gly Gly Glu Pro Val Gly Ser Phe Val Gln Pro Cys Leu
            580                 585                 590

Arg Pro Leu Met Pro Ala Ile Ala His Ala Leu Phe Met Asp Ile Thr
        595                 600                 605

His Asp Asn Glu Cys Pro Ile Val His Arg Ser Ala Tyr Asp Ala Leu
    610                 615                 620

Pro Ser Thr Thr Ile Val Ser Met Ala Cys Cys Ala Ser Gly Ser Thr
625                 630                 635                 640
```

```
Arg Gly Tyr Asp Glu Leu Val Pro His Gln Ile Ser Val Val Ser Glu
                645                 650                 655

Glu Arg Phe Tyr Thr Lys Trp Asn Pro Glu Ala Leu Pro Ser Asn Thr
            660                 665                 670

Gly Glu Val Asn Phe Gln Ser Gly Ile Ile Ala Ala Arg Cys Ala Ile
        675                 680                 685

Ser Lys Leu His Gln Glu Leu Gly Ala Lys Gly Phe Ile Gln Val Tyr
    690                 695                 700

Val Asp Gln Val Asp Glu Asp Ile Val Ala Val Thr Arg His Ser Pro
705                 710                 715                 720

Ser Ile His Gln Ser Val Val Ala Val Thr Arg Thr Ala Phe Arg Asn
                725                 730                 735

Pro Lys Thr Ser Phe Tyr Ser Lys Glu Val Pro Gln Met Cys Ile Pro
            740                 745                 750

Gly Lys Ile Glu Glu Val Val Leu Glu Ala Arg Thr Ile Glu Arg Asn
        755                 760                 765

Thr Lys Pro Tyr Arg Lys Asp Glu Asn Ser Ile Asn Gly Thr Pro Asp
    770                 775                 780

Ile Thr Val Glu Ile Arg Glu His Ile Gln Leu Asn Glu Ser Lys Ile
785                 790                 795                 800

Val Lys Gln Ala Gly Val Ala Thr Lys Gly Pro Asn Glu Tyr Ile Gln
                805                 810                 815

Glu Ile Glu Phe Glu Asn Leu Ser Pro Gly Ser Val Ile Ile Phe Arg
            820                 825                 830

Val Ser Leu Asp Pro His Ala Gln Val Ala Val Gly Ile Leu Arg Asn
        835                 840                 845

His Leu Thr Gln Phe Ser Pro His Phe Lys Ser Gly Ser Leu Ala Val
    850                 855                 860

Asp Asn Ala Asp Pro Ile Leu Lys Ile Pro Phe Ala Ser Leu Ala Tyr
865                 870                 875                 880

Arg Leu Thr Leu Ala Glu Leu Asn Gln Ile Leu Tyr Arg Cys Glu Ser
                885                 890                 895

Glu Glu Lys Glu Asp Gly Gly Gly Cys Tyr Asp Ile Pro Asn Trp Ser
            900                 905                 910

Ala Leu Lys Tyr Ala Gly Leu Gln Gly Leu Met Ser Val Leu Ala Glu
        915                 920                 925

Ile Arg Pro Lys Asn Asp Leu Gly His Pro Phe Cys Asn Asn Leu Arg
    930                 935                 940

Ser Gly Asp Trp Met Ile Asp Tyr Val Ser Asn Arg Leu Ile Ser Arg
945                 950                 955                 960

Ser Gly Thr Ile Ala Glu Val Gly Lys Trp Leu Gln Ala Met Phe Phe
                965                 970                 975

Tyr Leu Lys Gln Ile Pro Arg Tyr Leu Ile Pro Cys Tyr Phe Asp Ala
            980                 985                 990

Ile Leu Ile Gly Ala Tyr Thr Thr  Leu Leu Asp Thr Ala  Trp Lys Gln
        995                 1000                1005

Met Ser  Ser Phe Val Gln Asn  Gly Ser Thr Phe Val  Lys His Leu
    1010                1015                1020

Ser Leu  Gly Ser Val Gln Leu  Cys Gly Val Gly Lys  Phe Pro Ser
    1025                1030                1035

Leu Pro  Ile Leu Ser Pro Ala  Leu Met Asp Val Pro  Tyr Arg Leu
    1040                1045                1050

Asn Glu  Ile Thr Lys Glu Lys  Glu Gln Cys Cys Val  Ser Leu Ala
```

```
    1055                1060                1065

Ala Gly  Leu Pro His Phe Ser  Ser Gly Ile Phe Arg  Cys Trp Gly
    1070                1075                1080

Arg Asp  Thr Phe Ile Ala Leu  Arg Gly Ile Leu Leu  Ile Thr Gly
    1085                1090                1095

Arg Tyr  Val Glu Ala Arg Asn  Ile Ile Leu Ala Phe  Ala Gly Thr
    1100                1105                1110

Leu Arg  His Gly Leu Ile Pro  Asn Leu Leu Gly Glu  Gly Ile Tyr
    1115                1120                1125

Ala Arg  Tyr Asn Cys Arg Asp  Ala Val Trp Trp Trp  Leu Gln Cys
    1130                1135                1140

Ile Gln  Asp Tyr Cys Lys Met  Val Pro Asn Gly Leu  Asp Ile Leu
    1145                1150                1155

Lys Cys  Pro Val Ser Arg Met  Tyr Pro Thr Asp Asp  Ser Ala Pro
    1160                1165                1170

Leu Pro  Ala Gly Thr Leu Asp  Gln Pro Leu Phe Glu  Val Ile Gln
    1175                1180                1185

Glu Ala  Met Gln Lys His Met  Gln Gly Ile Gln Phe  Arg Glu Arg
    1190                1195                1200

Asn Ala  Gly Pro Gln Ile Asp  Arg Asn Met Lys Asp  Glu Gly Phe
    1205                1210                1215

Asn Ile  Thr Ala Gly Val Asp  Glu Glu Thr Gly Phe  Val Tyr Gly
    1220                1225                1230

Gly Asn  Arg Phe Asn Cys Gly  Thr Trp Met Asp Lys  Met Gly Glu
    1235                1240                1245

Ser Asp  Arg Ala Arg Asn Arg  Gly Ile Pro Ala Thr  Pro Arg Asp
    1250                1255                1260

Gly Ser  Ala Val Glu Ile Val  Gly Leu Ser Lys Ser  Ala Val Arg
    1265                1270                1275

Trp Leu  Leu Glu Leu Ser Lys  Lys Asn Ile Phe Pro  Tyr His Glu
    1280                1285                1290

Val Thr  Val Lys Arg His Gly  Lys Ala Ile Lys Val  Ser Tyr Asp
    1295                1300                1305

Glu Trp  Asn Arg Lys Ile Gln  Asp Asn Phe Glu Lys  Leu Phe His
    1310                1315                1320

Val Ser  Glu Asp Pro Ser Asp  Leu Asn Glu Lys His  Pro Asn Leu
    1325                1330                1335

Val His  Lys Arg Gly Ile Tyr  Lys Asp Ser Tyr Gly  Ala Ser Ser
    1340                1345                1350

Pro Trp  Cys Asp Tyr Gln Leu  Arg Pro Asn Phe Thr  Ile Ala Met
    1355                1360                1365

Val Val  Ala Pro Glu Leu Phe  Thr Thr Glu Lys Ala  Trp Lys Ala
    1370                1375                1380

Leu Glu  Ile Ala Glu Lys Lys  Leu Leu Gly Pro Leu  Gly Met Lys
    1385                1390                1395

Thr Leu  Asp Pro Asp Asp Met  Val Tyr Cys Gly Ile  Tyr Asp Asn
    1400                1405                1410

Ala Leu  Asp Asn Asp Asn Tyr  Asn Leu Ala Lys Gly  Phe Asn Tyr
    1415                1420                1425

His Gln  Gly Pro Glu Trp Leu  Trp Pro Ile Gly Tyr  Phe Leu Arg
    1430                1435                1440

Ala Lys  Leu Tyr Phe Ser Arg  Leu Met Gly Pro Glu  Thr Thr Ala
    1445                1450                1455
```

```
Lys Thr  Ile Val Leu Val Lys  Asn Val Leu Ser Arg  His Tyr Val
    1460                 1465                 1470

His Leu  Glu Arg Ser Pro Trp  Lys Gly Leu Pro Glu  Leu Thr Asn
    1475                 1480                 1485

Glu Asn  Ala Gln Tyr Cys Pro  Phe Ser Cys Glu Thr  Gln Ala Trp
    1490                 1495                 1500

Ser Ile  Ala Thr Ile Leu Glu  Thr Leu Tyr Asp Leu
    1505                 1510                 1515


<210> SEQ ID NO 41
<211> LENGTH: 1516
<212> TYPE: PRT
<213> ORGANISM: Homo sapiens

<400> SEQUENCE: 41

Met Ala Pro Ile Leu Ser Ile Asn Leu Phe Ile Gly Tyr Glu Leu Gln
1               5                   10                  15

Phe Arg Leu Gly Pro Thr Leu Gln Gly Lys Ala Val Thr Val Tyr Thr
            20                  25                  30

Asn Tyr Pro Phe Pro Gly Glu Thr Phe Asn Arg Glu Lys Phe Arg Ser
        35                  40                  45

Leu Asp Trp Glu Asn Pro Thr Glu Arg Glu Asp Asp Ser Asp Lys Tyr
    50                  55                  60

Cys Lys Leu Asn Leu Gln Gln Ser Gly Ser Phe Gln Tyr Tyr Phe Leu
65                  70                  75                  80

Gln Gly Asn Glu Lys Ser Gly Gly Gly Tyr Ile Val Val Asp Pro Ile
                85                  90                  95

Leu Arg Val Gly Ala Asp Asn His Val Leu Pro Leu Asp Cys Val Thr
            100                 105                 110

Leu Gln Thr Phe Leu Ala Lys Cys Leu Gly Pro Phe Asp Glu Trp Glu
        115                 120                 125

Ser Arg Leu Arg Val Ala Lys Glu Ser Gly Tyr Asn Met Ile His Phe
    130                 135                 140

Thr Pro Leu Gln Thr Leu Gly Leu Ser Arg Ser Cys Tyr Ser Leu Ala
145                 150                 155                 160

Asn Gln Leu Glu Leu Asn Pro Asp Phe Ser Arg Pro Asn Arg Lys Tyr
                165                 170                 175

Thr Trp Asn Asp Val Gly Gln Leu Val Glu Lys Leu Lys Lys Glu Trp
            180                 185                 190

Asn Val Ile Cys Ile Thr Asp Val Val Tyr Asn His Thr Ala Ala Asn
        195                 200                 205

Ser Lys Trp Ile Gln Glu His Pro Glu Cys Ala Tyr Asn Leu Val Asn
    210                 215                 220

Ser Pro His Leu Lys Pro Ala Trp Val Leu Asp Arg Ala Leu Trp Arg
225                 230                 235                 240

Phe Ser Cys Asp Val Ala Glu Gly Lys Tyr Lys Glu Lys Gly Ile Pro
                245                 250                 255

Ala Leu Ile Glu Asn Asp His His Met Asn Ser Ile Arg Lys Ile Ile
            260                 265                 270

Trp Glu Asp Ile Phe Pro Lys Leu Lys Leu Trp Glu Phe Phe Gln Val
        275                 280                 285

Asp Val Asn Lys Ala Val Glu Gln Phe Arg Arg Leu Leu Thr Gln Glu
    290                 295                 300

Asn Arg Arg Val Thr Lys Ser Asp Pro Asn Gln His Leu Thr Ile Ile
```

```
305                 310                 315                 320

Gln Asp Pro Glu Tyr Arg Arg Phe Gly Cys Thr Val Asp Met Asn Ile
                325                 330                 335

Ala Leu Thr Thr Phe Ile Pro His Asp Lys Gly Pro Ala Ala Ile Glu
            340                 345                 350

Glu Cys Cys Asn Trp Phe His Lys Arg Met Glu Glu Leu Asn Ser Glu
        355                 360                 365

Lys His Arg Leu Ile Asn Tyr His Gln Glu Gln Ala Val Asn Cys Leu
    370                 375                 380

Leu Gly Asn Val Phe Tyr Glu Arg Leu Ala Gly His Gly Pro Lys Leu
385                 390                 395                 400

Gly Pro Val Thr Arg Lys His Pro Leu Val Thr Arg Tyr Phe Thr Phe
                405                 410                 415

Pro Phe Glu Glu Ile Asp Phe Ser Met Glu Glu Ser Met Ile His Leu
            420                 425                 430

Pro Asn Lys Ala Cys Phe Leu Met Ala His Asn Gly Trp Val Met Gly
        435                 440                 445

Asp Asp Pro Leu Arg Asn Phe Ala Glu Pro Gly Ser Glu Val Tyr Leu
    450                 455                 460

Arg Arg Glu Leu Ile Cys Trp Gly Asp Ser Val Lys Leu Arg Tyr Gly
465                 470                 475                 480

Asn Lys Pro Glu Asp Cys Pro Tyr Leu Trp Ala His Met Lys Lys Tyr
                485                 490                 495

Thr Glu Ile Thr Ala Thr Tyr Phe Gln Gly Val Arg Leu Asp Asn Cys
            500                 505                 510

His Ser Thr Pro Leu His Val Ala Glu Tyr Met Leu Asp Ala Ala Arg
        515                 520                 525

Asn Leu Gln Pro Asn Leu Tyr Val Val Ala Glu Leu Phe Thr Gly Ser
    530                 535                 540

Glu Asp Leu Asp Asn Val Phe Val Thr Arg Leu Gly Ile Ser Ser Leu
545                 550                 555                 560

Ile Arg Glu Ala Met Ser Ala Tyr Asn Ser His Glu Glu Gly Arg Leu
                565                 570                 575

Val Tyr Arg Tyr Gly Gly Glu Pro Val Gly Ser Phe Val Gln Pro Cys
            580                 585                 590

Leu Arg Pro Leu Met Pro Ala Ile Ala His Ala Leu Phe Met Asp Ile
        595                 600                 605

Thr His Asp Asn Glu Cys Pro Ile Val His Arg Ser Ala Tyr Asp Ala
    610                 615                 620

Leu Pro Ser Thr Thr Ile Val Ser Met Ala Cys Cys Ala Ser Gly Ser
625                 630                 635                 640

Thr Arg Gly Tyr Asp Glu Leu Val Pro His Gln Ile Ser Val Val Ser
                645                 650                 655

Glu Glu Arg Phe Tyr Thr Lys Trp Asn Pro Glu Ala Leu Pro Ser Asn
            660                 665                 670

Thr Gly Glu Val Asn Phe Gln Ser Gly Ile Ile Ala Ala Arg Cys Ala
        675                 680                 685

Ile Ser Lys Leu His Gln Glu Leu Gly Ala Lys Gly Phe Ile Gln Val
    690                 695                 700

Tyr Val Asp Gln Val Asp Glu Asp Ile Val Ala Val Thr Arg His Ser
705                 710                 715                 720

Pro Ser Ile His Gln Ser Val Val Ala Val Thr Arg Thr Ala Phe Arg
                725                 730                 735
```

```
Asn Pro Lys Thr Ser Phe Tyr Ser Lys Glu Val Pro Gln Met Cys Ile
            740                 745                 750

Pro Gly Lys Ile Glu Glu Val Val Leu Glu Ala Arg Thr Ile Glu Arg
        755                 760                 765

Asn Thr Lys Pro Tyr Arg Lys Asp Glu Asn Ser Ile Asn Gly Thr Pro
    770                 775                 780

Asp Ile Thr Val Glu Ile Arg Glu His Ile Gln Leu Asn Glu Ser Lys
785                 790                 795                 800

Ile Val Lys Gln Ala Gly Val Ala Thr Lys Gly Pro Asn Glu Tyr Ile
                805                 810                 815

Gln Glu Ile Glu Phe Glu Asn Leu Ser Pro Gly Ser Val Ile Ile Phe
            820                 825                 830

Arg Val Ser Leu Asp Pro His Ala Gln Val Ala Val Gly Ile Leu Arg
        835                 840                 845

Asn His Leu Thr Gln Phe Ser Pro His Phe Lys Ser Gly Ser Leu Ala
    850                 855                 860

Val Asp Asn Ala Asp Pro Ile Leu Lys Ile Pro Phe Ala Ser Leu Ala
865                 870                 875                 880

Tyr Arg Leu Thr Leu Ala Glu Leu Asn Gln Ile Leu Tyr Arg Cys Glu
                885                 890                 895

Ser Glu Glu Lys Glu Asp Gly Gly Gly Cys Tyr Asp Ile Pro Asn Trp
            900                 905                 910

Ser Ala Leu Lys Tyr Ala Gly Leu Gln Gly Leu Met Ser Val Leu Ala
        915                 920                 925

Glu Ile Arg Pro Lys Asn Asp Leu Gly His Pro Phe Cys Asn Asn Leu
    930                 935                 940

Arg Ser Gly Asp Trp Met Ile Asp Tyr Val Ser Asn Arg Leu Ile Ser
945                 950                 955                 960

Arg Ser Gly Thr Ile Ala Glu Val Gly Lys Trp Leu Gln Ala Met Phe
                965                 970                 975

Phe Tyr Leu Lys Gln Ile Pro Arg Tyr Leu Ile Pro Cys Tyr Phe Asp
            980                 985                 990

Ala Ile Leu Ile Gly Ala Tyr Thr  Thr Leu Leu Asp Thr  Ala Trp Lys
        995                 1000                 1005

Gln Met  Ser Ser Phe Val Gln  Asn Gly Ser Thr Phe  Val Lys His
    1010                 1015                 1020

Leu Ser  Leu Gly Ser Val Gln  Leu Cys Gly Val Gly  Lys Phe Pro
    1025                 1030                 1035

Ser Leu  Pro Ile Leu Ser Pro  Ala Leu Met Asp Val  Pro Tyr Arg
    1040                 1045                 1050

Leu Asn  Glu Ile Thr Lys Glu  Lys Glu Gln Cys Cys  Val Ser Leu
    1055                 1060                 1065

Ala Ala  Gly Leu Pro His Phe  Ser Ser Gly Ile Phe  Arg Cys Trp
    1070                 1075                 1080

Gly Arg  Asp Thr Phe Ile Ala  Leu Arg Gly Ile Leu  Leu Ile Thr
    1085                 1090                 1095

Gly Arg  Tyr Val Glu Ala Arg  Asn Ile Ile Leu Ala  Phe Ala Gly
    1100                 1105                 1110

Thr Leu  Arg His Gly Leu Ile  Pro Asn Leu Leu Gly  Glu Gly Ile
    1115                 1120                 1125

Tyr Ala  Arg Tyr Asn Cys Arg  Asp Ala Val Trp Trp  Trp Leu Gln
    1130                 1135                 1140
```

```
Cys Ile  Gln Asp Tyr Cys Lys  Met Val Pro Asn Gly  Leu Asp Ile
    1145                 1150                 1155

Leu Lys  Cys Pro Val Ser Arg  Met Tyr Pro Thr Asp  Asp Ser Ala
    1160                 1165                 1170

Pro Leu  Pro Ala Gly Thr Leu  Asp Gln Pro Leu Phe  Glu Val Ile
    1175                 1180                 1185

Gln Glu  Ala Met Gln Lys His  Met Gln Gly Ile Gln  Phe Arg Glu
    1190                 1195                 1200

Arg Asn  Ala Gly Pro Gln Ile  Asp Arg Asn Met Lys  Asp Glu Gly
    1205                 1210                 1215

Phe Asn  Ile Thr Ala Gly Val  Asp Glu Glu Thr Gly  Phe Val Tyr
    1220                 1225                 1230

Gly Gly  Asn Arg Phe Asn Cys  Gly Thr Trp Met Asp  Lys Met Gly
    1235                 1240                 1245

Glu Ser  Asp Arg Ala Arg Asn  Arg Gly Ile Pro Ala  Thr Pro Arg
    1250                 1255                 1260

Asp Gly  Ser Ala Val Glu Ile  Val Gly Leu Ser Lys  Ser Ala Val
    1265                 1270                 1275

Arg Trp  Leu Leu Glu Leu Ser  Lys Lys Asn Ile Phe  Pro Tyr His
    1280                 1285                 1290

Glu Val  Thr Val Lys Arg His  Gly Lys Ala Ile Lys  Val Ser Tyr
    1295                 1300                 1305

Asp Glu  Trp Asn Arg Lys Ile  Gln Asp Asn Phe Glu  Lys Leu Phe
    1310                 1315                 1320

His Val  Ser Glu Asp Pro Ser  Asp Leu Asn Glu Lys  His Pro Asn
    1325                 1330                 1335

Leu Val  His Lys Arg Gly Ile  Tyr Lys Asp Ser Tyr  Gly Ala Ser
    1340                 1345                 1350

Ser Pro  Trp Cys Asp Tyr Gln  Leu Arg Pro Asn Phe  Thr Ile Ala
    1355                 1360                 1365

Met Val  Val Ala Pro Glu Leu  Phe Thr Thr Glu Lys  Ala Trp Lys
    1370                 1375                 1380

Ala Leu  Glu Ile Ala Glu Lys  Lys Leu Leu Gly Pro  Leu Gly Met
    1385                 1390                 1395

Lys Thr  Leu Asp Pro Asp Asp  Met Val Tyr Cys Gly  Ile Tyr Asp
    1400                 1405                 1410

Asn Ala  Leu Asp Asn Asp Asn  Tyr Asn Leu Ala Lys  Gly Phe Asn
    1415                 1420                 1425

Tyr His  Gln Gly Pro Glu Trp  Leu Trp Pro Ile Gly  Tyr Phe Leu
    1430                 1435                 1440

Arg Ala  Lys Leu Tyr Phe Ser  Arg Leu Met Gly Pro  Glu Thr Thr
    1445                 1450                 1455

Ala Lys  Thr Ile Val Leu Val  Lys Asn Val Leu Ser  Arg His Tyr
    1460                 1465                 1470

Val His  Leu Glu Arg Ser Pro  Trp Lys Gly Leu Pro  Glu Leu Thr
    1475                 1480                 1485

Asn Glu  Asn Ala Gln Tyr Cys  Pro Phe Ser Cys Glu  Thr Gln Ala
    1490                 1495                 1500

Trp Ser  Ile Ala Thr Ile Leu  Glu Thr Leu Tyr Asp  Leu
    1505                 1510                 1515
```

<210> SEQ ID NO 42
<211> LENGTH: 441
<212> TYPE: DNA

<213> ORGANISM: artificial
<220> FEATURE:
<223> OTHER INFORMATION: HBB2 intron

<400> SEQUENCE: 42
gtacacatat tgaccaaatc agggtaattt tgcatttgta attttaaaaa atgctttctt 60
cttttaatat actttttgt ttatcttatt tctaatactt tccctaatct ctttctttca 120
gggcaataat gatacaatgt atcatgcctc tttgcaccat tctaaagaat aacagtgata 180
atttctgggt taaggcaata gcaatatttc tgcatataaa tatttctgca tataaattgt 240
aactgatgta agaggtttca tattgctaat agcagctaca atccagctac cattctgctt 300
ttattttatg gttgggataa ggctggatta ttctgagtcc aagctaggcc cttttgctaa 360
tcatgttcat acctcttatc ttcctcccac agctcctggg caacgtgctg gtctgtgtgc 420
tggcccatca ctttggcaaa g 441

<210> SEQ ID NO 43
<211> LENGTH: 441
<212> TYPE: DNA
<213> ORGANISM: artificial
<220> FEATURE:
<223> OTHER INFORMATION: modified HBB2 intron

<400> SEQUENCE: 43
gtacacatat tgaccaaatc agggtaattt tgcatttgta attttaaaaa atgctttctt 60
cttttaatat actttttgt ttatcttatt tctaatactt tccctaatct ctttctttca 120
gggcaataat gatacaatgt atcatgcctc tttgcaccat tctaaagaat aacagtgata 180
atttctgggt taaggcaata gcaatatttc tgcatataaa tatttctgca tataaattgt 240
aactgatgta agaggtttca tattgctaat agcagctaca atccagctac cattctgctt 300
ttattttctg gttgggataa ggctggatta ttctgagtcc aagctaggcc cttttgctaa 360
tcttgttcat acctcttatc ttcctcccac agctcctggg caacctgctg gtctctctgc 420
tggcccatca ctttggcaaa g 441

<210> SEQ ID NO 44
<211> LENGTH: 1438
<212> TYPE: DNA
<213> ORGANISM: artificial
<220> FEATURE:
<223> OTHER INFORMATION: FIX intron

<400> SEQUENCE: 44
ggtttgtttc ctttttaaa atacattgag tatgcttgcc ttttagatat agaaatatct 60
gatgctgtct tcttcactaa attttgatta catgatttga cagcaatatt gaagagtcta 120
acagccagca cgcaggttgg taagtactgg ttctttgtta gctaggtttt cttcttcttc 180
atttttaaaa ctaaatagat cgacaatgct tatgatgcat ttatgtttaa taaacactgt 240
tcagttcatg atttggtcat gtaattcctg ttagaaaaca ttcatctcct tggtttaaaa 300
aaattaaaag tgggaaaaca aagaaatagc agaatatagt gaaaaaaaat aaccacatta 360
tttttgtttg gacttaccac tttgaaatca aaatgggaaa caaaagcaca aacaatggcc 420
ttatttacac aaaaagtctg attttaagat atatgacatt tcaaggtttc agaagtatgt 480
aatgaggtgt gtctctaatt ttttaaatta tatatcttca atttaaagtt ttagttaaaa 540
cataaagatt aacctttcat tagcaagctg ttagttatca ccaacgcttt tcatggatta 600
ggaaaaaatc attttgtctc tatgtcaaac atcttggagt tgatatttgg ggaaacacaa 660

```
tactcagttg agttccctag gggagaaaag cacgcttaag aattgacata aagagtagga    720

agttagctaa tgcaacatat atcactttgt tttttcacaa ctacagtgac tttatgtatt    780

tcccagagga aggcatacag ggaagaaatt atcccatttg gacaaacagc atgttctcac    840

aggaagcatt tatcacactt acttgtcaac tttctagaat caaatctagt agctgacagt    900

accaggatca ggggtgccaa ccctaagcac ccccagaaag ctgactggcc ctgtggttcc    960

cactccagac atgatgtcag ctgtgaaatc gacgtcgctg gaccataatt aggcttctgt   1020

tcttcaggag acatttgttc aaagtcattt gggcaaccat attctgaaaa cagcccagcc   1080

agggtgatgg atcactttgc aaagatcctc aatgagctat tttcaagtga tgacaaagtg   1140

tgaagttaac cgctcatttg agaactttct ttttcatcca aagtaaattc aaatatgatt   1200

agaaatctga ccttttatta ctggaattct cttgactaaa agtaaaattg aattttaatt   1260

cctaaatctc catgtgtata cagtactgtg ggaacatcac agattttggc tccatgccct   1320

aaagagaaat tggctttcag attatttgga ttaaaaacaa agactttctt aagagatgta   1380

aaattttcat gatgttttct tttttgctaa aactaaagaa ttattctttt acatttca     1438
```

```
<210> SEQ ID NO 45
<211> LENGTH: 1438
<212> TYPE: DNA
<213> ORGANISM: artificial
<220> FEATURE:
<223> OTHER INFORMATION: Modified FIX intron

<400> SEQUENCE: 45

ggtttgtttc ctttttttaaa atacattgag tatgcttgcc ttttagatat agaaatatct     60

gatgctgtct tcttcactaa attttgatta catgatttga cagcaatatt gaagagtcta    120

acagccagca cgcaggttgg taagtactgg ttctttgtta gctaggtttt cttcttcttc    180

atttttaaaa ctaaatagat cgacattgct tttgttgcat ttatgtttaa taaacactgt    240

tcagttcatg atttggtcat gtaattcctg ttagaaaaca ttcatctcct tggtttaaaa    300

aaattaaaag tgggaaaaca aagaaatagc agaatatagt gaaaaaaaat aaccacatta    360

tttttgtttg gacttaccac tttgaaatca aattgggaaa caaaagcaca aacaatggcc    420

ttatttacac aaaaagtctg attttaagat atatgacatt tcaaggtttc agaagtatgt    480

aatgaggtgt gtctctaatt ttttaaatta tatatcttca atttaaagtt ttagttaaaa    540

cataaagatt aacctttcat tagcaagctg ttagttatca ccaacgcttt tcatggatta    600

ggaaaaaatc attttgtctc tttgtcaaac atcttggagt tgatatttgg ggaaacacaa    660

tactcagttg agttccctag gggagaaaag cacgcttaag aattgacata aagagtagga    720

agttagctat tgcaacatat atcactttgt tttttcacaa ctacagtgac tttttgtatt    780

tcccagagga aggcatacag ggaagaaatt atcccatttg gacaaacagc ttgttctcac    840

aggaagcatt tatcacactt acttgtcaac tttctagaat caaatctagt agctgacagt    900

accaggatca ggggtgccaa ccctaagcac ccccagaaag ctgactggcc ctgtggttcc    960

cactccagac atgatgtcag ctgtgaaatc gacgtcgctg gaccataatt aggcttctgt   1020

tcttcaggag acatttgttc aaagtcattt gggcaaccat attctgaaaa cagcccagcc   1080

agggtgttgg atcactttgc aaagatcctc attgagctat tttcaagtgt tgacaaagtg   1140

tgaagttaac cgctcatttg agaactttct ttttcatcca aagtaaattc aaatatgatt   1200

agaaatctga ccttttatta ctggaattct cttgactaaa agtaaaattg aattttaatt   1260
```

```
cctaaatctc catgtgtata cagtactgtg ggaacatcac agattttggc tccatgccct   1320

aaagagaaat tggctttcag attatttgga ttaaaaacaa agactttctt aagagatgta   1380

aaattttctt gttgttttct tttttgctaa aactaaagaa ttattctttt acatttca     1438
```

<210> SEQ ID NO 46
<211> LENGTH: 881
<212> TYPE: DNA
<213> ORGANISM: artificial
<220> FEATURE:
<223> OTHER INFORMATION: Chicken beta-globin intron

<400> SEQUENCE: 46

```
gcgggagtcg ctgcgttgcc ttcgccccgt gccccgctcc gccgccgcct cgcgccgccc     60

gccccggctc tgactgaccg cgttactccc acaggtgagc gggcgggacg gcccttctcc    120

tccgggctgt aattagcgct tggtttaatg acggcttgtt tcttttctgt ggctgcgtga    180

aagccttgag gggctccggg agggcccttt gtgcgggggg agcggctcgg ggggtgcgtg    240

cgtgtgtgtg tgcgtgggga gcgccgcgtg cggctccgcg ctgcccggcg gctgtgagcg    300

ctgcgggcgc ggcgcggggc tttgtgcgct ccgcagtgtg cgcgagggga gcgcggccgg    360

gggcggtgcc ccgcggtgcg gggggggctg cgaggggaac aaaggctgcg tgcggggtgt    420

gtgcgtgggg gggtgagcag ggggtgtggg cgcgtcggtc gggctgcaac cccccctgca    480

cccccctccc cgagttgctg agcacggccc ggcttcgggt gcggggctcc gtacggggcg    540

tggcgcgggg ctcgccgtgc cgggcggggg gtggcggcag gtgggggtgc cgggcggggc    600

ggggccgcct cgggccgggg agggctcggg ggaggggcgc ggcggccccc ggagcgccgg    660

cggctgtcga ggcgcggcga gccgcagcca ttgcctttta tggtaatcgt gcgagagggc    720

gcagggactt cctttgtccc aaatctgtgc ggagccgaaa tctgggaggc gccgccgcac    780

cccctctagc gggcgcgggg cgaagcggtg cggcgccggc aggaaggaaa tgggcgggga    840

gggccttcgt gcgtcgccgc gccgccgtcc ccttctccct c                        881
```

<210> SEQ ID NO 47
<211> LENGTH: 881
<212> TYPE: DNA
<213> ORGANISM: artificial
<220> FEATURE:
<223> OTHER INFORMATION: modified chicken-beta globin intron

<400> SEQUENCE: 47

```
gcgggagtcg ctgcgttgcc ttcgccccgt gccccgctcc gccgccgcct cgcgccgccc     60

gccccggctc tgactgaccg cgttactccc acaggtgagc gggcgggacg gcccttctcc    120

tccgggctgt aattagcgct tggtttaatg acggcttgtt tcttttctgt ggctgcgtga    180

aagccttgag gggctccggg agggcccttt gtgcgggggg agcggctcgg ggggtgcgtg    240

cgtgtgtgtg tgcgtgggga gcgccgcgtg cggctccgcg ctgcccggcg gctgtgagcg    300

ctgcgggcgc ggcgcggggc tttgtgcgct ccgcagtgtg cgcgagggga gcgcggccgg    360

gggcggtgcc ccgcggtgcg gggggggctg cgaggggaac aaaggctgcg tgcggggtgt    420

gtgcgtgggg gggtgagcag ggggtgtggg cgcgtcggtc gggctgcaac cccccctgca    480

cccccctccc cgagttgctg agcacggccc ggcttcgggt gcggggctcc gtacggggcg    540

tggcgcgggg ctcgccgtgc cgggcggggg gtggcggcag gtgggggtgc cgggcggggc    600

ggggccgcct cgggccgggg agggctcggg ggaggggcgc ggcggccccc ggagcgccgg    660

cggctgtcga ggcgcggcga gccgcagcca ttgccttttt tggtaatcgt gcgagagggc    720
```

```
gcagggactt cctttgtccc aaatctgtgc ggagccgaaa tctgggaggc gccgccgcac    780

cccctctagc gggcgcgggg cgaagcggtg cggcgccggc aggaaggaat tgggcgggga    840

gggccttcgt gcgtcgccgc gccgccgtcc ccttctccct c                        881


<210> SEQ ID NO 48
<211> LENGTH: 1518
<212> TYPE: PRT
<213> ORGANISM: artificial
<220> FEATURE:
<223> OTHER INFORMATION: D1a + D2,3 hGDE

<400> SEQUENCE: 48

Met Glu Lys Leu Glu Lys Thr Leu Phe Arg Leu Glu Gln Gly Tyr Glu
1               5                   10                  15

Leu Gln Phe Arg Leu Gly Pro Thr Leu Gln Gly Lys Ala Val Thr Val
            20                  25                  30

Tyr Thr Asn Tyr Pro Phe Pro Gly Glu Thr Phe Asn Arg Glu Lys Phe
        35                  40                  45

Arg Ser Leu Asp Trp Glu Asn Pro Thr Glu Arg Glu Asp Asp Ser Asp
    50                  55                  60

Lys Tyr Cys Lys Leu Asn Leu Gln Gln Ser Gly Ser Phe Gln Tyr Tyr
65                  70                  75                  80

Phe Leu Gln Gly Asn Glu Lys Ser Gly Gly Gly Tyr Ile Val Val Asp
                85                  90                  95

Pro Ile Leu Arg Val Gly Ala Asp Asn His Val Leu Pro Leu Asp Cys
            100                 105                 110

Val Thr Leu Gln Thr Phe Leu Ala Lys Cys Leu Gly Pro Phe Asp Glu
        115                 120                 125

Trp Glu Ser Arg Leu Arg Val Ala Lys Glu Ser Gly Tyr Asn Met Ile
    130                 135                 140

His Phe Thr Pro Leu Gln Thr Leu Gly Leu Ser Arg Ser Cys Tyr Ser
145                 150                 155                 160

Leu Ala Asn Gln Leu Glu Leu Asn Pro Asp Phe Ser Arg Pro Asn Arg
                165                 170                 175

Lys Tyr Thr Trp Asn Asp Val Gly Gln Leu Val Glu Lys Leu Lys Lys
            180                 185                 190

Glu Trp Asn Val Ile Cys Ile Thr Asp Val Val Tyr Asn His Thr Ala
        195                 200                 205

Ala Asn Ser Lys Trp Ile Gln Glu His Pro Glu Cys Ala Tyr Asn Leu
    210                 215                 220

Val Asn Ser Pro His Leu Lys Pro Ala Trp Val Leu Asp Arg Ala Leu
225                 230                 235                 240

Trp Arg Phe Ser Cys Asp Val Ala Glu Gly Lys Tyr Lys Glu Lys Gly
                245                 250                 255

Ile Pro Ala Leu Ile Glu Asn Asp His His Met Asn Ser Ile Arg Lys
            260                 265                 270

Ile Ile Trp Glu Asp Ile Phe Pro Lys Leu Lys Leu Trp Glu Phe Phe
        275                 280                 285

Gln Val Asp Val Asn Lys Ala Val Glu Gln Phe Arg Arg Leu Leu Thr
    290                 295                 300

Gln Glu Asn Arg Arg Val Thr Lys Ser Asp Pro Asn Gln His Leu Thr
305                 310                 315                 320

Ile Ile Gln Asp Pro Glu Tyr Arg Arg Phe Gly Cys Thr Val Asp Met
                325                 330                 335
```

```
Asn Ile Ala Leu Thr Thr Phe Ile Pro His Asp Lys Gly Pro Ala Ala
            340                 345                 350

Ile Glu Glu Cys Cys Asn Trp Phe His Lys Arg Met Glu Glu Leu Asn
        355                 360                 365

Ser Glu Lys His Arg Leu Ile Asn Tyr His Gln Glu Gln Ala Val Asn
    370                 375                 380

Cys Leu Leu Gly Asn Val Phe Tyr Glu Arg Leu Ala Gly His Gly Pro
385                 390                 395                 400

Lys Leu Gly Pro Val Thr Arg Lys His Pro Leu Val Thr Arg Tyr Phe
                405                 410                 415

Thr Phe Pro Phe Glu Glu Ile Asp Phe Ser Met Glu Glu Ser Met Ile
            420                 425                 430

His Leu Pro Asn Lys Ala Cys Phe Leu Met Ala His Asn Gly Trp Val
        435                 440                 445

Met Gly Asp Asp Pro Leu Arg Asn Phe Ala Glu Pro Gly Ser Glu Val
    450                 455                 460

Tyr Leu Arg Arg Glu Leu Ile Cys Trp Gly Asp Ser Val Lys Leu Arg
465                 470                 475                 480

Tyr Gly Asn Lys Pro Glu Asp Cys Pro Tyr Leu Trp Ala His Met Lys
                485                 490                 495

Lys Tyr Thr Glu Ile Thr Ala Thr Tyr Phe Gln Gly Val Arg Leu Asp
            500                 505                 510

Asn Cys His Ser Thr Pro Leu His Val Ala Glu Tyr Met Leu Asp Ala
        515                 520                 525

Ala Arg Asn Leu Gln Pro Asn Leu Tyr Val Val Ala Glu Leu Phe Thr
    530                 535                 540

Gly Ser Glu Asp Leu Asp Asn Val Phe Val Thr Arg Leu Gly Ile Ser
545                 550                 555                 560

Ser Leu Ile Arg Glu Ala Met Ser Ala Tyr Asn Ser His Glu Glu Gly
                565                 570                 575

Arg Leu Val Tyr Arg Tyr Gly Gly Glu Pro Val Gly Ser Phe Val Gln
            580                 585                 590

Pro Cys Leu Arg Pro Leu Met Pro Ala Ile Ala His Ala Leu Phe Met
        595                 600                 605

Asp Ile Thr His Asp Asn Glu Cys Pro Ile Val His Arg Ser Ala Tyr
    610                 615                 620

Asp Ala Leu Pro Ser Thr Thr Ile Val Ser Met Ala Cys Cys Ala Ser
625                 630                 635                 640

Gly Ser Thr Arg Gly Tyr Asp Glu Leu Val Pro His Gln Ile Ser Val
                645                 650                 655

Val Ser Glu Glu Arg Phe Tyr Thr Lys Trp Asn Pro Glu Ala Leu Pro
            660                 665                 670

Ser Asn Thr Gly Glu Val Asn Phe Gln Ser Gly Ile Ile Ala Ala Arg
        675                 680                 685

Cys Ala Ile Ser Lys Leu His Gln Glu Leu Gly Ala Lys Gly Phe Ile
    690                 695                 700

Gln Val Tyr Val Asp Gln Val Asp Glu Asp Ile Val Ala Val Thr Arg
705                 710                 715                 720

His Ser Pro Ser Ile His Gln Ser Val Val Ala Val Thr Arg Thr Ala
                725                 730                 735

Phe Arg Asn Pro Lys Thr Ser Phe Tyr Ser Lys Glu Val Pro Gln Met
            740                 745                 750
```

```
Cys Ile Pro Gly Lys Ile Glu Glu Val Val Leu Glu Ala Arg Thr Ile
        755                 760                 765

Glu Arg Asn Thr Lys Pro Tyr Arg Lys Asp Glu Asn Ser Ile Asn Gly
    770                 775                 780

Thr Pro Asp Ile Thr Val Glu Ile Arg Glu His Ile Gln Leu Asn Glu
785                 790                 795                 800

Ser Lys Ile Val Lys Gln Ala Gly Val Ala Thr Lys Gly Pro Asn Glu
                805                 810                 815

Tyr Ile Gln Glu Ile Glu Phe Glu Asn Leu Ser Pro Gly Ser Val Ile
            820                 825                 830

Ile Phe Arg Val Ser Leu Asp Pro His Ala Gln Val Ala Val Gly Ile
        835                 840                 845

Leu Arg Asn His Leu Thr Gln Phe Ser Pro His Phe Lys Ser Gly Ser
    850                 855                 860

Leu Ala Val Asp Asn Ala Asp Pro Ile Leu Lys Ile Pro Phe Ala Ser
865                 870                 875                 880

Leu Ala Tyr Arg Leu Thr Leu Ala Glu Leu Asn Gln Ile Leu Tyr Arg
                885                 890                 895

Cys Glu Ser Glu Glu Lys Glu Asp Gly Gly Gly Cys Tyr Asp Ile Pro
            900                 905                 910

Asn Trp Ser Ala Leu Lys Tyr Ala Gly Leu Gln Gly Leu Met Ser Val
        915                 920                 925

Leu Ala Glu Ile Arg Pro Lys Asn Asp Leu Gly His Pro Phe Cys Asn
    930                 935                 940

Asn Leu Arg Ser Gly Asp Trp Met Ile Asp Tyr Val Ser Asn Arg Leu
945                 950                 955                 960

Ile Ser Arg Ser Gly Thr Ile Ala Glu Val Gly Lys Trp Leu Gln Ala
                965                 970                 975

Met Phe Phe Tyr Leu Lys Gln Ile Pro Arg Tyr Leu Ile Pro Cys Tyr
            980                 985                 990

Phe Asp Ala Ile Leu Ile Gly Ala  Tyr Thr Thr Leu Leu  Asp Thr Ala
        995                 1000                1005

Trp Lys  Gln Met Ser Ser Phe  Val Gln Asn Gly Ser  Thr Phe Val
    1010                1015                1020

Lys His  Leu Ser Leu Gly Ser  Val Gln Leu Cys Gly  Val Gly Lys
    1025                1030                1035

Phe Pro  Ser Leu Pro Ile Leu  Ser Pro Ala Leu Met  Asp Val Pro
    1040                1045                1050

Tyr Arg  Leu Asn Glu Ile Thr  Lys Glu Lys Glu Gln  Cys Cys Val
    1055                1060                1065

Ser Leu  Ala Ala Gly Leu Pro  His Phe Ser Ser Gly  Ile Phe Arg
    1070                1075                1080

Cys Trp  Gly Arg Asp Thr Phe  Ile Ala Leu Arg Gly  Ile Leu Leu
    1085                1090                1095

Ile Thr  Gly Arg Tyr Val Glu  Ala Arg Asn Ile Ile  Leu Ala Phe
    1100                1105                1110

Ala Gly  Thr Leu Arg His Gly  Leu Ile Pro Asn Leu  Leu Gly Glu
    1115                1120                1125

Gly Ile  Tyr Ala Arg Tyr Asn  Cys Arg Asp Ala Val  Trp Trp Trp
    1130                1135                1140

Leu Gln  Cys Ile Gln Asp Tyr  Cys Lys Met Val Pro  Asn Gly Leu
    1145                1150                1155

Asp Ile  Leu Lys Cys Pro Val  Ser Arg Met Tyr Pro  Thr Asp Asp
```

```
    1160                1165                1170

Ser Ala  Pro Leu Pro Ala Gly  Thr Leu Asp Gln Pro  Leu Phe Glu
    1175                1180                1185

Val Ile  Gln Glu Ala Met Gln  Lys His Met Gln Gly  Ile Gln Phe
    1190                1195                1200

Arg Glu  Arg Asn Ala Gly Pro  Gln Ile Asp Arg Asn  Met Lys Asp
    1205                1210                1215

Glu Gly  Phe Asn Ile Thr Ala  Gly Val Asp Glu Glu  Thr Gly Phe
    1220                1225                1230

Val Tyr  Gly Gly Asn Arg Phe  Asn Cys Gly Thr Trp  Met Asp Lys
    1235                1240                1245

Met Gly  Glu Ser Asp Arg Ala  Arg Asn Arg Gly Ile  Pro Ala Thr
    1250                1255                1260

Pro Arg  Asp Gly Ser Ala Val  Glu Ile Val Gly Leu  Ser Lys Ser
    1265                1270                1275

Ala Val  Arg Trp Leu Leu Glu  Leu Ser Lys Lys Asn  Ile Phe Pro
    1280                1285                1290

Tyr His  Glu Val Thr Val Lys  Arg His Gly Lys Ala  Ile Lys Val
    1295                1300                1305

Ser Tyr  Asp Glu Trp Asn Arg  Lys Ile Gln Asp Asn  Phe Glu Lys
    1310                1315                1320

Leu Phe  His Val Ser Glu Asp  Pro Ser Asp Leu Asn  Glu Lys His
    1325                1330                1335

Pro Asn  Leu Val His Lys Arg  Gly Ile Tyr Lys Asp  Ser Tyr Gly
    1340                1345                1350

Ala Ser  Ser Pro Trp Cys Asp  Tyr Gln Leu Arg Pro  Asn Phe Thr
    1355                1360                1365

Ile Ala  Met Val Val Ala Pro  Glu Leu Phe Thr Thr  Glu Lys Ala
    1370                1375                1380

Trp Lys  Ala Leu Glu Ile Ala  Glu Lys Lys Leu Leu  Gly Pro Leu
    1385                1390                1395

Gly Met  Lys Thr Leu Asp Pro  Asp Asp Met Val Tyr  Cys Gly Ile
    1400                1405                1410

Tyr Asp  Asn Ala Leu Asp Asn  Asp Asn Tyr Asn Leu  Ala Lys Gly
    1415                1420                1425

Phe Asn  Tyr His Gln Gly Pro  Glu Trp Leu Trp Pro  Ile Gly Tyr
    1430                1435                1440

Phe Leu  Arg Ala Lys Leu Tyr  Phe Ser Arg Leu Met  Gly Pro Glu
    1445                1450                1455

Thr Thr  Ala Lys Thr Ile Val  Leu Val Lys Asn Val  Leu Ser Arg
    1460                1465                1470

His Tyr  Val His Leu Glu Arg  Ser Pro Trp Lys Gly  Leu Pro Glu
    1475                1480                1485

Leu Thr  Asn Glu Asn Ala Gln  Tyr Cys Pro Phe Ser  Cys Glu Thr
    1490                1495                1500

Gln Ala  Trp Ser Ile Ala Thr  Ile Leu Glu Thr Leu  Tyr Asp Leu
    1505                1510                1515
```

<210> SEQ ID NO 49
<211> LENGTH: 1503
<212> TYPE: PRT
<213> ORGANISM: artificial
<220> FEATURE:
<223> OTHER INFORMATION: D1b1 + D2,3 hGDE

<400> SEQUENCE: 49

```
Met Leu Gln Phe Arg Leu Gly Pro Thr Leu Gln Gly Lys Ala Val Thr
1               5                   10                  15

Val Tyr Thr Asn Tyr Pro Phe Pro Gly Glu Thr Phe Asn Arg Glu Lys
            20                  25                  30

Phe Arg Ser Leu Asp Trp Glu Asn Pro Thr Glu Arg Glu Asp Asp Ser
        35                  40                  45

Asp Lys Tyr Cys Lys Leu Asn Leu Gln Gln Ser Gly Ser Phe Gln Tyr
    50                  55                  60

Tyr Phe Leu Gln Gly Asn Glu Lys Ser Gly Gly Gly Tyr Ile Val Val
65                  70                  75                  80

Asp Pro Ile Leu Arg Val Gly Ala Asp Asn His Val Leu Pro Leu Asp
                85                  90                  95

Cys Val Thr Leu Gln Thr Phe Leu Ala Lys Cys Leu Gly Pro Phe Asp
            100                 105                 110

Glu Trp Glu Ser Arg Leu Arg Val Ala Lys Glu Ser Gly Tyr Asn Met
        115                 120                 125

Ile His Phe Thr Pro Leu Gln Thr Leu Gly Leu Ser Arg Ser Cys Tyr
    130                 135                 140

Ser Leu Ala Asn Gln Leu Glu Leu Asn Pro Asp Phe Ser Arg Pro Asn
145                 150                 155                 160

Arg Lys Tyr Thr Trp Asn Asp Val Gly Gln Leu Val Glu Lys Leu Lys
                165                 170                 175

Lys Glu Trp Asn Val Ile Cys Ile Thr Asp Val Val Tyr Asn His Thr
            180                 185                 190

Ala Ala Asn Ser Lys Trp Ile Gln Glu His Pro Glu Cys Ala Tyr Asn
        195                 200                 205

Leu Val Asn Ser Pro His Leu Lys Pro Ala Trp Val Leu Asp Arg Ala
    210                 215                 220

Leu Trp Arg Phe Ser Cys Asp Val Ala Glu Gly Lys Tyr Lys Glu Lys
225                 230                 235                 240

Gly Ile Pro Ala Leu Ile Glu Asn Asp His His Met Asn Ser Ile Arg
                245                 250                 255

Lys Ile Ile Trp Glu Asp Ile Phe Pro Lys Leu Lys Leu Trp Glu Phe
            260                 265                 270

Phe Gln Val Asp Val Asn Lys Ala Val Glu Gln Phe Arg Arg Leu Leu
        275                 280                 285

Thr Gln Glu Asn Arg Arg Val Thr Lys Ser Asp Pro Asn Gln His Leu
    290                 295                 300

Thr Ile Ile Gln Asp Pro Glu Tyr Arg Arg Phe Gly Cys Thr Val Asp
305                 310                 315                 320

Met Asn Ile Ala Leu Thr Thr Phe Ile Pro His Asp Lys Gly Pro Ala
                325                 330                 335

Ala Ile Glu Glu Cys Cys Asn Trp Phe His Lys Arg Met Glu Glu Leu
            340                 345                 350

Asn Ser Glu Lys His Arg Leu Ile Asn Tyr His Gln Glu Gln Ala Val
        355                 360                 365

Asn Cys Leu Leu Gly Asn Val Phe Tyr Glu Arg Leu Ala Gly His Gly
    370                 375                 380

Pro Lys Leu Gly Pro Val Thr Arg Lys His Pro Leu Val Thr Arg Tyr
385                 390                 395                 400

Phe Thr Phe Pro Phe Glu Glu Ile Asp Phe Ser Met Glu Glu Ser Met
                405                 410                 415
```

```
Ile His Leu Pro Asn Lys Ala Cys Phe Leu Met Ala His Asn Gly Trp
            420                 425                 430

Val Met Gly Asp Asp Pro Leu Arg Asn Phe Ala Glu Pro Gly Ser Glu
        435                 440                 445

Val Tyr Leu Arg Arg Glu Leu Ile Cys Trp Gly Asp Ser Val Lys Leu
    450                 455                 460

Arg Tyr Gly Asn Lys Pro Glu Asp Cys Pro Tyr Leu Trp Ala His Met
465                 470                 475                 480

Lys Lys Tyr Thr Glu Ile Thr Ala Thr Tyr Phe Gln Gly Val Arg Leu
                485                 490                 495

Asp Asn Cys His Ser Thr Pro Leu His Val Ala Glu Tyr Met Leu Asp
            500                 505                 510

Ala Ala Arg Asn Leu Gln Pro Asn Leu Tyr Val Val Ala Glu Leu Phe
        515                 520                 525

Thr Gly Ser Glu Asp Leu Asp Asn Val Phe Val Thr Arg Leu Gly Ile
    530                 535                 540

Ser Ser Leu Ile Arg Glu Ala Met Ser Ala Tyr Asn Ser His Glu Glu
545                 550                 555                 560

Gly Arg Leu Val Tyr Arg Tyr Gly Gly Glu Pro Val Gly Ser Phe Val
                565                 570                 575

Gln Pro Cys Leu Arg Pro Leu Met Pro Ala Ile Ala His Ala Leu Phe
            580                 585                 590

Met Asp Ile Thr His Asp Asn Glu Cys Pro Ile Val His Arg Ser Ala
        595                 600                 605

Tyr Asp Ala Leu Pro Ser Thr Thr Ile Val Ser Met Ala Cys Cys Ala
    610                 615                 620

Ser Gly Ser Thr Arg Gly Tyr Asp Glu Leu Val Pro His Gln Ile Ser
625                 630                 635                 640

Val Val Ser Glu Glu Arg Phe Tyr Thr Lys Trp Asn Pro Glu Ala Leu
                645                 650                 655

Pro Ser Asn Thr Gly Glu Val Asn Phe Gln Ser Gly Ile Ile Ala Ala
            660                 665                 670

Arg Cys Ala Ile Ser Lys Leu His Gln Glu Leu Gly Ala Lys Gly Phe
        675                 680                 685

Ile Gln Val Tyr Val Asp Gln Val Asp Glu Asp Ile Val Ala Val Thr
    690                 695                 700

Arg His Ser Pro Ser Ile His Gln Ser Val Val Ala Val Thr Arg Thr
705                 710                 715                 720

Ala Phe Arg Asn Pro Lys Thr Ser Phe Tyr Ser Lys Glu Val Pro Gln
                725                 730                 735

Met Cys Ile Pro Gly Lys Ile Glu Glu Val Val Leu Glu Ala Arg Thr
            740                 745                 750

Ile Glu Arg Asn Thr Lys Pro Tyr Arg Lys Asp Glu Asn Ser Ile Asn
        755                 760                 765

Gly Thr Pro Asp Ile Thr Val Glu Ile Arg Glu His Ile Gln Leu Asn
    770                 775                 780

Glu Ser Lys Ile Val Lys Gln Ala Gly Val Ala Thr Lys Gly Pro Asn
785                 790                 795                 800

Glu Tyr Ile Gln Glu Ile Glu Phe Glu Asn Leu Ser Pro Gly Ser Val
                805                 810                 815

Ile Ile Phe Arg Val Ser Leu Asp Pro His Ala Gln Val Ala Val Gly
            820                 825                 830
```

```
Ile Leu Arg Asn His Leu Thr Gln Phe Ser Pro His Phe Lys Ser Gly
        835                 840                 845

Ser Leu Ala Val Asp Asn Ala Asp Pro Ile Leu Lys Ile Pro Phe Ala
    850                 855                 860

Ser Leu Ala Tyr Arg Leu Thr Leu Ala Glu Leu Asn Gln Ile Leu Tyr
865                 870                 875                 880

Arg Cys Glu Ser Glu Glu Lys Glu Asp Gly Gly Gly Cys Tyr Asp Ile
                885                 890                 895

Pro Asn Trp Ser Ala Leu Lys Tyr Ala Gly Leu Gln Gly Leu Met Ser
            900                 905                 910

Val Leu Ala Glu Ile Arg Pro Lys Asn Asp Leu Gly His Pro Phe Cys
        915                 920                 925

Asn Asn Leu Arg Ser Gly Asp Trp Met Ile Asp Tyr Val Ser Asn Arg
    930                 935                 940

Leu Ile Ser Arg Ser Gly Thr Ile Ala Glu Val Gly Lys Trp Leu Gln
945                 950                 955                 960

Ala Met Phe Phe Tyr Leu Lys Gln Ile Pro Arg Tyr Leu Ile Pro Cys
                965                 970                 975

Tyr Phe Asp Ala Ile Leu Ile Gly Ala Tyr Thr Thr Leu Leu Asp Thr
            980                 985                 990

Ala Trp Lys Gln Met Ser Ser Phe  Val Gln Asn Gly Ser  Thr Phe Val
        995                 1000                 1005

Lys His  Leu Ser Leu Gly Ser  Val Gln Leu Cys Gly  Val Gly Lys
    1010                 1015                 1020

Phe Pro  Ser Leu Pro Ile Leu  Ser Pro Ala Leu Met  Asp Val Pro
    1025                 1030                 1035

Tyr Arg  Leu Asn Glu Ile Thr  Lys Glu Lys Glu Gln  Cys Cys Val
    1040                 1045                 1050

Ser Leu  Ala Ala Gly Leu Pro  His Phe Ser Ser Gly  Ile Phe Arg
    1055                 1060                 1065

Cys Trp  Gly Arg Asp Thr Phe  Ile Ala Leu Arg Gly  Ile Leu Leu
    1070                 1075                 1080

Ile Thr  Gly Arg Tyr Val Glu  Ala Arg Asn Ile Ile  Leu Ala Phe
    1085                 1090                 1095

Ala Gly  Thr Leu Arg His Gly  Leu Ile Pro Asn Leu  Leu Gly Glu
    1100                 1105                 1110

Gly Ile  Tyr Ala Arg Tyr Asn  Cys Arg Asp Ala Val  Trp Trp Trp
    1115                 1120                 1125

Leu Gln  Cys Ile Gln Asp Tyr  Cys Lys Met Val Pro  Asn Gly Leu
    1130                 1135                 1140

Asp Ile  Leu Lys Cys Pro Val  Ser Arg Met Tyr Pro  Thr Asp Asp
    1145                 1150                 1155

Ser Ala  Pro Leu Pro Ala Gly  Thr Leu Asp Gln Pro  Leu Phe Glu
    1160                 1165                 1170

Val Ile  Gln Glu Ala Met Gln  Lys His Met Gln Gly  Ile Gln Phe
    1175                 1180                 1185

Arg Glu  Arg Asn Ala Gly Pro  Gln Ile Asp Arg Asn  Met Lys Asp
    1190                 1195                 1200

Glu Gly  Phe Asn Ile Thr Ala  Gly Val Asp Glu Glu  Thr Gly Phe
    1205                 1210                 1215

Val Tyr  Gly Gly Asn Arg Phe  Asn Cys Gly Thr Trp  Met Asp Lys
    1220                 1225                 1230

Met Gly  Glu Ser Asp Arg Ala  Arg Asn Arg Gly Ile  Pro Ala Thr
```

```
    1235                1240                1245

Pro Arg  Asp Gly Ser Ala Val  Glu Ile Val Gly Leu  Ser Lys Ser
    1250                1255                1260

Ala Val  Arg Trp Leu Leu Glu  Leu Ser Lys Lys Asn  Ile Phe Pro
    1265                1270                1275

Tyr His  Glu Val Thr Val Lys  Arg His Gly Lys Ala  Ile Lys Val
    1280                1285                1290

Ser Tyr  Asp Glu Trp Asn Arg  Lys Ile Gln Asp Asn  Phe Glu Lys
    1295                1300                1305

Leu Phe  His Val Ser Glu Asp  Pro Ser Asp Leu Asn  Glu Lys His
    1310                1315                1320

Pro Asn  Leu Val His Lys Arg  Gly Ile Tyr Lys Asp  Ser Tyr Gly
    1325                1330                1335

Ala Ser  Ser Pro Trp Cys Asp  Tyr Gln Leu Arg Pro  Asn Phe Thr
    1340                1345                1350

Ile Ala  Met Val Val Ala Pro  Glu Leu Phe Thr Thr  Glu Lys Ala
    1355                1360                1365

Trp Lys  Ala Leu Glu Ile Ala  Glu Lys Lys Leu Leu  Gly Pro Leu
    1370                1375                1380

Gly Met  Lys Thr Leu Asp Pro  Asp Asp Met Val Tyr  Cys Gly Ile
    1385                1390                1395

Tyr Asp  Asn Ala Leu Asp Asn  Asp Asn Tyr Asn Leu  Ala Lys Gly
    1400                1405                1410

Phe Asn  Tyr His Gln Gly Pro  Glu Trp Leu Trp Pro  Ile Gly Tyr
    1415                1420                1425

Phe Leu  Arg Ala Lys Leu Tyr  Phe Ser Arg Leu Met  Gly Pro Glu
    1430                1435                1440

Thr Thr  Ala Lys Thr Ile Val  Leu Val Lys Asn Val  Leu Ser Arg
    1445                1450                1455

His Tyr  Val His Leu Glu Arg  Ser Pro Trp Lys Gly  Leu Pro Glu
    1460                1465                1470

Leu Thr  Asn Glu Asn Ala Gln  Tyr Cys Pro Phe Ser  Cys Glu Thr
    1475                1480                1485

Gln Ala  Trp Ser Ile Ala Thr  Ile Leu Glu Thr Leu  Tyr Asp Leu
    1490                1495                1500


<210> SEQ ID NO 50
<211> LENGTH: 1452
<212> TYPE: PRT
<213> ORGANISM: artificial
<220> FEATURE:
<223> OTHER INFORMATION: D1b2 + D2,3 hGDE

<400> SEQUENCE: 50

Met Lys Leu Asn Leu Gln Gln Ser Gly Ser Phe Gln Tyr Tyr Phe Leu
1               5                   10                  15

Gln Gly Asn Glu Lys Ser Gly Gly Gly Tyr Ile Val Val Asp Pro Ile
            20                  25                  30

Leu Arg Val Gly Ala Asp Asn His Val Leu Pro Leu Asp Cys Val Thr
        35                  40                  45

Leu Gln Thr Phe Leu Ala Lys Cys Leu Gly Pro Phe Asp Glu Trp Glu
    50                  55                  60

Ser Arg Leu Arg Val Ala Lys Glu Ser Gly Tyr Asn Met Ile His Phe
65                  70                  75                  80

Thr Pro Leu Gln Thr Leu Gly Leu Ser Arg Ser Cys Tyr Ser Leu Ala
```

```
                85                  90                  95

Asn Gln Leu Glu Leu Asn Pro Asp Phe Ser Arg Pro Asn Arg Lys Tyr
            100                 105                 110

Thr Trp Asn Asp Val Gly Gln Leu Val Glu Lys Leu Lys Lys Glu Trp
        115                 120                 125

Asn Val Ile Cys Ile Thr Asp Val Val Tyr Asn His Thr Ala Ala Asn
    130                 135                 140

Ser Lys Trp Ile Gln Glu His Pro Glu Cys Ala Tyr Asn Leu Val Asn
145                 150                 155                 160

Ser Pro His Leu Lys Pro Ala Trp Val Leu Asp Arg Ala Leu Trp Arg
                165                 170                 175

Phe Ser Cys Asp Val Ala Glu Gly Lys Tyr Lys Glu Lys Gly Ile Pro
            180                 185                 190

Ala Leu Ile Glu Asn Asp His His Met Asn Ser Ile Arg Lys Ile Ile
        195                 200                 205

Trp Glu Asp Ile Phe Pro Lys Leu Lys Leu Trp Glu Phe Phe Gln Val
    210                 215                 220

Asp Val Asn Lys Ala Val Glu Gln Phe Arg Arg Leu Leu Thr Gln Glu
225                 230                 235                 240

Asn Arg Arg Val Thr Lys Ser Asp Pro Asn Gln His Leu Thr Ile Ile
                245                 250                 255

Gln Asp Pro Glu Tyr Arg Arg Phe Gly Cys Thr Val Asp Met Asn Ile
            260                 265                 270

Ala Leu Thr Thr Phe Ile Pro His Asp Lys Gly Pro Ala Ala Ile Glu
        275                 280                 285

Glu Cys Cys Asn Trp Phe His Lys Arg Met Glu Glu Leu Asn Ser Glu
    290                 295                 300

Lys His Arg Leu Ile Asn Tyr His Gln Glu Gln Ala Val Asn Cys Leu
305                 310                 315                 320

Leu Gly Asn Val Phe Tyr Glu Arg Leu Ala Gly His Gly Pro Lys Leu
                325                 330                 335

Gly Pro Val Thr Arg Lys His Pro Leu Val Thr Arg Tyr Phe Thr Phe
            340                 345                 350

Pro Phe Glu Glu Ile Asp Phe Ser Met Glu Glu Ser Met Ile His Leu
        355                 360                 365

Pro Asn Lys Ala Cys Phe Leu Met Ala His Asn Gly Trp Val Met Gly
    370                 375                 380

Asp Asp Pro Leu Arg Asn Phe Ala Glu Pro Gly Ser Glu Val Tyr Leu
385                 390                 395                 400

Arg Arg Glu Leu Ile Cys Trp Gly Asp Ser Val Lys Leu Arg Tyr Gly
                405                 410                 415

Asn Lys Pro Glu Asp Cys Pro Tyr Leu Trp Ala His Met Lys Lys Tyr
            420                 425                 430

Thr Glu Ile Thr Ala Thr Tyr Phe Gln Gly Val Arg Leu Asp Asn Cys
        435                 440                 445

His Ser Thr Pro Leu His Val Ala Glu Tyr Met Leu Asp Ala Ala Arg
    450                 455                 460

Asn Leu Gln Pro Asn Leu Tyr Val Val Ala Glu Leu Phe Thr Gly Ser
465                 470                 475                 480

Glu Asp Leu Asp Asn Val Phe Val Thr Arg Leu Gly Ile Ser Ser Leu
                485                 490                 495

Ile Arg Glu Ala Met Ser Ala Tyr Asn Ser His Glu Glu Gly Arg Leu
            500                 505                 510
```

```
Val Tyr Arg Tyr Gly Gly Glu Pro Val Gly Ser Phe Val Gln Pro Cys
        515                 520                 525

Leu Arg Pro Leu Met Pro Ala Ile Ala His Ala Leu Phe Met Asp Ile
    530                 535                 540

Thr His Asp Asn Glu Cys Pro Ile Val His Arg Ser Ala Tyr Asp Ala
545                 550                 555                 560

Leu Pro Ser Thr Thr Ile Val Ser Met Ala Cys Cys Ala Ser Gly Ser
                565                 570                 575

Thr Arg Gly Tyr Asp Glu Leu Val Pro His Gln Ile Ser Val Val Ser
            580                 585                 590

Glu Glu Arg Phe Tyr Thr Lys Trp Asn Pro Glu Ala Leu Pro Ser Asn
        595                 600                 605

Thr Gly Glu Val Asn Phe Gln Ser Gly Ile Ile Ala Ala Arg Cys Ala
    610                 615                 620

Ile Ser Lys Leu His Gln Glu Leu Gly Ala Lys Gly Phe Ile Gln Val
625                 630                 635                 640

Tyr Val Asp Gln Val Asp Glu Asp Ile Val Ala Val Thr Arg His Ser
                645                 650                 655

Pro Ser Ile His Gln Ser Val Val Ala Val Thr Arg Thr Ala Phe Arg
            660                 665                 670

Asn Pro Lys Thr Ser Phe Tyr Ser Lys Glu Val Pro Gln Met Cys Ile
        675                 680                 685

Pro Gly Lys Ile Glu Glu Val Val Leu Glu Ala Arg Thr Ile Glu Arg
    690                 695                 700

Asn Thr Lys Pro Tyr Arg Lys Asp Glu Asn Ser Ile Asn Gly Thr Pro
705                 710                 715                 720

Asp Ile Thr Val Glu Ile Arg Glu His Ile Gln Leu Asn Glu Ser Lys
                725                 730                 735

Ile Val Lys Gln Ala Gly Val Ala Thr Lys Gly Pro Asn Glu Tyr Ile
            740                 745                 750

Gln Glu Ile Glu Phe Glu Asn Leu Ser Pro Gly Ser Val Ile Ile Phe
        755                 760                 765

Arg Val Ser Leu Asp Pro His Ala Gln Val Ala Val Gly Ile Leu Arg
    770                 775                 780

Asn His Leu Thr Gln Phe Ser Pro His Phe Lys Ser Gly Ser Leu Ala
785                 790                 795                 800

Val Asp Asn Ala Asp Pro Ile Leu Lys Ile Pro Phe Ala Ser Leu Ala
                805                 810                 815

Tyr Arg Leu Thr Leu Ala Glu Leu Asn Gln Ile Leu Tyr Arg Cys Glu
            820                 825                 830

Ser Glu Glu Lys Glu Asp Gly Gly Gly Cys Tyr Asp Ile Pro Asn Trp
        835                 840                 845

Ser Ala Leu Lys Tyr Ala Gly Leu Gln Gly Leu Met Ser Val Leu Ala
    850                 855                 860

Glu Ile Arg Pro Lys Asn Asp Leu Gly His Pro Phe Cys Asn Asn Leu
865                 870                 875                 880

Arg Ser Gly Asp Trp Met Ile Asp Tyr Val Ser Asn Arg Leu Ile Ser
                885                 890                 895

Arg Ser Gly Thr Ile Ala Glu Val Gly Lys Trp Leu Gln Ala Met Phe
            900                 905                 910

Phe Tyr Leu Lys Gln Ile Pro Arg Tyr Leu Ile Pro Cys Tyr Phe Asp
        915                 920                 925
```

```
Ala Ile Leu Ile Gly Ala Tyr Thr Thr Leu Leu Asp Thr Ala Trp Lys
    930                 935                 940

Gln Met Ser Ser Phe Val Gln Asn Gly Ser Thr Phe Val Lys His Leu
945                 950                 955                 960

Ser Leu Gly Ser Val Gln Leu Cys Gly Val Gly Lys Phe Pro Ser Leu
                965                 970                 975

Pro Ile Leu Ser Pro Ala Leu Met Asp Val Pro Tyr Arg Leu Asn Glu
            980                 985                 990

Ile Thr Lys Glu Lys Glu Gln Cys  Cys Val Ser Leu Ala  Ala Gly Leu
        995                 1000                1005

Pro His  Phe Ser Ser Gly Ile  Phe Arg Cys Trp Gly  Arg Asp Thr
    1010                1015                1020

Phe Ile  Ala Leu Arg Gly Ile  Leu Leu Ile Thr Gly  Arg Tyr Val
    1025                1030                1035

Glu Ala  Arg Asn Ile Ile Leu  Ala Phe Ala Gly Thr  Leu Arg His
    1040                1045                1050

Gly Leu  Ile Pro Asn Leu Leu  Gly Glu Gly Ile Tyr  Ala Arg Tyr
    1055                1060                1065

Asn Cys  Arg Asp Ala Val Trp  Trp Trp Leu Gln Cys  Ile Gln Asp
    1070                1075                1080

Tyr Cys  Lys Met Val Pro Asn  Gly Leu Asp Ile Leu  Lys Cys Pro
    1085                1090                1095

Val Ser  Arg Met Tyr Pro Thr  Asp Asp Ser Ala Pro  Leu Pro Ala
    1100                1105                1110

Gly Thr  Leu Asp Gln Pro Leu  Phe Glu Val Ile Gln  Glu Ala Met
    1115                1120                1125

Gln Lys  His Met Gln Gly Ile  Gln Phe Arg Glu Arg  Asn Ala Gly
    1130                1135                1140

Pro Gln  Ile Asp Arg Asn Met  Lys Asp Glu Gly Phe  Asn Ile Thr
    1145                1150                1155

Ala Gly  Val Asp Glu Glu Thr  Gly Phe Val Tyr Gly  Gly Asn Arg
    1160                1165                1170

Phe Asn  Cys Gly Thr Trp Met  Asp Lys Met Gly Glu  Ser Asp Arg
    1175                1180                1185

Ala Arg  Asn Arg Gly Ile Pro  Ala Thr Pro Arg Asp  Gly Ser Ala
    1190                1195                1200

Val Glu  Ile Val Gly Leu Ser  Lys Ser Ala Val Arg  Trp Leu Leu
    1205                1210                1215

Glu Leu  Ser Lys Lys Asn Ile  Phe Pro Tyr His Glu  Val Thr Val
    1220                1225                1230

Lys Arg  His Gly Lys Ala Ile  Lys Val Ser Tyr Asp  Glu Trp Asn
    1235                1240                1245

Arg Lys  Ile Gln Asp Asn Phe  Glu Lys Leu Phe His  Val Ser Glu
    1250                1255                1260

Asp Pro  Ser Asp Leu Asn Glu  Lys His Pro Asn Leu  Val His Lys
    1265                1270                1275

Arg Gly  Ile Tyr Lys Asp Ser  Tyr Gly Ala Ser Ser  Pro Trp Cys
    1280                1285                1290

Asp Tyr  Gln Leu Arg Pro Asn  Phe Thr Ile Ala Met  Val Val Ala
    1295                1300                1305

Pro Glu  Leu Phe Thr Thr Glu  Lys Ala Trp Lys Ala  Leu Glu Ile
    1310                1315                1320

Ala Glu  Lys Lys Leu Leu Gly  Pro Leu Gly Met Lys  Thr Leu Asp
```

```
    1325                1330                1335

Pro Asp  Asp Met Val Tyr Cys  Gly Ile Tyr Asp Asn  Ala Leu Asp
    1340                1345                1350

Asn Asp  Asn Tyr Asn Leu Ala  Lys Gly Phe Asn Tyr  His Gln Gly
    1355                1360                1365

Pro Glu  Trp Leu Trp Pro Ile  Gly Tyr Phe Leu Arg  Ala Lys Leu
    1370                1375                1380

Tyr Phe  Ser Arg Leu Met Gly  Pro Glu Thr Thr Ala  Lys Thr Ile
    1385                1390                1395

Val Leu  Val Lys Asn Val Leu  Ser Arg His Tyr Val  His Leu Glu
    1400                1405                1410

Arg Ser  Pro Trp Lys Gly Leu  Pro Glu Leu Thr Asn  Glu Asn Ala
    1415                1420                1425

Gln Tyr  Cys Pro Phe Ser Cys  Glu Thr Gln Ala Trp  Ser Ile Ala
    1430                1435                1440

Thr Ile  Leu Glu Thr Leu Tyr  Asp Leu
    1445                1450


<210> SEQ ID NO 51
<211> LENGTH: 1430
<212> TYPE: PRT
<213> ORGANISM: artificial
<220> FEATURE:
<223> OTHER INFORMATION: D1b3 + D2,3 hGDE

<400> SEQUENCE: 51

Met Gly Gly Tyr Ile Val Val Asp Pro Ile Leu Arg Val Gly Ala Asp
1               5                   10                  15

Asn His Val Leu Pro Leu Asp Cys Val Thr Leu Gln Thr Phe Leu Ala
            20                  25                  30

Lys Cys Leu Gly Pro Phe Asp Glu Trp Glu Ser Arg Leu Arg Val Ala
        35                  40                  45

Lys Glu Ser Gly Tyr Asn Met Ile His Phe Thr Pro Leu Gln Thr Leu
    50                  55                  60

Gly Leu Ser Arg Ser Cys Tyr Ser Leu Ala Asn Gln Leu Glu Leu Asn
65                  70                  75                  80

Pro Asp Phe Ser Arg Pro Asn Arg Lys Tyr Thr Trp Asn Asp Val Gly
                85                  90                  95

Gln Leu Val Glu Lys Leu Lys Lys Glu Trp Asn Val Ile Cys Ile Thr
            100                 105                 110

Asp Val Val Tyr Asn His Thr Ala Ala Asn Ser Lys Trp Ile Gln Glu
        115                 120                 125

His Pro Glu Cys Ala Tyr Asn Leu Val Asn Ser Pro His Leu Lys Pro
    130                 135                 140

Ala Trp Val Leu Asp Arg Ala Leu Trp Arg Phe Ser Cys Asp Val Ala
145                 150                 155                 160

Glu Gly Lys Tyr Lys Glu Lys Gly Ile Pro Ala Leu Ile Glu Asn Asp
                165                 170                 175

His His Met Asn Ser Ile Arg Lys Ile Ile Trp Glu Asp Ile Phe Pro
            180                 185                 190

Lys Leu Lys Leu Trp Glu Phe Phe Gln Val Asp Val Asn Lys Ala Val
        195                 200                 205

Glu Gln Phe Arg Arg Leu Leu Thr Gln Glu Asn Arg Arg Val Thr Lys
    210                 215                 220

Ser Asp Pro Asn Gln His Leu Thr Ile Ile Gln Asp Pro Glu Tyr Arg
```

```
225                 230                 235                 240

Arg Phe Gly Cys Thr Val Asp Met Asn Ile Ala Leu Thr Thr Phe Ile
                245                 250                 255

Pro His Asp Lys Gly Pro Ala Ala Ile Glu Glu Cys Cys Asn Trp Phe
            260                 265                 270

His Lys Arg Met Glu Glu Leu Asn Ser Glu Lys His Arg Leu Ile Asn
        275                 280                 285

Tyr His Gln Glu Gln Ala Val Asn Cys Leu Leu Gly Asn Val Phe Tyr
    290                 295                 300

Glu Arg Leu Ala Gly His Gly Pro Lys Leu Gly Pro Val Thr Arg Lys
305                 310                 315                 320

His Pro Leu Val Thr Arg Tyr Phe Thr Phe Pro Phe Glu Glu Ile Asp
                325                 330                 335

Phe Ser Met Glu Glu Ser Met Ile His Leu Pro Asn Lys Ala Cys Phe
            340                 345                 350

Leu Met Ala His Asn Gly Trp Val Met Gly Asp Asp Pro Leu Arg Asn
        355                 360                 365

Phe Ala Glu Pro Gly Ser Glu Val Tyr Leu Arg Arg Glu Leu Ile Cys
    370                 375                 380

Trp Gly Asp Ser Val Lys Leu Arg Tyr Gly Asn Lys Pro Glu Asp Cys
385                 390                 395                 400

Pro Tyr Leu Trp Ala His Met Lys Lys Tyr Thr Glu Ile Thr Ala Thr
                405                 410                 415

Tyr Phe Gln Gly Val Arg Leu Asp Asn Cys His Ser Thr Pro Leu His
            420                 425                 430

Val Ala Glu Tyr Met Leu Asp Ala Ala Arg Asn Leu Gln Pro Asn Leu
        435                 440                 445

Tyr Val Val Ala Glu Leu Phe Thr Gly Ser Glu Asp Leu Asp Asn Val
    450                 455                 460

Phe Val Thr Arg Leu Gly Ile Ser Ser Leu Ile Arg Glu Ala Met Ser
465                 470                 475                 480

Ala Tyr Asn Ser His Glu Glu Gly Arg Leu Val Tyr Arg Tyr Gly Gly
                485                 490                 495

Glu Pro Val Gly Ser Phe Val Gln Pro Cys Leu Arg Pro Leu Met Pro
            500                 505                 510

Ala Ile Ala His Ala Leu Phe Met Asp Ile Thr His Asp Asn Glu Cys
        515                 520                 525

Pro Ile Val His Arg Ser Ala Tyr Asp Ala Leu Pro Ser Thr Thr Ile
    530                 535                 540

Val Ser Met Ala Cys Cys Ala Ser Gly Ser Thr Arg Gly Tyr Asp Glu
545                 550                 555                 560

Leu Val Pro His Gln Ile Ser Val Val Ser Glu Glu Arg Phe Tyr Thr
                565                 570                 575

Lys Trp Asn Pro Glu Ala Leu Pro Ser Asn Thr Gly Glu Val Asn Phe
            580                 585                 590

Gln Ser Gly Ile Ile Ala Ala Arg Cys Ala Ile Ser Lys Leu His Gln
        595                 600                 605

Glu Leu Gly Ala Lys Gly Phe Ile Gln Val Tyr Val Asp Gln Val Asp
    610                 615                 620

Glu Asp Ile Val Ala Val Thr Arg His Ser Pro Ser Ile His Gln Ser
625                 630                 635                 640

Val Val Ala Val Thr Arg Thr Ala Phe Arg Asn Pro Lys Thr Ser Phe
                645                 650                 655
```

```
Tyr Ser Lys Glu Val Pro Gln Met Cys Ile Pro Gly Lys Ile Glu Glu
            660                 665                 670

Val Val Leu Glu Ala Arg Thr Ile Glu Arg Asn Thr Lys Pro Tyr Arg
        675                 680                 685

Lys Asp Glu Asn Ser Ile Asn Gly Thr Pro Asp Ile Thr Val Glu Ile
    690                 695                 700

Arg Glu His Ile Gln Leu Asn Glu Ser Lys Ile Val Lys Gln Ala Gly
705                 710                 715                 720

Val Ala Thr Lys Gly Pro Asn Glu Tyr Ile Gln Glu Ile Glu Phe Glu
                725                 730                 735

Asn Leu Ser Pro Gly Ser Val Ile Ile Phe Arg Val Ser Leu Asp Pro
            740                 745                 750

His Ala Gln Val Ala Val Gly Ile Leu Arg Asn His Leu Thr Gln Phe
        755                 760                 765

Ser Pro His Phe Lys Ser Gly Ser Leu Ala Val Asp Asn Ala Asp Pro
    770                 775                 780

Ile Leu Lys Ile Pro Phe Ala Ser Leu Ala Tyr Arg Leu Thr Leu Ala
785                 790                 795                 800

Glu Leu Asn Gln Ile Leu Tyr Arg Cys Glu Ser Glu Glu Lys Glu Asp
                805                 810                 815

Gly Gly Gly Cys Tyr Asp Ile Pro Asn Trp Ser Ala Leu Lys Tyr Ala
            820                 825                 830

Gly Leu Gln Gly Leu Met Ser Val Leu Ala Glu Ile Arg Pro Lys Asn
        835                 840                 845

Asp Leu Gly His Pro Phe Cys Asn Asn Leu Arg Ser Gly Asp Trp Met
    850                 855                 860

Ile Asp Tyr Val Ser Asn Arg Leu Ile Ser Arg Ser Gly Thr Ile Ala
865                 870                 875                 880

Glu Val Gly Lys Trp Leu Gln Ala Met Phe Phe Tyr Leu Lys Gln Ile
                885                 890                 895

Pro Arg Tyr Leu Ile Pro Cys Tyr Phe Asp Ala Ile Leu Ile Gly Ala
            900                 905                 910

Tyr Thr Thr Leu Leu Asp Thr Ala Trp Lys Gln Met Ser Ser Phe Val
        915                 920                 925

Gln Asn Gly Ser Thr Phe Val Lys His Leu Ser Leu Gly Ser Val Gln
    930                 935                 940

Leu Cys Gly Val Gly Lys Phe Pro Ser Leu Pro Ile Leu Ser Pro Ala
945                 950                 955                 960

Leu Met Asp Val Pro Tyr Arg Leu Asn Glu Ile Thr Lys Glu Lys Glu
                965                 970                 975

Gln Cys Cys Val Ser Leu Ala Ala Gly Leu Pro His Phe Ser Ser Gly
            980                 985                 990

Ile Phe Arg Cys Trp Gly Arg Asp  Thr Phe Ile Ala Leu  Arg Gly Ile
        995                 1000                1005

Leu Leu  Ile Thr Gly Arg Tyr  Val Glu Ala Arg Asn  Ile Ile Leu
    1010                 1015                 1020

Ala Phe  Ala Gly Thr Leu Arg  His Gly Leu Ile Pro  Asn Leu Leu
    1025                 1030                 1035

Gly Glu  Gly Ile Tyr Ala Arg  Tyr Asn Cys Arg Asp  Ala Val Trp
    1040                 1045                 1050

Trp Trp  Leu Gln Cys Ile Gln  Asp Tyr Cys Lys Met  Val Pro Asn
    1055                 1060                 1065
```

```
Gly Leu  Asp Ile Leu Lys Cys  Pro Val Ser Arg Met  Tyr Pro Thr
    1070                 1075                 1080

Asp Asp  Ser Ala Pro Leu Pro  Ala Gly Thr Leu Asp  Gln Pro Leu
    1085                 1090                 1095

Phe Glu  Val Ile Gln Glu Ala  Met Gln Lys His Met  Gln Gly Ile
    1100                 1105                 1110

Gln Phe  Arg Glu Arg Asn Ala  Gly Pro Gln Ile Asp  Arg Asn Met
    1115                 1120                 1125

Lys Asp  Glu Gly Phe Asn Ile  Thr Ala Gly Val Asp  Glu Glu Thr
    1130                 1135                 1140

Gly Phe  Val Tyr Gly Gly Asn  Arg Phe Asn Cys Gly  Thr Trp Met
    1145                 1150                 1155

Asp Lys  Met Gly Glu Ser Asp  Arg Ala Arg Asn Arg  Gly Ile Pro
    1160                 1165                 1170

Ala Thr  Pro Arg Asp Gly Ser  Ala Val Glu Ile Val  Gly Leu Ser
    1175                 1180                 1185

Lys Ser  Ala Val Arg Trp Leu  Leu Glu Leu Ser Lys  Lys Asn Ile
    1190                 1195                 1200

Phe Pro  Tyr His Glu Val Thr  Val Lys Arg His Gly  Lys Ala Ile
    1205                 1210                 1215

Lys Val  Ser Tyr Asp Glu Trp  Asn Arg Lys Ile Gln  Asp Asn Phe
    1220                 1225                 1230

Glu Lys  Leu Phe His Val Ser  Glu Asp Pro Ser Asp  Leu Asn Glu
    1235                 1240                 1245

Lys His  Pro Asn Leu Val His  Lys Arg Gly Ile Tyr  Lys Asp Ser
    1250                 1255                 1260

Tyr Gly  Ala Ser Ser Pro Trp  Cys Asp Tyr Gln Leu  Arg Pro Asn
    1265                 1270                 1275

Phe Thr  Ile Ala Met Val Val  Ala Pro Glu Leu Phe  Thr Thr Glu
    1280                 1285                 1290

Lys Ala  Trp Lys Ala Leu Glu  Ile Ala Glu Lys Lys  Leu Leu Gly
    1295                 1300                 1305

Pro Leu  Gly Met Lys Thr Leu  Asp Pro Asp Asp Met  Val Tyr Cys
    1310                 1315                 1320

Gly Ile  Tyr Asp Asn Ala Leu  Asp Asn Asp Asn Tyr  Asn Leu Ala
    1325                 1330                 1335

Lys Gly  Phe Asn Tyr His Gln  Gly Pro Glu Trp Leu  Trp Pro Ile
    1340                 1345                 1350

Gly Tyr  Phe Leu Arg Ala Lys  Leu Tyr Phe Ser Arg  Leu Met Gly
    1355                 1360                 1365

Pro Glu  Thr Thr Ala Lys Thr  Ile Val Leu Val Lys  Asn Val Leu
    1370                 1375                 1380

Ser Arg  His Tyr Val His Leu  Glu Arg Ser Pro Trp  Lys Gly Leu
    1385                 1390                 1395

Pro Glu  Leu Thr Asn Glu Asn  Ala Gln Tyr Cys Pro  Phe Ser Cys
    1400                 1405                 1410

Glu Thr  Gln Ala Trp Ser Ile  Ala Thr Ile Leu Glu  Thr Leu Tyr
    1415                 1420                 1425

Asp Leu
    1430
```

<210> SEQ ID NO 52
<211> LENGTH: 1404
<212> TYPE: PRT

<213> ORGANISM: artificial
<220> FEATURE:
<223> OTHER INFORMATION: D1c + D2,3 hGDE

<400> SEQUENCE: 52

```
Met Gln Thr Phe Leu Ala Lys Cys Leu Gly Pro Phe Asp Glu Trp Glu
1               5                   10                  15

Ser Arg Leu Arg Val Ala Lys Glu Ser Gly Tyr Asn Met Ile His Phe
            20                  25                  30

Thr Pro Leu Gln Thr Leu Gly Leu Ser Arg Ser Cys Tyr Ser Leu Ala
        35                  40                  45

Asn Gln Leu Glu Leu Asn Pro Asp Phe Ser Arg Pro Asn Arg Lys Tyr
    50                  55                  60

Thr Trp Asn Asp Val Gly Gln Leu Val Glu Lys Leu Lys Lys Glu Trp
65                  70                  75                  80

Asn Val Ile Cys Ile Thr Asp Val Val Tyr Asn His Thr Ala Ala Asn
                85                  90                  95

Ser Lys Trp Ile Gln Glu His Pro Glu Cys Ala Tyr Asn Leu Val Asn
            100                 105                 110

Ser Pro His Leu Lys Pro Ala Trp Val Leu Asp Arg Ala Leu Trp Arg
        115                 120                 125

Phe Ser Cys Asp Val Ala Glu Gly Lys Tyr Lys Glu Lys Gly Ile Pro
    130                 135                 140

Ala Leu Ile Glu Asn Asp His His Met Asn Ser Ile Arg Lys Ile Ile
145                 150                 155                 160

Trp Glu Asp Ile Phe Pro Lys Leu Lys Leu Trp Glu Phe Phe Gln Val
                165                 170                 175

Asp Val Asn Lys Ala Val Glu Gln Phe Arg Arg Leu Leu Thr Gln Glu
            180                 185                 190

Asn Arg Arg Val Thr Lys Ser Asp Pro Asn Gln His Leu Thr Ile Ile
        195                 200                 205

Gln Asp Pro Glu Tyr Arg Arg Phe Gly Cys Thr Val Asp Met Asn Ile
    210                 215                 220

Ala Leu Thr Thr Phe Ile Pro His Asp Lys Gly Pro Ala Ala Ile Glu
225                 230                 235                 240

Glu Cys Cys Asn Trp Phe His Lys Arg Met Glu Glu Leu Asn Ser Glu
                245                 250                 255

Lys His Arg Leu Ile Asn Tyr His Gln Glu Gln Ala Val Asn Cys Leu
            260                 265                 270

Leu Gly Asn Val Phe Tyr Glu Arg Leu Ala Gly His Gly Pro Lys Leu
        275                 280                 285

Gly Pro Val Thr Arg Lys His Pro Leu Val Thr Arg Tyr Phe Thr Phe
    290                 295                 300

Pro Phe Glu Glu Ile Asp Phe Ser Met Glu Glu Ser Met Ile His Leu
305                 310                 315                 320

Pro Asn Lys Ala Cys Phe Leu Met Ala His Asn Gly Trp Val Met Gly
                325                 330                 335

Asp Asp Pro Leu Arg Asn Phe Ala Glu Pro Gly Ser Glu Val Tyr Leu
            340                 345                 350

Arg Arg Glu Leu Ile Cys Trp Gly Asp Ser Val Lys Leu Arg Tyr Gly
        355                 360                 365

Asn Lys Pro Glu Asp Cys Pro Tyr Leu Trp Ala His Met Lys Lys Tyr
    370                 375                 380

Thr Glu Ile Thr Ala Thr Tyr Phe Gln Gly Val Arg Leu Asp Asn Cys
```

-continued

```
385                 390                 395                 400

His Ser Thr Pro Leu His Val Ala Glu Tyr Met Leu Asp Ala Ala Arg
                405                 410                 415

Asn Leu Gln Pro Asn Leu Tyr Val Val Ala Glu Leu Phe Thr Gly Ser
            420                 425                 430

Glu Asp Leu Asp Asn Val Phe Val Thr Arg Leu Gly Ile Ser Ser Leu
        435                 440                 445

Ile Arg Glu Ala Met Ser Ala Tyr Asn Ser His Glu Glu Gly Arg Leu
    450                 455                 460

Val Tyr Arg Tyr Gly Gly Glu Pro Val Gly Ser Phe Val Gln Pro Cys
465                 470                 475                 480

Leu Arg Pro Leu Met Pro Ala Ile Ala His Ala Leu Phe Met Asp Ile
                485                 490                 495

Thr His Asp Asn Glu Cys Pro Ile Val His Arg Ser Ala Tyr Asp Ala
            500                 505                 510

Leu Pro Ser Thr Thr Ile Val Ser Met Ala Cys Cys Ala Ser Gly Ser
        515                 520                 525

Thr Arg Gly Tyr Asp Glu Leu Val Pro His Gln Ile Ser Val Val Ser
    530                 535                 540

Glu Glu Arg Phe Tyr Thr Lys Trp Asn Pro Glu Ala Leu Pro Ser Asn
545                 550                 555                 560

Thr Gly Glu Val Asn Phe Gln Ser Gly Ile Ile Ala Ala Arg Cys Ala
                565                 570                 575

Ile Ser Lys Leu His Gln Glu Leu Gly Ala Lys Gly Phe Ile Gln Val
            580                 585                 590

Tyr Val Asp Gln Val Asp Glu Asp Ile Val Ala Val Thr Arg His Ser
        595                 600                 605

Pro Ser Ile His Gln Ser Val Val Ala Val Thr Arg Thr Ala Phe Arg
    610                 615                 620

Asn Pro Lys Thr Ser Phe Tyr Ser Lys Glu Val Pro Gln Met Cys Ile
625                 630                 635                 640

Pro Gly Lys Ile Glu Glu Val Val Leu Glu Ala Arg Thr Ile Glu Arg
                645                 650                 655

Asn Thr Lys Pro Tyr Arg Lys Asp Glu Asn Ser Ile Asn Gly Thr Pro
            660                 665                 670

Asp Ile Thr Val Glu Ile Arg Glu His Ile Gln Leu Asn Glu Ser Lys
        675                 680                 685

Ile Val Lys Gln Ala Gly Val Ala Thr Lys Gly Pro Asn Glu Tyr Ile
    690                 695                 700

Gln Glu Ile Glu Phe Glu Asn Leu Ser Pro Gly Ser Val Ile Ile Phe
705                 710                 715                 720

Arg Val Ser Leu Asp Pro His Ala Gln Val Ala Val Gly Ile Leu Arg
                725                 730                 735

Asn His Leu Thr Gln Phe Ser Pro His Phe Lys Ser Gly Ser Leu Ala
            740                 745                 750

Val Asp Asn Ala Asp Pro Ile Leu Lys Ile Pro Phe Ala Ser Leu Ala
        755                 760                 765

Tyr Arg Leu Thr Leu Ala Glu Leu Asn Gln Ile Leu Tyr Arg Cys Glu
    770                 775                 780

Ser Glu Glu Lys Glu Asp Gly Gly Gly Cys Tyr Asp Ile Pro Asn Trp
785                 790                 795                 800

Ser Ala Leu Lys Tyr Ala Gly Leu Gln Gly Leu Met Ser Val Leu Ala
                805                 810                 815
```

```
Glu Ile Arg Pro Lys Asn Asp Leu Gly His Pro Phe Cys Asn Asn Leu
            820                 825                 830

Arg Ser Gly Asp Trp Met Ile Asp Tyr Val Ser Asn Arg Leu Ile Ser
        835                 840                 845

Arg Ser Gly Thr Ile Ala Glu Val Gly Lys Trp Leu Gln Ala Met Phe
    850                 855                 860

Phe Tyr Leu Lys Gln Ile Pro Arg Tyr Leu Ile Pro Cys Tyr Phe Asp
865                 870                 875                 880

Ala Ile Leu Ile Gly Ala Tyr Thr Thr Leu Leu Asp Thr Ala Trp Lys
                885                 890                 895

Gln Met Ser Ser Phe Val Gln Asn Gly Ser Thr Phe Val Lys His Leu
            900                 905                 910

Ser Leu Gly Ser Val Gln Leu Cys Gly Val Gly Lys Phe Pro Ser Leu
        915                 920                 925

Pro Ile Leu Ser Pro Ala Leu Met Asp Val Pro Tyr Arg Leu Asn Glu
    930                 935                 940

Ile Thr Lys Glu Lys Glu Gln Cys Cys Val Ser Leu Ala Ala Gly Leu
945                 950                 955                 960

Pro His Phe Ser Ser Gly Ile Phe Arg Cys Trp Gly Arg Asp Thr Phe
                965                 970                 975

Ile Ala Leu Arg Gly Ile Leu Leu Ile Thr Gly Arg Tyr Val Glu Ala
            980                 985                 990

Arg Asn Ile Ile Leu Ala Phe Ala  Gly Thr Leu Arg His  Gly Leu Ile
        995                 1000                 1005

Pro Asn  Leu Leu Gly Glu Gly  Ile Tyr Ala Arg Tyr  Asn Cys Arg
    1010                 1015                 1020

Asp Ala  Val Trp Trp Trp Leu  Gln Cys Ile Gln Asp  Tyr Cys Lys
    1025                 1030                 1035

Met Val  Pro Asn Gly Leu Asp  Ile Leu Lys Cys Pro  Val Ser Arg
    1040                 1045                 1050

Met Tyr  Pro Thr Asp Asp Ser  Ala Pro Leu Pro Ala  Gly Thr Leu
    1055                 1060                 1065

Asp Gln  Pro Leu Phe Glu Val  Ile Gln Glu Ala Met  Gln Lys His
    1070                 1075                 1080

Met Gln  Gly Ile Gln Phe Arg  Glu Arg Asn Ala Gly  Pro Gln Ile
    1085                 1090                 1095

Asp Arg  Asn Met Lys Asp Glu  Gly Phe Asn Ile Thr  Ala Gly Val
    1100                 1105                 1110

Asp Glu  Glu Thr Gly Phe Val  Tyr Gly Gly Asn Arg  Phe Asn Cys
    1115                 1120                 1125

Gly Thr  Trp Met Asp Lys Met  Gly Glu Ser Asp Arg  Ala Arg Asn
    1130                 1135                 1140

Arg Gly  Ile Pro Ala Thr Pro  Arg Asp Gly Ser Ala  Val Glu Ile
    1145                 1150                 1155

Val Gly  Leu Ser Lys Ser Ala  Val Arg Trp Leu Leu  Glu Leu Ser
    1160                 1165                 1170

Lys Lys  Asn Ile Phe Pro Tyr  His Glu Val Thr Val  Lys Arg His
    1175                 1180                 1185

Gly Lys  Ala Ile Lys Val Ser  Tyr Asp Glu Trp Asn  Arg Lys Ile
    1190                 1195                 1200

Gln Asp  Asn Phe Glu Lys Leu  Phe His Val Ser Glu  Asp Pro Ser
    1205                 1210                 1215
```

```
Asp Leu  Asn Glu Lys His Pro  Asn Leu Val His Lys  Arg Gly Ile
    1220                 1225                 1230

Tyr Lys  Asp Ser Tyr Gly Ala  Ser Ser Pro Trp Cys  Asp Tyr Gln
    1235                 1240                 1245

Leu Arg  Pro Asn Phe Thr Ile  Ala Met Val Val Ala  Pro Glu Leu
    1250                 1255                 1260

Phe Thr  Thr Glu Lys Ala Trp  Lys Ala Leu Glu Ile  Ala Glu Lys
    1265                 1270                 1275

Lys Leu  Leu Gly Pro Leu Gly  Met Lys Thr Leu Asp  Pro Asp Asp
    1280                 1285                 1290

Met Val  Tyr Cys Gly Ile Tyr  Asp Asn Ala Leu Asp  Asn Asp Asn
    1295                 1300                 1305

Tyr Asn  Leu Ala Lys Gly Phe  Asn Tyr His Gln Gly  Pro Glu Trp
    1310                 1315                 1320

Leu Trp  Pro Ile Gly Tyr Phe  Leu Arg Ala Lys Leu  Tyr Phe Ser
    1325                 1330                 1335

Arg Leu  Met Gly Pro Glu Thr  Thr Ala Lys Thr Ile  Val Leu Val
    1340                 1345                 1350

Lys Asn  Val Leu Ser Arg His  Tyr Val His Leu Glu  Arg Ser Pro
    1355                 1360                 1365

Trp Lys  Gly Leu Pro Glu Leu  Thr Asn Glu Asn Ala  Gln Tyr Cys
    1370                 1375                 1380

Pro Phe  Ser Cys Glu Thr Gln  Ala Trp Ser Ile Ala  Thr Ile Leu
    1385                 1390                 1395

Glu Thr  Leu Tyr Asp Leu
    1400
```

```
<210> SEQ ID NO 53
<211> LENGTH: 4557
<212> TYPE: DNA
<213> ORGANISM: artificial
<220> FEATURE:
<223> OTHER INFORMATION: D1a + D2,3 hGDE

<400> SEQUENCE: 53

atggaaaagc tggaaaagac cctgttccgg ctcgagcagg gctacgagct gcagtttaga     60

ctgggcccta cactgcaggg caaagccgtg accgtgtaca caaactaccc cttccctggc    120

gaaaccttca accgcgagaa gttcagaagc ctggactggg agaaccccac cgagagagag    180

gacgacagcg acaagtactg caagctgaac ctgcagcaga gcggctcctt ccagtactac    240

ttcctgcaag gcaacgagaa gtccggcgga ggctacatcg tggtggaccc tattctgaga    300

gtgggcgccg acaatcacgt gctgcctctg gattgtgtga ccctgcagac cttcctggcc    360

aagtgtctgg gccctttcga tgagtgggag agcagactgc gcgtggccaa agaaagcggc    420

tacaacatga tccacttcac ccctctgcag accctgggcc tgagcagaag ctgttacagc    480

ctggccaacc agctggaact gaaccccgac ttcagcagac ccaaccggaa gtacacctgg    540

aacgatgtgg gccagctggt ggaaaaactg aagaaagaat ggaacgtgat ctgcatcacc    600

gacgtggtgt acaaccacac cgccgccaac agcaagtgga tccaagagca ccctgagtgc    660

gcctacaacc tggtcaacag ccctcacctg aaacctgcct gggtgctcga tagagccctg    720

tggcggttta gctgtgatgt ggccgagggc aagtacaaag agaagggcat ccccgctctg    780

atcgagaacg accaccacat gaacagcatc cggaagatca tctgggaaga tattttcccc    840

aagctgaagc tgtgggagtt cttccaggtg gacgtgaaca aggccgtgga acagttcaga    900
```

```
cggctgctga cccaagagaa cagaagagtg accaagagcg accccaacca gcacctgacc    960
atcattcagg accccgagta tcggagattc ggctgcaccg tggacatgaa tatcgccctg   1020
accaccttca ttccccacga caaaggacct gccgccatcg aggaatgctg caactggttc   1080
cacaagcgga tggaagaatt gaacagcgag aagcaccggc tgatcaacta ccaccaagag   1140
caggccgtga actgcctgct gggcaacgtg ttctatgaga gactggccgg acacggccct   1200
aagctgggac ctgtgacaag aaagcaccct ctggttaccc ggtacttcac ctttccattc   1260
gaagagatcg acttctccat ggaagagagc atgatccatc tgcctaacaa ggcctgcttc   1320
ctgatggctc acaacggctg ggttatgggc gacgaccctc tgagaaattt cgccgagcct   1380
ggcagcgagg tgtacctgag aagagaactg atctgttggg gcgacagcgt gaagctgaga   1440
tacggcaaca agcccgagga ctgcccttac ctgtgggccc atatgaagaa gtacacagag   1500
atcaccgcca cctactttca gggcgtcaga ctggacaact gccacagcac acctctgcac   1560
gtggccgagt acatgctgga cgccgctaga aatctgcagc ccaacctgta tgtggtggcc   1620
gagctgttta ccggctccga ggacctggac aatgtgttcg tgaccagact gggcatcagc   1680
agcctgatca gagaagccat gtccgcctac aatagccacg aagagggcag actggtgtac   1740
agatatggcg gcgagcctgt gggcagcttc gttcagcctt gtctgaggcc tctgatgccc   1800
gccattgctc acgccctgtt catggacatc acccacgata acgagtgccc catcgtgcac   1860
agaagcgcct acgacgctct gcctagcacc accattgtgt ccatggcctg ttgtgccagc   1920
ggcagcacaa gaggctatga cgaactggtg ccccaccaga tttccgtggt gtccgaggaa   1980
cggttctaca ccaagtggaa ccccgaggct ctgcccagca ataccggcga agtgaatttc   2040
cagagcggca tcattgccgc cagatgcgcc atcagcaagc tgcaccaaga actgggcgcc   2100
aagggcttca ttcaggtgta cgtggaccag gtcgacgagg acattgtggc cgtgacaaga   2160
cacagcccca gcatccatca gagcgtggtg gctgtgacca gaaccgcctt cagaaacccc   2220
aagaccagct tctacagcaa agaggtgccc cagatgtgca tccccggcaa gattgaggaa   2280
gtggtgctcg aggcccggac catcgagaga aacaccaagc cttaccggaa ggacgagaac   2340
tccatcaacg gcacccctga catcaccgtg gaaatcagag agcacatcca gctcaacgag   2400
agcaagatcg tgaaacaggc cggcgtggcc acaaagggcc ccaacgagta tatccaagag   2460
attgagttcg agaatctgag ccccggcagc gtgatcatct tcagagtgtc cctggatcct   2520
cacgctcagg tggccgtggg catcctgaga aatcacctga cacagttcag cccacacttc   2580
aagagcggaa gcctggccgt ggacaacgcc gatcctatcc tgaagatccc cttcgcctct   2640
ctggcctaca gactgacact ggctgagctg aaccagatcc tgtacagatg cgagtccgaa   2700
gagaaagagg atggcggagg ctgctacgac atccccaatt ggagcgccct gaagtatgcc   2760
ggactgcagg gactgatgtc tgtgctggcc gagatcagac ccaagaacga cctgggacac   2820
cccttctgca acaacctgag atccggcgac tggatgatcg actacgtgtc caacagactg   2880
atcagcagat ccggcacaat cgccgaagtc ggcaaatggc tgcaggccat gttcttctac   2940
ctgaagcaga tccctcggta tctgatcccc tgctacttcg acgccatcct gatcggcgcc   3000
tacaccacac tgctggatac cgcctggaag cagatgtcca gcttcgtgca gaacggcagc   3060
accttcgtga agcacctgtc tctgggaagc gtgcagctgt gtggcgtggg caaatttccc   3120
agcctgccta tcctgtctcc tgcactgatg gacgtgccct accggctgaa tgagatcacc   3180
aaagaaaaag agcagtgctg cgtcagcctg gctgctggcc tgcctcattt ttccagcggc   3240
atcttccggt gttggggcag agacaccttt attgccctga gaggcatcct gctgattacc   3300
```

```
ggcagatacg tggaagcccg gaacatcatc ctggcctttg ccggcacact gcggcacgga   3360
ctgattccta atctgctcgg cgagggcatc tacgccagat acaactgcag agatgccgtg   3420
tggtggtggc tccagtgcat ccaggactac tgcaagatgg tgcccaacgg cctggacatc   3480
ctgaagtgcc ctgtgtccag aatgtaccct accgacgata gcgcccctct gcctgccgga   3540
acacttgacc agcctctgtt cgaagtgatt caagaggcca tgcagaaaca catgcaggga   3600
atccagtttc gcgagcggaa tgccggacct cagatcgaca gaaacatgaa ggatgagggc   3660
ttcaacatca ccgctggcgt ggacgaagag acaggctttg tgtacggcgg caaccggttc   3720
aattgcggca cctggatgga caagatgggc gagtctgacc gggccagaaa cagaggaatt   3780
cccgccacac ctagagatgg cagcgctgtg gaaatcgtgg gcctgtctaa gtctgctgtg   3840
cggtggctgc tcgaactgag caagaagaat atctttccgt accacgaagt gaccgtgaag   3900
cggcacggca aggccatcaa ggtgtcctac gacgagtgga acagaaagat ccaggacaac   3960
ttcgaaaagc tgttccatgt gtctgaggac cccagcgacc tgaacgaaaa gcaccccaac   4020
ctggtgcaca agcgcggcat ctacaaggac agctacggcg cctcttctcc ttggtgcgat   4080
taccagctgc ggcccaactt caccattgcc atggtggttg cccctgagct gttcaccaca   4140
gagaaggcct ggaaggccct ggaaatcgcc gagaagaaac tgctgggccc tctgggcatg   4200
aagacactgg accccgacga catggtgtac tgcggaatct acgacaacgc cctggataac   4260
gacaactaca atctggccaa ggggttcaat taccatcagg gacccgagtg gctgtggcct   4320
atcggctatt tcctgcgggc caagctgtac ttctccagac tgatgggccc tgagacaacc   4380
gccaagacaa tcgtgctcgt gaagaacgtg ctgagccggc actatgtgca cctggaaaga   4440
agcccctgga agggactgcc cgagctgacc aatgagaacg cccagtactg ccccttcagc   4500
tgcgaaacac aggcctggtc tatcgccacc atcctggaaa ccctgtacga cctgtga      4557
```

<210> SEQ ID NO 54
<211> LENGTH: 4512
<212> TYPE: DNA
<213> ORGANISM: artificial
<220> FEATURE:
<223> OTHER INFORMATION: D1b1 + D2,3 hGDE

<400> SEQUENCE: 54

```
atgctgcagt ttagactggg ccctacactg cagggcaaag ccgtgaccgt gtacacaaac     60
taccccttcc ctggcgaaac cttcaaccgc gagaagttca gaagcctgga ctgggagaac    120
cccaccgaga gagaggacga cagcgacaag tactgcaagc tgaacctgca gcagagcggc    180
tccttccagt actacttcct gcaaggcaac gagaagtccg gcggaggcta catcgtggtg    240
gaccctattc tgagagtggg cgccgacaat cacgtgctgc ctctggattg tgtgaccctg    300
cagaccttcc tggccaagtg tctgggccct ttcgatgagt gggagagcag actgcgcgtg    360
gccaaagaaa gcggctacaa catgatccac ttcacccctc tgcagaccct gggcctgagc    420
agaagctgtt acagcctggc caaccagctg gaactgaacc ccgacttcag cagacccaac    480
cggaagtaca cctggaacga tgtgggccag ctggtggaaa aactgaagaa agaatggaac    540
gtgatctgca tcaccgacgt ggtgtacaac cacaccgccg ccaacagcaa gtggatccaa    600
gagcaccctg agtgcgccta caacctggtc aacagccctc acctgaaacc tgcctgggtg    660
ctcgatagag ccctgtggcg gtttagctgt gatgtggccg agggcaagta caaagagaag    720
ggcatccccg ctctgatcga gaacgaccac cacatgaaca gcatccggaa gatcatctgg    780
```

```
gaagatattt tccccaagct gaagctgtgg gagttcttcc aggtggacgt gaacaaggcc    840
gtggaacagt tcagacggct gctgacccaa gagaacagaa gagtgaccaa gagcgacccc    900
aaccagcacc tgaccatcat tcaggacccc gagtatcgga gattcggctg caccgtggac    960
atgaatatcg ccctgaccac cttcattccc cacgacaaag gacctgccgc catcgaggaa   1020
tgctgcaact ggttccacaa gcggatggaa gaattgaaca gcgagaagca ccggctgatc   1080
aactaccacc aagagcaggc cgtgaactgc ctgctgggca acgtgttcta tgagagactg   1140
gccggacacg gccctaagct gggacctgtg acaagaaagc accctctggt tacccggtac   1200
ttcacctttc cattcgaaga gatcgacttc tccatggaag agagcatgat ccatctgcct   1260
aacaaggcct gcttcctgat ggctcacaac ggctgggtta tgggcgacga ccctctgaga   1320
aatttcgccg agcctggcag cgaggtgtac ctgagaagag aactgatctg ttggggcgac   1380
agcgtgaagc tgagatacgg caacaagccc gaggactgcc cttacctgtg ggcccatatg   1440
aagaagtaca cagagatcac cgccacctac tttcagggcg tcagactgga caactgccac   1500
agcacacctc tgcacgtggc cgagtacatg ctggacgccg ctagaaatct gcagcccaac   1560
ctgtatgtgg tggccgagct gtttaccggc tccgaggacc tggacaatgt gttcgtgacc   1620
agactgggca tcagcagcct gatcagagaa gccatgtccg cctacaatag ccacgaagag   1680
ggcagactgg tgtacagata tggcggcgag cctgtgggca gcttcgttca gccttgtctg   1740
aggcctctga tgcccgccat tgctcacgcc ctgttcatgg acatcaccca cgataacgag   1800
tgccccatcg tgcacagaag cgcctacgac gctctgccta gcaccaccat tgtgtccatg   1860
gcctgttgtg ccagcggcag cacaagaggc tatgacgaac tggtgcccca ccagatttcc   1920
gtggtgtccg aggaacggtt ctacaccaag tggaaccccg aggctctgcc cagcaatacc   1980
ggcgaagtga atttccagag cggcatcatt gccgccagat gcgccatcag caagctgcac   2040
caagaactgg gcgccaaggg cttcattcag gtgtacgtgg accaggtcga cgaggacatt   2100
gtggccgtga caagacacag ccccagcatc catcagagcg tggtggctgt gaccagaacc   2160
gccttcagaa accccaagac cagcttctac agcaaagagg tgccccagat gtgcatcccc   2220
ggcaagattg aggaagtggt gctcgaggcc cggaccatcg agagaaacac caagccttac   2280
cggaaggacg agaactccat caacggcacc cctgacatca ccgtggaaat cagagagcac   2340
atccagctca acgagagcaa gatcgtgaaa caggccggcg tggccacaaa gggccccaac   2400
gagtatatcc aagagattga gttcgagaat ctgagccccg gcagcgtgat catcttcaga   2460
gtgtccctgg atcctcacgc tcaggtggcc gtgggcatcc tgagaaatca cctgacacag   2520
ttcagcccac acttcaagag cggaagcctg gccgtggaca acgccgatcc tatcctgaag   2580
atccccttcg cctctctggc ctacagactg acactggctg agctgaacca gatcctgtac   2640
agatgcgagt ccgaagagaa agaggatggc ggaggctgct acgacatccc caattggagc   2700
gccctgaagt atgccggact gcagggactg atgtctgtgc tggccgagat cagacccaag   2760
aacgacctgg gacacccctt ctgcaacaac ctgagatccg gcgactggat gatcgactac   2820
gtgtccaaca gactgatcag cagatccggc acaatcgccg aagtcggcaa atggctgcag   2880
gccatgttct tctacctgaa gcagatccct cggtatctga tcccctgcta cttcgacgcc   2940
atcctgatcg gcgcctacac cacactgctg gataccgcct ggaagcagat gtccagcttc   3000
gtgcagaacg gcagcacctt cgtgaagcac ctgtctctgg gaagcgtgca gctgtgtggc   3060
gtgggcaaat tcccagcct gcctatcctg tctcctgcac tgatggacgt gccctaccgg    3120
ctgaatgaga tcaccaaaga aaaagagcag tgctgcgtca gcctggctgc tggcctgcct   3180
```

```
catttttcca gcggcatctt ccggtgttgg ggcagagaca cctttattgc cctgagaggc   3240

atcctgctga ttaccggcag atacgtggaa gcccggaaca tcatcctggc ctttgccggc   3300

acactgcggc acggactgat tcctaatctg ctcggcgagg gcatctacgc cagatacaac   3360

tgcagagatg ccgtgtggtg gtggctccag tgcatccagg actactgcaa gatggtgccc   3420

aacggcctgg acatcctgaa gtgccctgtg tccagaatgt accctaccga cgatagcgcc   3480

cctctgcctg ccggaacact tgaccagcct ctgttcgaag tgattcaaga ggccatgcag   3540

aaacacatgc agggaatcca gtttcgcgag cggaatgccg gacctcagat cgacagaaac   3600

atgaaggatg agggcttcaa catcaccgct ggcgtggacg aagagacagg ctttgtgtac   3660

ggcggcaacc ggttcaattg cggcacctgg atggacaaga tgggcgagtc tgaccgggcc   3720

agaaacagag gaattcccgc cacacctaga gatggcagcg ctgtggaaat cgtgggcctg   3780

tctaagtctg ctgtgcggtg gctgctcgaa ctgagcaaga agaatatctt tccgtaccac   3840

gaagtgaccg tgaagcggca cggcaaggcc atcaaggtgt cctacgacga gtggaacaga   3900

aagatccagg acaacttcga aaagctgttc catgtgtctg aggaccccag cgacctgaac   3960

gaaaagcacc ccaacctggt gcacaagcgc ggcatctaca aggacagcta cggcgcctct   4020

tctccttggt gcgattacca gctgcggccc aacttcacca ttgccatggt ggttgcccct   4080

gagctgttca ccacagagaa ggcctggaag gccctggaaa tcgccgagaa gaaactgctg   4140

ggccctctgg gcatgaagac actggacccc gacgacatgg tgtactgcgg aatctacgac   4200

aacgccctgg ataacgacaa ctacaatctg gccaaggggt tcaattacca tcagggaccc   4260

gagtggctgt ggcctatcgg ctatttcctg cgggccaagc tgtacttctc cagactgatg   4320

ggccctgaga caaccgccaa gacaatcgtg ctcgtgaaga acgtgctgag ccggcactat   4380

gtgcacctgg aaagaagccc ctggaaggga ctgcccgagc tgaccaatga gaacgcccag   4440

tactgcccct tcagctgcga aacacaggcc tggtctatcg ccaccatcct ggaaaccctg   4500

tacgacctgt ga                                                        4512
```

```
<210> SEQ ID NO 55
<211> LENGTH: 4359
<212> TYPE: DNA
<213> ORGANISM: artificial
<220> FEATURE:
<223> OTHER INFORMATION: D1b2 + D2,3 hGDE

<400> SEQUENCE: 55

atgaagctga acctgcagca gagcggctcc ttccagtact acttcctgca aggcaacgag     60

aagtccggcg gaggctacat cgtggtggac cctattctga gagtgggcgc cgacaatcac    120

gtgctgcctc tggattgtgt gaccctgcag accttcctgg ccaagtgtct gggccctttc    180

gatgagtggg agagcagact gcgcgtggcc aaagaaagcg gctacaacat gatccacttc    240

acccctctgc agaccctggg cctgagcaga agctgttaca gcctggccaa ccagctggaa    300

ctgaaccccg acttcagcag acccaaccgg aagtacacct ggaacgatgt gggccagctg    360

gtggaaaaac tgaagaaaga atggaacgtg atctgcatca ccgacgtggt gtacaaccac    420

accgccgcca acagcaagtg gatccaagag caccctgagt gcgcctacaa cctggtcaac    480

agccctcacc tgaaacctgc ctgggtgctc gatagagccc tgtggcggtt tagctgtgat    540

gtggccgagg gcaagtacaa agagaagggc atccccgctc tgatcgagaa cgaccaccac    600

atgaacagca tccggaagat catctgggaa gatattttcc ccaagctgaa gctgtgggag    660
```

```
ttcttccagg tggacgtgaa caaggccgtg gaacagttca gacggctgct gacccaagag    720
aacagaagag tgaccaagag cgaccccaac cagcacctga ccatcattca ggaccccgag    780
tatcggagat tcggctgcac cgtggacatg aatatcgccc tgaccacctt cattccccac    840
gacaaaggac ctgccgccat cgaggaatgc tgcaactggt tccacaagcg gatggaagaa    900
ttgaacagcg agaagcaccg gctgatcaac taccaccaag agcaggccgt gaactgcctg    960
ctgggcaacg tgttctatga gagactggcc ggacacggcc ctaagctggg acctgtgaca   1020
agaaagcacc ctctggttac ccggtacttc acctttccat tcgaagagat cgacttctcc   1080
atggaagaga gcatgatcca tctgcctaac aaggcctgct tcctgatggc tcacaacggc   1140
tgggttatgg gcgacgaccc tctgagaaat ttcgccgagc ctggcagcga ggtgtacctg   1200
agaagagaac tgatctgttg ggcgacagc gtgaagctga gatacggcaa caagcccgag   1260
gactgccctt acctgtgggc ccatatgaag aagtacacag agatcaccgc cacctacttt   1320
cagggcgtca gactggacaa ctgccacagc acacctctgc acgtggccga gtacatgctg   1380
gacgccgcta gaaatctgca gcccaacctg tatgtggtgg ccgagctgtt taccggctcc   1440
gaggacctgg acaatgtgtt cgtgaccaga ctgggcatca gcagcctgat cagagaagcc   1500
atgtccgcct acaatagcca cgaagagggc agactggtgt acagatatgg cggcgagcct   1560
gtgggcagct tcgttcagcc ttgtctgagg cctctgatgc ccgccattgc tcacgccctg   1620
ttcatggaca tcacccacga taacgagtgc cccatcgtgc acagaagcgc ctacgacgct   1680
ctgcctagca ccaccattgt gtccatggcc tgttgtgcca gcggcagcac aagaggctat   1740
gacgaactgg tgccccacca gatttccgtg gtgtccgagg aacggttcta caccaagtgg   1800
aaccccgagg ctctgcccag caataccggc gaagtgaatt tccagagcgg catcattgcc   1860
gccagatgcg ccatcagcaa gctgcaccaa gaactgggcg ccaagggctt cattcaggtg   1920
tacgtggacc aggtcgacga ggacattgtg gccgtgacaa gacacagccc cagcatccat   1980
cagagcgtgg tggctgtgac cagaaccgcc ttcagaaacc ccaagaccag cttctacagc   2040
aaagaggtgc cccagatgtg catccccggc aagattgagg aagtggtgct cgaggcccgg   2100
accatcgaga gaaacaccaa gccttaccgg aaggacgaga actccatcaa cggcacccct   2160
gacatcaccg tggaaatcag agagcacatc cagctcaacg agagcaagat cgtgaaacag   2220
gccggcgtgg ccacaaaggg ccccaacgag tatatccaag agattgagtt cgagaatctg   2280
agccccggca gcgtgatcat cttcagagtg tccctggatc ctcacgctca ggtggccgtg   2340
ggcatcctga gaaatcacct gacacagttc agcccacact tcaagagcgg aagcctggcc   2400
gtggacaacg ccgatcctat cctgaagatc cccttcgcct ctctggccta cagactgaca   2460
ctggctgagc tgaaccagat cctgtacaga tgcgagtccg aagagaaaga ggatggcgga   2520
ggctgctacg acatccccaa ttggagcgcc ctgaagtatg ccggactgca gggactgatg   2580
tctgtgctgg ccgagatcag acccaagaac gacctgggac acccccttctg caacaacctg   2640
agatccggcg actggatgat cgactacgtg tccaacagac tgatcagcag atccggcaca   2700
atcgccgaag tcggcaaatg gctgcaggcc atgttcttct acctgaagca gatccctcgg   2760
tatctgatcc cctgctactt cgacgccatc ctgatcggcg cctacaccac actgctggat   2820
accgcctgga agcagatgtc cagcttcgtg cagaacggca gcaccttcgt gaagcacctg   2880
tctctgggaa gcgtgcagct gtgtggcgtg ggcaaatttc ccagcctgcc tatcctgtct   2940
cctgcactga tggacgtgcc ctaccggctg aatgagatca ccaaagaaaa agagcagtgc   3000
tgcgtcagcc tggctgctgg cctgcctcat ttttccagcg gcatcttccg gtgttggggc   3060
```

```
agagacacct ttattgccct gagaggcatc ctgctgatta ccggcagata cgtggaagcc   3120

cggaacatca tcctggcctt tgccggcaca ctgcggcacg gactgattcc taatctgctc   3180

ggcgagggca tctacgccag atacaactgc agagatgccg tgtggtggtg gctccagtgc   3240

atccaggact actgcaagat ggtgcccaac ggcctggaca tcctgaagtg ccctgtgtcc   3300

agaatgtacc ctaccgacga tagcgcccct ctgcctgccg gaacacttga ccagcctctg   3360

ttcgaagtga ttcaagaggc catgcagaaa cacatgcagg gaatccagtt tcgcgagcgg   3420

aatgccggac ctcagatcga cagaaacatg aaggatgagg gcttcaacat caccgctggc   3480

gtggacgaag agacaggctt tgtgtacggc ggcaaccggt tcaattgcgg cacctggatg   3540

gacaagatgg gcgagtctga ccgggccaga aacagaggaa ttcccgccac acctagagat   3600

ggcagcgctg tggaaatcgt gggcctgtct aagtctgctg tgcggtggct gctcgaactg   3660

agcaagaaga atatctttcc gtaccacgaa gtgaccgtga agcggcacgg caaggccatc   3720

aaggtgtcct acgacgagtg gaacagaaag atccaggaca acttcgaaaa gctgttccat   3780

gtgtctgagg accccagcga cctgaacgaa aagcacccca acctggtgca caagcgcggc   3840

atctacaagg acagctacgg cgcctcttct ccttggtgcg attaccagct gcggcccaac   3900

ttcaccattg ccatggtggt tgcccctgag ctgttcacca cagagaaggc ctggaaggcc   3960

ctggaaatcg ccgagaagaa actgctgggc cctctgggca tgaagacact ggaccccgac   4020

gacatggtgt actgcggaat ctacgacaac gccctggata acgacaacta caatctggcc   4080

aaggggttca attaccatca gggacccgag tggctgtggc ctatcggcta tttcctgcgg   4140

gccaagctgt acttctccag actgatgggc cctgagacaa ccgccaagac aatcgtgctc   4200

gtgaagaacg tgctgagccg gcactatgtg cacctggaaa gaagcccctg gaagggactg   4260

cccgagctga ccaatgagaa cgcccagtac tgccccttca gctgcgaaac acaggcctgg   4320

tctatcgcca ccatcctgga aaccctgtac gacctgtga                          4359
```

<210> SEQ ID NO 56
<211> LENGTH: 4293
<212> TYPE: DNA
<213> ORGANISM: artificial
<220> FEATURE:
<223> OTHER INFORMATION: D1b3 + D2,3 hGDE

<400> SEQUENCE: 56

```
atgggaggct acatcgtggt ggaccctatt ctgagagtgg gcgccgacaa tcacgtgctg     60

cctctggatt gtgtgaccct gcagaccttc ctggccaagt gtctgggccc tttcgatgag    120

tgggagagca gactgcgcgt ggccaaagaa agcggctaca acatgatcca cttcacccct    180

ctgcagaccc tgggcctgag cagaagctgt tacagcctgg ccaaccagct ggaactgaac    240

cccgacttca gcagacccaa ccggaagtac acctggaacg atgtgggcca gctggtggaa    300

aaactgaaga aagaatggaa cgtgatctgc atcaccgacg tggtgtacaa ccacaccgcc    360

gccaacagca agtggatcca agagcaccct gagtgcgcct acaacctggt caacagccct    420

cacctgaaac ctgcctgggt gctcgataga gccctgtggc ggtttagctg tgatgtggcc    480

gagggcaagt acaaagagaa gggcatcccc gctctgatcg agaacgacca ccacatgaac    540

agcatccgga agatcatctg ggaagatatt ttccccaagc tgaagctgtg ggagttcttc    600

caggtggacg tgaacaaggc cgtggaacag ttcagacggc tgctgaccca agagaacaga    660

agagtgacca agagcgaccc caaccagcac ctgaccatca ttcaggaccc cgagtatcgg    720
```

```
agattcggct gcaccgtgga catgaatatc gccctgacca ccttcattcc ccacgacaaa    780
ggacctgccg ccatcgagga atgctgcaac tggttccaca agcggatgga agaattgaac    840
agcgagaagc accggctgat caactaccac caagagcagg ccgtgaactg cctgctgggc    900
aacgtgttct atgagagact ggccggacac ggccctaagc tgggacctgt gacaagaaag    960
caccctctgg ttacccggta cttcaccttt ccattcgaag agatcgactt ctccatggaa   1020
gagagcatga tccatctgcc taacaaggcc tgcttcctga tggctcacaa cggctgggtt   1080
atgggcgacg accctctgag aaatttcgcc gagcctggca gcgaggtgta cctgagaaga   1140
gaactgatct gttggggcga cagcgtgaag ctgagatacg gcaacaagcc cgaggactgc   1200
ccttacctgt gggcccatat gaagaagtac acagagatca ccgccaccta ctttcagggc   1260
gtcagactgg acaactgcca cagcacacct ctgcacgtgg ccgagtacat gctggacgcc   1320
gctagaaatc tgcagcccaa cctgtatgtg gtggccgagc tgtttaccgg ctccgaggac   1380
ctggacaatg tgttcgtgac cagactgggc atcagcagcc tgatcagaga agccatgtcc   1440
gcctacaata gccacgaaga gggcagactg gtgtacagat atggcggcga gcctgtgggc   1500
agcttcgttc agccttgtct gaggcctctg atgcccgcca ttgctcacgc cctgttcatg   1560
gacatcaccc acgataacga gtgccccatc gtgcacagaa gcgcctacga cgctctgcct   1620
agcaccacca ttgtgtccat ggcctgttgt gccagcggca gcacaagagg ctatgacgaa   1680
ctggtgcccc accagatttc cgtggtgtcc gaggaacggt tctacaccaa gtggaacccc   1740
gaggctctgc ccagcaatac cggcgaagtg aatttccaga gcggcatcat tgccgccaga   1800
tgcgccatca gcaagctgca ccaagaactg ggcgccaagg gcttcattca ggtgtacgtg   1860
gaccaggtcg acgaggacat tgtggccgtg acaagacaca gccccagcat ccatcagagc   1920
gtggtggctg tgaccagaac cgccttcaga aaccccaaga ccagcttcta cagcaaagag   1980
gtgccccaga tgtgcatccc cggcaagatt gaggaagtgg tgctcgaggc ccggaccatc   2040
gagagaaaca ccaagcctta ccggaaggac gagaactcca tcaacggcac ccctgacatc   2100
accgtggaaa tcagagagca catccagctc aacgagagca agatcgtgaa acaggccggc   2160
gtggccacaa agggccccaa cgagtatatc caagagattg agttcgagaa tctgagcccc   2220
ggcagcgtga tcatcttcag agtgtccctg gatcctcacg ctcaggtggc cgtgggcatc   2280
ctgagaaatc acctgacaca gttcagccca cacttcaaga gcggaagcct ggccgtggac   2340
aacgccgatc ctatcctgaa gatccccttc gcctctctgg cctacagact gacactggct   2400
gagctgaacc agatcctgta cagatgcgag tccgaagaga aagaggatgg cggaggctgc   2460
tacgacatcc ccaattggag cgccctgaag tatgccggac tgcagggact gatgtctgtg   2520
ctggccgaga tcagacccaa gaacgacctg ggacacccct tctgcaacaa cctgagatcc   2580
ggcgactgga tgatcgacta cgtgtccaac agactgatca gcagatccgg cacaatcgcc   2640
gaagtcggca aatggctgca ggccatgttc ttctacctga agcagatccc tcggtatctg   2700
atcccctgct acttcgacgc catcctgatc ggcgcctaca ccacactgct ggataccgcc   2760
tggaagcaga tgtccagctt cgtgcagaac ggcagcacct tcgtgaagca cctgtctctg   2820
ggaagcgtgc agctgtgtgg cgtgggcaaa tttcccagcc tgcctatcct gtctcctgca   2880
ctgatggacg tgccctaccg gctgaatgag atcaccaaag aaaaagagca gtgctgcgtc   2940
agcctggctg ctggcctgcc tcatttttcc agcggcatct tccggtgttg gggcagagac   3000
acctttattg ccctgagagg catcctgctg attaccggca gatacgtgga agcccggaac   3060
atcatcctgg cctttgccgg cacactgcgg cacggactga ttcctaatct gctcggcgag   3120
```

ggcatctacg ccagatacaa ctgcagagat gccgtgtggt ggtggctcca gtgcatccag 3180
gactactgca agatggtgcc caacggcctg gacatcctga agtgccctgt gtccagaatg 3240
taccctaccg acgatagcgc ccctctgcct gccggaacac ttgaccagcc tctgttcgaa 3300
gtgattcaag aggccatgca gaaacacatg cagggaatcc agtttcgcga gcggaatgcc 3360
ggacctcaga tcgacagaaa catgaaggat gagggcttca acatcaccgc tggcgtggac 3420
gaagagacag gctttgtgta cggcggcaac cggttcaatt gcggcacctg gatggacaag 3480
atgggcgagt ctgaccgggc cagaaacaga ggaattcccg ccacacctag agatggcagc 3540
gctgtggaaa tcgtgggcct gtctaagtct gctgtgcggt ggctgctcga actgagcaag 3600
aagaatatct ttccgtacca cgaagtgacc gtgaagcggc acggcaaggc catcaaggtg 3660
tcctacgacg agtggaacag aaagatccag gacaacttcg aaaagctgtt ccatgtgtct 3720
gaggacccca gcgacctgaa cgaaaagcac cccaacctgg tgcacaagcg cggcatctac 3780
aaggacagct acggcgcctc ttctccttgg tgcgattacc agctgcggcc caacttcacc 3840
attgccatgg tggttgcccc tgagctgttc accacagaga aggcctggaa ggccctggaa 3900
atcgccgaga agaaactgct gggccctctg ggcatgaaga cactggaccc cgacgacatg 3960
gtgtactgcg gaatctacga caacgccctg gataacgaca actacaatct ggccaagggg 4020
ttcaattacc atcagggacc cgagtggctg tggcctatcg gctatttcct gcgggccaag 4080
ctgtacttct ccagactgat gggccctgag acaaccgcca agacaatcgt gctcgtgaag 4140
aacgtgctga gccggcacta tgtgcacctg gaaagaagcc cctggaaggg actgcccgag 4200
ctgaccaatg agaacgccca gtactgcccc ttcagctgcg aaacacaggc ctggtctatc 4260
gccaccatcc tggaaaccct gtacgacctg tga 4293

<210> SEQ ID NO 57
<211> LENGTH: 4215
<212> TYPE: DNA
<213> ORGANISM: artificial
<220> FEATURE:
<223> OTHER INFORMATION: D1c + D2,3 hGDE

<400> SEQUENCE: 57
atgcagacct tcctggccaa gtgtctgggc cctttcgatg agtgggagag cagactgcgc 60
gtggccaaag aaagcggcta caacatgatc cacttcaccc ctctgcagac cctgggcctg 120
agcagaagct gttacagcct ggccaaccag ctggaactga accccgactt cagcagaccc 180
aaccggaagt acacctggaa cgatgtgggc cagctggtgg aaaaactgaa gaaagaatgg 240
aacgtgatct gcatcaccga cgtggtgtac aaccacaccg ccgccaacag caagtggatc 300
caagagcacc ctgagtgcgc ctacaacctg gtcaacagcc ctcacctgaa acctgcctgg 360
gtgctcgata gagccctgtg gcggtttagc tgtgatgtgg ccgagggcaa gtacaaagag 420
aagggcatcc ccgctctgat cgagaacgac caccacatga acagcatccg gaagatcatc 480
tgggaagata ttttccccaa gctgaagctg tgggagttct tccaggtgga cgtgaacaag 540
gccgtggaac agttcagacg gctgctgacc caagagaaca gaagagtgac caagagcgac 600
cccaaccagc acctgaccat cattcaggac cccgagtatc ggagattcgg ctgcaccgtg 660
gacatgaata tcgccctgac caccttcatt ccccacgaca aaggacctgc cgccatcgag 720
gaatgctgca actggttcca caagcggatg gaagaattga acagcgagaa gcaccggctg 780
atcaactacc accaagagca ggccgtgaac tgcctgctgg gcaacgtgtt ctatgagaga 840

```
ctggccggac acggccctaa gctgggacct gtgacaagaa agcaccctct ggttacccgg    900
tacttcacct ttccattcga agagatcgac ttctccatgg aagagagcat gatccatctg    960
cctaacaagg cctgcttcct gatggctcac aacggctggg ttatgggcga cgaccctctg   1020
agaaatttcg ccgagcctgg cagcgaggtg tacctgagaa gagaactgat ctgttggggc   1080
gacagcgtga agctgagata cggcaacaag cccgaggact gcccttacct gtgggcccat   1140
atgaagaagt acacagagat caccgccacc tactttcagg gcgtcagact ggacaactgc   1200
cacagcacac ctctgcacgt ggccgagtac atgctggacg ccgctagaaa tctgcagccc   1260
aacctgtatg tggtggccga gctgtttacc ggctccgagg acctggacaa tgtgttcgtg   1320
accagactgg gcatcagcag cctgatcaga gaagccatgt ccgcctacaa tagccacgaa   1380
gagggcagac tggtgtacag atatggcggc gagcctgtgg gcagcttcgt tcagccttgt   1440
ctgaggcctc tgatgcccgc cattgctcac gccctgttca tggacatcac ccacgataac   1500
gagtgcccca tcgtgcacag aagcgcctac gacgctctgc ctagcaccac cattgtgtcc   1560
atggcctgtt gtgccagcgg cagcacaaga ggctatgacg aactggtgcc ccaccagatt   1620
tccgtggtgt ccgaggaacg gttctacacc aagtggaacc ccgaggctct gcccagcaat   1680
accggcgaag tgaatttcca gagcggcatc attgccgcca gatgcgccat cagcaagctg   1740
caccaagaac tgggcgccaa gggcttcatt caggtgtacg tggaccaggt cgacgaggac   1800
attgtggccg tgacaagaca cagccccagc atccatcaga gcgtggtggc tgtgaccaga   1860
accgccttca gaaaccccaa gaccagcttc tacagcaaag aggtgcccca gatgtgcatc   1920
cccggcaaga ttgaggaagt ggtgctcgag gcccggacca tcgagagaaa caccaagcct   1980
taccggaagg acgagaactc catcaacggc accccctgaca tcaccgtgga aatcagagag   2040
cacatccagc tcaacgagag caagatcgtg aaacaggccg gcgtggccac aaagggcccc   2100
aacgagtata tccaagagat tgagttcgag aatctgagcc ccggcagcgt gatcatcttc   2160
agagtgtccc tggatcctca cgctcaggtg gccgtgggca tcctgagaaa tcacctgaca   2220
cagttcagcc cacacttcaa gagcggaagc ctggccgtgg acaacgccga tcctatcctg   2280
aagatcccct tcgcctctct ggcctacaga ctgacactgg ctgagctgaa ccagatcctg   2340
tacagatgcg agtccgaaga gaaagaggat ggcggaggct gctacgacat ccccaattgg   2400
agcgccctga agtatgccgg actgcaggga ctgatgtctg tgctggccga gatcagaccc   2460
aagaacgacc tgggacaccc cttctgcaac aacctgagat ccggcgactg gatgatcgac   2520
tacgtgtcca acagactgat cagcagatcc ggcacaatcg ccgaagtcgg caaatggctg   2580
caggccatgt tcttctacct gaagcagatc cctcggtatc tgatcccctg ctacttcgac   2640
gccatcctga tcggcgccta caccacactg ctggataccg cctggaagca gatgtccagc   2700
ttcgtgcaga acggcagcac cttcgtgaag cacctgtctc tgggaagcgt gcagctgtgt   2760
ggcgtgggca aatttcccag cctgcctatc ctgtctcctg cactgatgga cgtgccctac   2820
cggctgaatg agatcaccaa agaaaaagag cagtgctgcg tcagcctggc tgctggcctg   2880
cctcattttt ccagcggcat cttccggtgt tggggcagag acacctttat tgccctgaga   2940
ggcatcctgc tgattaccgg cagatacgtg gaagcccgga acatcatcct ggcctttgcc   3000
ggcacactgc ggcacggact gattcctaat ctgctcggcg agggcatcta cgccagatac   3060
aactgcagag atgccgtgtg gtggtggctc cagtgcatcc aggactactg caagatggtg   3120
cccaacggcc tggacatcct gaagtgccct gtgtccagaa tgtaccctac cgacgatagc   3180
gcccctctgc ctgccggaac acttgaccag cctctgttcg aagtgattca agaggccatg   3240
```

```
cagaaacaca tgcagggaat ccagtttcgc gagcggaatg ccggacctca gatcgacaga   3300

aacatgaagg atgagggctt caacatcacc gctggcgtgg acgaagagac aggctttgtg   3360

tacggcggca accggttcaa ttgcggcacc tggatggaca agatgggcga gtctgaccgg   3420

gccagaaaca gaggaattcc cgccacacct agagatggca gcgctgtgga aatcgtgggc   3480

ctgtctaagt ctgctgtgcg gtggctgctc gaactgagca agaagaatat ctttccgtac   3540

cacgaagtga ccgtgaagcg gcacggcaag gccatcaagg tgtcctacga cgagtggaac   3600

agaaagatcc aggacaactt cgaaaagctg ttccatgtgt ctgaggaccc cagcgacctg   3660

aacgaaaagc accccaacct ggtgcacaag cgcggcatct acaaggacag ctacggcgcc   3720

tcttctcctt ggtgcgatta ccagctgcgg cccaacttca ccattgccat ggtggttgcc   3780

cctgagctgt tcaccacaga gaaggcctgg aaggccctgg aaatcgccga gaagaaactg   3840

ctgggccctc tgggcatgaa gacactggac cccgacgaca tggtgtactg cggaatctac   3900

gacaacgccc tggataacga caactacaat ctggccaagg ggttcaatta ccatcaggga   3960

cccgagtggc tgtggcctat cggctatttc ctgcgggcca agctgtactt ctccagactg   4020

atgggccctg agacaaccgc caagacaatc gtgctcgtga agaacgtgct gagccggcac   4080

tatgtgcacc tggaaagaag cccctggaag ggactgcccg agctgaccaa tgagaacgcc   4140

cagtactgcc ccttcagctg cgaaacacag gcctggtcta tcgccaccat cctggaaacc   4200

ctgtacgacc tgtga                                                    4215
```

<210> SEQ ID NO 58
<211> LENGTH: 17
<212> TYPE: DNA
<213> ORGANISM: artificial
<220> FEATURE:
<223> OTHER INFORMATION: sNRP1 polyadenylation signal

<400> SEQUENCE: 58

```
aaataaaata cgaaatg                                                    17
```

<210> SEQ ID NO 59
<211> LENGTH: 4557
<212> TYPE: DNA
<213> ORGANISM: artificial
<220> FEATURE:
<223> OTHER INFORMATION: delta-9 GDE (isoform 1 (SEQ ID NO:1); wt version)

<400> SEQUENCE: 59

```
atggagaaac tggaaaagac cctcttcaga cttgaacaag ggtatgagct acagttccga     60

ttaggcccaa ctttacaggg aaaagcagtt accgtgtata caaattaccc atttcctgga    120

gaaacattta atagagaaaa attccgttct ctggattggg aaaatccaac agaaagagaa    180

gatgattctg ataaatactg taaacttaat ctgcaacaat ctggttcatt tcagtattat    240

ttccttcaag gaaatgagaa aagtggtgga ggttacatag ttgtggaccc cattttacgt    300

gttggtgctg ataatcatgt gctacccttg gactgtgtta ctcttcagac atttttagct    360

aagtgtttgg gaccttttga tgaatgggaa agcagactta gggttgcaaa agaatcaggc    420

tacaacatga ttcattttac cccattgcag actcttggac tatctaggtc atgctactcc    480

cttgccaatc agttagaatt aaatcctgac ttttcaagac ctaatagaaa gtatacctgg    540

aatgatgttg gacagctagt ggaaaaatta aaaaaggaat ggaatgttat ttgtattact    600

gatgttgtct acaatcatac tgctgctaat agtaaatgga tccaggaaca tccagaatgt    660
```

```
gcctataatc ttgtaaattc tccacactta aaacctgcct gggtcttaga cagagcactt    720
tggcgtttct cctgtgatgt tgcagaaggg aaatacaaag aaaagggaat acctgctttg    780
attgaaaatg atcaccatat gaactccatc cgaaaaataa tttgggagga tatttttcca    840
aagcttaaac tctgggaatt tttccaagta gatgtcaaca aagcggttga gcaatttaga    900
agacttctta cacaagaaaa taggcgagta accaagtctg atccaaacca acaccttacg    960
attattcaag atcctgaata cagacggttt ggctgtactg tagatatgaa cattgcacta   1020
acgactttca taccacatga caaggggcca gcagcaattg aagaatgctg taattggttt   1080
cataaaagaa tggaggaatt aaattcagag aagcatcgac tcattaacta tcatcaggaa   1140
caggcagtta attgcctttt gggaaatgtg ttttatgaac gactggctgg ccatggtcca   1200
aaactaggac ctgtcactag aaagcatcct ttagttacca ggtattttac tttcccattt   1260
gaagagatag acttctccat ggaagaatct atgattcatc tgccaaataa agcttgtttt   1320
ctgatggcac acaatggatg ggtaatggga gatgatcctc ttcgaaactt tgctgaaccg   1380
ggttcagaag tttacctaag gagagaactt atttgctggg gagacagtgt taaattacgc   1440
tatgggaata aaccagagga ctgtccttat ctctgggcac acatgaaaaa atacactgaa   1500
ataactgcaa cttatttcca gggagtacgt cttgataact gccactcaac acctcttcac   1560
gtagctgagt acatgttgga tgctgctagg aatttgcaac ccaatttata tgtagtagct   1620
gaactgttca caggaagtga ggacctagac aatgtctttg ttactagact gggcattagt   1680
tccttaataa gagaggcaat gagtgcatat aatagtcatg aagagggcag attagtttac   1740
cgatatggag gagaacctgt tggatccttt gttcagccct gtttgaggcc tttaatgcca   1800
gctattgcac atgccctgtt tatggatatt acgcatgata atgagtgtcc tattgtgcat   1860
agatcagcgt atgatgctct tccaagtact acaattgttt ctatggcatg ttgtgctagt   1920
ggaagtacaa gaggctatga tgaattagtg cctcatcaga tttcagtggt ttctgaagaa   1980
cggttttaca ctaagtggaa tcctgaagca ttgccttcaa acacaggtga agttaatttc   2040
caaagcggca ttattgcagc caggtgtgct atcagtaaac ttcatcagga gcttggagcc   2100
aagggtttta ttcaggtgta tgtggatcaa gttgatgaag acatagtggc agtaacaaga   2160
cactcaccta gcatccatca gtctgttgtg gctgtaacta gaactgcttt caggaatccc   2220
aagacttcat tttacagcaa ggaagtgcct caaatgtgca tccctggcaa aattgaagaa   2280
gtagttcttg aagctagaac tattgagaga aacacgaaac cttataggaa ggatgaaaat   2340
tcaatcaatg gaacaccaga tatcacagta gaaattagag aacatattca gcttaatgaa   2400
agtaaaattg ttaaacaagc tggagttgcc acaaaagggc ccaatgaata tattcaagaa   2460
atagaatttg aaaacttgtc tccaggaagt gttattatat tcagagttag tcttgatcca   2520
catgcacaag tcgctgttgg cattcttcga aatcatctga cacaattcag tcctcacttt   2580
aaatctggca gcctagctgt tgacaatgca gatcctatat taaaaattcc ttttgcttct   2640
cttgcctata gattaacttt ggctgagcta aatcagatcc tttaccgatg tgaatcagaa   2700
gaaaaggaag atggtggagg gtgctatgac ataccaaact ggtcagccct taaatatgca   2760
ggtcttcaag gtttaatgtc tgtattggca gaaataagac caaagaatga cttggggcat   2820
cctttttgta ataatttgag gtctggagat tggatgattg actatgtcag taaccggctt   2880
atttcacgat caggaactat tgctgaagtt ggtaaatggt tgcaggctat gttcttctac   2940
ctgaagcaga tcccacgtta ccttatccca tgttactttg atgctatatt aattggtgca   3000
```

```
tataccactc ttctggatac agcatggaag cagatgtcaa gctttgttca gaatggttca   3060
acctttgtga aacacctttc attgggttca gttcaactgt gtggagtagg aaaattccct   3120
tccctgccaa ttctttcacc tgccctaatg gatgtacctt ataggttaaa tgagatcaca   3180
aaagaaaagg agcaatgttg tgtttctcta gctgcaggct tacctcattt ttcttctggt   3240
attttccgct gctggggaag ggatactttt attgcactta gaggtatact gctgattact   3300
ggacgctatg tagaagccag gaatattatt ttagcatttg cgggtaccct gaggcatggt   3360
ctcattccta atctactggg tgaaggaatt tatgccagat acaattgtcg ggatgctgtg   3420
tggtggtggc tgcagtgtat ccaggattac tgtaaaatgg ttccaaatgg actagacatt   3480
ctcaagtgcc cagtttccag aatgtatcct acagatgatt ctgctccttt gcctgctggc   3540
acactggatc agccattgtt tgaagtcata caggaagcaa tgcaaaaaca catgcagggc   3600
atacagttcc gagaaaggaa tgctggtccc cagatagatc gaaacatgaa ggacgaaggt   3660
tttaatataa ctgcaggagt tgatgaagaa acaggatttg tttatggagg aaatcgtttc   3720
aattgtggca catggatgga taaaatggga gaaagtgaca gagctagaaa cagaggaatc   3780
ccagccacac caagagatgg gtctgctgtg gaaattgtgg gcctgagtaa atctgctgtt   3840
cgctggttgc tggaattatc caaaaaaaat attttccctt atcatgaagt cacagtaaaa   3900
agacatggaa aggctataaa ggtctcatat gatgagtgga acagaaaaat acaagacaac   3960
tttgaaaagc tatttcatgt ttccgaagac ccttcagatt taaatgaaaa gcatccaaat   4020
ctggttcaca aacgtggcat atacaaagat agttatggag cttcaagtcc ttggtgtgac   4080
tatcagctca ggcctaattt taccatagca atggttgtgg cccctgagct ctttactaca   4140
gaaaaagcat ggaaagcttt ggagattgca gaaaaaaaat tgcttggtcc ccttggcatg   4200
aaaactttag atccagatga tatggtttac tgtggaattt atgacaacgc attagacaat   4260
gacaactaca atcttgctaa aggtttcaat tatcaccaag gacctgagtg gctgtggcct   4320
attgggtatt ttcttcgtgc aaaattatat ttttccagat tgatgggccc ggagactact   4380
gcaaagacta tagttttggt taaaaatgtt ctttcccgac attatgttca tcttgagaga   4440
tccccttgga aaggacttcc agaactgacc aatgagaatg cccagtactg tcctttcagc   4500
tgtgaaacac aagcctggtc aattgctact attcttgaga cactttatga tttatag      4557
```

```
<210> SEQ ID NO 60
<211> LENGTH: 4512
<212> TYPE: DNA
<213> ORGANISM: artificial
<220> FEATURE:
<223> OTHER INFORMATION: delta-10 GDE (isoform 1 (SEQ ID NO:1); wt
      version)

<400> SEQUENCE: 60
```

```
atgctacagt tccgattagg cccaacttta cagggaaaag cagttaccgt gtatacaaat     60
tacccatttc ctggagaaac atttaataga gaaaaattcc gttctctgga ttgggaaaat    120
ccaacagaaa gagaagatga ttctgataaa tactgtaaac ttaatctgca acaatctggt    180
tcatttcagt attatttcct tcaaggaaat gagaaaagtg gtggaggtta catagttgtg    240
gaccccattt tacgtgttgg tgctgataat catgtgctac ccttggactg tgttactctt    300
cagacatttt tagctaagtg tttgggacct tttgatgaat gggaaagcag acttagggtt    360
gcaaaagaat caggctacaa catgattcat tttaccccat tgcagactct tggactatct    420
aggtcatgct actcccttgc caatcagtta gaattaaatc ctgacttttc aagacctaat    480
```

```
agaaagtata cctggaatga tgttggacag ctagtggaaa aattaaaaaa ggaatggaat    540
gttatttgta ttactgatgt tgtctacaat catactgctg ctaatagtaa atggatccag    600
gaacatccag aatgtgccta taatcttgta aattctccac acttaaaacc tgcctgggtc    660
ttagacagag cactttggcg tttctcctgt gatgttgcag aagggaaata caaagaaaag    720
ggaataccctg ctttgattga aaatgatcac catatgaact ccatccgaaa aataatttgg   780
gaggatattt ttccaaagct taaactctgg gaatttttcc aagtagatgt caacaaagcg    840
gttgagcaat ttagaagact tcttacacaa gaaaataggc gagtaaccaa gtctgatcca    900
aaccaacacc ttacgattat tcaagatcct gaatacagac ggtttggctg tactgtagat    960
atgaacattg cactaacgac tttcatacca catgacaagg ggccagcagc aattgaagaa   1020
tgctgtaatt ggtttcataa aagaatggag gaattaaatt cagagaagca tcgactcatt   1080
aactatcatc aggaacaggc agttaattgc cttttgggaa atgtgtttta tgaacgactg   1140
gctggccatg gtccaaaact aggacctgtc actagaaagc atcctttagt taccaggtat   1200
tttactttcc catttgaaga gatagacttc tccatggaag aatctatgat tcatctgcca   1260
aataaagctt gttttctgat ggcacacaat ggatgggtaa tgggagatga tcctcttcga   1320
aactttgctg aaccgggttc agaagtttac ctaaggagag aacttatttg ctggggagac   1380
agtgttaaat tacgctatgg gaataaacca gaggactgtc cttatctctg ggcacacatg   1440
aaaaaataca ctgaaataac tgcaacttat ttccagggag tacgtcttga taactgccac   1500
tcaacacctc ttcacgtagc tgagtacatg ttggatgctg ctaggaattt gcaacccaat   1560
ttatatgtag tagctgaact gttcacagga agtgaggacc tagacaatgt ctttgttact   1620
agactgggca ttagttcctt aataagagag gcaatgagtg catataatag tcatgaagag   1680
ggcagattag tttaccgata tggaggagaa cctgttggat cctttgttca gccctgtttg   1740
aggcctttaa tgccagctat tgcacatgcc ctgtttatgg atattacgca tgataatgag   1800
tgtcctattg tgcatagatc agcgtatgat gctcttccaa gtactacaat tgtttctatg   1860
gcatgttgtg ctagtggaag tacaagaggc tatgatgaat tagtgcctca tcagatttca   1920
gtggtttctg aagaacggtt ttacactaag tggaatcctg aagcattgcc ttcaaacaca   1980
ggtgaagtta atttccaaag cggcattatt gcagccaggt gtgctatcag taaacttcat   2040
caggagcttg gagccaaggg ttttattcag gtgtatgtgg atcaagttga tgaagacata   2100
gtggcagtaa caagacactc acctagcatc catcagtctg ttgtggctgt aactagaact   2160
gctttcagga atcccaagac ttcattttac agcaaggaag tgcctcaaat gtgcatccct   2220
ggcaaaattg aagaagtagt tcttgaagct agaactattg agagaaacac gaaaccttat   2280
aggaaggatg aaaattcaat caatggaaca ccagatatca cagtagaaat tagagaacat   2340
attcagctta atgaaagtaa aattgttaaa caagctggag ttgccacaaa agggcccaat   2400
gaatatattc aagaaataga atttgaaaac ttgtctccag gaagtgttat tatattcaga   2460
gttagtcttg atccacatgc acaagtcgct gttggcattc ttcgaaatca tctgacacaa   2520
ttcagtcctc actttaaatc tggcagccta gctgttgaca atgcagatcc tatattaaaa   2580
attccttttg cttctcttgc ctatagatta actttggctg agctaaatca gatcctttac   2640
cgatgtgaat cagaagaaaa ggaagatggt ggagggtgct atgacatacc aaactggtca   2700
gcccttaaat atgcaggtct tcaaggttta atgtctgtat tggcagaaat aagaccaaag   2760
aatgacttgg ggcatccttt ttgtaataat ttgaggtctg gagattggat gattgactat   2820
gtcagtaacc ggcttatttc acgatcagga actattgctg aagttggtaa atggttgcag   2880
```

```
gctatgttct tctacctgaa gcagatccca cgttacctta tcccatgtta ctttgatgct   2940

atattaattg gtgcatatac cactcttctg gatacagcat ggaagcagat gtcaagcttt   3000

gttcagaatg gttcaacctt tgtgaaacac ctttcattgg gttcagttca actgtgtgga   3060

gtaggaaaat tcccttccct gccaattctt tcacctgccc taatggatgt accttatagg   3120

ttaaatgaga tcacaaaaga aaaggagcaa tgttgtgttt ctctagctgc aggcttacct   3180

catttttctt ctggtatttt ccgctgctgg ggaagggata cttttattgc acttagaggt   3240

atactgctga ttactggacg ctatgtagaa gccaggaata ttattttagc atttgcgggt   3300

accctgaggc atggtctcat tcctaatcta ctgggtgaag gaatttatgc cagatacaat   3360

tgtcgggatg ctgtgtggtg gtggctgcag tgtatccagg attactgtaa aatggttcca   3420

aatggactag acattctcaa gtgcccagtt tccagaatgt atcctacaga tgattctgct   3480

cctttgcctg ctggcacact ggatcagcca ttgtttgaag tcatacagga agcaatgcaa   3540

aaacacatgc agggcataca gttccgagaa aggaatgctg gtccccagat agatcgaaac   3600

atgaaggacg aaggttttaa tataactgca ggagttgatg aagaaacagg atttgtttat   3660

ggaggaaatc gtttcaattg tggcacatgg atggataaaa tgggagaaag tgacagagct   3720

agaaacagag gaatcccagc cacaccaaga gatgggtctg ctgtggaaat tgtgggcctg   3780

agtaaatctg ctgttcgctg gttgctggaa ttatccaaaa aaaatatttt cccttatcat   3840

gaagtcacag taaaaagaca tggaaaggct ataaaggtct catatgatga gtggaacaga   3900

aaaatacaag acaactttga aaagctattt catgtttccg aagacccttc agatttaaat   3960

gaaaagcatc caaatctggt tcacaaacgt ggcatataca aagatagtta tggagcttca   4020

agtccttggt gtgactatca gctcaggcct aattttacca tagcaatggt tgtggcccct   4080

gagctcttta ctacagaaaa agcatggaaa gctttggaga ttgcagaaaa aaaattgctt   4140

ggtccccttg gcatgaaaac tttagatcca gatgatatgg tttactgtgg aatttatgac   4200

aacgcattag acaatgacaa ctacaatctt gctaaaggtt tcaattatca ccaaggacct   4260

gagtggctgt ggcctattgg gtattttctt cgtgcaaaat tatatttttc cagattgatg   4320

ggcccggaga ctactgcaaa gactatagtt ttggttaaaa atgttctttc ccgacattat   4380

gttcatcttg agagatcccc ttggaaagga cttccagaac tgaccaatga gaatgcccag   4440

tactgtcctt tcagctgtga aacacaagcc tggtcaattg ctactattct tgagacactt   4500

tatgatttat ag                                                       4512
```

<210> SEQ ID NO 61
<211> LENGTH: 4359
<212> TYPE: DNA
<213> ORGANISM: artificial
<220> FEATURE:
<223> OTHER INFORMATION: delta-11 GDE (isoform 1 (SEQ ID NO:1); wt version)

<400> SEQUENCE: 61

```
atgaaactta atctgcaaca atctggttca tttcagtatt atttccttca aggaaatgag     60

aaaagtggtg gaggttacat agttgtggac cccattttac gtgttggtgc tgataatcat    120

gtgctaccct tggactgtgt tactcttcag acatttttag ctaagtgttt gggacctttt    180

gatgaatggg aaagcagact tagggttgca aaagaatcag gctacaacat gattcatttt    240

accccattgc agactcttgg actatctagg tcatgctact cccttgccaa tcagttagaa    300

ttaaatcctg acttttcaag acctaataga aagtatacct ggaatgatgt tggacagcta    360
```

```
gtggaaaaat taaaaaagga atggaatgtt atttgtatta ctgatgttgt ctacaatcat    420
actgctgcta atagtaaatg gatccaggaa catccagaat gtgcctataa tcttgtaaat    480
tctccacact taaaacctgc ctgggtctta gacagagcac tttggcgttt ctcctgtgat    540
gttgcagaag ggaaatacaa agaaaaggga atacctgctt tgattgaaaa tgatcaccat    600
atgaactcca tccgaaaaat aatttgggag gatatttttc caaagcttaa actctgggaa    660
tttttccaag tagatgtcaa caaagcggtt gagcaattta gaagacttct tacacaagaa    720
aataggcgag taaccaagtc tgatccaaac caacacctta cgattattca agatcctgaa    780
tacagacggt ttggctgtac tgtagatatg aacattgcac taacgacttt cataccacat    840
gacaaggggc cagcagcaat tgaagaatgc tgtaattggt ttcataaaag aatggaggaa    900
ttaaattcag agaagcatcg actcattaac tatcatcagg aacaggcagt taattgcctt    960
ttgggaaatg tgttttatga acgactggct ggccatggtc caaaactagg acctgtcact   1020
agaaagcatc ctttagttac caggtatttt actttcccat ttgaagagat agacttctcc   1080
atggaagaat ctatgattca tctgccaaat aaagcttgtt ttctgatggc acacaatgga   1140
tgggtaatgg gagatgatcc tcttcgaaac tttgctgaac cgggttcaga agtttaccta   1200
aggagagaac ttatttgctg gggagacagt gttaaattac gctatgggaa taaaccagag   1260
gactgtcctt atctctgggc acacatgaaa aaatacactg aaataactgc aacttatttc   1320
cagggagtac gtcttgataa ctgccactca acacctcttc acgtagctga gtacatgttg   1380
gatgctgcta ggaatttgca acccaattta tatgtagtag ctgaactgtt cacaggaagt   1440
gaggacctag acaatgtctt tgttactaga ctgggcatta gttccttaat aagagaggca   1500
atgagtgcat ataatagtca tgaagagggc agattagttt accgatatgg aggagaacct   1560
gttggatcct ttgttcagcc ctgtttgagg cctttaatgc cagctattgc acatgccctg   1620
tttatggata ttacgcatga taatgagtgt cctattgtgc atagatcagc gtatgatgct   1680
cttccaagta ctacaattgt ttctatggca tgttgtgcta gtggaagtac aagaggctat   1740
gatgaattag tgcctcatca gatttcagtg gtttctgaag aacggtttta cactaagtgg   1800
aatcctgaag cattgccttc aaacacaggt gaagttaatt tccaaagcgg cattattgca   1860
gccaggtgtg ctatcagtaa acttcatcag gagcttggag ccaagggttt tattcaggtg   1920
tatgtggatc aagttgatga agacatagtg gcagtaacaa gacactcacc tagcatccat   1980
cagtctgttg tggctgtaac tagaactgct ttcaggaatc ccaagacttc attttacagc   2040
aaggaagtgc ctcaaatgtg catccctggc aaaattgaag aagtagttct tgaagctaga   2100
actattgaga gaaacacgaa accttatagg aaggatgaaa attcaatcaa tggaacacca   2160
gatatcacag tagaaattag agaacatatt cagcttaatg aaagtaaaat tgttaaacaa   2220
gctggagttg ccacaaaagg gcccaatgaa tatattcaag aaatagaatt tgaaaacttg   2280
tctccaggaa gtgttattat attcagagtt agtcttgatc cacatgcaca agtcgctgtt   2340
ggcattcttc gaaatcatct gacacaattc agtcctcact ttaaatctgg cagcctagct   2400
gttgacaatg cagatcctat attaaaaatt ccttttgctt ctcttgccta tagattaact   2460
ttggctgagc taaatcagat cctttaccga tgtgaatcag aagaaaagga agatggtgga   2520
gggtgctatg acataccaaa ctggtcagcc cttaaatatg caggtcttca aggtttaatg   2580
tctgtattgg cagaaataag accaaagaat gacttggggc atcctttttg taataatttg   2640
aggtctggag attggatgat tgactatgtc agtaaccggc ttatttcacg atcaggaact   2700
```

```
attgctgaag ttggtaaatg gttgcaggct atgttcttct acctgaagca gatcccacgt   2760
taccttatcc catgttactt tgatgctata ttaattggtg catataccac tcttctggat   2820
acagcatgga agcagatgtc aagctttgtt cagaatggtt caacctttgt gaaacacctt   2880
tcattgggtt cagttcaact gtgtggagta ggaaaattcc cttccctgcc aattctttca   2940
cctgccctaa tggatgtacc ttataggtta aatgagatca caaaagaaaa ggagcaatgt   3000
tgtgtttctc tagctgcagg cttacctcat ttttcttctg gtatttttccg ctgctgggga   3060
agggatactt ttattgcact tagaggtata ctgctgatta ctggacgcta tgtagaagcc   3120
aggaatatta ttttagcatt tgcgggtacc ctgaggcatg gtctcattcc taatctactg   3180
ggtgaaggaa tttatgccag atacaattgt cgggatgctg tgtggtggtg gctgcagtgt   3240
atccaggatt actgtaaaat ggttccaaat ggactagaca ttctcaagtg cccagtttcc   3300
agaatgtatc ctacagatga ttctgctcct ttgcctgctg gcacactgga tcagccattg   3360
tttgaagtca tacaggaagc aatgcaaaaa cacatgcagg gcatacagtt ccgagaaagg   3420
aatgctggtc cccagataga tcgaaacatg aaggacgaag gttttaatat aactgcagga   3480
gttgatgaag aaacaggatt tgtttatgga ggaaatcgtt tcaattgtgg cacatggatg   3540
gataaaatgg gagaaagtga cagagctaga aacagaggaa tcccagccac accaagagat   3600
gggtctgctg tggaaattgt gggcctgagt aaatctgctg ttcgctggtt gctggaatta   3660
tccaaaaaaa atattttccc ttatcatgaa gtcacagtaa aaagacatgg aaaggctata   3720
aaggtctcat atgatgagtg gaacagaaaa atacaagaca actttgaaaa gctatttcat   3780
gtttccgaag acccttcaga tttaaatgaa aagcatccaa atctggttca caaacgtggc   3840
atatacaaag atagttatgg agcttcaagt ccttggtgtg actatcagct caggcctaat   3900
tttaccatag caatggttgt ggccccctgag ctctttacta cagaaaaagc atggaaagct   3960
ttggagattg cagaaaaaaa attgcttggt cccctttggca tgaaaacttt agatccagat   4020
gatatggttt actgtggaat ttatgacaac gcattagaca atgacaacta caatcttgct   4080
aaaggtttca attatcacca aggacctgag tggctgtggc ctattgggta ttttcttcgt   4140
gcaaaattat atttttccag attgatgggc ccggagacta ctgcaaagac tatagttttg   4200
gttaaaaatg ttctttcccg acattatgtt catcttgaga gatccccttg gaaaggactt   4260
ccagaactga ccaatgagaa tgcccagtac tgtcctttca gctgtgaaac acaagcctgg   4320
tcaattgcta ctattcttga gacactttat gatttatag                         4359
```

<210> SEQ ID NO 62
<211> LENGTH: 4293
<212> TYPE: DNA
<213> ORGANISM: artificial
<220> FEATURE:
<223> OTHER INFORMATION: delta-12 GDE (isoform 1 (SEQ ID NO:1); wt version)

<400> SEQUENCE: 62

```
atgggaggtt acatagttgt ggaccccatt ttacgtgttg gtgctgataa tcatgtgcta     60
cccttggact gtgttactct tcagacattt ttagctaagt gtttgggacc ttttgatgaa    120
tgggaaagca gacttagggt tgcaaaagaa tcaggctaca acatgattca ttttacccca    180
ttgcagactc ttggactatc taggtcatgc tactcccttg ccaatcagtt agaattaaat    240
cctgactttt caagacctaa tagaaagtat acctggaatg atgttggaca gctagtggaa    300
aaattaaaaa aggaatggaa tgttatttgt attactgatg ttgtctacaa tcatactgct    360
```

```
gctaatagta aatggatcca ggaacatcca gaatgtgcct ataatcttgt aaattctcca    420
cacttaaaac ctgcctgggt cttagacaga gcactttggc gtttctcctg tgatgttgca    480
gaagggaaat acaaagaaaa gggaatacct gctttgattg aaaatgatca ccatatgaac    540
tccatccgaa aaataatttg ggaggatatt tttccaaagc ttaaactctg ggaatttttc    600
caagtagatg tcaacaaagc ggttgagcaa tttagaagac ttcttacaca agaaaatagg    660
cgagtaacca agtctgatcc aaaccaacac cttacgatta ttcaagatcc tgaatacaga    720
cggtttggct gtactgtaga tatgaacatt gcactaacga ctttcatacc acatgacaag    780
gggccagcag caattgaaga atgctgtaat tggtttcata aaagaatgga ggaattaaat    840
tcagagaagc atcgactcat taactatcat caggaacagg cagttaattg ccttttggga    900
aatgtgtttt atgaacgact ggctggccat ggtccaaaac taggacctgt cactagaaag    960
catcctttag ttaccaggta ttttactttc ccatttgaag agatagactt ctccatggaa   1020
gaatctatga ttcatctgcc aaataaagct tgttttctga tggcacacaa tggatgggta   1080
atgggagatg atcctcttcg aaactttgct gaaccgggtt cagaagttta cctaaggaga   1140
gaacttattt gctggggaga cagtgttaaa ttacgctatg ggaataaacc agaggactgt   1200
ccttatctct gggcacacat gaaaaaatac actgaaataa ctgcaactta tttccaggga   1260
gtacgtcttg ataactgcca ctcaacacct cttcacgtag ctgagtacat gttggatgct   1320
gctaggaatt tgcaacccaa tttatatgta gtagctgaac tgttcacagg aagtgaggac   1380
ctagacaatg tctttgttac tagactgggc attagttcct taataagaga ggcaatgagt   1440
gcatataata gtcatgaaga gggcagatta gtttaccgat atggaggaga acctgttgga   1500
tcctttgttc agccctgttt gaggccttta atgccagcta ttgcacatgc cctgtttatg   1560
gatattacgc atgataatga gtgtcctatt gtgcatagat cagcgtatga tgctcttcca   1620
agtactacaa ttgtttctat ggcatgttgt gctagtggaa gtacaagagg ctatgatgaa   1680
ttagtgcctc atcagatttc agtggtttct gaagaacggt tttacactaa gtggaatcct   1740
gaagcattgc cttcaaacac aggtgaagtt aatttccaaa gcggcattat tgcagccagg   1800
tgtgctatca gtaaacttca tcaggagctt ggagccaagg gttttattca ggtgtatgtg   1860
gatcaagttg atgaagacat agtggcagta acaagacact cacctagcat ccatcagtct   1920
gttgtggctg taactagaac tgctttcagg aatcccaaga cttcatttta cagcaaggaa   1980
gtgcctcaaa tgtgcatccc tggcaaaatt gaagaagtag ttcttgaagc tagaactatt   2040
gagagaaaca cgaaacctta taggaaggat gaaaattcaa tcaatggaac accagatatc   2100
acagtagaaa ttagagaaca tattcagctt aatgaaagta aaattgttaa acaagctgga   2160
gttgccacaa aagggcccaa tgaatatatt caagaaatag aatttgaaaa cttgtctcca   2220
ggaagtgtta ttatattcag agttagtctt gatccacatg cacaagtcgc tgttggcatt   2280
cttcgaaatc atctgacaca attcagtcct cactttaaat ctggcagcct agctgttgac   2340
aatgcagatc ctatattaaa aattcctttt gcttctcttg cctatagatt aactttggct   2400
gagctaaatc agatccttta ccgatgtgaa tcagaagaaa aggaagatgg tggagggtgc   2460
tatgacatac caaactggtc agcccttaaa tatgcaggtc ttcaaggttt aatgtctgta   2520
ttggcagaaa taagaccaaa gaatgacttg gggcatcctt tttgtaataa tttgaggtct   2580
ggagattgga tgattgacta tgtcagtaac cggcttattt cacgatcagg aactattgct   2640
gaagttggta aatggttgca ggctatgttc ttctacctga agcagatccc acgttacctt   2700
atcccatgtt actttgatgc tatattaatt ggtgcatata ccactcttct ggatacagca   2760
```

```
tggaagcaga tgtcaagctt tgttcagaat ggttcaacct ttgtgaaaca cctttcattg   2820
ggttcagttc aactgtgtgg agtaggaaaa ttcccttccc tgccaattct ttcacctgcc   2880
ctaatggatg taccttatag gttaaatgag atcacaaaag aaaaggagca atgttgtgtt   2940
tctctagctg caggcttacc tcatttttct tctggtattt tccgctgctg ggaagggat    3000
acttttattg cacttagagg tatactgctg attactggac gctatgtaga agccaggaat   3060
attattttag catttgcggg taccctgagg catggtctca ttcctaatct actgggtgaa   3120
ggaatttatg ccagatacaa ttgtcgggat gctgtgtggt ggtggctgca gtgtatccag   3180
gattactgta aaatggttcc aaatggacta gacattctca agtgcccagt ttccagaatg   3240
tatcctacag atgattctgc tcctttgcct gctggcacac tggatcagcc attgtttgaa   3300
gtcatacagg aagcaatgca aaaacacatg cagggcatac agttccgaga aaggaatgct   3360
ggtccccaga tagatcgaaa catgaaggac gaaggtttta atataactgc aggagttgat   3420
gaagaaacag gatttgttta tggaggaaat cgtttcaatt gtggcacatg gatggataaa   3480
atgggagaaa gtgacagagc tagaaacaga ggaatcccag ccacaccaag agatgggtct   3540
gctgtggaaa ttgtgggcct gagtaaatct gctgttcgct ggttgctgga attatccaaa   3600
aaaaatattt tcccttatca tgaagtcaca gtaaaaagac atggaaaggc tataaaggtc   3660
tcatatgatg agtggaacag aaaaatacaa gacaactttg aaaagctatt tcatgtttcc   3720
gaagaccctt cagatttaaa tgaaaagcat ccaaatctgg ttcacaaacg tggcatatac   3780
aaagatagtt atggagcttc aagtccttgg tgtgactatc agctcaggcc taattttacc   3840
atagcaatgg ttgtggcccc tgagctcttt actacagaaa aagcatggaa agctttggag   3900
attgcagaaa aaaaattgct tggtcccctt ggcatgaaaa ctttagatcc agatgatatg   3960
gtttactgtg gaatttatga caacgcatta gacaatgaca actacaatct tgctaaaggt   4020
ttcaattatc accaaggacc tgagtggctg tggcctattg ggtattttct tcgtgcaaaa   4080
ttatattttt ccagattgat gggcccggag actactgcaa agactatagt tttggttaaa   4140
aatgttcttt cccgacatta tgttcatctt gagagatccc cttggaaagg acttccagaa   4200
ctgaccaatg agaatgccca gtactgtcct ttcagctgtg aaacacaagc ctggtcaatt   4260
gctactattc ttgagacact ttatgattta tag                                4293
```

<210> SEQ ID NO 63
<211> LENGTH: 4215
<212> TYPE: DNA
<213> ORGANISM: artificial
<220> FEATURE:
<223> OTHER INFORMATION: delta-13 GDE (isoform 1 (SEQ ID NO:1); wt version)

<400> SEQUENCE: 63

```
atgcagacat ttttagctaa gtgtttggga ccttttgatg aatgggaaag cagacttagg     60
gttgcaaaag aatcaggcta caacatgatt cattttaccc cattgcagac tcttggacta    120
tctaggtcat gctactccct tgccaatcag ttagaattaa atcctgactt ttcaagacct    180
aatagaaagt atacctggaa tgatgttgga cagctagtgg aaaaattaaa aaaggaatgg    240
aatgttattt gtattactga tgttgtctac aatcatactg ctgctaatag taaatggatc    300
caggaacatc cagaatgtgc ctataatctt gtaaattctc cacacttaaa acctgcctgg    360
gtcttagaca gagcactttg gcgtttctcc tgtgatgttg cagaagggaa atacaaagaa    420
aagggaatac ctgctttgat tgaaaatgat caccatatga actccatccg aaaaataatt    480
```

```
tgggaggata tttttccaaa gcttaaactc tgggaatttt tccaagtaga tgtcaacaaa    540
gcggttgagc aatttagaag acttcttaca caagaaaata ggcgagtaac caagtctgat    600
ccaaaccaac accttacgat tattcaagat cctgaataca gacggtttgg ctgtactgta    660
gatatgaaca ttgcactaac gactttcata ccacatgaca aggggccagc agcaattgaa    720
gaatgctgta attggtttca taaaagaatg gaggaattaa attcagagaa gcatcgactc    780
attaactatc atcaggaaca ggcagttaat tgccttttgg gaaatgtgtt ttatgaacga    840
ctggctggcc atggtccaaa actaggacct gtcactagaa agcatccttt agttaccagg    900
tattttactt tcccatttga agagatagac ttctccatgg aagaatctat gattcatctg    960
ccaaataaag cttgttttct gatggcacac aatggatggg taatgggaga tgatcctctt   1020
cgaaactttg ctgaaccggg ttcagaagtt tacctaagga gagaacttat ttgctgggga   1080
gacagtgtta aattacgcta tgggaataaa ccagaggact gtccttatct ctgggcacac   1140
atgaaaaaat acactgaaat aactgcaact tatttccagg gagtacgtct tgataactgc   1200
cactcaacac ctcttcacgt agctgagtac atgttggatg ctgctaggaa tttgcaaccc   1260
aatttatatg tagtagctga actgttcaca ggaagtgagg acctagacaa tgtctttgtt   1320
actagactgg gcattagttc cttaataaga gaggcaatga gtgcatataa tagtcatgaa   1380
gagggcagat tagtttaccg atatggagga gaacctgttg gatcctttgt tcagccctgt   1440
ttgaggcctt taatgccagc tattgcacat gccctgttta tggatattac gcatgataat   1500
gagtgtccta ttgtgcatag atcagcgtat gatgctcttc caagtactac aattgtttct   1560
atggcatgtt gtgctagtgg aagtacaaga ggctatgatg aattagtgcc tcatcagatt   1620
tcagtggttt ctgaagaacg gttttacact aagtggaatc ctgaagcatt gccttcaaac   1680
acaggtgaag ttaatttcca aagcggcatt attgcagcca ggtgtgctat cagtaaactt   1740
catcaggagc ttggagccaa gggttttatt caggtgtatg tggatcaagt tgatgaagac   1800
atagtggcag taacaagaca ctcacctagc atccatcagt ctgttgtggc tgtaactaga   1860
actgctttca ggaatcccaa gacttcattt tacagcaagg aagtgcctca aatgtgcatc   1920
cctggcaaaa ttgaagaagt agttcttgaa gctagaacta ttgagagaaa cacgaaacct   1980
tataggaagg atgaaaattc aatcaatgga acaccagata tcacagtaga aattagagaa   2040
catattcagc ttaatgaaag taaaattgtt aaacaagctg gagttgccac aaaagggccc   2100
aatgaatata ttcaagaaat agaatttgaa aacttgtctc caggaagtgt tattatattc   2160
agagttagtc ttgatccaca tgcacaagtc gctgttggca ttcttcgaaa tcatctgaca   2220
caattcagtc ctcactttaa atctggcagc ctagctgttg acaatgcaga tcctatatta   2280
aaaattcctt ttgcttctct tgcctataga ttaactttgg ctgagctaaa tcagatcctt   2340
taccgatgtg aatcagaaga aaaggaagat ggtggagggt gctatgacat accaaactgg   2400
tcagccctta aatatgcagg tcttcaaggt ttaatgtctg tattggcaga aataagacca   2460
aagaatgact tggggcatcc tttttgtaat aatttgaggt ctggagattg gatgattgac   2520
tatgtcagta accggcttat ttcacgatca ggaactattg ctgaagttgg taaatggttg   2580
caggctatgt tcttctacct gaagcagatc ccacgttacc ttatcccatg ttactttgat   2640
gctatattaa ttggtgcata taccactctt ctggatacag catggaagca gatgtcaagc   2700
tttgttcaga atggttcaac ctttgtgaaa cacctttcat tgggttcagt tcaactgtgt   2760
ggagtaggaa aattcccttc cctgccaatt ctttcacctg ccctaatgga tgtaccttat   2820
```

-continued

```
aggttaaatg agatcacaaa agaaaaggag caatgttgtg tttctctagc tgcaggctta   2880

cctcattttt cttctggtat tttccgctgc tggggaaggg atacttttat tgcacttaga   2940

ggtatactgc tgattactgg acgctatgta gaagccagga atattatttt agcatttgcg   3000

ggtaccctga ggcatggtct cattcctaat ctactgggtg aaggaattta tgccagatac   3060

aattgtcggg atgctgtgtg gtggtggctg cagtgtatcc aggattactg taaaatggtt   3120

ccaaatggac tagacattct caagtgccca gtttccagaa tgtatcctac agatgattct   3180

gctcctttgc ctgctggcac actggatcag ccattgtttg aagtcataca ggaagcaatg   3240

caaaaacaca tgcagggcat acagttccga gaaaggaatg ctggtcccca gatagatcga   3300

aacatgaagg acgaaggttt taatataact gcaggagttg atgaagaaac aggatttgtt   3360

tatggaggaa atcgtttcaa ttgtggcaca tggatggata aaatgggaga aagtgacaga   3420

gctagaaaca gaggaatccc agccacacca agagatgggt ctgctgtgga aattgtgggc   3480

ctgagtaaat ctgctgttcg ctggttgctg gaattatcca aaaaaaatat tttcccttat   3540

catgaagtca cagtaaaaag acatggaaag gctataaagg tctcatatga tgagtggaac   3600

agaaaaatac aagacaactt tgaaaagcta tttcatgttt ccgaagaccc ttcagattta   3660

aatgaaaagc atccaaatct ggttcacaaa cgtggcatat acaaagatag ttatggagct   3720

tcaagtcctt ggtgtgacta tcagctcagg cctaatttta ccatagcaat ggttgtggcc   3780

cctgagctct ttactacaga aaaagcatgg aaagctttgg agattgcaga aaaaaaattg   3840

cttggtcccc ttggcatgaa aactttagat ccagatgata tggtttactg tggaatttat   3900

gacaacgcat tagacaatga caactacaat cttgctaaag gtttcaatta tcaccaagga   3960

cctgagtggc tgtggcctat tgggtatttt cttcgtgcaa aattatattt ttccagattg   4020

atgggcccgg agactactgc aaagactata gttttggtta aaaatgttct ttcccgacat   4080

tatgttcatc ttgagagatc cccttggaaa ggacttccag aactgaccaa tgagaatgcc   4140

cagtactgtc ctttcagctg tgaaacacaa gcctggtcaa ttgctactat tcttgagaca   4200

ctttatgatt tatag                                                    4215
```